US012570668B2

(12) United States Patent
Morales et al.

(10) Patent No.: US 12,570,668 B2
(45) Date of Patent: Mar. 10, 2026

(54) SINGLE MOLECULE COMPOUNDS PROVIDING MULTI-TARGET INHIBITION OF BTK AND OTHER PROTEINS AND METHODS OF USE THEREOF

(71) Applicant: SignalRx Pharmaceuticals, Inc., Cumming, GA (US)

(72) Inventors: Guillermo A. Morales, Oro Valley, AZ (US); Joseph R. Garlich, Cape Coral, FL (US); Donald L. Durden, Charlotte, NC (US)

(73) Assignee: SignalRx Pharmaceuticals, Inc., Cumming, GA (US)

( * ) Notice: Subject to any disclaimer, the term of this patent is extended or adjusted under 35 U.S.C. 154(b) by 1177 days.

(21) Appl. No.: 17/262,358

(22) PCT Filed: Jul. 22, 2019

(86) PCT No.: PCT/US2019/042753

§ 371 (c)(1),
(2) Date: Jan. 22, 2021

(87) PCT Pub. No.: WO2020/023340

PCT Pub. Date: Jan. 30, 2020

(65) Prior Publication Data

US 2021/0300939 A1 Sep. 30, 2021

Related U.S. Application Data

(60) Provisional application No. 62/702,233, filed on Jul. 23, 2018.

(51) Int. Cl.
*C07D 495/04* (2006.01)
*A61P 35/00* (2006.01)

(52) U.S. Cl.
CPC ............ *C07D 495/04* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 8,557,807 | B2 * | 10/2013 | Morales | A61P 35/02 544/122 |
| 9,505,780 | B2 | 11/2016 | Morales et al. | |
| 9,550,790 | B2 * | 1/2017 | Morales | C07K 5/10 |
| 9,981,983 | B2 * | 5/2018 | Morales | A61K 31/381 |

(Continued)

FOREIGN PATENT DOCUMENTS

| | | |
|---|---|---|
| WO | WO 2018/140730 | 2/2018 |
| WO | WO 2018/226739 | 12/2018 |
| WO | WO 2018/236971 | 12/2018 |

OTHER PUBLICATIONS (Batlevi et al., Annals of Oncology, vol. 28, Issue 9, 2017, pp. 2047-2049) (Year: 2017).*

*Primary Examiner* — Jeffrey S Lundgren
*Assistant Examiner* — Anthony Joseph Seitz
(74) *Attorney, Agent, or Firm* — TDW Patents & Consulting LLC; Thomas D. Webster

(57) ABSTRACT

The invention relates to compounds useful for inhibiting BTK and at least one other protein and to methods of treating diseases including cancer by administration of a compound(s) of Formula I-IV or pharmaceutically acceptable salts thereof as defined herein.

19 Claims, 7 Drawing Sheets

(56) References Cited

U.S. PATENT DOCUMENTS

| | | | | |
|---|---|---|---|---|
| 10,174,032 | B2 | 1/2019 | Morales et al. | |
| 10,308,662 | B2 * | 6/2019 | Durden ................ | A61K 31/538 |
| 11,472,814 | B2 * | 10/2022 | Morales .................. | A61P 35/00 |
| 2023/0165873 | A1 * | 6/2023 | Durden .............. | A61K 31/7068<br>514/210.21 |
| 2024/0043445 | A1 * | 2/2024 | Morales .................. | A61P 29/00 |

* cited by examiner

SINGLE MOLECULE COMPOUNDS PROVIDING MULTI-TARGET INHIBITION OF BTK AND OTHER PROTEINS AND METHODS OF USE THEREOF

FIELD OF THE INVENTION

The present invention relates to thienopyranone and furanopyranone compounds and methods of treating diseases in mammals including humans by administering a compound(s) of the invention. In one aspect of the invention, a compound or composition is administered to provide therapeutic benefit by inhibiting Bruton's Tyrosine Kinase ("BTK") and at least one other kinase such as but not limited to PI3K, and/or an epigenetic regulator such as bromodomain containing proteins.

BACKGROUND

Bruton's tyrosine kinase (BTK) is a nonreceptor cytoplasmic tyrosine kinase which has been demonstrated to be critical for B-cell differentiation, proliferation, maturation, apoptosis, and cell migration. BTK is expressed in all hematopoietic lineage cells except for T-cells and plasma cells. From a signaling standpoint BTK is downstream of the B-cell antigen receptor (BCR) and becomes active when BCR is activated. BTK is believed to be critical in the initiation, survival, and progression of B cell lymphoproliferative diseases (J. Wu et al., Journal of Hematology & Oncology, 2016, volume 9 DOI 10.1186/s13045-016-0313-y). BTK inhibitors are thought to be suitable drugs for treatment of hematopoetic cancers and also solid tumors (J. Molina-Cerrilo, Cancer Treatment Reviews 2017, volume 58, pp 41-50) as well as autoimmune disease such as rheumatoid arthritis (L. A. Honigberg PNAS, 2010, volume 107, #20 pp 13075-13080). More recently, other diseases beyond B cell malignancies have been proposed as targets for BTK inhibitors (A. Berglof et al. Scandinavian Journal of Immunology 2015, volume 82, pp 208-217). Lastly, therapeutic antitumor immunity enhancement by checkpoint blockage was demonstrated by BTK inhibition (I. Sagiv-Barfi et al. PNAS, online Feb. 17, 2015; doi 10.1073). Two BTK inhibitors have been approved by the FDA for cancer treatment, Imbruvica R: (ibrutinib, formerly PCI-32765) in 2013 and Calquence R: (acalabrutinib) in 2017.

It should be noted that both of these BTK inhibitors possess an electrophilic group (alpha-beta unsaturated amide) thought to react with the sulfhydryl group of cysteine C481 of the BTK catalytic site in a mechanism called irreversible inhibition due to a covalent bond being formed (carbon-sulfur bond via Michael addition reaction). A mechanism of resistance to such BTK inhibitors is thought to be a mutation of the BTK protein such that the cysteine (C481) is replaced by a serine residue (S481). This new amino acid residue prevents these BTK inhibitors from covalently binding to the BTK mutants and thus becoming very reduced potency reversible BTK inhibitors. For example, ibrutinib exhibited an almost 500-fold decrease in potency towards the C481S mutant BTK versus native BTK (J. Wu et al., Journal of Hematology & Oncology, 2016, volume 9 DOI 10.1186/s13045-016-0313-y). The prevelance of such mutations is almost nonexistent in ibrutinib-naïve patients which indicates that the mutation arises via selection during treatment with ibrutinib. Despite FDA approval, ibrutinib induces undesirable side effects such as bleeding, rash, diarrhea, and atrial fibrillation. Thus, there remains a need for BTK inhibitors possessing fewer side effects and less susceptibility to resistance.

Protein kinases play an important role in regulating most cellular functions including proliferation, cell cycle, cell metabolism, survival/apoptosis, DNA damage repair, cell motility, and response to the microenvironment. Not surprisingly, kinases have been identified as oncogenes. For example, kinases such as c-Src, c-Abl, mitogen activad protein (MAP) kinase, phosphotidylinositol-3-kinase (PI3-K, PI3K, PI-3 kinase), AKT (also known as PKB), and the epidermal growth factor receptor (EGFR) are commonly activated in cancer cells and are known to contribute to tumorigenesis. Many of these mutations occur in the same signaling pathway. For example, HER-kinase family members (HER1 [EGFR], HER3, and HER4) transmit signals through MAP kinase and PI-3 kinase to promote cell proliferation.

PI3 kinases are a large family of lipid kinases comprising roughly 16 members divided into 3 classes based on sequence homology and the particular product formed by enzyme catalysis. The class I PI3 kinases are composed of 2 subunits: a 110 kd catalytic subunit and an 85 kd regulatory subunit. Class I PI-3 kinases are involved in important signal transduction events downstream of cytokines, integrins, growth factors and immunoreceptors, and control of this pathway may lead to important therapeutic effects. Inhibition of class I PI3 kinase induces apoptosis, blocks tumor induced angiogenesis in vivo, and increases radiosensitivity in certain tumors.

Molecular and genetic studies have demonstrated a strong correlation between the PI3 kinase pathway (also known as PI3K-AKT pathway) and a variety of diseases in humans such as inflammation, autoimmune conditions, and cancers (P. Workman et al., Nat. Biotechnol. 2006, 24, 794-796). The PI3 kinase pathway controls a number of cellular functions including cell growth, metabolism, differentiation, and apoptosis. Many types of cancer are thought to arise in response to abnormalities in signal transduction pathways of which the PI-3 kinase pathway is a major example.

The PI3 kinase pathway comprises a number of enzymes including PI3 kinase, PTEN (Phosphatase and Tensin homolog deleted on chromosome 10), and AKT (a serine/threonine kinase) all of which are involved in producing and maintaining intracellular levels of second messenger molecule PtdIns(3,4,5)P3 (Phosphatidylinositol (3,4,5)-trisphosphate or PIP3). Homeostasis in the levels of this important second messenger is maintained by the interaction between PI3 kinase and PTEN. When either PI3 kinase or PTEN are mutated and/or reduced in activity PIP3 levels are perturbed which may act as a trigger in the development of cancer. Indeed, both PI3 kinase and PTEN have been found to be mutated in multiple cancers including glioblastoma, ovarian, breast, endometrial, hepatic, melanoma, gut, lung, renal cell, thyroid and lymphoid cancer. Multiple studies have now shown that p110α, which is a Class IA isoform of the regulatory subunit of PI-3 kinase, is frequently over-expressed and mutated in many cancers including gliomas, colon, brain, breast, lung, prostate, gynecological and other tumor types (Y. Samuels et al., Science 2004, 304, 554). Thus, a rational approach to treating cancer relates to developing drugs that act on kinases including those of the PI3 kinase pathway.

Another putative mechanism for cancers involving kinase dependency involves the loss of a negative regulator. Perhaps the best example of this comes from tumors with mutations in the PTEN tumor suppressor gene. This gene, which is mutated or deleted in a number of different cancers, encodes a lipid phosphatase that regulates signaling through the PI3 kinase pathway. Specifically, PTEN dephosphorylates PIP3, the product of PI3 kinase (See L. C. Cantley et al., Proc. Natl. Acad. Sci. 1999, 96, 4240-4245). As a consequence of PTEN loss and the resultant increase in PIP3 levels, signal propagation through downstream kinases such as AKT is constitutively elevated. Preclinical studies suggest that this indirect mode of constitutive kinase activation in tumor cells (i.e., through loss of the PTEN suppressor gene), creates a kinase dependency analogous to that seen in tumors with direct, activating mutations in the kinase itself.

Genetic and biochemical evidence from several animal model systems has established that constitutive levels of AKT can regulate TOR (mTOR in mammalian systems) through phosphorylation of the tuberous sclerosis complex (K. Inoki et al., Nat. Cell Biol. 2002, 4, 648-657). Hence, tumors with loss-of-function mutations in PTEN exhibit constitutive activation of AKT, as well as other downstream kinases such as mTOR. Many such tumors in murine models have been shown to be sensitive to mTOR inhibitors (M. S. Neshat et al., Proc. Natl. Acad. Sci. 2001, 98, 10314-10319).

At the cytocellular level, the induction and/or progression of cancer appears to involve a sub-population of cells within a tumor known as cancer stem cells. Within a population of cancer cells there exist a small number of cells that are capable of fully re-establishing a tumor. These cells are called cancer stem cells and are thought to be responsible for the inability to cure cancer with current drugs. Cancer stem cells are characterized as having enhanced drug efflux properties, lacking in cell cycle progression (quiescent), and possessing resistance to anoikis (apoptosis upon experiencing loss of anchorage). Cancer stem cells have been described in the literature in solid tumor types, for example, see the review and references incorporated therein by J. E. Visvader et al., Nat. Rev. Cancer 2008, 8, 755-768: "Cancer Stem Cells in Solid Tumors: accumulating evidence and unresolved questions". Non-solid tumor cancer stem cells have also been reviewed recently, for example, see the review and references incorporated therein by J. E. Dick et al., Blood 2008, 112, 4793-4807: "Stem cell concepts renew cancer research". To date, the only approved cancer therapeutic drug that decreases cancer stem cells is Lapatinib which was shown to decrease the number of breast cancer stem cells in biopsies of women with breast tumors possessing high levels of HER2 protein (decreased from 11% down to 5% of cells) (C. Schmidt et al., J. Natl. Cancer I. 2008, 100, 694-695: "Lapatinib Study Supports Cancer Stem Cell Hypothesis, Encourages Industry Research"). More recently, PI3K inhibitors have also been shown to preferentially target cancer stem cells (PI3K/mTOR Dual Inhibitor VS-5584 Preferentially Targets Cancer Stem Cells, Vihren N. Kolev, Quentin G. Wright, Christian M. Vidal, Jennifer E. Ring, Irina M. Shapiro, Jill Ricono, David T. Weaver, Mahesh V. Padval, Jonathan A. Pachter and Qunli Xu, Cancer Res. Jan. 14, 2015, 75 (2), 446-455). Thus, inhibition of PI3K may provide an effective strategy to inhibit cancer stem cells.

While therapeutic agents that act as modulators of signaling pathways are of clear therapeutic interest as agonists or antagonists of particular enzymes within a signaling pathway, e.g., inhibitors of PI3 kinase, recent evidence indicates that independent mechanisms exist for providing therapeutic efficacy including, for example, oxidative stress. The generation of oxidative stress in cancer cells is a recent but well described cancer treatment approach. Examples of agents that induce oxidation stress include clinically evaluated compounds such as buthionine sulfoximine/melphalan, imexon, arsenic trioxide, and motexafin gadolinium, and the like (See e.g. R. H. Engel et al., Front. Biosci 2006, 11, 300-312: "Oxidative Stress and Apoptosis: a new treatment paradigm in cancer"). Chromenones such as LY294002 and the related analog LY3035111 have been reported to induce apoptosis in tumor cells due to intracellular hydrogen peroxide production independent of their PI3 kinase inhibition activity (T. W. Poh et al., Cancer Res. 2005, 65, 6264-6274: "LY294002 and LY303511 Sensitize Tumor Cells to Drug-Induced Apoptosis via Intracellular Hydrogen Peroxide Production Independent of the Phosphoinositide 3-Kinase-Akt Pathway"). The ability to induce oxidative stress in cancer cells is a positive attribute for an anticancer agent. Oxidative stress induction has also been demonstrated to enhance sensitivity of prostate cancer cells to non-apopototic concentrations of the chemotherapeutic agent Vincristine.

LY294002 [2-(4-morpholinyl)-8-phenyl-4H-1-benzopyran-4-one] is a potent, non-selective inhibitor of PI3 kinases with an $IC_{50}$ of 1.4 μM (C. J. Vlahos et al., J. Biol. Chem. 1994, 269, 5241-5248). While LY294002 is an effective inhibitor of PI3 kinase, it has several undesirable attributes for clinical use including lack of aqueous solubility, poor pharmacokinetics, unacceptable toxicity, lack of tissue specificity, rapid metabolism in animals, and a synthetic route that involves the use of carbon disulfide, a highly toxic compound. As such, LY294002 has never been developed for clinical use.

In addition to defects in one or more kinase pathways, a growing list of diseases including cancer can arise by epigenetically-induced changes in gene expression and cellular phenotype by mechanisms other than changes in DNA nucleotide sequence. Epigenetic effects can be controlled by three types of proteins: the writers (i.e., DNA methyltransferase which adds methyl groups to DNA), the erasers (i.e., histone deacetylase, HDAC, which removes acetyl groups from histones), and the readers (i.e., BET bromodomain proteins such as BRD2, BRD3, BRD4 and BRDT). Bromodomain proteins serve as "readers" to recruit regulatory enzymes such as "writers" and "erasers" which lead to regulation of gene expression. Inhibitors of bromodomain proteins are potentially useful in the treatment of a variety of diseases including obesity, inflammation, and cancer (A. C. Belkina et al., Nat. Rev. Cancer 2012, 12, 465-477). The BET bromodomain protein BRD4 is a current target to inhibit in cancer and a number of inhibitors are known and in development (Wadhwa E, Nicolaides T. Bromodomain Inhibitor Review: "Bromodomain and Extra-terminal Family Protein Inhibitors as a Potential New Therapy in Central Nervous System Tumors". Muacevic A, Adler J R, eds. Cureus. 2016, 8 (5), e620. doi: 10.7759/cureus.620).

BET inhibitors act as acetylated lysine mimetics that disrupt the binding interaction of BET proteins with acetylated lysine residues on histones (D. S. Hewings et al., J. Med. Chem. 2012, 55, 9393-9413). This leads to suppression of transcription of a number of key genes involved in cancer including c-MYC, MYCN, BCL-2, and some NF-kB-dependent genes (J. E. Delmore et al., Cell 2011, 146, 904-917) (A. Puissant et al., Cancer Discov. 2013, 3, 308-323). Most B-cell malignancies are associated with the activation of the c-MYC gene which is partially controlled by the PI3 kinase-AKT-GSK3beta signaling axis (J. E. Delmore et al., Cell 2011, 146, 904-917). MYC (encompassing c-MYC and MYCN) is an oncoprotein that has proven difficult to inhibit using small molecule approaches (E. V. Prochownik et al., Genes Cancer 2010, 1, 650-659). Recently, it has been shown that BET inhibition prevents the transcription of MYCN (A. Puissant et al., Cancer Discov.

2013, 3, 308-323), and blocking PI3K enhances MYC degradation (L. Chesler et al., Cancer Res. 2006, 66, 8139-8146). Therefore, a single molecule that inhibits both PI3K and bromodomain proteins would provide a more effective way to inhibit MYC activity. Additional support for inhibiting both bromodomain proteins such as BRD4 and kinases including PI3K and BTK comes from recent reports of synthetic lethality of cancer cells with such a combination (M. Ramadoss and V. Mahadevan, Drug Discovery Today, vol. 23, #1, January 2018 p 76). Moreover, compounds such as Compound 0 (aka "Compd 0": shown below) have been demonstrated to be potent dual inhibitors of BRD4 and PI3K with less toxicity than the combination of two single inhibitors (e.g., a PI3K inhibitor plus a separate BRD4 inhibitor) (see (U.S. Pat. Nos. 8,557,807, 9,505,780, Morales et al., J. Med. Chem. 2013, and Andrews et al., PNAS Feb. 14, 2017, vol. 114, no. 7, pp E1072-E108: the entire contents of which are herein incorporated by reference). Several reported BET inhibitors contain the 3,5-dimethylisoxazole chemotype as the acetyl-lysine mimetic moiety (D. S. Hewings, J. Med. Chem. 2011, 54, 6761-6770) (D. S. Hewings et al., J. Med. Chem. 2012, 55, 9393-9413) (D. S. Hewings et al., J. Med. Chem. 2013, 56, 3217-3227).

Compound 0

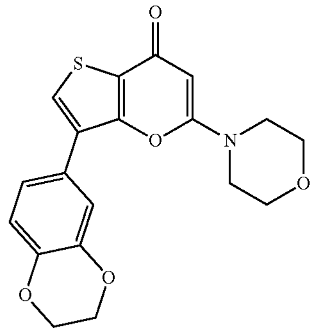

A growing body of evidence indicates that resistance to BTK inhibitors can be overcome by use of a combination of PI3K inhibitors or by using a BTK inhibitor in combination with a PI3K inhibitor.

For example, effectiveness was demonstrated in preclinical models of ABC-DLBCL patients by administering a BTK inhibitor in combination with an alpha/delta PI3K inhibitor as compared with a delta-PI3K inhibitor alone (J. Paul et al., "Molecular mechanisms and combination strategies with PI3K and BTK inhibitors to overcome intrinsic and acquired resistance in preclinical models of ABC-DLBCL": Hematological Oncology, 2017:35: 403-404. doi: 10.1002/hon.2439_179). The mechanism underlying the enhanced benefit provided by the combination was elaborated in a subsequent study showing sustained complete responses in in vivo mouse models (J. Paul et al., Cancer Cell, 2017, volume 31 pp 64-78).

Also, the combination of ibrutinib (BTK inhibitor) with umbralisib (PI3K inhibitor) demonstrated good efficacy in a phase I/IB dose-escalation study in patients with B-cell malignancies (see European Hematology Association Annual Congress Jul. 20 2017 "Hitting BTK PI3K pays of in B-cell malignancies": https://www.mdedge.com/hematologynews/article/140843/mantle-cell-lymphoma/hitting-btk-pi3k-pays-b-cell-malignancies).

Moreover, the improved efficacy from the combination of a BTK inhibitor (acalabrutinib) with delta PI3K inhibition (ACP-319) in chronic lymphocytic leukemia (CLL) cell lines and mouse models has been described (C. U. Niemann et al., Clin. Cancer Res. 2017 Oct. 1; 23 (19): 5814-5823. doi: 10.1158/1078-0432.CCR-17-0650. Epub 2017 Jun. 23). Also, selective inhibition of PI3K delta/gamma was shown to overcome ibrutinib resistance resulting from treatment-induced BTK C481S mutation. These results suggest that a combination of PI3K inhibition and BTK inhibition may be effective in treating chronic lymphocytic leukemia (CLL) and related B-cell lymphoproliferative disorders (S. Dong et al., Blood, 2014, volume 124, p 3583-3586).

Lastly, in mantle cell lymphoma it has been shown that resistance to BTK inhibition arises when the Cys residue at position 481 of BTK mutates to Ser (C481S) and that this resistance can be overcome by the use of PI3K inhibitors (D. Chiron et al., "Cell-cycle reprogramming for PI3K inhibition overrides a relapse-specific C481S BTK mutation revealed by longitudinal functional genomics in mantle cell lymphoma", Cancer Discovery, 2014 September: 4 (9): 1022-35).

Thus, there is a growing body of evidence that supports using a combination of BTK and PI3K inhibitors in treating various B-cell malignancies both to block resistance to BTK inhibition and improve efficacy.

A combined use of a bromodomain inhibitor (CPI203) with a BTK inhibitor (ibrutinib) was demonstrated to have a synergistic effect in both in vitro and in vivo studies using ABC-DLBCL cell types (M. Ceribelli et al., PNAS USA 2014). Similarly, combining a bromodomain inhibitor (GS-5829) with a BTK inhibitor (GS-4059) resulted in synergistic efficacy in in vitro studies using the TMD8 ABC-DLBCL cell type (J. Bates et al., "The Combination of a BET Inhibitor (GS-5829) and a BTK Inhibitor (GS-4059) Potentiates DLBCL Cell Line Cell Death and Reduces Expression of MYC, IL-10, and IL-6 in Vitro", Blood December 2016, 128 (22) 5116)). Additionally, the bromodomain inhibitor OTX015 (formerly MK-8628) showed enhanced in vivo antitumor activity in an ABC-DLBCL cell line (SU-DHL-2) when combined with the BTK inhibitor Ibrutinib (E. Gaudiol et al., "Bromodomain inhibitor OTX015 combined with targeted agents shows strong in vivo antitumor activity in lymphoma": Oncotarget, 2016, volume 7, number 36: www.impactjournals.com/oncotarget/).

While treatments involving inhibition of BTK, PI3K, and bromodomain by administering separate agents hold considerable promise, in practice additive unwanted off-target toxicities from the combination of individual inhibitors has revealed significant problems with this strategy. In a recent clinical trial, the PI3K inhibitor BKM120 was co-administered with the PARP inhibitor Olaparib. The combination of these two agents resulted in significant toxicity issues, and the maximum tolerated dose of the PI3K inhibitor was only half the amount achievable by administration of BKM120 as a single agent (see Matulonis U. et al., "Phase I of oral BLK120 or BLY719 and olaparib for high-grade serous ovarian cancer or triple-negative breast cancer: final results of the BMK120 plus olaparib cohort", 106th Annual Meeting of the American Association for Cancer Research: April 18-22: AACR: 2015).

Off-target toxicities represent a major hurdle when administering multiple single molecule inhibitors. A more nuanced approach involves administering multi-target single molecule inhibitors which are potentially advantageous over combinations of single-target inhibitors for a number of reasons including: a) simpler straightforward clinical development, b) reduced development costs: c) lower toxicity: d) lower non-target side effects due to non-target drug interactions: e) wider therapeutic index, e) simultaneous target inhibition to provide greater efficacy (versus combinations of agents suffering from differing ADME dynamics): f) lower financial costs to patients and the healthcare system: g) increased efficacy and longer durations of response; and h) accelerated drug development.

Single-molecule, multi-target inhibition can avoid some of the problems arising from differing ADME properties associated with administering separate agents such as dose limiting toxicity resulting from additive off-target toxicities of the individual drugs. In addition, a single molecule, multi-target inhibitor could dramatically simplify taking medications and improve patient compliance. For example, a patient whose treatment includes inhibition of multiple targets would generally take separate medicines to achieve inhibition of each target, whereas a single molecule, multi-target inhibitor could achieve the same objective with just a single medication.

Moreover, there is a current need to inhibit as many cancer targets as toxicity will allow, and using drugs that inhibit multiple cancer targets, such as the compounds of the invention, may be the only way to achieve more sophisticated effective combinations. There remains a need for single molecule, multi-target inhibitors of kinases including inhibitors of BTK and at least one other protein including but not limited to PI3K and/or a bromodomain protein such as BRD4 to provide effective treatments for diseases.

Macrophages are key immune infiltrates in solid tumors and serve as major drivers behind tumor growth, immune suppression, and inhibition of adaptive immune responses in the tumor microenvironment (TME). Recent reported results suggest that BRD4 regulates the immunosuppressive myeloid TME, and BET inhibitors and especially dual PI3K/BRD4 inhibitors such as those compounds of the invention represent therapeutic strategies for treating cancers or other diseases driven by the macrophage dependent immunosuppressive TME (Joshi et al., Mol Cancer Ther: 18 (6) June 2019).

In addition to cancer there are non-cancer diseases that can be addressed by the compounds of the invention including, for example, fibrotic disease or fibrosis. Fibrosis is the formation of excess fibrous connective tissue in an organ or tissue in a reparative or reactive process. Several signaling pathways contribute to the development of both fibrosis and lung cancer. The phosphoinositide 3-kinase (PI3K) pathway is activated in both pulmonary cancer (Annu Rev Pathol 2009; 4: 127-150) and idiopathic pulmonary fibrosis (IPF) (Thorax 2016; 71:701-711 & Scientific Reports 2017:7: 14272). Additionally PI3K inhibition has proven effective against IPF in in vivo preclinical studies (Am J Pathol 2010:176:679-686) along with promising results of PI3K inhibition in a Phase 1 clinical trial for IPF administered orally (European Respiratory Journal 2019 (in press); see https://erj.ersjournals.com/content/early/2018/12/14/13993003.01992-2018); however, the PI3K inhibitor suffered from a limited therapeutic window and the patients suffered diarrhea along with increases in insulin and glucose levels. The bromodomain 4 (BRD4) pathway is also reported to drive IPF pathology (Am J Pathol 2013, 183: 470-479) and the inhibition of BRD4 is reported to inhibit fibrosis in bleomycin-induced lung fibrosis models (Am J Pathol 2013, 183:470-479; Mol Pharmacol 2013:83:283-293 and Am J Respir Crit Care Med 2019:199: A5879). Further, BRD4 inhibition in an aging model of lung fibrosis reduced markers of fibrosis (Am J Respir Crit Care Med 2019:199:A5879). Lastly, several studies and reviews have highlighted similarities between IPF and cancer (Thorax 2016:71:675-676). Therefore, compounds of the invention are expected to be useful in treating fibrotic disease including but not limited to IPF by inhibiting both BRD4 and PI3K.

SUMMARY OF THE INVENTION

The present invention relates to thienopyranone and furanopyranone compounds that are useful as inhibitors of BTK and at least one other target protein including an anti-cancer target protein for the treatment and/or prevention of diseases including cancer.

In particular, the present invention relates to new thienopyranone and furanopyranone compounds, conjugates, and pharmaceutical compositions thereof, and use of the compounds as therapeutic agents including as anticancer and antitumor agents for the treatment of disorders including but not limited to cancer. Some of the compounds disclosed in this application can be prepared by methods described in U.S. Pat. Nos. 8,557,807 and 9,505,780, and in Morales et al., J. Med. Chem. 2013, the entire contents of which are herein incorporated by reference.

In one aspect, the present invention relates to methods for treating diseases in mammals including humans by administering a therapeutically effective amount of a compound of Formula I or a pharmaceutically acceptable salt thereof:

Formula I

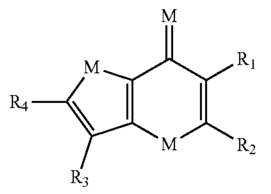

wherein M is independently oxygen (O) or sulfur(S);

R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1, morpholine, thiomorpholine, or piperazine;

R3 is selected from R1;

R4 is selected from R1; and where R1-R4 may independently contain varying amounts of isotopic substitution.

These and other objects of the invention are evidenced by the summary of the invention, the description of the preferred embodiments and the claims.

DETAILED DESCRIPTION

A. Definitions

Figure 1A:
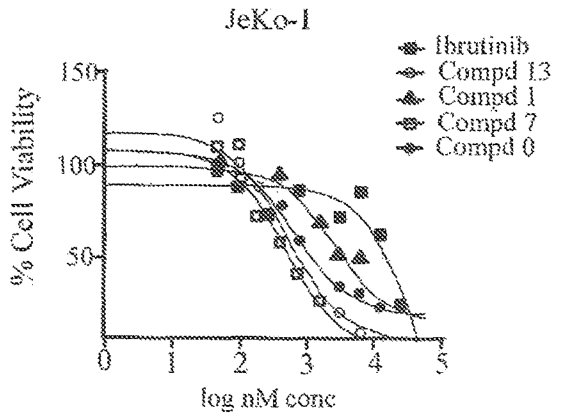
FIG. 1A shows the inhibitory effects of compounds of the invention including Compds 0, 1, 7, and 13 and Ibrutinib in JeKo-1 cells, a human mantle cell lymphoma cell line.

As used herein, the term "disease" or "condition" refers to a variety of health abnormalities and/or conditions in a mammal including a human as generally understood, for example, in the medical profession, and further as described herein.

"Cancer" refers to cellular-proliferative disease states, including cancers with loss of function somatic or germline mutations in BRCA 1/2, and cancers without loss of function mutations in BRCA 1/2 (i.e., "BRCA wild type" or "BRCA competent") including but not limited to medulloblastoma (MB) and neuroblastoma (NB), and further including the following cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma: Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma): Genitourinary tract: kidney (adenocarcinoma, Wilms tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma): Liver: hepatoma (hepatocellular carcinoma), cholangiocarcinoma, hepatoblastoma, angiosarcoma, hepatocellular adenoma, hemangioma: Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors: Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma): Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma): Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]: Skin: malignant melanoma, basal cell carcinoma, squamous cell carcinoma, Kaposi's sarcoma, moles dysplastic nevi, lipoma, angioma, dermatofibroma, keloids, psoriasis: Adrenal Glands: neuroblastoma; and breast cancer.

The term "cancerous cell" as provided herein, includes a cell affected by any one of the cancers identified herein. The term "cancer stem cell" refers to a subpopulation of cells in a solid or non-solid tumor that demonstrate enhanced drug efflux properties, are lacking in cell cycle progression, and are resistant to anoikis.

As used herein, the term "branched" refers to a group containing from 1 to 24 backbone atoms wherein the backbone chain of the group contains one or more subordinate branches from the main chain. Preferred branched groups herein contain from 1 to 12 backbone atoms. Examples of branched groups include, but are not limited to, isobutyl, t-butyl, isopropyl, $—CH_2CH_2CH(CH_3)CH_2CH_3$, $—CH_2CH(CH_2CH_3)CH_2CH_3$, $—CH_2CH_2C(CH_3)$ $2CH_3$, $—CH_2CH_2C(CH_3)_3$ and the like.

The term "unbranched" as used herein refers to a group containing from 1 to 24 backbone atoms wherein the backbone chain of the group extends in a direct line. Preferred unbranched groups herein contain from 1 to 12 backbone atoms.

The term "cyclic" or "cyclo" as used herein alone or in combination refers to a group having one or more closed rings, whether unsaturated or saturated, possessing rings of from 3 to 12 backbone atoms, preferably 3 to 7 backbone atoms.

The term "lower" as used herein refers to a group with 1 to 6 backbone atoms.

The term "saturated" as used herein refers to a group where all available valence bonds of the backbone atoms are attached to other atoms. Representative examples of saturated groups include, but are not limited to, butyl, cyclohexyl, piperidine and the like.

The term "unsaturated" as used herein refers to a group where at least one available valence bond of two adjacent backbone atoms is not attached to other atoms. Representative examples of unsaturated groups include, but are not limited to, $—CH_2CH_2CH{=}CH_2$, phenyl, pyrrole and the like.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "aromatic" as used herein refers to an unsaturated cyclic hydrocarbon group which may be substituted or unsubstituted having 4n+2 delocalized π(pi) electrons. The term aromatic further includes aromatic groups, which comprise a nitrogen atom replacing one or more carbons of the hydrocarbon backbone. Examples of aromatic groups include, but are not limited to, phenyl, naphthyl, thienyl, furanyl, pyridinyl, (is) oxazolyl and the like.

The term "substituted" as used herein refers to a group having one or more hydrogens or other atoms removed from a carbon or suitable heteroatom and replaced with a further group. Preferred substituted groups herein are substituted with one to five, most preferably one to three substituents. An atom with two substituents is denoted with "di" whereas an atom with more than two substituents is denoted by "poly." Representative examples of such substituents include, but are not limited to aliphatic groups, aromatic groups, alkyl, alkenyl, alkynyl, aryl, alkoxy, halo, aryloxy, carbonyl, acryl, cyano, amino, amide, nitro, phosphate-containing groups, sulfur-containing groups, hydroxyl, alkylcarbonyloxy, arylcarbonyloxy, alkoxy carbonyloxy, aryloxy carbonyloxy, alkylcarbonyl, arylcarbonyl, alkoxy carbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

As described herein, compounds of the invention may contain "optionally substituted" moieties. In general, the term "substituted", whether preceded by the term "optionally" or not. means that one or more hydrogens of the designated moiety are replaced with a suitable substituent. Unless otherwise indicated. an "optionally substituted" group may have a suitable substituent at each substitutable position of the group, and when more than one position in any given structure may be substituted with more than one substituent selected from a specified group. the substituent may be either the same or different at each position. Combinations of substituents envisioned under this invention are preferably those that result in the formation of stable or chemically feasible compounds. The term "stable". as used herein, refers to compounds that are not substantially altered when subjected to conditions to allow for their production. detection, and. in certain embodiments. their recovery, purification, and use for one or more of the purposes disclosed herein.

The terms "optionally substituted". "optionally substituted alkyl". "optionally substituted alkenyl". "optionally substituted alkynyl". "optionally substituted carbocyclic". "optionally substituted aryl". "optionally substituted heteroaryl". "optionally substituted heterocyclic". and any other optionally substituted group as used herein, refer to groups that are substituted or unsubstituted by independent replacement of one, two, or three or more of the hydrogen atoms thereon with substituents including, but not limited to:—F, —Cl, —Br, —I, —OH, protected hydroxy, alkoxy, oxo, thiooxo, $—NO_2$, —CN, $—CF_3$, $—N_3$, $—NH_2$, protected amino, —NH-alkyl, —NH-alkenyl, —NH-alkynyl, —NH-cycloalkyl, —NH-aryl, —NH-heteroaryl, —NH-heterocyclic, -dialkylamino,-diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, $—CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —$NHC(O)NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, —$NHC(S)NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —$NHC(NH)NH_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl-$SO_2NH_2$, —$SO_2NH$-alkyl, —$SO_2NH$-alkenyl, —$SO_2NH$-alkynyl, —$SO_2NH$-cycloalkyl, —$SO_2NH$-aryl, —$SO_2NH$-heteroaryl, —$SO_2NH$-heterocycloalkyl, —$NHSO_2$-alkyl, —$NHSO_2$-alkenyl, —$NHSO_2$-alkynyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$,-alkyl,-alkenyl,-alkynyl,-aryl,-arylalkyl,-heteroaryl,-heteroarylalkyl,-heterocycloalkyl,-cycloalkyl,-carbocyclic,-heterocyclic, polyalkoxyalkyl, polyalkoxy, methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

The term "unsubstituted" as used herein refers to a group that does not have any further groups attached thereto or substituted therefore.

The term "alkyl" as used herein, alone or in combination, refers to a branched or unbranched, saturated aliphatic group. The alkyl radical may be optionally substituted independently with one or more substituents described herein. Lower alkyl refers to alkyl groups of from one to six carbon atoms. Examples of lower alkyl groups include methyl, ethyl, propyl. isopropyl, butyl, s-butyl, t-butyl, isobutyl, pentyl, and the like. Higher alkyl refers to alkyl groups containing more than seven carbon atoms. A "Co" alkyl (as in "Co—Co-alkyl") is a covalent bond. Exemplary alkyl groups are those of $C_{20}$ or below. In this application, alkyl refers to alkanyl, alkenyl, and alkynyl residues (and combinations thereof); it is intended to include vinyl, allyl. isoprenyl, and the like. Thus, when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example. "propyl" or "$C_3$ alkyl" each include n-propyl, propenyl, and isopropyl. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetracosyl and the like. The terms "alkyl" or "alk" as used herein refer to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)$ 3), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)$ $2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)$ $(CH_2CH_2CH_3)_2$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)$ $(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. The cycloalkyl radical may be optionally substituted independently with one or more substituents described herein. Bicyclic carbocycles having 7 to 12 atoms can be arranged, for example, as a bicyclo[4,5], [5,5], [5,6] or [6,6] system, and bicyclic carbocycles having 9) or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "alkenyl" as used herein alone or in combination refers to a branched or unbranched, unsaturated aliphatic group containing at least one carbon-carbon double bond which may occur at any stable point along the chain. The alkenyl radical may be optionally substituted independently with one or more substituents described herein, and includes radicals having "cis" and "trans" orientations, or alternatively, "E" and "Z" orientations. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain. The alkynyl radical may be optionally substituted independently with one or more substituents described herein. Representative examples of alkynyl groups include, but are not limited to, ethynyl, propynyl, propargyl, butynyl, hexynyl, decynyl and the like.

The term "aryl" as used herein alone or in combination refers to a substituted or unsubstituted aromatic group, which may be optionally fused to other aromatic or non-aromatic cyclic groups. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heteroaryl" and "heteroar-", used alone or as part of a larger moiety, e.g., "heteroaralkyl", or "heteroaralkoxy", refer to groups having 5 to 18 ring atoms, preferably 5, 6, 7, 9, or 14 ring atoms; having 6, 10, or 14 (pi) electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridavinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

The term "alkoxy" as used herein alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

The term "aryloxy" as used herein alone or in combination refers to an aryl group bound through a single terminal ether linkage.

The terms "halogen", "halo" and "hal" as used herein refer to monovalent atoms of fluorine, chlorine, bromine, iodine and astatine.

The term "hetero" or "heteroatom" as used herein combination refers to a group that includes one or more atoms of any element other than carbon or hydrogen. Representative examples of hetero groups include, but are not limited to, those groups that contain heteroatoms including, but not limited to, nitrogen, oxygen, sulfur and phosphorus.

The term "heterocycle" or "heterocyclyl" or "heterocyclic ring" or "heterocyclic" as used herein refers to a cyclic group containing one or more heteroatoms. The heterocyclic radical may be optionally substituted independently with one or more substituents described herein. Representative examples of heterocycles include, but are not limited to, pyridine, piperidine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical" are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "covalent inhibitor" means an inhibitor of a target protein that forms a chemical bond by the sharing of electrons between atoms especially between sulfur atoms on a protein and the beta-carbon of an alpha-beta-unsaturated system present in the inhibitor small molecule typically through the use of Michael addition. The term "electrophile" means a positively charged or neutral species having vacant orbitals that are attracted to an electron rich centre (termed nucleophile). Electrophile groups on a covalent inhibitor participate in a chemical reaction by accepting an electron pair in order to bond to a nucleophile. The term "Michael addition" means the nucleophilic addition of a carbanion or another nucleophile to an $\alpha,\beta$-unsaturated carbonyl compound. The term "covalent inhibitor" also means an inhibitor of a target protein that forms a chemical bond by the nucleophilic displacement of a leaving group (e.g., chlorine) on a primary or secondary carbon such as alpha-chloroacetamide, (preferably an alpha-chlorofluoroacetamide group) of the inhibitor by a sulfur atom of the protein, for example cysteine or methionine (Naoya Shindo et al., Nature Chemical Biology. Vol. 15. March 2019 pp 250-258 and reference therein).

The term "substituent" means any group selected from H, F, Cl, Br, I, alkyl, alkenyl, alkynyl, carbocycle, aryl, heterocycle, heteroaryl, formyl, nitro, cyano, amino, amide, carboxylic acid, carboxylic ester, carboxyl amide, reverse carboxyl amide, halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally' substituted aryl, optionally substituted heteroaryl, alkylaminoalkyl, dialkylaminoalkyl, carboxy, carboxy ester, —C(O)$NR^5R''$ (where $R^5$ is hydrogen or alkyl and R" is hydrogen, alkyl, aryl, or heterocyclyl), —$NR^5C(O)R''$ (where $R^5$ is hydrogen or alkyl and R" is alkyl, aryl, or heterocyclyl), amino, alkylamino, dialkylamino, and —$NHS(O)_2R'$ (where R' is alkyl, aryl, or heteroaryl).

The term "carbonyl" or "carboxy" as used herein alone or in combination refers to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

The term "carbamate" as used herein alone or in combination refers to an ester group represented by the general structure —NH(CO)O—. Carbamate esters may have alkyl or aryl groups substituted on the nitrogen, or the amide function.

The term "cyanate" "isocyanate", "thiocyanate", or "isothiocyanate" as used herein alone or in combination refers to an oxygen- or sulfur-carbon double bond carbon-nitrogen double bond. Representative examples of cyano groups include, but are not limited to, isocyanate, isothiocyanate and the like.

The term "cyano", "cyanide", "isocyanide", "nitrile", or "isonitrile" as used herein alone or in combination refers to a carbon-nitrogen triple bond.

The term "amino" as used herein alone or in combination refers to a group containing a backbone nitrogen atom. Representative examples of amino groups include, but are not limited to, alkylamino, dialkylamino, arylamino, diarylamino, alkylarylamino, alkylcarbonylamino, arylcarbonylamino, carbamoyl, ureido and the like.

The term "phosphate-containing group" as used herein refers to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphorany lidenes, phosphorosos and the like.

The term "sulfur-containing group" as used herein refers to a group containing a sulfur atom. Representative examples include, but are not limited to, sulfhydryls, sulfenos, sulfinos, sulfinyls, sulfos, sulfonyls, thios, thioxos and the like.

The term "optional" or "optionally" as used herein means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and substituted alkyl.

The term "targeting agent" as used herein means any compound of the invention or moiety attached to a compound of the invention allowing an increase in concentration of the compound at a site of treatment, for example, a tumor site. Exemplary targeting agents include but are not limited to carbohydrates, peptides, vitamins, and antibodies.

As used herein, the term "multi-target inhibitor" or "multi-target agent" refers to a single molecule having the capacity to interact with BTK and at least one other protein target including but not limited to PI3K or a bromodomain protein including but not limited to BRD4 in vitro or in vivo including the capacity to inhibit the activity or normal function of said targets, e.g., to inhibit binding and/or enzymatic activity of BTK and PI3K.

As used herein, the term "dual inhibitor" refers to a single molecule that interacts with and/or inhibits the activity or normal function of two different target proteins, for example, BTK and PI3K or BTK and BRD4 in vivo or in vitro.

The term "effective amount" or "effective concentration" when used in reference to a compound, product, or composition as provided herein, means a sufficient amount of the compound, product or composition to provide the desired pharmaceutical or therapeutic result. The exact amount required will vary depending on the particular compound, product or composition used, its mode of administration and the like. Thus, it is not always possible to specify an exact "effective amount." However, an appropriate effective amount may be determined by one of ordinary skill in the art informed by the instant disclosure using only routine experimentation.

The term "hydrolyzable" as used herein refers to whether the group is capable of or prone to hydrolysis (i.e., splitting of the molecule or group into two or more new molecules or groups).

The term "pharmaceutically acceptable salt" of a compound of the instant invention (e.g., Formula I) is one which is the acid addition salt of a basic compound of the invention with an inorganic or organic acid which affords a physiologically acceptable anion or which is the salt formed by an acidic compound of the invention with a base which affords a physiologically acceptable cation.

The term "prodrug" or "procompound" as used in this application refers to a precursor or derivative form of a compound of the invention that may be less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "conjugate" as used herein refers to a compound that has been formed by the joining of two or more compounds via either a covalent or non-covalent bond.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "metabolite" is a product of a compound or salt thereof produced by metabolism in the body. Metabolites of a compound may be identified using routine techniques known in the art, and their activities determined using tests such as those described herein. Such products may result, for example, from oxidation, reduction, hydrolysis, amidation, deamidation, esterification, deesterification, enzymatic cleavage, and the like, of an administered compound. Accordingly, the invention includes metabolites of compounds of the invention produced in vivo in a mammal including a human or produced in vitro.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If a compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If a compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the terms "treatment", "treat", and "treating" refer to preventing, reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (i.e., in light of family history, symptoms and genetic or other susceptibility factors). Treatment may also be continued after symptoms have resolved, for example, to prevent or delay their recurrence.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxy carbonyl (BOC), benzyloxy carbonyl (CBZ) and 9-fluorenylmethylenoxy carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include, but are not limited to, phenylsulfonylethyl, cyanoethyl, 2-(trimethylsilyl)ethyl, 2-(trimethylsilyl) ethoxy methyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" include compounds disclosed herein including but not limited to those of Formulas I-IV and stereoisomers, geometric isomers, tautomers, solvates, metabolites, and pharmaceutically acceptable salts, prodrugs, and conjugates thereof.

The term "TP scaffold" or "Thienopyranone scaffold" refers to a compound of general Formula I-IV where M of the 5-membered ring is S.

The term "Furanopyranone scaffold" refers to a compound of Formula I-IV where M of the 5-membered ring is O.

As used herein, the term "PI3K inhibiting" as applied to a compound of the invention means that a compound inhibits the normal or wild-type function of PI3K, i.e., enzymatic activity, in vivo and/or in vitro (e.g., PI3Kα, PI3 Kβ, PI3Kγ, PI3Kδ) with an $IC_{50}$ value of less than or equal to 50 μM in an appropriate in vitro assay.

As used herein, the term "BTK inhibiting" as applied to a compound of the invention means that a compound inhibits the mutant, normal or wild-type function of BTK in vivo and/or in vitro with an $IC_{50}$ value of less than or equal to 50 μM in an appropriate in vitro assay.

As used herein, the term "Bromodomain inhibiting" as applied to a compound of the invention means that a compound inhibits the normal or wild-type function of a Bromodomain protein, in vivo and/or in vitro (e.g., BRD4) with an $IC_{50}$ value of less than or equal to 50 μM in an appropriate in vitro assay.

B. Compounds

The present invention relates in part to single molecule, multitargeting compounds of Formula I and their use in therapeutic methods to treat and/or prevent diseases including cancer by inhibiting BTK and at least one other protein such as, but not limited to, PI3K and/or BRD4:

Formula I

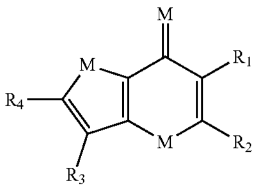

wherein M is independently oxygen (O) or sulfur(S);

R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1, morpholine, thiomorpholine, or piperazine;

R3 is selected from R1; and

R4 is selected from R1.

R1-R4 of Formula I may independently contain varying amounts of isotopic substitution.

Representative examples of compounds of Formula I are shown in Table 1.

TABLE 1

Representative compounds of Formula I.

| Compound No. | MW | Structure |
| --- | --- | --- |
| 1 | 382.4 | 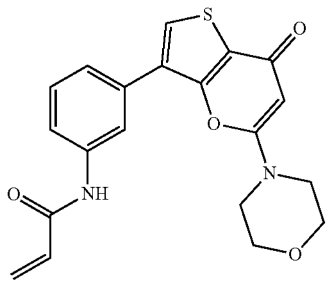 [SMILES: C=CC(=O)Nc1cccc(-c2csc3c(=O)cc(N4CCOCC4)oc23)c1] |
| 2 | 398.5 | 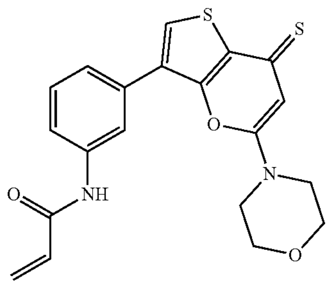 [SMILES: C=CC(=O)Nc1cccc(-c2csc3c(=S)cc(N4CCOCC4)oc23)c1] |
| 3 | 381.5 | 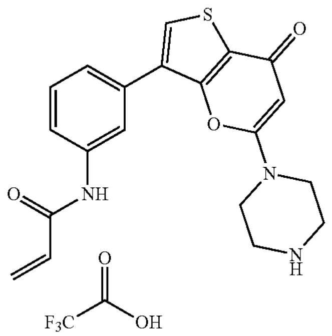 |

TABLE 1-continued
| Representative compounds of Formula I. | | |
|---|---|---|
| Compound No. | MW | Structure |
| 4 | 523.6 | 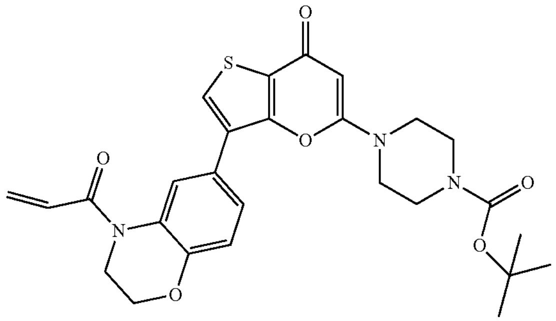 [SMILES: C=CC(=O)N1CCOc2ccc(-c3csc4c(=O)cc(N5CCN(C(=O)OC(C)(C)C)CC5)oc34)cc21] |
| 5 | 423.1 | 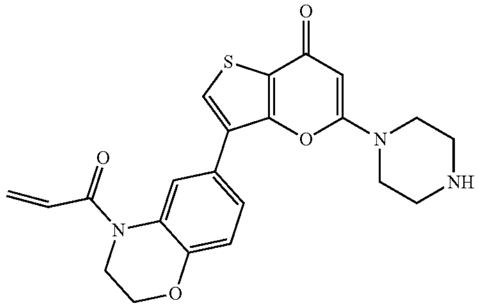 [SMILES: C=CC(=O)N1CCOc2ccc(-c3csc4c(=O)cc(N5CCNCC5)oc34)cc21] |
| 6 | 437.5 | 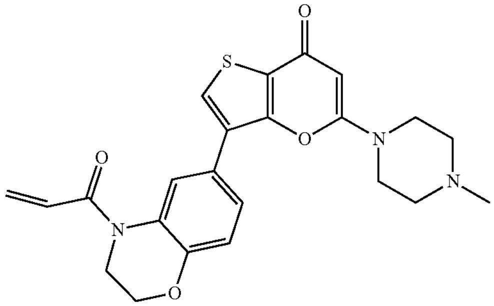 [SMILES: C=CC(=O)N1CCOc2ccc(-c3csc4c(=O)cc(N5CCN(C)CC5)oc34)cc21] |
| 7 | 474.5 | 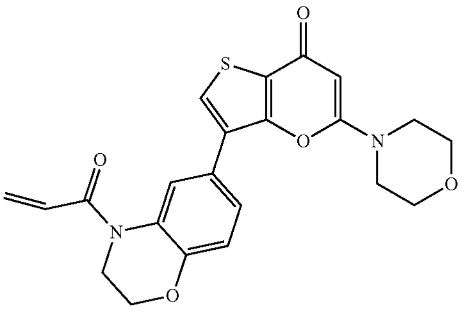 [SMILES: C=CC(=O)N1CCOc2ccc(-c3csc4c(=O)cc(N5CCOCC5)oc34)cc21] |

TABLE 1-continued
| Representative compounds of Formula I. | | |
|---|---|---|
| Compound No. | MW | Structure |
| 8 | 412.5 | 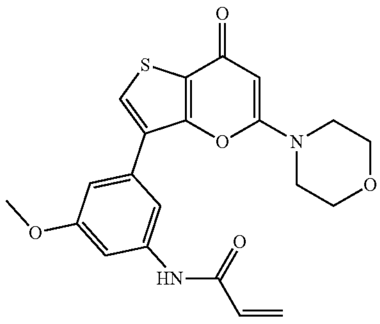 [SMILES: C=CC(=O)Nc1cc(OC)cc(-c2csc3c(=O)cc(N4CCOCC4)oc23)c1] |
| 9 | 412.5 | 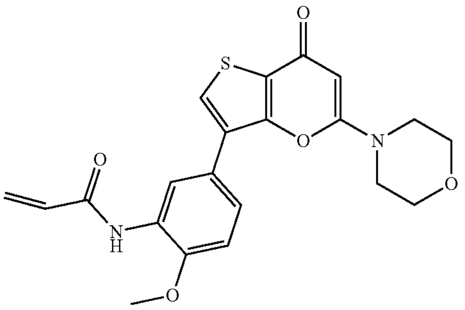 [SMILES: C=CC(=O)Nc1cc(-c2csc3c(=O)cc(N4CCOCC4)oc23)ccc1OC] |
| 10 | 452.2 | 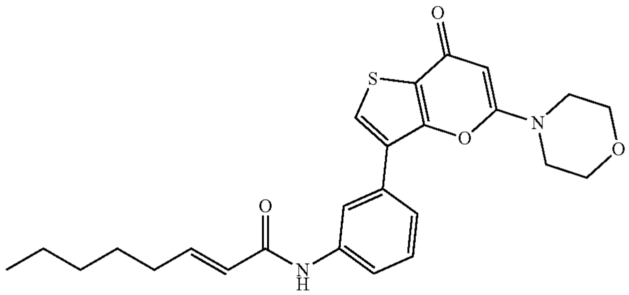 [SMILES: CCCCC/C=C/C(=O)Nc1cccc(-c2csc3c(=O)cc(N4CCOCC4)oc23)c1] |
| 11 | 447.5 | 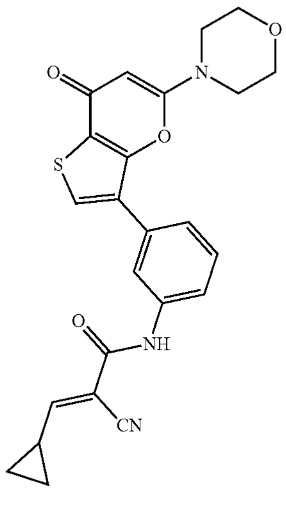 [SMILES: N#C/C(=C\C1CC1)C(=O)Nc1cccc(-c2csc3c(=O)cc(N4CCOCC4)oc23)c1] |

TABLE 1-continued
| Representative compounds of Formula I. | | |
|---|---|---|
| Compound No. | MW | Structure |
| 12 | 394.4 | 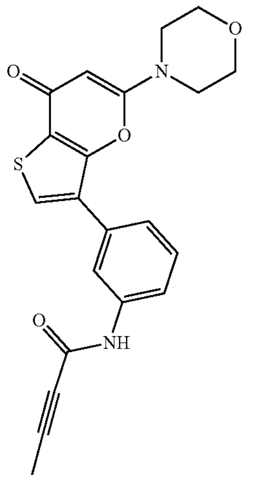 [SMILES: CC#CC(=O)Nc1cccc(-c2csc3c(=O)cc(N4CCOCC4)oc23)c1] |
| 13 | 382.4 | 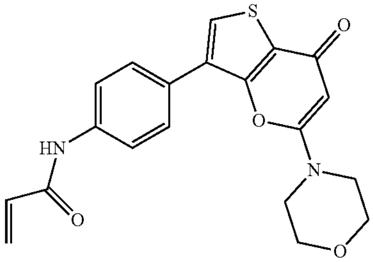 [SMILES: C=CC(=O)Nc1ccc(-c2csc3c(=O)cc(N4CCOCC4)oc23)cc1] |
| 14 | 452.5 | 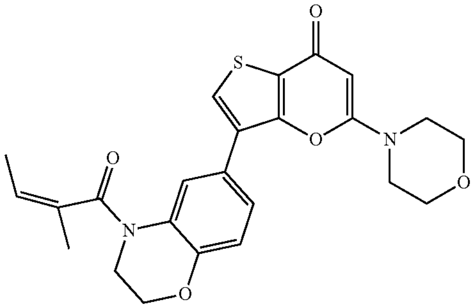 [SMILES: C/C=C(/C)C(=O)N1CCOc2ccc(-c3csc4c(=O)cc(N5CCOCC5)oc34)cc21] |
| 15 | 438.5 | 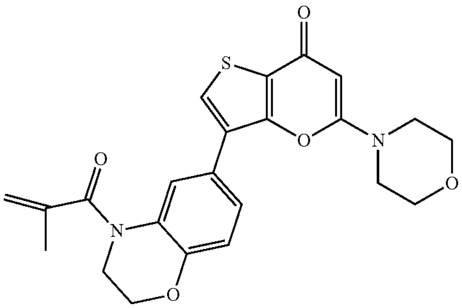 [SMILES: C=C(C)C(=O)N1CCOc2ccc(-c3csc4c(=O)cc(N5CCOCC5)oc34)cc21] |

TABLE 1-continued
| Representative compounds of Formula I. | | |
|---|---|---|
| Compound No. | MW | Structure |
| 16 | 452.5 | 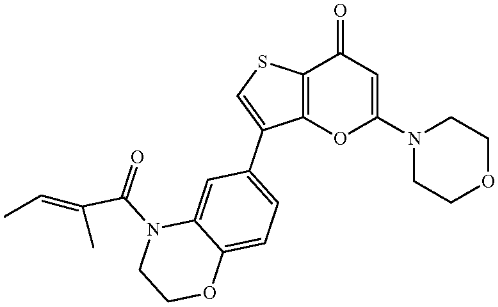 [SMILES: C/C=C(\C)C(=O)N1CCOc2ccc(-c3csc4c(=O)cc(N5CCOCC5)oc34)cc21] |
| 17 | 438.5 | 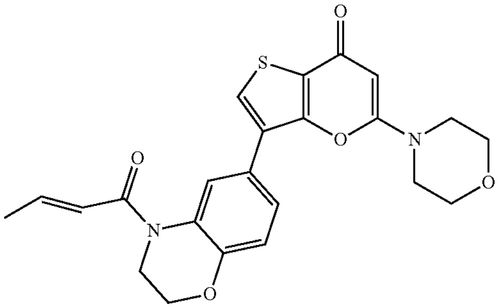 [SMILES: C/C=C/C(=O)N1CCOc2ccc(-c3csc4c(=O)cc(N5CCOCC5)oc34)cc21] |
| 18 | 464.5 | 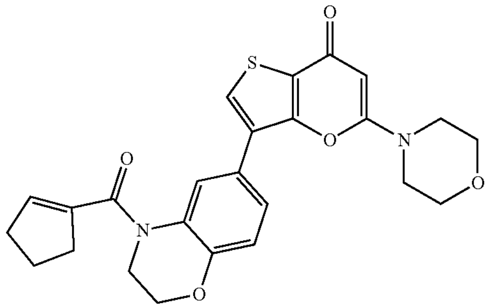 [SMILES: O=C(C1=CCCC1)N1CCOc2ccc(-c3csc4c(=O)cc(N5CCOCC5)oc34)cc21] |
| 19 | 438.5 | 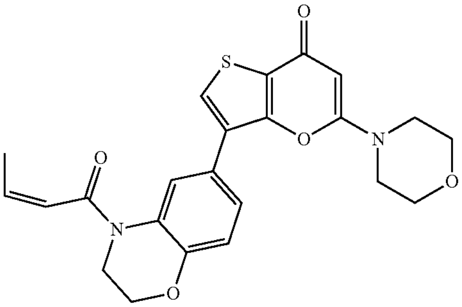 [SMILES: C/C=C\C(=O)N1CCOc2ccc(-c3csc4c(=O)cc(N5CCOCC5)oc34)cc21] |
| 20 | 478.6 | 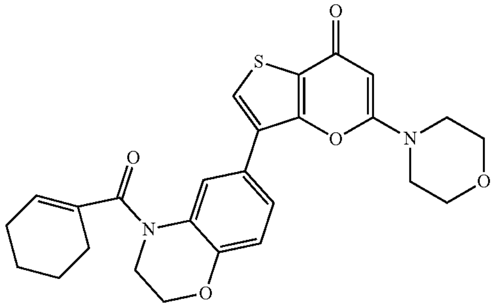 [SMILES: O=C(C1=CCCCC1)N1CCOc2ccc(-c3csc4c(=O)cc(N5CCOCC5)oc34)cc21] |

TABLE 1-continued

Representative compounds of Formula I.

| Compound No. | MW | Structure |
| --- | --- | --- |
| 21 | 460.5 | 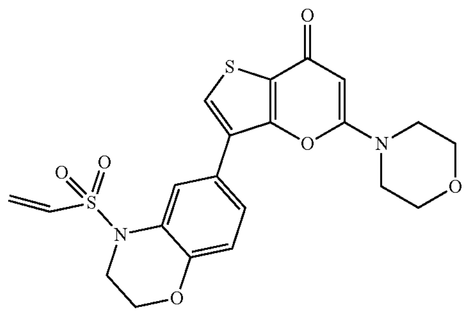 [SMILES: C=CS(=O)(=O)N1CCOc2ccc(-c3csc4c(=O)cc(N5CCOCC5)oc34)cc21] |
| 22 | 426.5 | 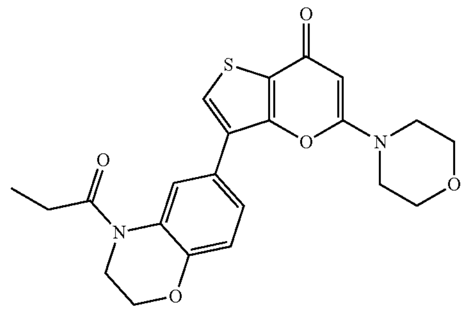 [SMILES: CCC(=O)N1CCOc2ccc(-c3csc4c(=O)cc(N5CCOCC5)oc34)cc21] |
| 23 | 382.4 | 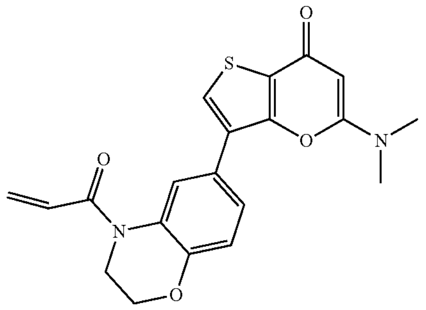 [SMILES: C=CC(=O)N1CCOc2ccc(-c3csc4c(=O)cc(N(C)C)oc34)cc21] |

The present invention also provides compounds of Formula II and methods of administering those compounds to a mammal in need thereof including, but not limited to, compounds that inhibit BTK and at least one other protein such as, but not limited to, PI3K and/or BRD4:

Formula II

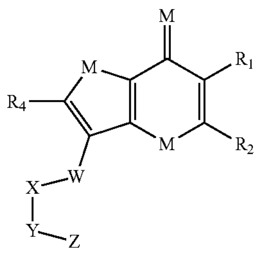

wherein M is independently O or S;

R1 and R2 and R4 are as described for Formula I;

W is null, NR1, O, S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

X is null or O, N, NR1 or S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

provided that if W is N, O, or S then X cannot be N, O, or S; and if X is N, O, or S then W cannot be N, O, or S;

Y is null, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate; and Z is a BTK covalent binding group such as but not limited to Michael acceptors, olefin, substituted olefin, acetylenic, and substituted acetylenic as well as alpha-chloroacetaminde and chlorofluroacetamide groups.

Representative compounds of Formula II are shown in Table 2.

TABLE 2

Representative examples of compounds of Formula II.

| No. | Structure |
|---|---|
| II-1 | 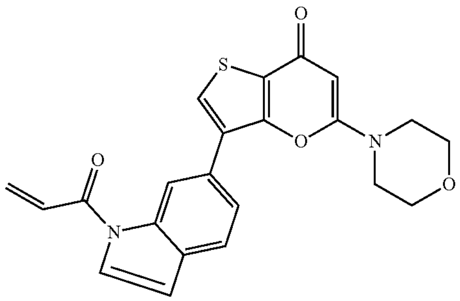 [SMILES: C=CC(=O)n1ccc2ccc(-c3csc4c(=O)cc(N5CCOCC5)oc34)cc21] |
| II-2 | 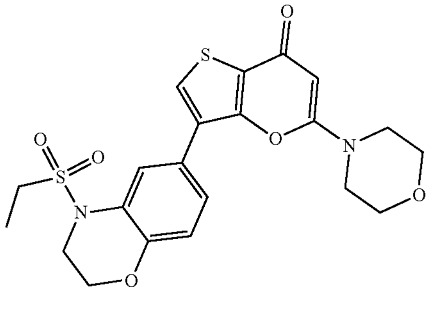 [SMILES: CCS(=O)(=O)N1CCOc2ccc(-c3csc4c(=O)cc(N5CCOCC5)oc34)cc21] |

TABLE 2-continued
| Representative examples of compounds of Formula II. | |
|---|---|
| No. | Structure |
| II-3 | 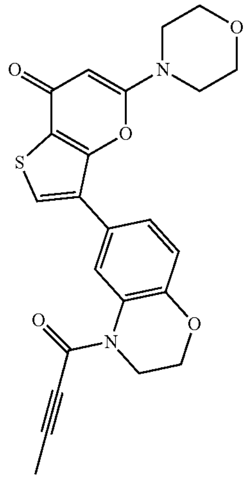 |
| II-4 | 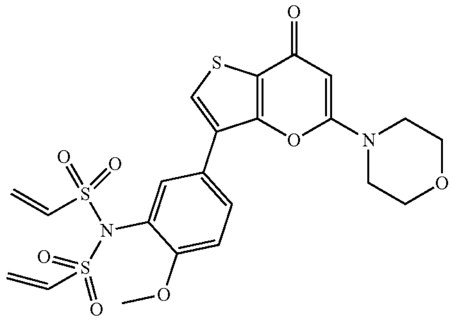 [SMILES: C=CS(=O)(=O)N(c1cc(-c2csc3c(=O)cc(N4CCOCC4)oc23)ccc1OC)S(=O)(=O)C=C] |
| II-5 | 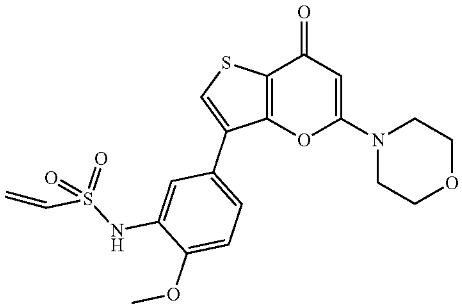 [SMILES: C=CS(=O)(=O)Nc1cc(-c2csc3c(=O)cc(N4CCOCC4)oc23)ccc1OC] |
| II-6 | 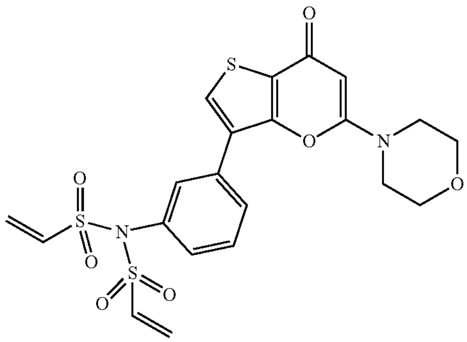 [SMILES: C=CS(=O)(=O)N(c1cccc(-c2csc3c(=O)cc(N4CCOCC4)oc23)c1)S(=O)(=O)C=C] |

TABLE 2-continued
| No. | Structure |
|---|---|
| | Representative examples of compounds of Formula II. |
| II-7 | 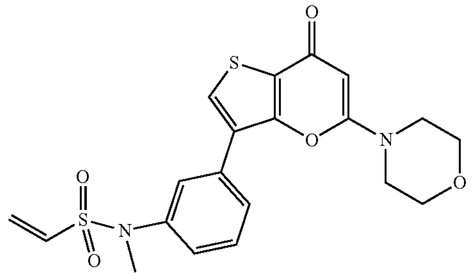 [SMILES: C=CS(=O)(=O)N(C)c1cccc(-c2csc3c(=O)cc(N4CCOCC4)oc23)c1] |
| II-8 | 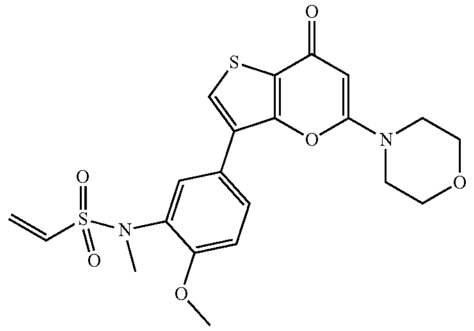 [SMILES: C=CS(=O)(=O)N(C)c1cc(-c2csc3c(=O)cc(N4CCOCC4)oc23)ccc1OC] |
| II-9 | 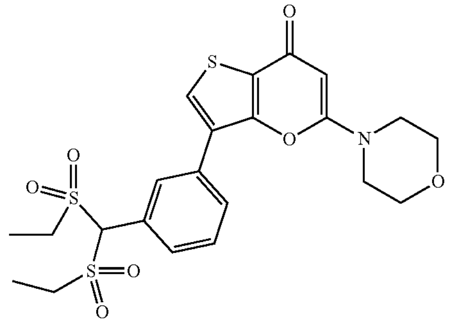 [SMILES: CCS(=O)(=O)C(c1cccc(-c2csc3c(=O)cc(N4CCOCC4)oc23)c1)S(=O)(=O)CC] |
| II-10 | 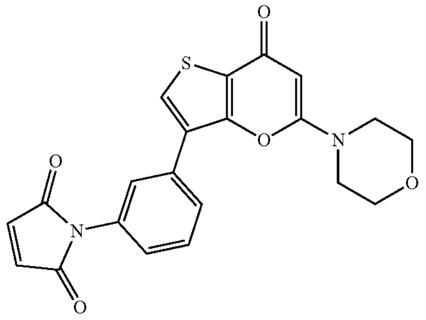 [SMILES: O=C1C=CC(=O)N1c1cccc(-c2csc3c(=O)cc(N4CCOCC4)oc23)c1] |
| II-11 | 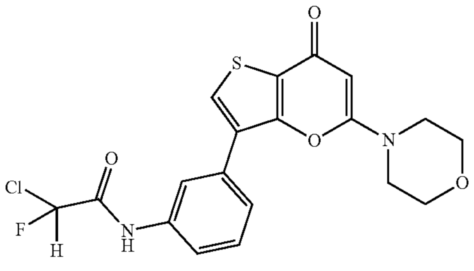 [SMILES: O=C(Nc1cccc(-c2csc3c(=O)cc(N4CCOCC4)oc23)c1)C(F)Cl] |

TABLE 2-continued
| Representative examples of compounds of Formula II. | |
|---|---|
| No. | Structure |
| II-12 | 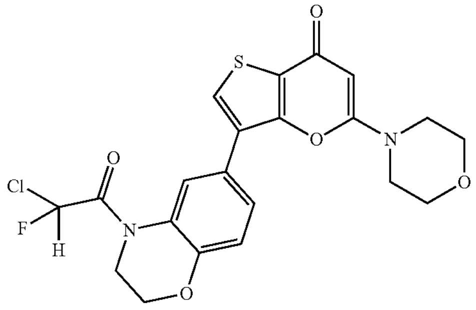 [SMILES: O=C(C(F)Cl)N1CCOc2ccc(-c3csc4c(=O)cc(N5CCOCC5)oc34)cc21] |
| II-13 | 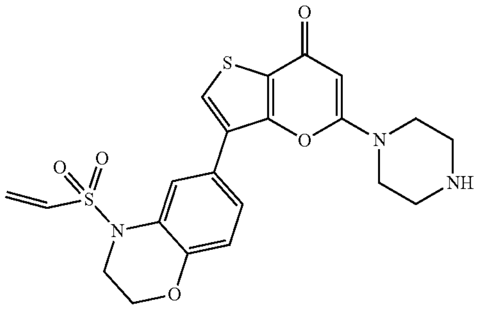 [SMILES: C=CS(=O)(=O)N1CCOc2ccc(-c3csc4c(=O)cc(N5CCNCC5)oc34)cc21] |
| II-14 | 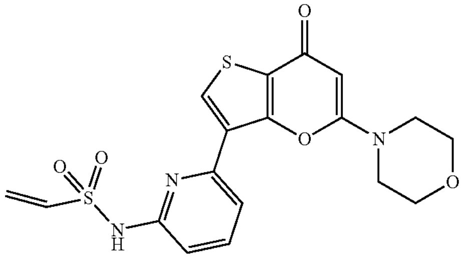 [SMILES: C=CS(=O)(=O)Nc1cccc(-c2csc3c(=O)cc(N4CCOCC4)oc23)n1] |
| II-15 | 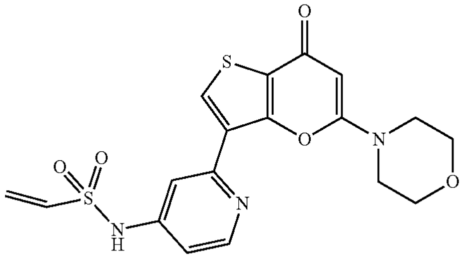 [SMILES: C=CS(=O)(=O)Nc1ccnc(-c2csc3c(=O)cc(N4CCOCC4)oc23)c1] |
| II-16 | 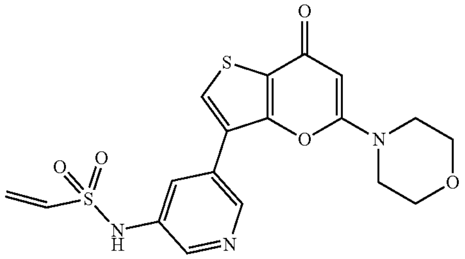 [SMILES: C=CS(=O)(=O)Nc1cncc(-c2csc3c(=O)cc(N4CCOCC4)oc23)c1] |

TABLE 2-continued
| Representative examples of compounds of Formula II. | |
|---|---|
| No. | Structure |
| II-17 | 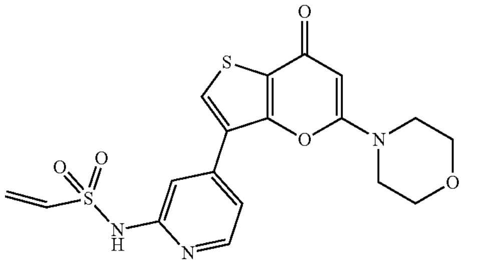 [SMILES: C=CS(=O)(=O)Nc1cc(-c2csc3c(=O)cc(N4CCOCC4)oc23)ccn1] |
| II-18 | 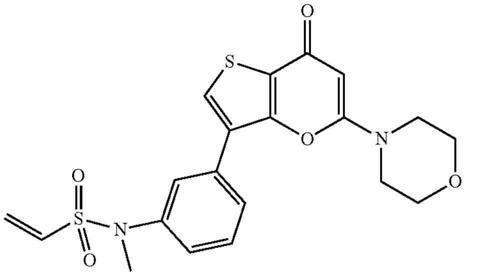 [SMILES: C=CS(=O)(=O)N(C)c1cccc(-c2csc3c(=O)cc(N4CCOCC4)oc23)c1] |
| II-19 | 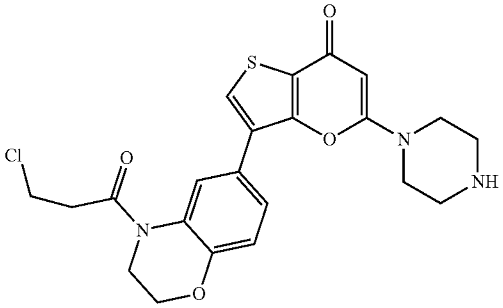 [SMILES: O=C(CCCl)N1CCOc2ccc(-c3csc4c(=O)cc(N5CCNCC5)oc34)cc21] |
| II-20 | 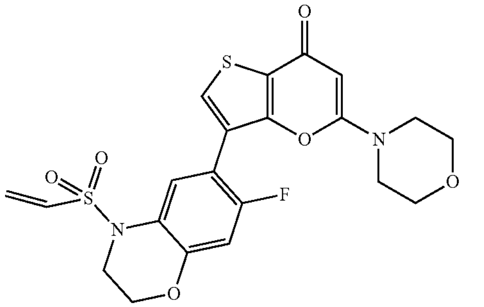 [SMILES: C=CS(=O)(=O)N1CCOc2cc(F)c(-c3csc4c(=O)cc(N5CCOCC5)oc34)cc21] |
| II-21 | 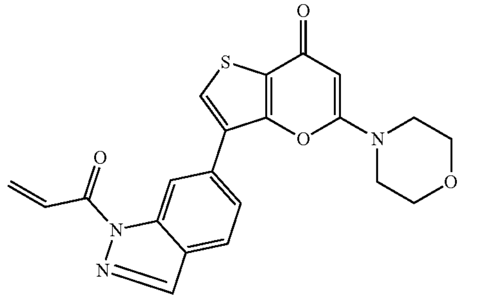 |

TABLE 2-continued
| Representative examples of compounds of Formula II. | |
|---|---|
| No. | Structure |
| II-22 | 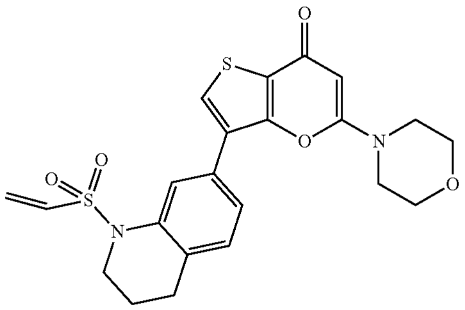 [SMILES: C=CS(=O)(=O)N1CCCc2ccc(-c3csc4c(=O)cc(N5CCOCC5)oc34)cc21] |
| II-23 | 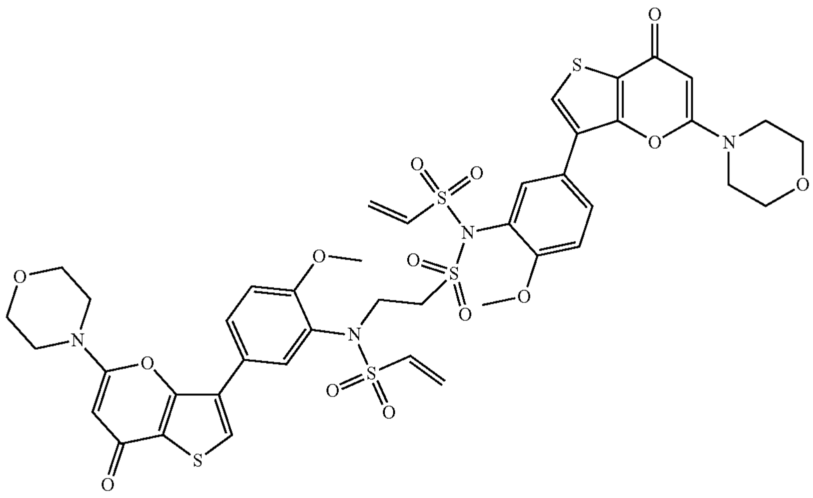 [SMILES: C=CS(=O)(=O)N(CCS(=O)(=O)N(c1cc(-c2csc3c(=O)cc(N4CCOCC4)oc23)ccc1OC)S(=O)(=O)C=C)c1cc(-c2csc3c(=O)cc(N4CCOCC4)oc23)ccc1OC] |
| II-24 | 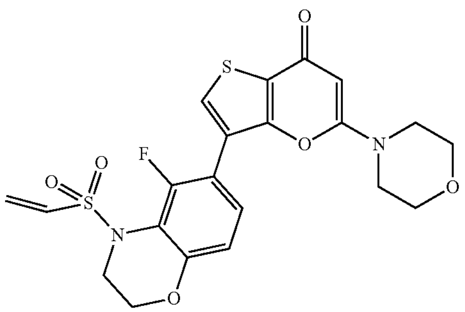 [SMILES: C=CS(=O)(=O)N1CCOc2ccc(-c3csc4c(=O)cc(N5CCOCC5)oc34)c(F)c21] |

The present invention also provides compounds of Formula III and methods of administering those compounds to a mammal in need thereof including, but not limited to, compounds that inhibit BTK and at least one other protein such as but not limited to PI3K and/or BRD4:

Formula III

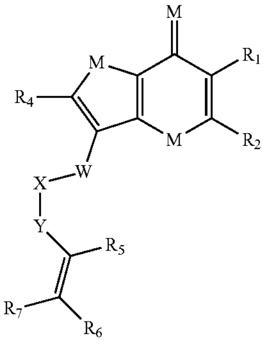

wherein M is independently O or S;

R1, R2, and R4 are as described for Formula I;

W is null, NR1, O, S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

X is null or O, N, NR1 or S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

provided that if W is N, O, or S then X cannot be N, O, or S; and if X is N, O, or S then W cannot be N, O, or S;

Y is null, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate; and R5, R6, R7 are independently selected from R1 as described in Formula I.

Representative examples of compounds of Formula III are shown in Table 3 below.

TABLE 3

Representative examples of compounds of Formula III.

| No. | Structure |
| --- | --- |
| III-1 | 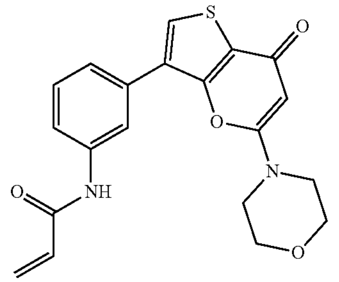 |
| III-2 | 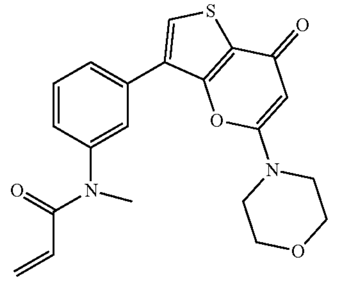 [SMILES: C=CC(=O)N(C)c1cccc(-c2csc3c(=O)cc(N4CCOCC4)oc23)c1] |
| III-3 | 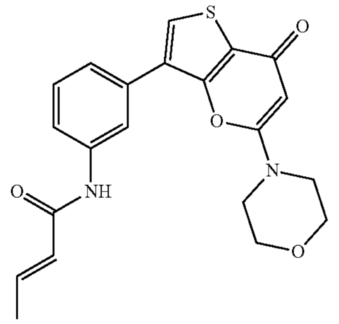 [SMILES: C/C=C/C(=O)Nc1cccc(-c2csc3c(=O)cc(N4CCOCC4)oc23)c1] |

TABLE 3-continued
| Representative examples of compounds of Formula III. | |
|---|---|
| No. | Structure |
| III-4 | 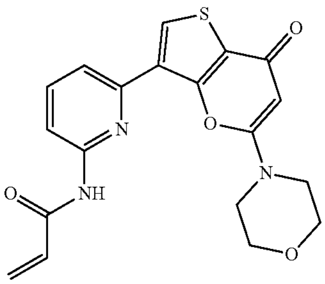 |
| III-5 | 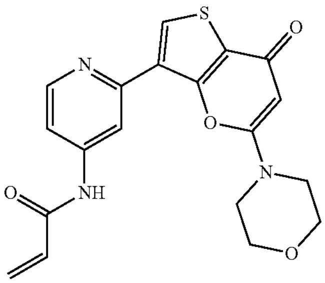 |
| III-6 | 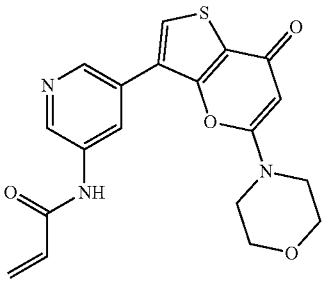 |
| III-7 | 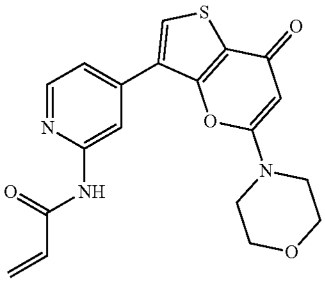 |
| III-8 | 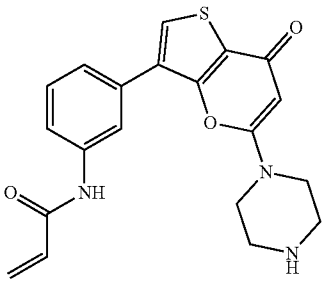 |
TABLE 3-continued
| Representative examples of compounds of Formula III. | |
|---|---|
| No. | Structure |
| III-9 | 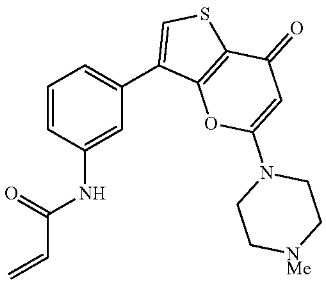 |
| III-10 | 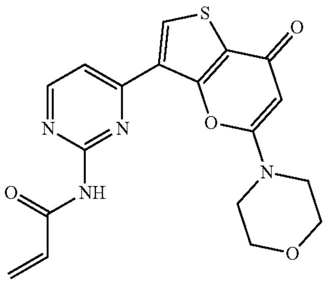 |
| III-11 | 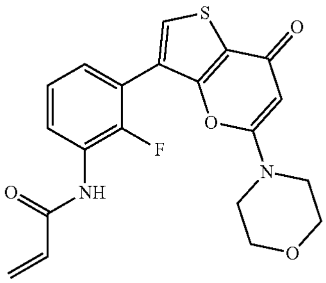 |
| III-12 | 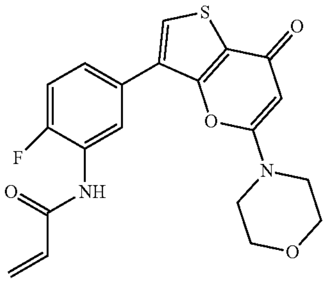 |
| III-13 | 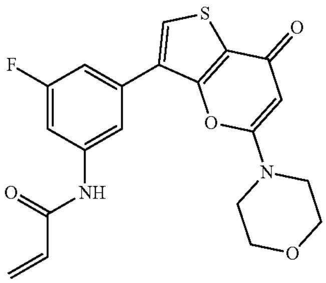 |

TABLE 3-continued
Representative examples of compounds of Formula III.
| No. | Structure |
|---|---|
| III-14 | 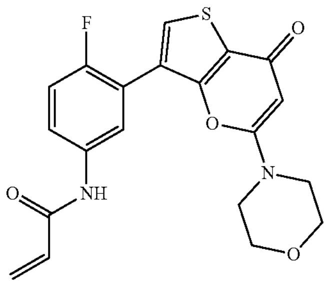 |
| III-15 | 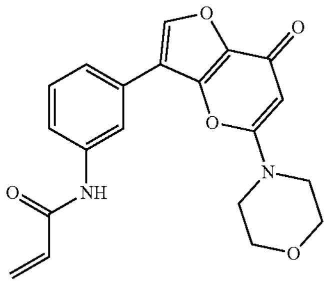 |
| III-16 | 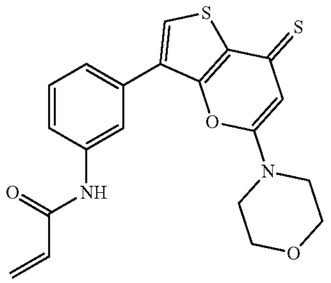 |
| III-17 | 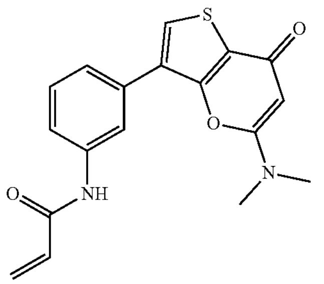 [SMILES: C=CC(=O)Nc1cccc(-c2csc3c(=O)cc(N(C)C)oc23)c1] |
| III-18 | 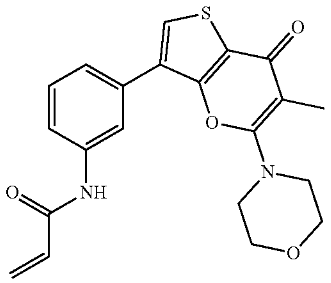 [SMILES: C=CC(=O)Nc1cccc(-c2csc3c(=O)c(C)c(N4CCOCC4)oc23)c1] |
TABLE 3-continued
Representative examples of compounds of Formula III.
| No. | Structure |
|---|---|
| III-19 | 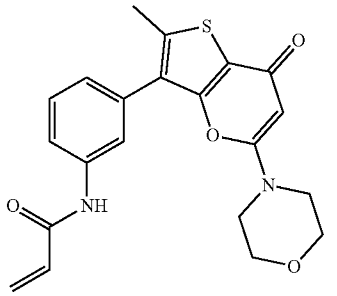 [SMILES: C=CC(=O)Nc1cccc(-c2c(C)sc3c(=O)cc(N4CCOCC4)oc23)c1] |
| III-20 | 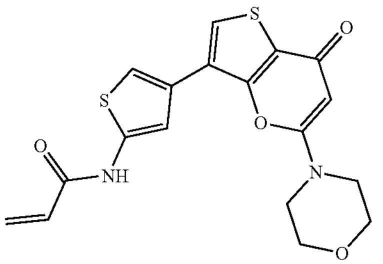 [SMILES: C=CC(=O)Nc1cc(-c2csc3c(=O)cc(N4CCOCC4)oc23)cs1] |
| III-21 | 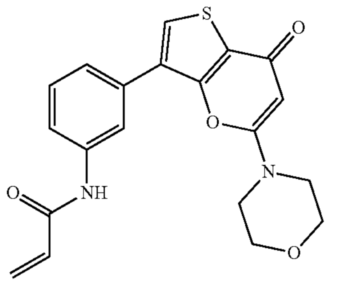 |
| III-22 | 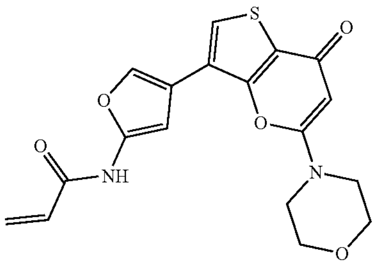 [SMILES: C=CC(=O)Nc1cc(-c2csc3c(=O)cc(N4CCOCC4)oc23)co1] |
| III-23 | 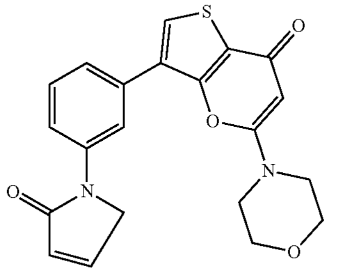 [SMILES: O=C1C=CCN1c1cccc(-c2csc3c(=O)cc(N4CCOCC4)oc23)c1] |

TABLE 3-continued
| Representative examples of compounds of Formula III. | |
|---|---|
| No. | Structure |
| III-24 | 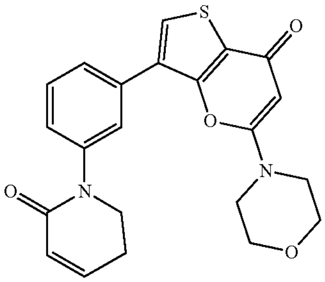 [SMILES: O=C1C=CCCN1c1cccc(-c2csc3c(=O)cc(N4CCOCC4)oc23)c1] |
| III-25 | 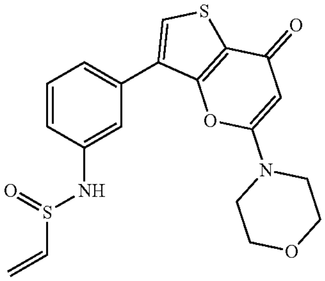 |
| III-26 | 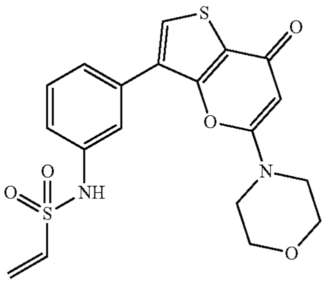 [SMILES: C=CS(=O)(=O)Nc1cccc(-c2csc3c(=O)cc(N4CCOCC4)oc23)c1] |
| III-27 | 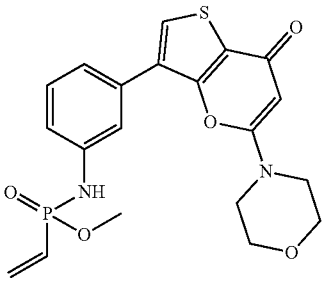 [SMILES: C=CP(=O)(Nc1cccc(-c2csc3c(=O)cc(N4CCOCC4)oc23)c1)OC] |
| III-28 | 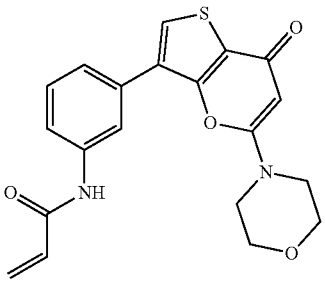 |
TABLE 3-continued
| Representative examples of compounds of Formula III. | |
|---|---|
| No. | Structure |
| III-29 | 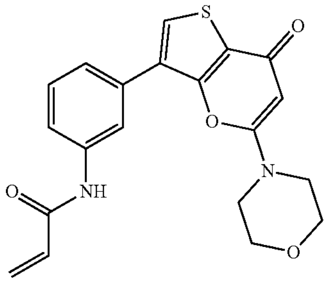 |
| III-30 | 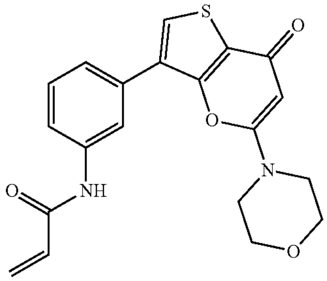 |
| III-31 | 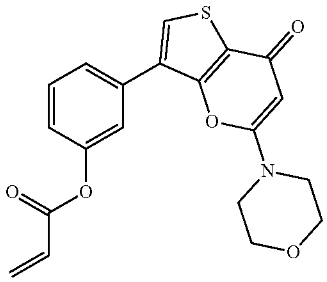 |
| III-32 | 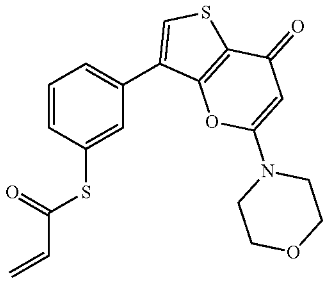 |
| III-33 | 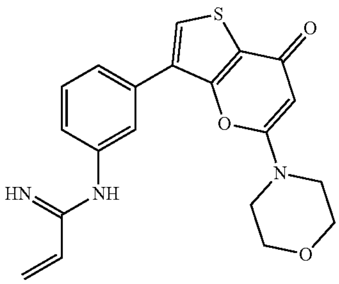 [SMILES: C=CC(=N)Nc1cccc(-c2csc3c(=O)cc(N4CCOCC4)oc23)c1] |

TABLE 3-continued
Representative examples of compounds of Formula III.
| No. | Structure |
| --- | --- |
| III-34 | 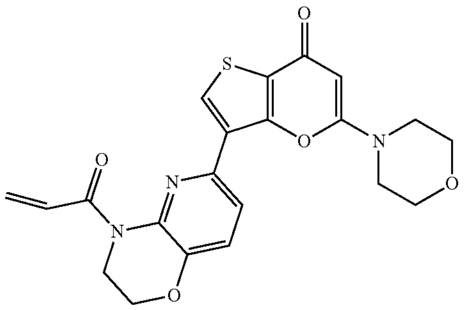 [SMILES: C=CC(=O)N1CCOc2ccc(-c3csc4c(=O)cc(N5CCOCC5)oc34)nc21] |
| III-35 | 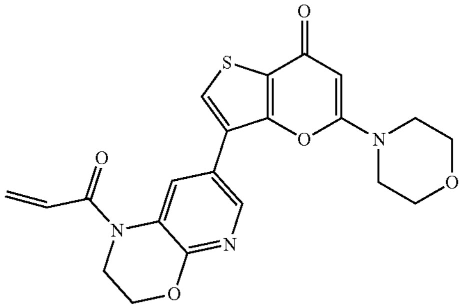 [SMILES: C=CC(=O)N1CCOc2ncc(-c3csc4c(=O)cc(N5CCOCC5)oc34)cc21] |
| III-36 | 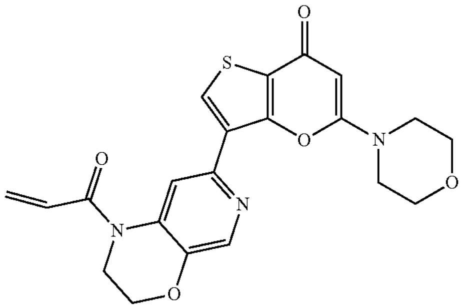 [SMILES: C=CC(=O)N1CCOc2cnc(-c3csc4c(=O)cc(N5CCOCC5)oc34)cc21] |
| III-37 | 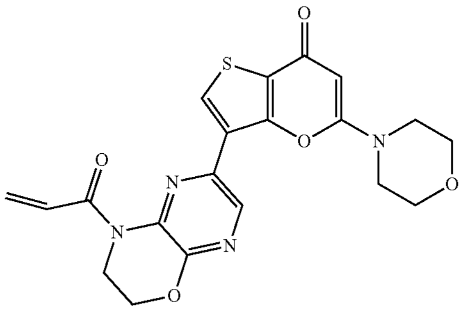 |
| III-38 | 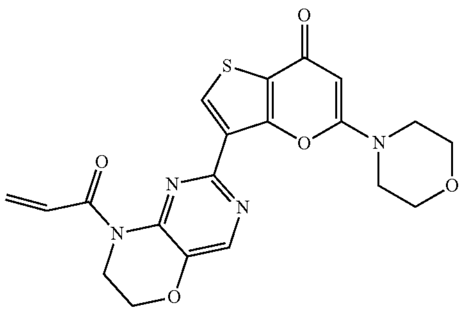 [SMILES: C=CC(=O)N1CCOc2cnc(-c3csc4c(=O)cc(N5CCOCC5)oc34)nc21] |
TABLE 3-continued
Representative examples of compounds of Formula III.
| No. | Structure |
| --- | --- |
| III-39 | 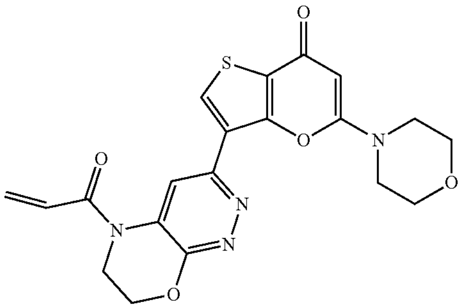 [SMILES: C=CC(=O)N1CCOc2nnc(-c3csc4c(=O)cc(N5CCOCC5)oc34)cc21] |
| III-40 | 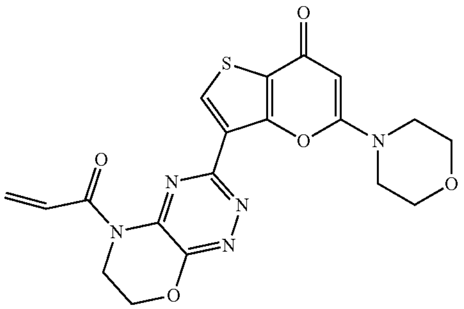 [SMILES: C=CC(=O)N1CCOc2nnc(-c3csc4c(=O)cc(N5CCOCC5)oc34)nc21] |
| III-41 | 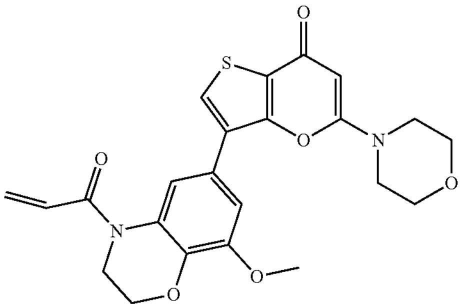 [SMILES: C=CC(=O)N1CCOc2c(OC)cc(-c3csc4c(=O)cc(N5CCOCC5)oc34)cc21] |
| III-42 | 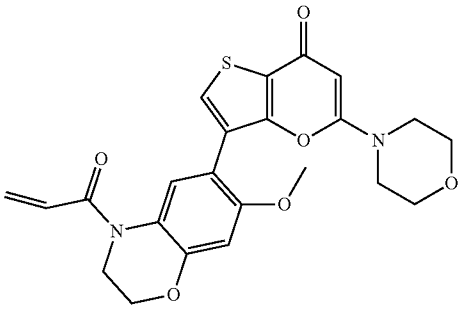 [SMILES: C=CC(=O)N1CCOc2cc(OC)c(-c3csc4c(=O)cc(N5CCOCC5)oc34)cc21] |

TABLE 3-continued
Representative examples of compounds of Formula III.
| No. | Structure |
| --- | --- |
| III-44 | 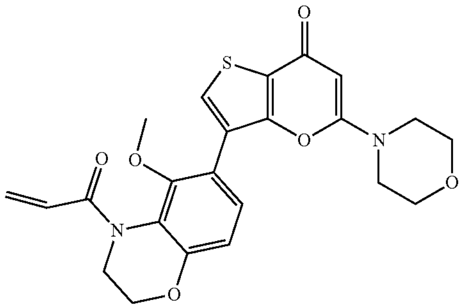 [SMILES: C=CC(=O)N1CCOc2ccc(-c3csc4c(=O)cc(N5CCOCC5)oc34)c(OC)c21] |
| III-45 | 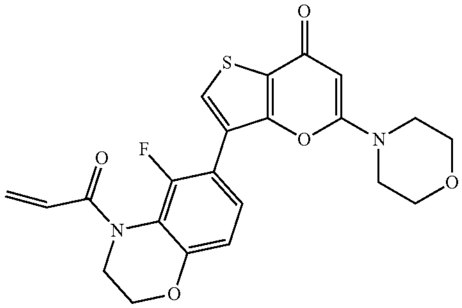 [SMILES: C=CC(=O)N1CCOc2ccc(-c3csc4c(=O)cc(N5CCOCC5)oc34)c(F)c21] |
| III-46 | 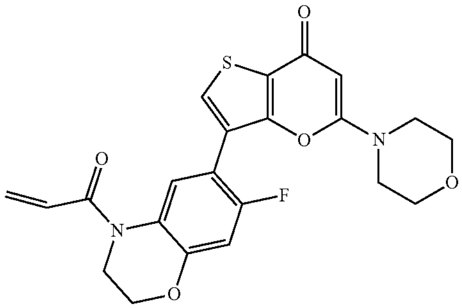 [SMILES: C=CC(=O)N1CCOc2cc(F)c(-c3csc4c(=O)cc(N5CCOCC5)oc34)cc21] |
| III-47 | 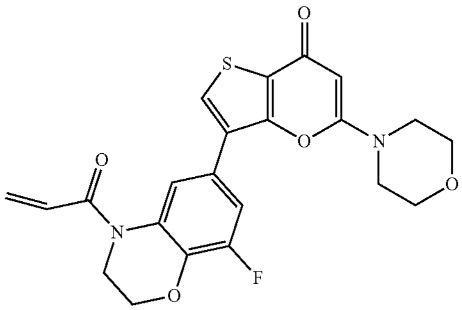 [SMILES: C=CC(=O)N1CCOc2c(F)cc(-c3csc4c(=O)cc(N5CCOCC5)oc34)cc21] |
| III-48 | 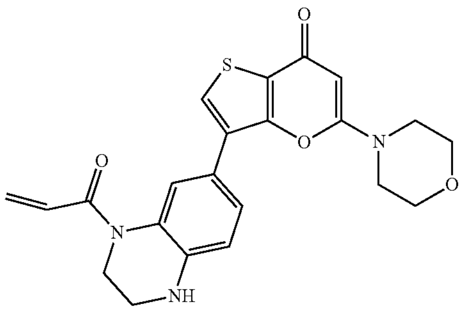 [SMILES: C=CC(=O)N1CCNc2ccc(-c3csc4c(=O)cc(N5CCOCC5)oc34)cc21] |
TABLE 3-continued
Representative examples of compounds of Formula III.
| No. | Structure |
| --- | --- |
| III-49 | 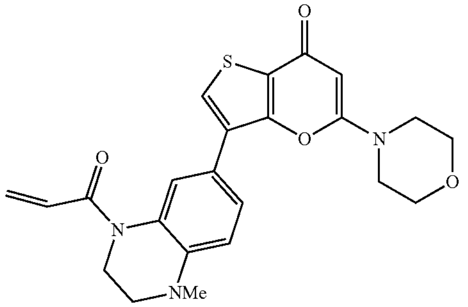 [SMILES: C=CC(=O)N1CCN(C)c2ccc(-c3csc4c(=O)cc(N5CCOCC5)oc34)cc21] |
| III-50 | 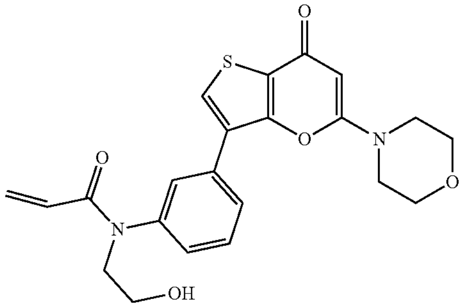 [SMILES: C=CC(=O)N(CCO)c1cccc(-c2csc3c(=O)cc(N4CCOCC4)oc23)c1] |
| III-51 | 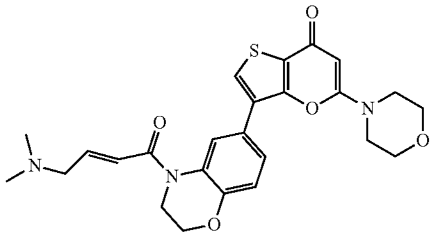 [SMILES: CN(C)C/C=C/C(=O)N1CCOc2ccc(-c3csc4c(=O)cc(N5CCOCC5)oc34)cc21] |
| III-52 | 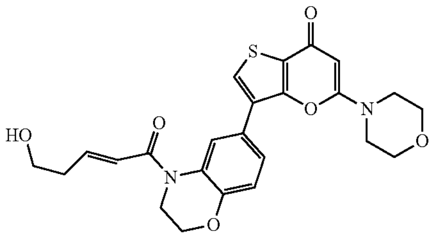 |
| III-53 | 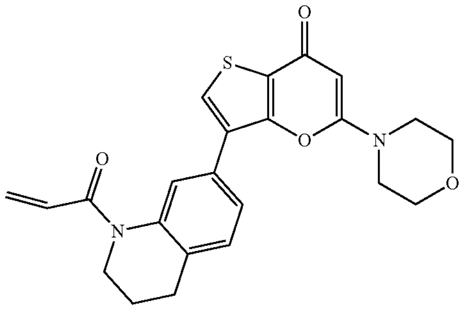 [SMILES: C=CC(=O)N1CCCc2ccc(-c3csc4c(=O)cc(N5CCOCC5)oc34)cc21] |

TABLE 3-continued
| Representative examples of compounds of Formula III. | |
|---|---|
| No. | Structure |
| III-54 | 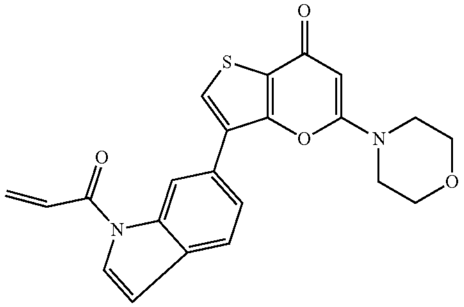 [SMILES: C=CC(=O)n1ccc2ccc(-c3csc4c(=O)cc(N5CCOCC5)oc34)cc21] |
| III-55 | 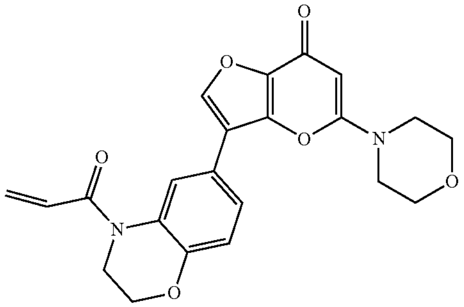 |
| III-56 | 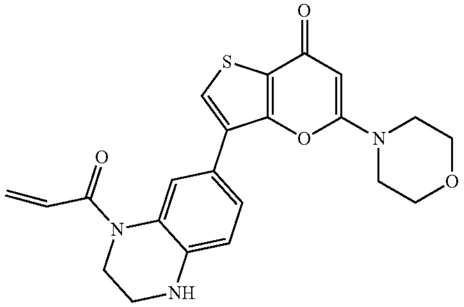 [SMILES: C=CC(=O)N1CCNc2ccc(-c3csc4c(=O)cc(N5CCOCC5)oc34)cc21] |
| III-57 | 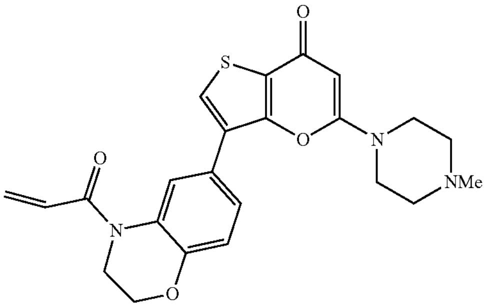 [SMILES: C=CC(=O)N1CCOc2ccc(-c3csc4c(=O)cc(N5CCN(C)CC5)oc34)cc21] |
| III-58 | 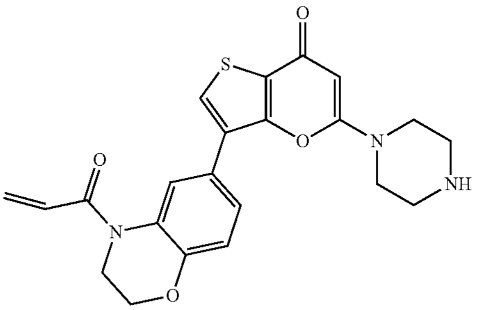 [SMILES: C=CC(=O)N1CCOc2ccc(-c3csc4c(=O)cc(N5CCNCC5)oc34)cc21] |
TABLE 3-continued
| Representative examples of compounds of Formula III. | |
|---|---|
| No. | Structure |
| III-59 | 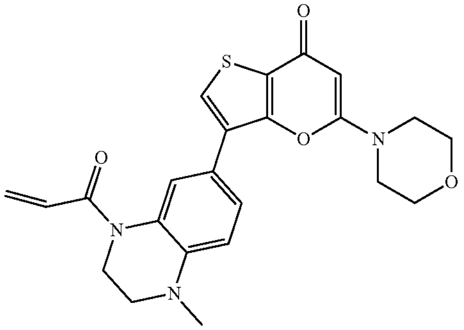 [SMILES: C=CC(=O)N1CCN(C)c2ccc(-c3csc4c(=O)cc(N5CCOCC5)oc34)cc21] |
| III-60 | 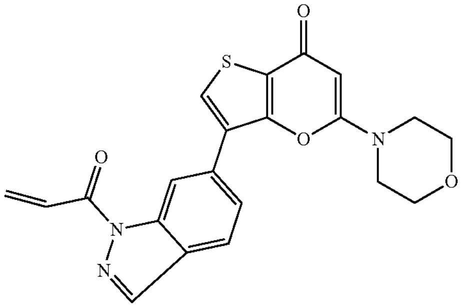 [SMILES: C=CC(=O)n1ncc2ccc(-c3csc4c(=O)cc(N5CCOCC5)oc34)cc21] |
| III-61 | 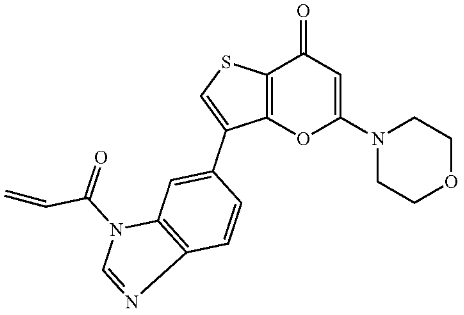 [SMILES: C=CC(=O)n1cnc2ccc(-c3csc4c(=O)cc(N5CCOCC5)oc34)cc21] |
| III-62 | 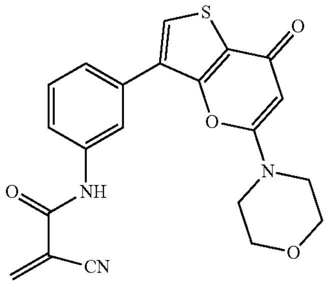 [SMILES: C=C(C#N)C(=O)Nc1cccc(-c2csc3c(=O)cc(N4CCOCC4)oc23)c1] |

TABLE 3-continued

| Representative examples of compounds of Formula III. | |
|---|---|
| No. | Structure |
| III-63 | 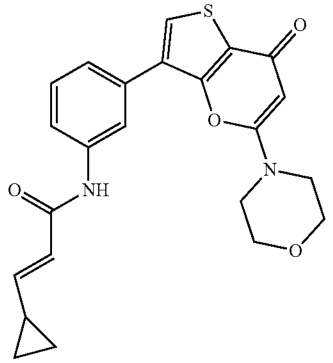 [SMILES: O=C(/C=C/C1CC1)Nc1cccc(-c2csc3c(=O)cc(N4CCOCC4)oc23)c1] |
| III-64 | 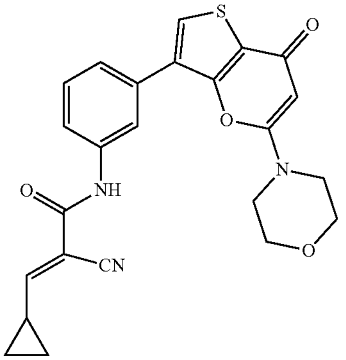 [SMILES: N#C/C(=C\C1CC1)C(=O)Nc1cccc(-c2csc3c(=O)cc(N4CCOCC4)oc23)c1] |

It should be noted that a variety of different substituents in different positions can be arranged on the aromatic group of the "W" or "X" moiety in Formula III some of which are exemplified in the Table 2 above. Additionally, the connection between the 5-membered ring of the thienopyran or furanopyran ring can include a variety of different linkers in various attachment positions (ortho, meta, para for a six membered ring for example) represented by the W—X—Y group in Formula III, some of which are exemplified in the Table 2 above. These permutations are synthetically accessible to one skilled in the art.

The present invention also provides compounds of Formula IV and methods of administering compounds of Formula IV to a mammal in need thereof including, but not limited to, compounds that inhibit BTK and at least one other protein such as, but not limited to, PI3K and/or BRD4:

Formula IV

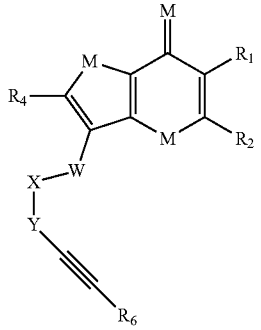

wherein M is independently O or S;

R1, R2, and R4 are as described for Formula I;

W is null, NR1, O, S, $CH_2$, Ar, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

X is null or O, N, NR1 or S, $CH_2$, Ar, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

provided that if W is N, O, or S then X cannot be N, O, or S; and if X is N, O, or S then W cannot be N, O, or S;

Y is null, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

Ar is aryl, heteroaryl, or heterocyclic bearing one, two, three or four substituents on the Ar ring independently selected from: H. F. Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, reverse sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, and substituted carbamate; and R8 is selected from R1 as defined in Formula I.

Representative examples of compounds of Formula IV are shown in Table 4 below.

TABLE 4

Representative examples of compounds of Formula IV.

| No. | Structure |
|---|---|
| IV-1 | 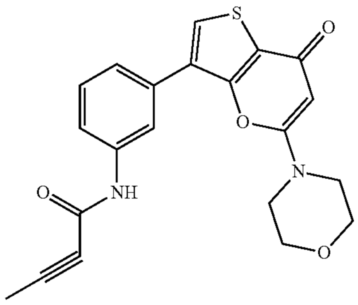 [SMILES: CC#CC(=O)Nc1cccc(-c2csc3c(=O)cc(N4CCOCC4)oc23)c1] |
| IV-2 | 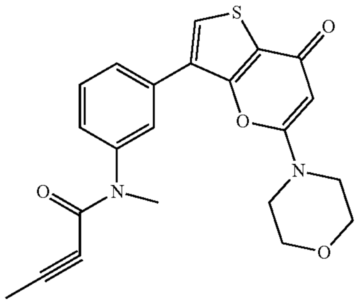 [SMILES: CC#CC(=O)N(C)c1cccc(-c2csc3c(=O)cc(N4CCOCC4)oc23)c1] |
| IV-3 | 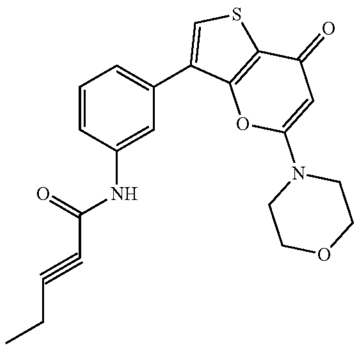 [SMILES: CCC#CC(=O)Nc1cccc(-c2csc3c(=O)cc(N4CCOCC4)oc23)c1] |

TABLE 4-continued

Representative examples of compounds of Formula IV.

| No. | Structure |
|---|---|
| IV-4 | 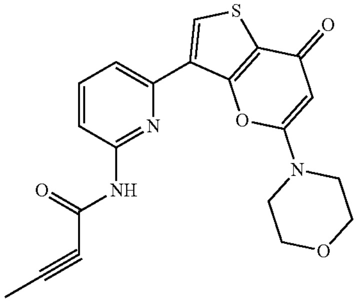 |
| IV-5 | 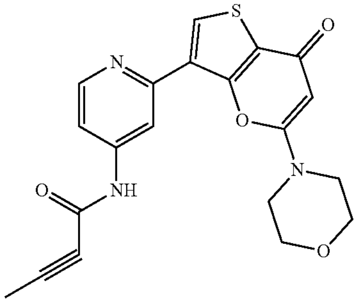 [SMILES: CC#CC(=O)Nc1ccnc(-c2csc3c(=O)cc(N4CCOCC4)oc23)c1] |
| IV-6 | 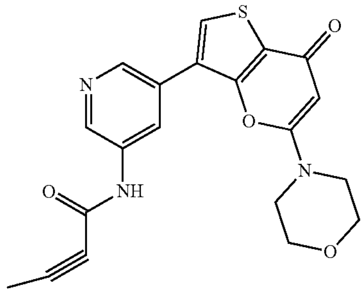 [SMILES: CC#CC(=O)Nc1cncc(-c2csc3c(=O)cc(N4CCOCC4)oc23)c1] |
| IV-7 | 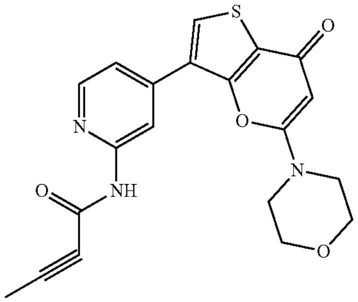 |
| IV-8 | 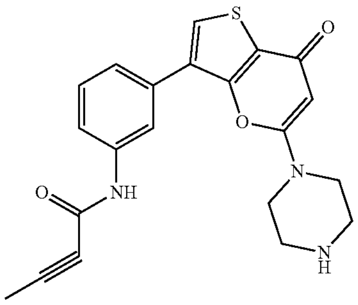 [SMILES: CC#CC(=O)Nc1cccc(-c2csc3c(=O)cc(N4CCNCC4)oc23)c1] |

TABLE 4-continued
Representative examples of compounds of Formula IV.
| No. | Structure |
|---|---|
| IV-9 | 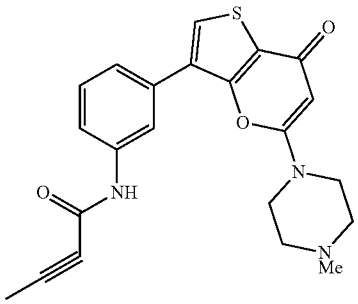 [SMILES: CC#CC(=O)Nc1cccc(-c2csc3c(=O)cc(N4CCN(C)CC4)oc23)c1] |
| IV-10 | 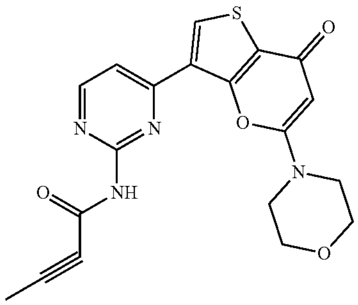 [SMILES: CC#CC(=O)Nc1nccc(-c2csc3c(=O)cc(N4CCOCC4)oc23)n1] |
| IV-11 | 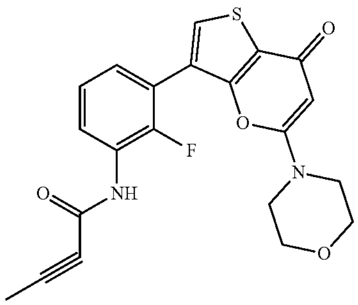 [SMILES: CC#CC(=O)Nc1cccc(-c2csc3c(=O)cc(N4CCOCC4)oc23)c1F] |
| IV-12 | 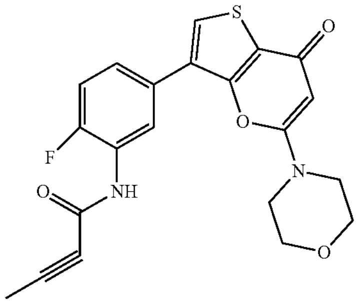 [SMILES: CC#CC(=O)Nc1cc(-c2csc3c(=O)cc(N4CCOCC4)oc23)ccc1F] |
| IV-13 | 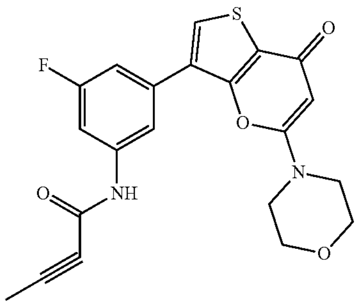 |
TABLE 4-continued
Representative examples of compounds of Formula IV.
| No. | Structure |
|---|---|
| IV-14 | 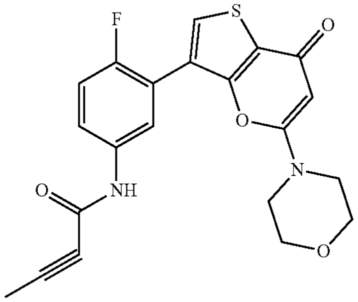 [SMILES: CC#CC(=O)Nc1ccc(F)c(-c2csc3c(=O)cc(N4CCOCC4)oc23)c1] |
| IV-15 | 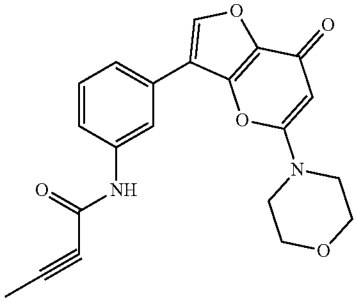 [SMILES: CC#CC(=O)Nc1cccc(-c2coc3c(=O)cc(N4CCOCC4)oc23)c1] |
| IV-16 | 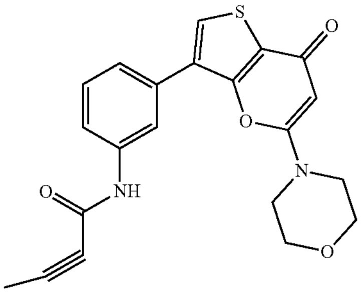 [SMILES: CC#CC(=O)Nc1cccc(-c2csc3c(=O)cc(N4CCOCC4)oc23)c1] |
| IV-17 | 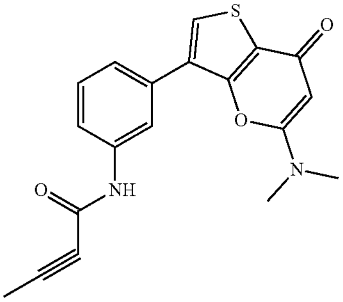 [SMILES: CC#CC(=O)Nc1cccc(-c2csc3c(=O)cc(N(C)C)oc23)c1] |
| IV-18 | 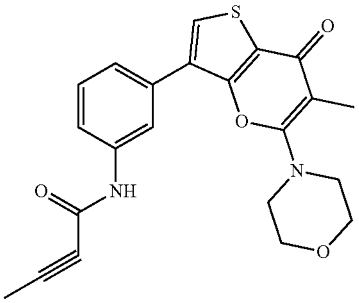 [SMILES: CC#CC(=O)Nc1cccc(-c2csc3c(=O)c(C)c(N4CCOCC4)oc23)c1] |

TABLE 4-continued
| Representative examples of compounds of Formula IV. | |
|---|---|
| No. | Structure |
| IV-19 | 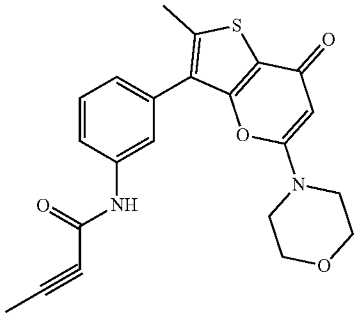 [SMILES: CC#CC(=O)Nc1cccc(-c2c(C)sc3c(=O)cc(N4CCOCC4)oc23)c1] |
| IV-20 | 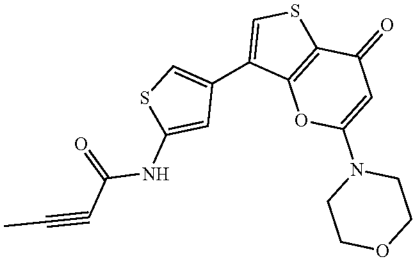 [SMILES: CC#CC(=O)Nc1cc(-c2csc3c(=O)cc(N4CCOCC4)oc23)cs1] |
| IV-21 | 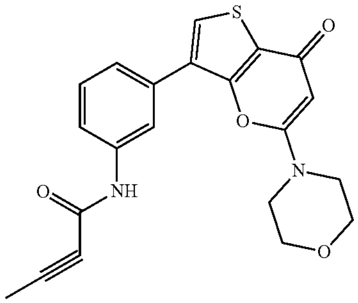 [SMILES: CC#CC(=O)Nc1cccc(-c2csc3c(=O)cc(N4CCOCC4)oc23)c1] |
| IV-22 | 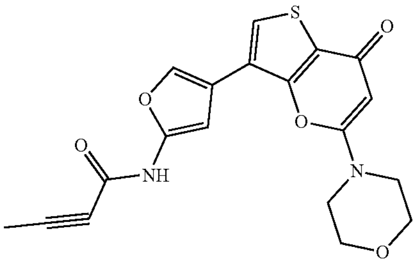 |
| IV-23 | 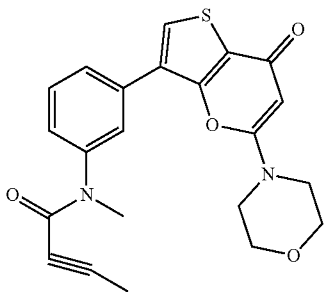 [SMILES: CC#CC(=O)N(C)c1cccc(-c2csc3c(=O)cc(N4CCOCC4)oc23)c1] |
TABLE 4-continued
| Representative examples of compounds of Formula IV. | |
|---|---|
| No. | Structure |
| IV-24 | 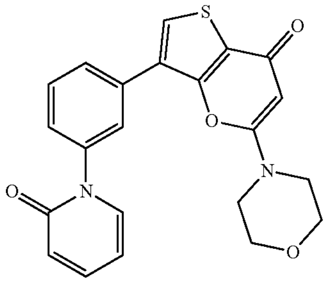 [SMILES: O=c1cc(N2CCOCC2)oc2c(-c3cccc(-n4ccccc4=O)c3)csc12] |
| IV-25 | 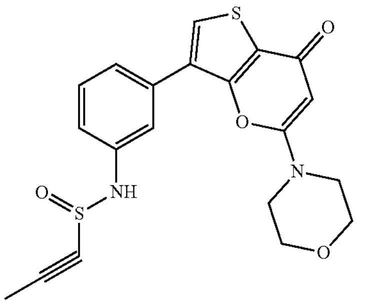 [SMILES: CC#CS(=O)Nc1cccc(-c2csc3c(=O)cc(N4CCOCC4)oc23)c1] |
| IV-26 | 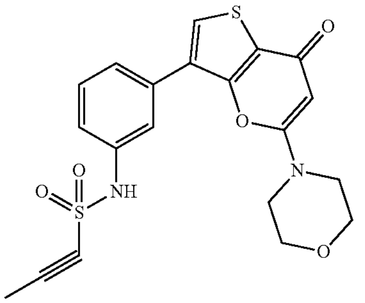 [SMILES: CC#CS(=O)(=O)Nc1cccc(-c2csc3c(=O)cc(N4CCOCC4)oc23)c1] |
| IV-27 | 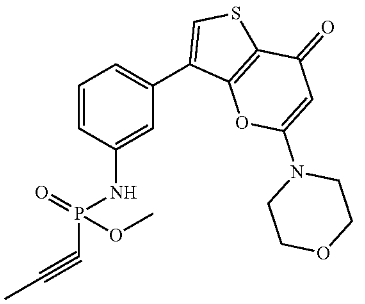 [SMILES: CC#CP(=O)(Nc1cccc(-c2csc3c(=O)cc(N4CCOCC4)oc23)c1)OC] |
| IV-28 | 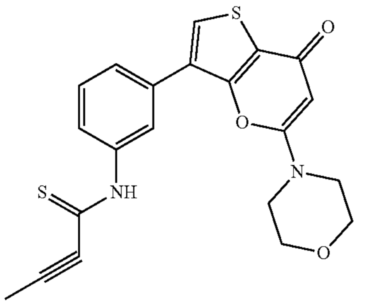 |

TABLE 4-continued
| Representative examples of compounds of Formula IV. | |
|---|---|
| No. | Structure |
| IV-29 | 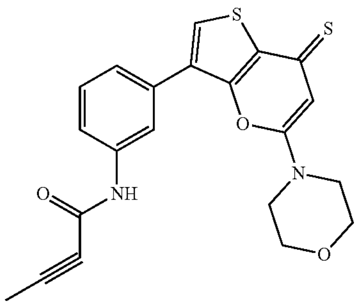 [SMILES: CC#CC(=O)Nc1cccc(-c2csc3c(=S)cc(N4CCOCC4)oc23)c1] |
| IV-30 | 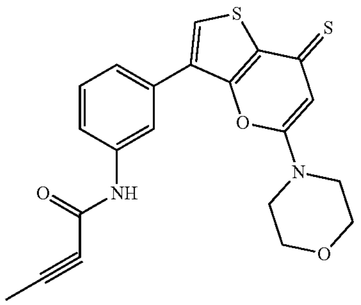 [SMILES: CC#CC(=O)Nc1cccc(-c2csc3c(=S)cc(N4CCOCC4)oc23)c1] |
| IV-31 | 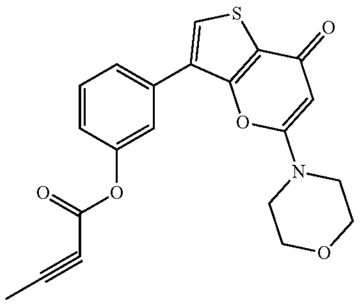 |
| IV-32 | 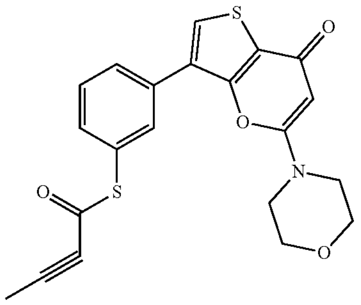 [SMILES: CC#CC(=O)Sc1cccc(-c2csc3c(=O)cc(N4CCOCC4)oc23)c1] |
| IV-33 | 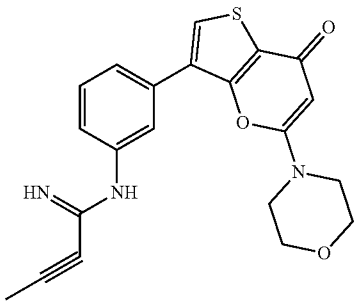 [SMILES: CC#CC(=N)Nc1cccc(-c2csc3c(=O)cc(N4CCOCC4)oc23)c1] |
TABLE 4-continued
| Representative examples of compounds of Formula IV. | |
|---|---|
| No. | Structure |
| IV-34 | 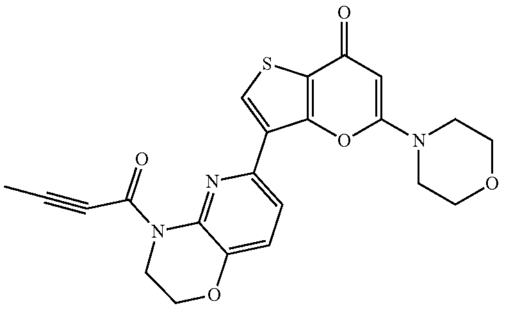 |
| IV-35 | 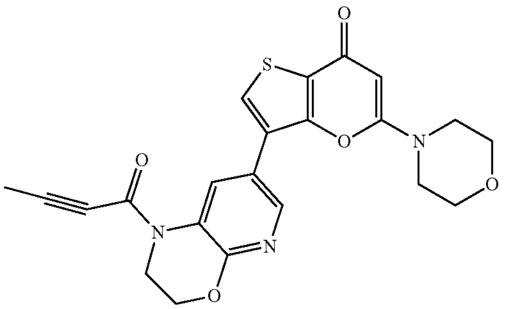 |
| IV-36 | 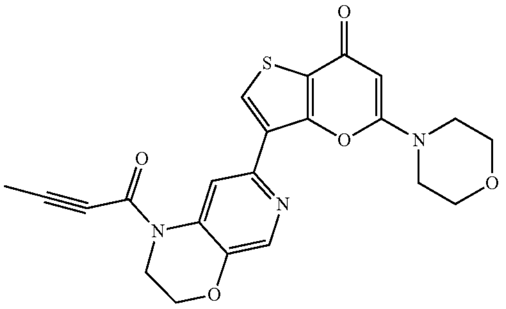 |
| IV-37 | 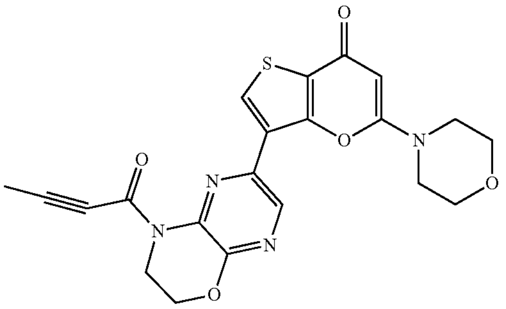 |
| IV-38 | 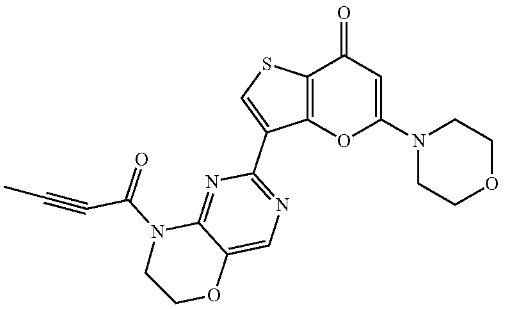 |

TABLE 4-continued
Representative examples of compounds of Formula IV.
| No. | Structure |
| --- | --- |
| IV-39 | 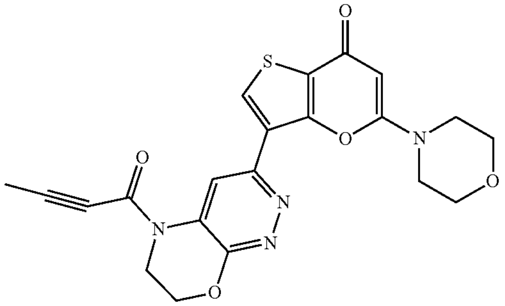 |
| IV-40 | 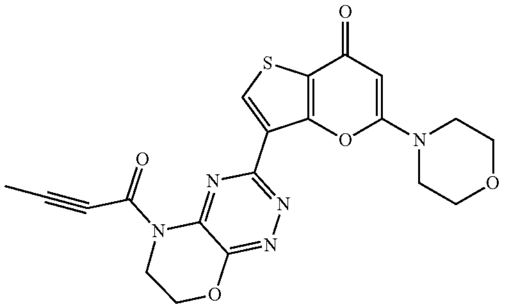 |
| IV-41 | 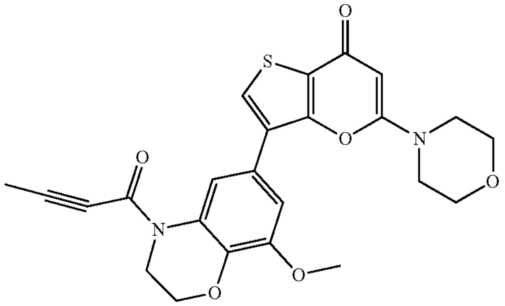 |
| IV-42 | 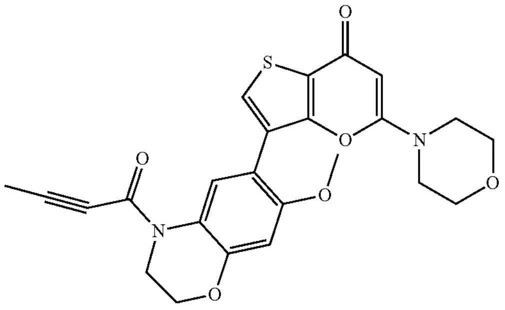 [SMILES: CC#CC(=O)N1CCOc2cc(OC)c(-c3csc4c(=O)cc(N5CCOCC5)oc34)cc21] |
TABLE 4-continued
Representative examples of compounds of Formula IV.
| No. | Structure |
| --- | --- |
| IV-44 | 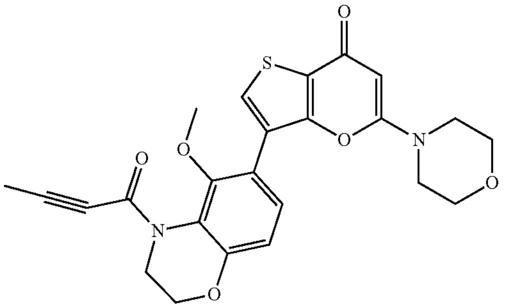 |
| IV-45 | 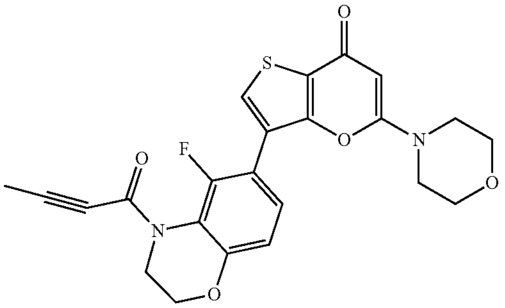 |
| IV-46 | 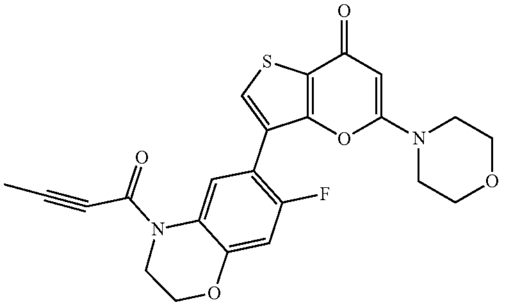 |
| IV-47 | 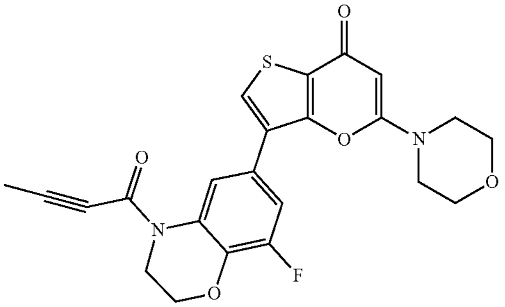 |
| IV-48 | 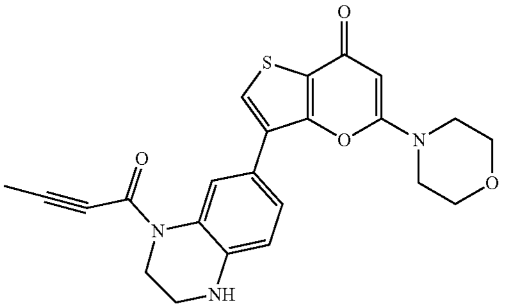 [SMILES: CC#CC(=O)N1CCNc2ccc(-c3csc4c(=O)cc(N5CCOCC5)oc34)cc21] |

TABLE 4-continued
| Representative examples of compounds of Formula IV. | |
|---|---|
| No. | Structure |
| IV-49 | 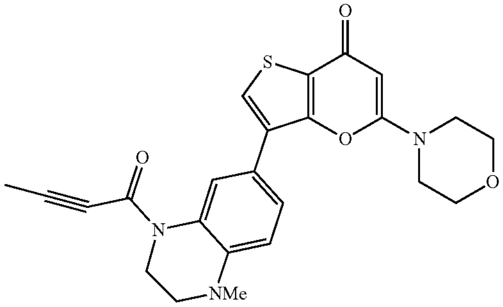 [SMILES: CC#CC(=O)N1CCN(C)c2ccc(-c3csc4c(=O)cc(N5CCOCC5)oc34)cc21] |
| IV-50 | 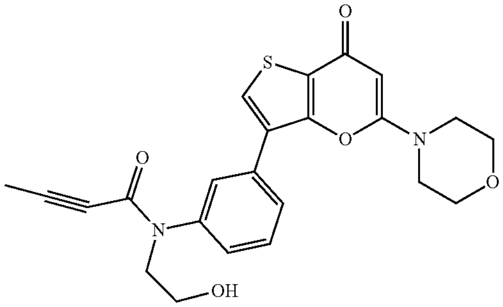 [SMILES: CC#CC(=O)N(CCO)c1cccc(-c2csc3c(=O)cc(N4CCOCC4)oc23)c1] |
| IV-51 | 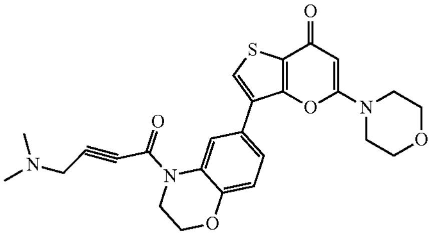 [SMILES: CN(C)CC#CC(=O)N1CCOc2ccc(-c3csc4c(=O)cc(N5CCOCC5)oc34)cc21] |
| IV-52 | 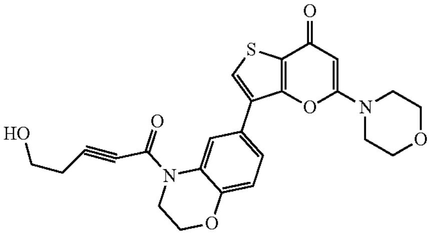 [SMILES: O=C(C#CCCO)N1CCOc2ccc(-c3csc4c(=O)cc(N5CCOCC5)oc34)cc21] |
| IV-53 | 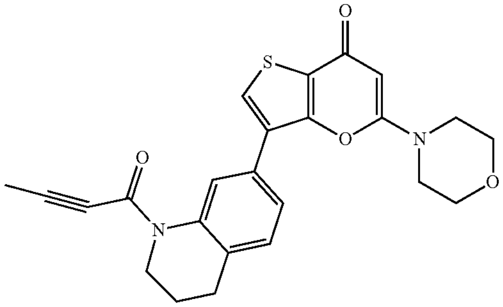 [SMILES: CC#CC(=O)N1CCCc2ccc(-c3csc4c(=O)cc(N5CCOCC5)oc34)cc21] |
TABLE 4-continued
| Representative examples of compounds of Formula IV. | |
|---|---|
| No. | Structure |
| IV-54 | 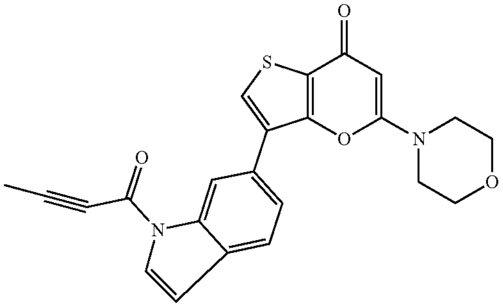 [SMILES: CC#CC(=O)n1ccc2ccc(-c3csc4c(=O)cc(N5CCOCC5)oc34)cc21] |
| IV-55 | 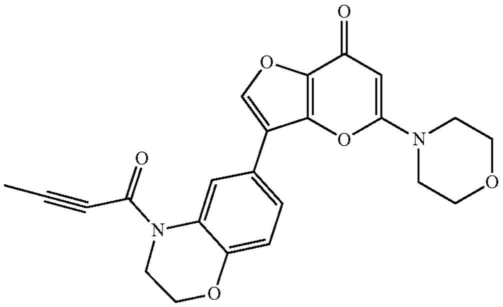 [SMILES: CC#CC(=O)N1CCOc2ccc(-c3coc4c(=O)cc(N5CCOCC5)oc34)cc21] |
| IV-56 | 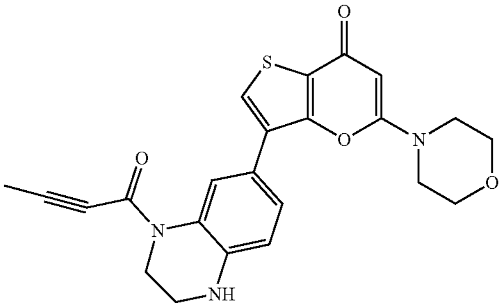 [SMILES: CC#CC(=O)N1CCNc2ccc(-c3csc4c(=O)cc(N5CCOCC5)oc34)cc21] |
| IV-57 | 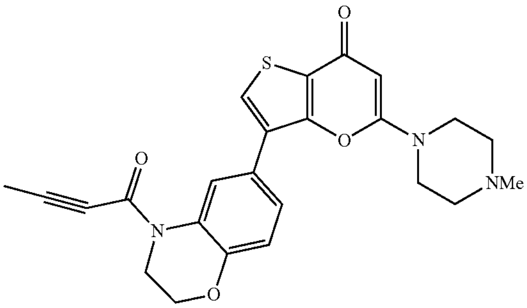 [SMILES: CC#CC(=O)N1CCOc2ccc(-c3csc4c(=O)cc(N5CCN(C)CC5)oc34)cc21] |
| IV-58 | 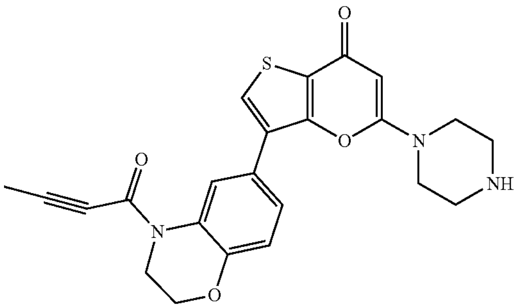 [SMILES: CC#CC(=O)N1CCOc2ccc(-c3csc4c(=O)cc(N5CCNCC5)oc34)cc21] |

TABLE 4-continued

Representative examples of compounds of Formula IV.

| No. | Structure |
|---|---|
| IV-59 | 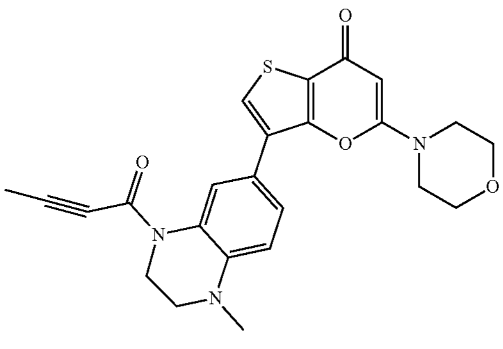 [SMILES: CC#CC(=O)N1CCN(C)c2ccc(-c3csc4c(=O)cc(N5CCOCC5)oc34)cc21] |
| IV-60 | 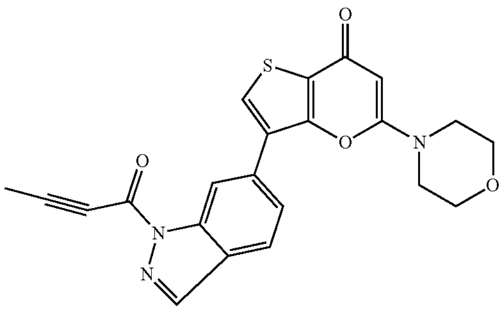 [SMILES: CC#CC(=O)n1ncc2ccc(-c3csc4c(=O)cc(N5CCOCC5)oc34)cc21] |
| IV-61 | 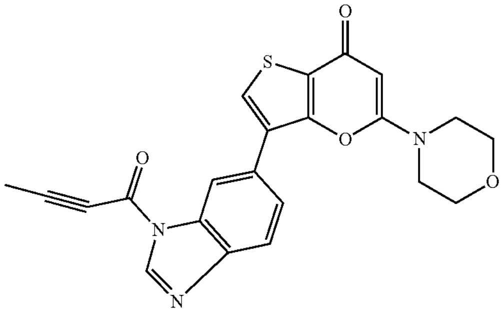 [SMILES: CC#CC(=O)n1cnc2ccc(-c3csc4c(=O)cc(N5CCOCC5)oc34)cc21] |

It should be noted that the connection between the 5-membered ring of the thienopyran or furanopyran ring can be provided by a variety of different linkers in various attachment positions (for example, ortho, meta, para for a six membered ring) represented by the W—X group in Formula IV, some of which are exemplified in the Table 3 above. These permutations are readily synthetically accessible to one skilled in the art.

In another aspect of the invention, a pharmaceutically acceptable salt of a compound of the invention is one which is the acid addition salt of a basic compound of Formula I-IV with an inorganic or organic acid which affords a physiologically acceptable anion, or which is the salt formed by an acidic compound of Formula I-IV with a base which affords a physiologically acceptable cation. Examples of such acids and bases are provided hereinbelow.

Another aspect of the invention relates to methods of using a pharmaceutical formulation comprising a compound of Formulas I-IV in association with a pharmaceutically acceptable carrier, diluent or excipient, a compound of Formula I-IV (or a pharmaceutically acceptable salt thereof), as provided in any of the descriptions herein.

In addition, compounds (or salts thereof) of the present invention are useful as an active ingredient in the manufacture of a medicament for the treatment of diseases including, but not limited to, cancer, and/or for inhibiting BTK and at least one other protein including but not limited to PI3K and a bromodomain protein for the treatment of diseases including but not limited to cancer.

The present invention also provides a method for treating a disease in a human or other mammal including, but not limited to, cancer by administering a therapeutically effective amount of a compound(s) of the invention including compound(s) or composition(s) of Formula I-IV or conjugate or prodrug thereof having any of the definitions herein.

The present invention further provides a method for inhibiting BTK and at least one other protein including but not limited to PI3K and a bromodomain protein in a mammal in need thereof by administering an effective amount of a compound of Formula I-IV, or conjugate or prodrug thereof having any of the definitions herein.

Further, the present invention provides a method of inhibiting tumor growth comprising administering to a mammal in need of treatment, a therapeutically effective amount of a compound of Formula I-IV, or conjugate or prodrug thereof.

Also, there is provided a compound of Formula I-IV (or conjugate, prodrug, or salt thereof) having any of the definitions herein for use as an anticancer agent.

In addition, there is provided use of a compound of Formula I-IV having any of the definitions herein for the manufacture of a medicament for the treatment of a disease described herein including, but not limited to, cancer.

As an additional feature of the invention there is provided a pharmaceutical formulation comprising in association with a pharmaceutically acceptable carrier, diluent or excipient, a conjugate of a compound of Formula I-IV (or of a pharmaceutically acceptable salt thereof) as provided in any of the descriptions herein.

The present invention also includes isotopically-labeled compounds of Formulas I-IV and use of such compounds, as well as pharmaceutically acceptable salts thereof where one or more atoms of the compound are replaced by a corresponding isotope. Examples of isotopes that can be incorporated into compounds of the invention include isotopes of hydrogen, carbon, nitrogen, oxygen, phosphorous, fluorine and chlorine. Compounds of the present disclosure, conjugates thereof, and pharmaceutically acceptable salts of said compounds or of said conjugates which contain the aforementioned isotopes and/or other isotopes of other atoms are included within the scope of this disclosure. Certain isotopically-labeled compounds of the present disclosure, for example those into which radioactive isotopes, such as $^{2}H$, $^{3}H$, $^{14}C$, $^{15}N$, $^{32}P$ and $^{131}I$ are incorporated, are useful in drug and/or substrate tissue distribution assays for example when imaging tumors. Fluorine-18 ($^{18}F$) is particularly preferred for the ease of preparation and detectability it provides. Isotopically labeled compounds of the invention can generally be prepared by carrying out the procedures disclosed in the Schemes and/or in the Examples and Preparations below, by substituting a readily available isotopically labeled reagent for a non-isotopically labeled reagent.

It will be appreciated that certain compounds of Formula I-IV (or salts, procompounds, conjugates, etc.) may exist in, and be isolated in, isomeric forms, including tautomeric forms, cis- or trans-isomers, as well as optically active, racemic, enantiomeric or diastereomeric forms. It is to be understood that the present invention encompasses a compound of Formula I-IV in any of the tautomeric forms or as a mixture thereof; or as a mixture of diastereomers, as well as in the form of an individual diastereomer, and that the present invention encompasses a compound of Formula I-IV as a mixture of enantiomers, as well as in the form of an individual enantiomer, any of which mixtures or form desirably possesses inhibitory properties against kinases including but not limited to PI3 kinase, it being well known in the art how to prepare or isolate particular forms and how to determine inhibitory properties against kinases by standard tests including those described herein below.

In addition, a compound of Formula I-IV (or salt, procompound, conjugate thereof, etc.) may exhibit polymorphism or may form a solvate with water or an organic solvent. The present invention also encompasses any such polymorphic form, any solvate or any mixture thereof.

The methods of the invention include manufacturing and administering a pharmaceutically acceptable salt of a compound of Formula I-IV. A basic compound of the invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxy benzoate, methoxy benzoate, phthalate, sulfonate, xylenesulfonate, phenylacetate, phenylpropionate, phenylbutyrate, citrate, lactate, gamma-hydroxy butyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

C.1. Synthesis of Compounds and Conjugates

Compounds of the invention may be prepared according to the examples provided herein as well as by processes known in the chemical arts and described, for example, in U.S. Pat. No. 8,557,807 and references cited therein, as well as in G. A. Morales et al., J. Med. Chem. 2013, 56, 1922-1939, the entire contents of which are herein incorporated by reference. Starting materials and intermediates used to prepare a compound of the invention are either commercially available or can be readily prepared by one of ordinary skill in the art. Compounds and conjugates described herein and used in the therapeutic methods of the invention can be made, for example, by procedures disclosed in U.S. Pat. No. 6,949,537; 7,662,977; 7,396,828; 8,557,807; and 9,505,780; and in U.S. patent application Ser. Nos. 14/702,816, and 15/297,293, the entire contents of which are herein incorporated by reference. Thio compounds can be made from oxygen analogs as described in the art, for example by using Lawesson's reagent as described in Morales et al., J. Med. Chem. 2013. Furan analogs of the thiophene-pyranone compounds (termed thienopyranones) can be made, for example, by the general schemes outlined below where the key intermediate "g" is prepared and utilized. Intermediate "g" is then further elaborated to the oxygen analog of "compound 6" as described in Morales et al., J. Med. Chem. 2013 (reference incorporated herein) which is designated below as compound "i". Compound "i" can then be reacted via couplings with boronates to make the final substituted furanopyranones of the invention. Alternatively, the bromine atom in compound "i" can be converted to a boron derivative and then coupled with aryl or heteroaryl bromides or iodides to make furanopyranones of the invention.

A reaction scheme is shown below for preparing furanopyranones of the invention via the key furan intermediate "g" and subsequent conversion to compound "i" which is then further reacted to produce compounds of the invention:

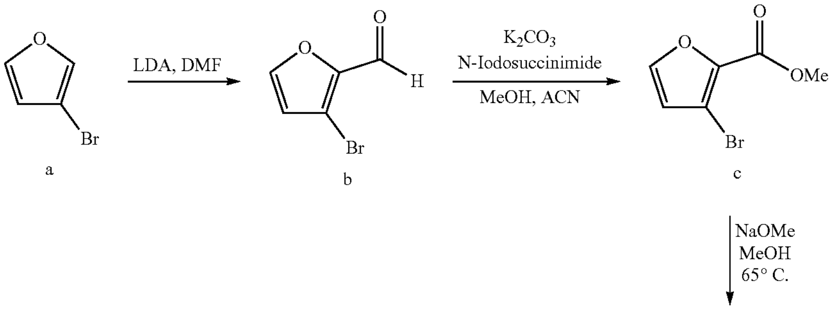

a b c

-continued
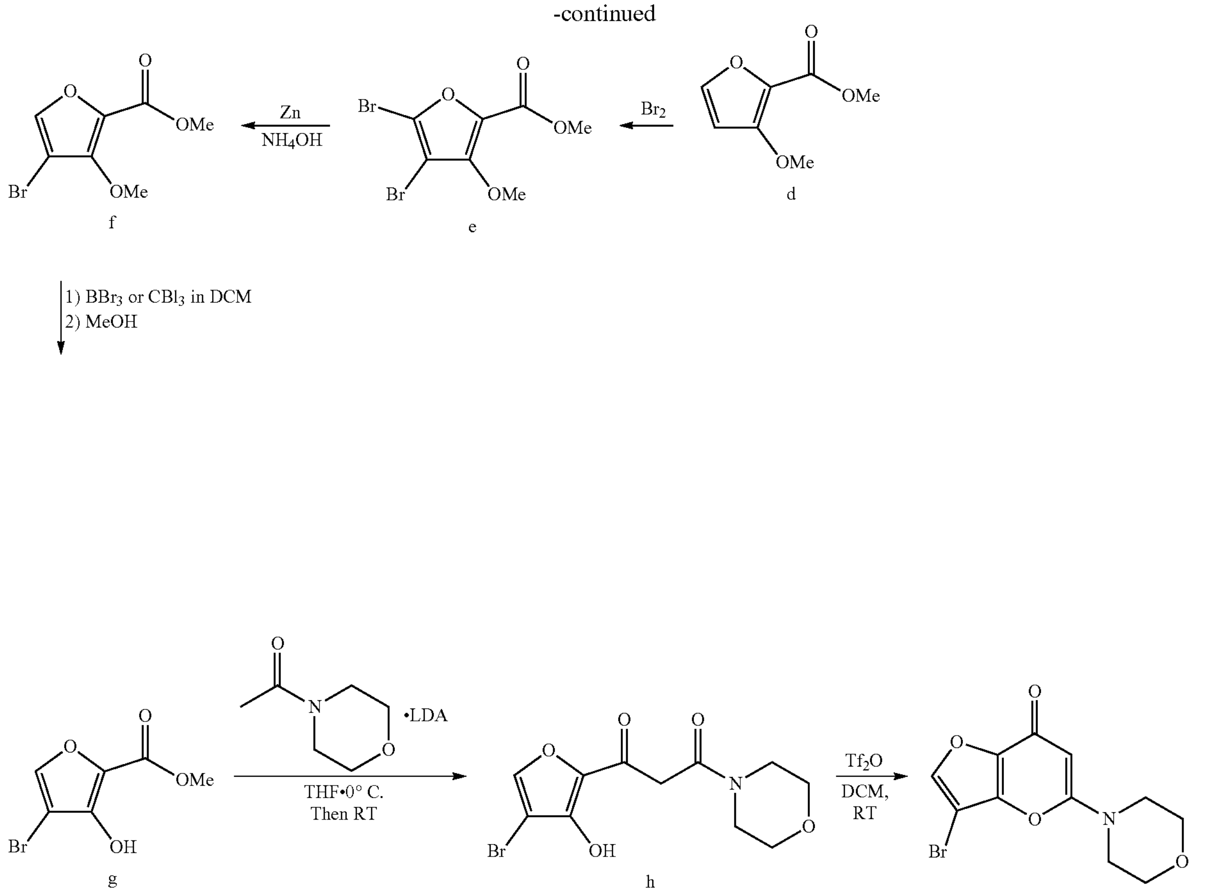
d, e, f, g, h, i
An expanded reaction scheme for introducing substituents at R4 of furan-based compounds of the invention are based on methods described in US20120022059-A1 which are herein incorporated by reference and shown below:
And to add $R_4$ groups
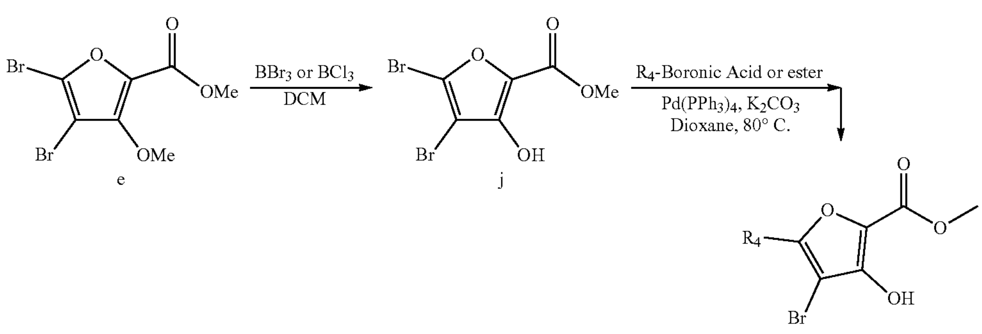
e, j
k
US Patent
US-20120022059-A1

Scheme for introducing substituents at R4 of TP scaffold core.

The selective introduction of substituents at the R4 position of thiophene containing compounds of the invention is based on the synthesis of molecule "m" (R4 is pyrazole) starting from molecule "l" as disclosed in published US Patent Application 2016/0287561, the entire contents of which is herein incorporated by reference.

And to add $R_4$ groups

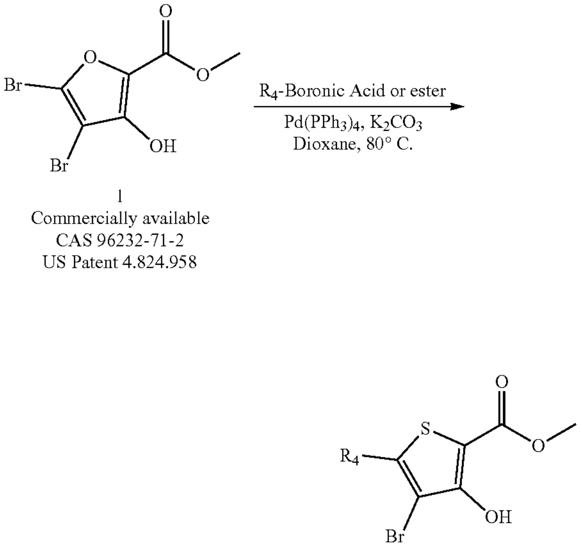

l
Commercially available
CAS 96232-71-2
US Patent 4.824.958 m
US Patent Application
US 2016/0287561

An additional scheme to obtain furanopyranones is shown below using $NaN_3$ to arrive at the key bromo-hydroxy-furan "g" which can then be used to make intermediate "i" and subsequent elaboration to compounds of the invention:

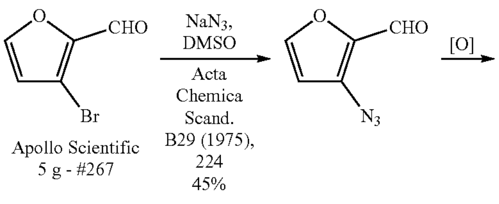

Apollo Scientific
5 g - #267

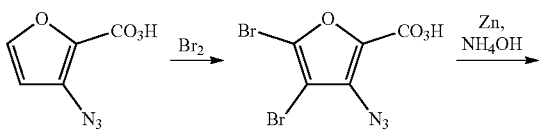

-continued

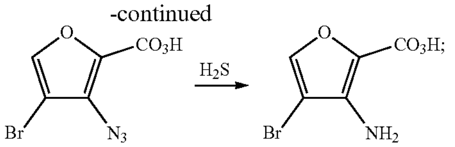

CAS 1206181-37-4
Patent:
WO2010/17748
A2, 2010

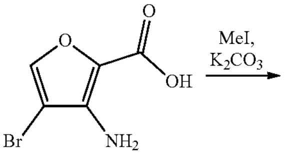

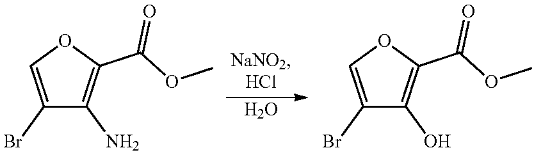

Compounds of the invention having various R2 substituents other than morpholine are made using, for example, acetylated amines, acetylated alcohols, or other methyl ketones in place of the acetyl morpholine. For example, use of acetone in the reaction scheme would give R2=methyl group. Also, compounds of the invention with various R1 substituents are made using substituted ketones or substituted acetyl morpholine, for example, use of propionylmorpholine would yield R1=methyl group.

An exemplary scheme for synthesizing compounds of Formula I is shown below:

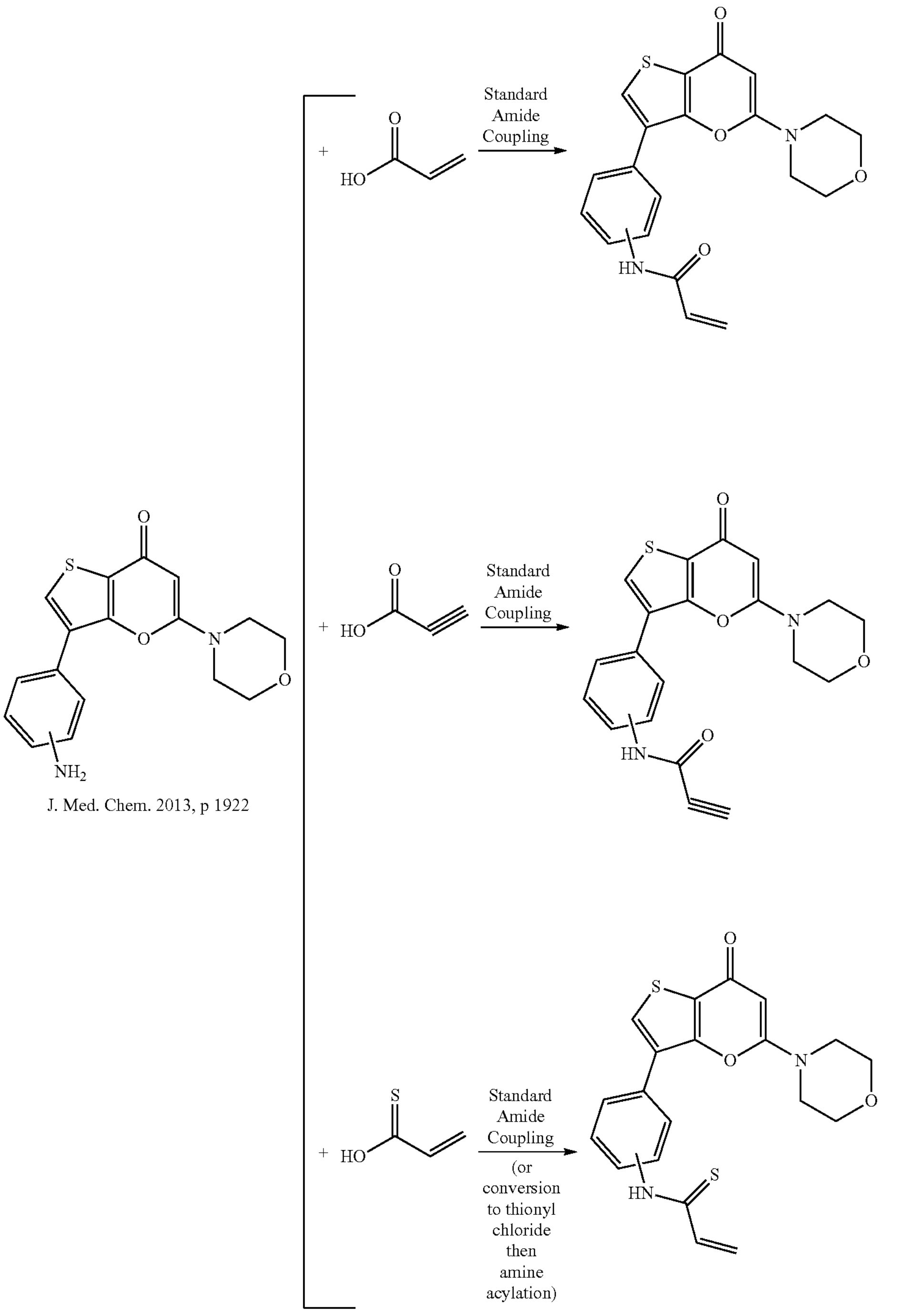

A specific example of a dual BTK/PI3K inhibitor of Formula I, II and III is illustrated by Compound 7 which was synthesized by the method described in Example 1. The use of different alpha-beta unsaturated acids (or acid halides) in this procedure in the last step results in differently substituted analogs of Compound 7. Preparation examples of compounds of the invention of Formula I, II, and III are described in the Examples 1-9, and 19-20.

Compounds of Formula IV can be made by the reaction scheme provided in Example 10 showing the synthesis of Compound 12 as representative of compounds of Formula IV.

Compounds used in methods of the invention, or their pharmaceutically acceptable salts, may have asymmetric carbon atoms or quaternized nitrogen atoms in their structure. It will be appreciated that certain compounds of Formula I-IV (or salts, conjugates, etc.) may exist in, and be isolated in, isomeric forms, including tautomeric forms, cisor trans-isomers, as well as optically active, racemic, enantiomeric, or diastereomeric forms. It is to be understood that the present invention encompasses a compound of Formula I-IV in any of the tautomeric forms or as a mixture thereof; or as a mixture of diastereomers, as well as in the form of an individual diastereomer, and that the present invention encompasses a compound of Formula I-IV as a mixture of enantiomers, as well as in the form of an individual enantiomer, any of which mixtures or form possesses inhibitory properties against kinases, for example PI3 kinases. The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of compounds of the invention. The carbonyl of the chromone is converted to the thione moiety as described above by reaction with Lawesson's reagent, or other ketone to thioketone conversion conditions known to those skilled in the art.

The compounds of the invention or their pharmaceutically acceptable salts, may contain enhanced levels of naturally occurring stable isotopes in their structure. Some elements like phosphorus and fluorine only exist naturally as a single isotope, with a natural abundance of 100%. However, other elements that may appear in compounds of the invention exist naturally in the abundances listed in the Table 4 below:

TABLE 5

| Isotopic abundances. | | |
|---|---|---|
| Isotope | % nat. abundance | atomic mass |
| $^{1}H$ | 99.985 | 1.007825 |
| $^{2}H$ | 0.015 | 2.0140 |
| $^{12}C$ | 98.89 | 12 (definition) |
| $^{13}C$ | 1.11 | 13.00335 |
| $^{14}N$ | 99.64 | 14.00307 |
| $^{15}N$ | 0.36 | 15.00011 |
| $^{16}O$ | 99.76 | 15.99491 |
| $^{17}O$ | 0.04 | 16.99913 |
| $^{18}O$ | 0.2 | 17.99916 |
| $^{32}S$ | 95.0 | 31.97207 |
| $^{33}S$ | 0.76 | 32.97146 |
| $^{34}S$ | 4.22 | 33.96786 |
| $^{37}Cl$ | 24.23 | |
| $^{g35}Cl$ | 75.77 | 34.96885 |
| $^{79}Br$ | 50.69 | 78.9183 |
| $^{81}Br$ | 49.31 | 80.9163 |

(Source: https://en.wikipedia.org/wiki/Natural_abundance)

Compounds of the invention include those intentionally synthesized to contain higher percentages of the minor natural isotope up to 100%. For example, the R2 group of Formula I could be a fully deuterated ($^{2}H$) morpholino group prepared by substituting in commercially available deuterated morpholine (see http://shop.isotope.com/productdetails.aspx?itemno=DLM-3484-PK for 98% 2H morpholine) for morpholine in the overall synthesis. Other isotopically enriched starting materials and intermediates can also be incorporated by one skilled in the art into the other R groups of Formula 1. Such deuterated pharmaceutical compounds are known to those skilled in the art (e.g. see U.S. Pat. No. 9,676,790 B2 and references therein) and are incorporated by reference herein. Enriched stable isotopic starting materials for preparing isotopically enriched compounds of the invention are available from several vendors including Cambridge Isotope Laboratories Inc. (http://www.isotope.com/index.cfm), Isoflex (https://www.isoflex.com/), and CDN Isotopes (https://cdnisotopes.com/).

D. Formulations

As an additional aspect of the invention there is provided a pharmaceutical formulation or composition comprising in association with a pharmaceutically acceptable carrier, diluent or excipient, a compound of the invention, e.g., a compound of Formula I-IV (or a pharmaceutically acceptable salt or procompound or conjugate thereof) as provided in any of the descriptions herein for use in a method of the invention. Compositions of the present invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions used in the methods of the present invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxy benzoate and sorbic acid.

Compositions used in the methods of the present invention may also be formulated as suppositories, which may contain suppository bases including, but not limited to, cocoa butter or glycerides. Compositions of the present invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of the present invention may also be formulated transdermal formulations comprising aqueous or non-aqueous vehicles including, but not limited to, creams, ointments, lotions, pastes, medicated plaster, patch, or membrane.

Compositions used in the methods of the present invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions used in the methods of the present invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions used in the methods of the present invention may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh et al., U.S. Pat. No. 4,621,023 of Redziniak et al., or U.S. Pat. No. 4,508,703 of Redziniak et al., can be used. Other suitable formulations can employ niosomes. Niosomes are lipid vesicles similar to liposomes, with membranes consisting largely of non-ionic lipids, some forms of which are effective for transporting compounds across the stratum corneum.

The following formulation examples are illustrative only and are not intended to limit the scope of the compounds used in the methods of the invention in any way. The phrase "active ingredient" refers herein to a compound according to Formula I-IV or a pharmaceutically acceptable salt, procompound, conjugate, or solvate thereof.

Formulation 1: Tablet containing the following components:

| Ingredient | Amount (mg/tablet) |
|---|---|
| Active ingredient | 250 |
| Dried starch | 200 |
| Magnesium stearate | 10 |
| Total | 460 mg |

Formulation 2: Capsule containing the following components:

| Ingredient | Amount (mg/tablet) |
|---|---|
| Active ingredient | 60 |
| Dried starch | 44 |
| Magnesium stearate | 1.5 |
| Microcrystalline cellulose | 44 |
| Total | 150 mg |

Parenteral dosage forms for administration to patients by various routes including, but not limited to, subcutaneous, intravenous (including bolus injection), intramuscular, and intra-arterial are also contemplated by the present invention. Parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the invention are well known to those skilled in the art. Examples include, but are not limited to: Water for Injection USP: aqueous vehicles such as, but not limited to, Sodium Chloride Injection, Ringer's Injection, Dextrose Injection, Dextrose and Sodium Chloride Injection, and Lactated Ringer's Injection: water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

An example parenteral composition for use in a method of the invention may be intended for dilution with aqueous solution(s) comprising for example 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8.

E. Therapeutic Use

In another embodiment of the present invention, a compound or composition of the invention is administered to a mammal in need thereof including a human to treat or prevent a disease including, but not limited to, cancer by administering a therapeutically effective dose of a compound of Formula I-IV. Without intending to be bound by theory, it is believed that the therapeutic effectiveness of a compound of the invention involves simultaneous inhibition, for example, of BTK and PI3K, or BTK and a bromodomain protein such as BRD4 with a single molecule. Inhibiting BTK and PI3K or a bromodomain protein with a single drug provides a sophisticated combination therapy for patients resulting in more effective and durable clinical benefits.

In one aspect, a compound of the invention provides therapeutic benefit by inhibiting BTK and at least one other protein including but not limited to PI3K and bromodomain protein.

In another aspect, the invention relates to a method for inhibiting BTK in a mammal by administering a compound of the invention.

In another aspect, the invention relates to a method for inhibiting PI3K in a mammal by administering a compound of the invention.

In another aspect, the invention relates to a method for inhibiting a bromodomain protein in a mammal by administering a compound of the invention.

In another aspect, the invention relates to a method for inhibiting BTK and PI3K, or BTK and a bromodomain protein in at least one cell at the same time in a mammal by administering a compound of the invention.

In another aspect, the invention relates to a method for inhibiting BTK and at least one of PI3K and a bromodomain protein with a single compound of the invention in each cell at the same time wherein the inhibition achieved is superior in a greater percentage of cells than that achieved by a combination of inhibitors of those same targets.

In another aspect, the present invention provides a method for enhancing the chemosensitivity of tumor cells comprising administering to a patient in need thereof a therapeutically effective amount of a compound of Formula I-IV.

In another aspect, the present invention provides a method for enhancing the radiosensitivity of tumor cells comprising administering to a patient in need thereof a therapeutically effective amount of a compound of Formula I-IV.

In another aspect, the present invention provides a method for inhibiting or reducing tumor growth comprising administering to a patient in need thereof a therapeutically effective amount of a compound of a compound of Formula I-IV.

In another aspect, the present invention provides a method for inducing oxidative stress in tumor cells comprising administering to a patient in need thereof a therapeutically effective amount of a compound of Formula I-IV.

In another aspect, the present invention provides a method for inhibiting or reducing tumor growth by inhibiting cancer stem cell growth and/or proliferation comprising administering to a patient in need thereof a therapeutically effective amount of a compound of Formula I-IV.

In another aspect, the present invention provides a method for inhibiting tumor induced angiogenesis comprising administering to a patient in need thereof a therapeutically effective amount of a compound of Formula I-IV.

Further, the present invention provides a method for inhibiting angiogenesis associated with cancer comprising administering to a patient in need thereof a therapeutically effective amount of a compound of Formula I-IV.

In yet another aspect, the present invention provides a therapeutic method for increasing apoptosis in cancer cells and cancerous tumors comprising administering to a patient in need thereof a therapeutically effective amount of a compound of Formula I-IV.

The present invention also provides a method of treating cancer comprising administering to a patient in need thereof a therapeutically effective amount of a compound of Formula I-IV.

In another aspect, a compound of the invention provides dual inhibitory activity against BTK and PI3K, or BTK and a bromodomain protein such as BRD4 to treat lymphoid malignancy in particular B cell driven lymphoma and leukemias.

The BTK, PI3K, and/or bromodomain inhibitory activity of a compound of the invention can be determined by methods known to the skilled artisan, or by procuring relevant analysis by a commercial vendor offering such services. For example, in vitro kinase inhibition (e.g., PI3K inhibition) can be determined by a standard kinase inhibition assay using labeled ATP to determine if a test compound inhibits the transfer of phosphate from ATP to the kinase substrate. In vivo, PI3K inhibition can be determined from target tissue biopsies by standard tissue processing in which cells are disrupted and Western Blot analysis is performed to determine the presence or absence of pAKT (substrate of PI3K) relative to a control sample. PI3K inhibition assays and BTK inhibition assays are known in the art and can be procured commercially through vendors such as Reaction Biology (Malvern, PA). The activity of a compound of the invention as an inhibitor of a bromodomain-containing protein, such as a BET protein, including BRD2, BRD3, BRD4, and/or BRDT, or an isoform or mutant thereof, may be determined in vitro, in vivo, or in a cell line. In vitro assays include assays that determine inhibition of bromodomain-containing proteins. Alternatively, inhibitor binding may be determined by running a competition experiment where a provided compound is incubated with a bromodomain-containing protein, such as a BET protein bound to known ligands, labeled or unlabeled. In vitro bromodomain inhibition assays can be performed using Alpha Screen Technology (Perkin Elmer Life and Analytical Sciences, Shelton, CT). In vivo bromodomain inhibition can be determined indirectly by evaluating the amount of a protein whose gene transcription is influenced or controlled by the bromodomain protein, for example, MYCN protein transcription is controlled by BRD4 (J. E. Delmore et al., Cell 2011, 146, 904-917: A. Puissant, Cancer Discov. 2013, 3, 308-323).

In certain embodiments, the invention provides a method for treating a disorder (as described above) in a mammal, comprising administering to a subject in need thereof, a therapeutically effective amount of a compound of the invention. The identification of those patients who are in need of treatment for the disorders described herein is within the ability and knowledge of one skilled in the art. Certain of the methods for identification of patients who are at risk of developing the above disorders which can be treated by a method of the invention are appreciated in the medical arts including, for example, family history and the presence of risk factors associated with development of the disease state.

Assessing the efficacy of a treatment in a patient may include determining the pre-treatment extent of a disorder by methods known in the art (i.e., determining tumor size or screening for tumor markers where the cell proliferative disorder is cancer), then administering a therapeutically effective amount of a compound of the invention, to the patient. Following an appropriate period of time after administration (e.g., 1 day, 1 week, 2 weeks, one month, six months), the extent of the disorder is again determined. Modulation (e.g., decrease) in the extent or invasiveness of the disorder (e.g., reduced tumor size) would indicate efficacy of the treatment. The extent or invasiveness of the disorder may be determined periodically throughout treatment. For example, the extent or invasiveness of the disorder may be assessed every few hours, days or weeks to assess the further efficacy of the treatment. A decrease in extent or invasiveness of the disorder would indicate that the treatment is efficacious. The methods described may be used to screen or select patients that may benefit from treatment with a compound of the invention.

A variety of cancers may be treated according to a method of the present invention. Exemplary cancers treatable according to the present invention include, but are not limited to: carcinoma of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma): hematopoietic tumors of lymphoid lineage including leukemia, acute lymphocytic leukemia, acute lymphoblastic leukemia, B-cell lymphoma. T-cell lymphoma. Hodgkin's lymphoma, non-Hodgkin's lymphoma, hairy cell lymphoma, histiocytic lymphoma, and Burkett's lymphoma: hematopoietic tumors of myeloid lineage including acute and chronic myelogenous leukemias, myelodysplastic syndrome, myeloid leukemia, and promyelocytic leukemia: tumors of the central and peripheral nervous system including astrocytoma, medulloblastoma, neuroblastoma, glioma, and schwannomas: tumors of mesenchymal origin including fibrosarcoma, rhabdomyosarcoma, and osteosarcoma; and other tumors including melanoma, xeroderma pigmentosum, keratoacanthoma, seminoma, thyroid follicular cancer, and teratocarcinoma. The methods of the invention may also be used to treat accelerated or metastatic cancers of the bladder, pancreatic cancer, prostate cancer, non-small cell lung cancer, colorectal cancer, and breast cancer.

Additional cancers treatable using an effective amount of a compound of Formula I-IV include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia. AIDS-related lymphoma, alveolar rhabdomyosarcoma, alveolar soft part sarcoma, ameloblastic fibroma. anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia. B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer. Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma. follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma. gallbladder cancer, gastric cancer, hairy cell leukemia, hemangioblastoma, head and neck cancer, hemangiopericytoma, hematological malignancy, hepatoblastoma, hepatosplenic T-cell lymphoma. Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma. lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, Merkle cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma. rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom macroglobulinemia, Warthin's tumor, and Wilms' tumor.

A therapeutic method according to the invention may be performed simultaneously or metronomically with other anti-cancer treatments such as chemotherapy and/or radiation therapy. The term "simultaneous" or "simultaneously" as used herein, means that the other anti-cancer treatment and a compound(s) of the present invention are administered within 48 hours, preferably 24 hours, more preferably 12 hours, yet more preferably 6 hours, and most preferably 3 hours or less, of each other. The term "metronomically" as used herein refers to administration of a compound(s) of the invention at times different from chemotherapy and/or radiation therapy, and at a certain frequency relative to repeat administration and/or the chemotherapy regimen.

Chemotherapy treatment may comprise administration of a cytotoxic agent or cytostatic agent, or combination thereof. Cytotoxic agents prevent cancer cells from multiplying by: (1) interfering with the cell's ability to replicate DNA, and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include but are not limited to the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide: antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine: natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®:), mithramycin, deoxyco-formycin, mitomycin-c, 1-asparaginase, interferons (preferably IFN—. alpha.), etoposide, and teniposide. Other proliferative cytotoxic agents are navelbene, CPT-11, anastrozole, letrozole, capecitabine, raloxifene, cyclophosphamide, ifosamide, and droloxifene.

Microtubule affecting agents interfere with cellular mitosis and are well known in the art for their cytotoxic activity. Microtubule affecting agents that are useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see R. F. Service, Science 1996, 274, 2009) estramustine, nocodazole, MAP4, and the like. Examples of such agents are also described in J. C. Bulinski et al., J. Cell Sci. 1997, 110, 3055-3064: D. Panda et al., Proc. Natl. Acad. Sci. USA 1997, 94, 10560-10564; P. F. Mühlradt et al., Cancer Res. 1997, 57, 3344-3346; K. C. Nicolaou et al., Nature 1997, 387, 268-272; R. J. Vasquez et al., Mol. Biol. Cell. 1997, 8, 973-985; and D. Panda et al., J. Biol. Chem. 1996, 271, 29807-29812.

Other suitable cytotoxic agents include but are not limited to epipodophyllotoxin: an antineoplastic enzyme: a topoisomerase inhibitor: procarbazine: mitoxantrone: platinum coordination complexes such as cis-platin and carboplatin: biological response modifiers: growth inhibitors: antihormonal therapeutic agents: leucovorin: tegafur; and haematopoietic growth factors.

Cytostatic agents that may be used according to methods of the invention include, but are not limited to, hormones and steroids (including synthetic analogs): 17 alpha-ethinylestradiol, diethylstilbestrol, testosterone, prednisone, fluoxymesterone, dromostanolone propionate, testolactone, megestrol acetate, methylprednisolone, methyl-testosterone, prednisolone, triamcinolone, chlorotrianisene, hydroxyprogesterone, aminoglutethimide, estramustine, medroxyprogesterone acetate, leuprolide, flutamide, toremifene, zoladex. Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are ImClone antibody C225 immunospecific for the EGFR, and Src inhibitors. Also suitable for use as a cytostatic agent is Casodex R: (bicalutamide, AstraZeneca) which renders androgen-dependent carcinomas non-proliferative. Yet another example of a cytostatic agent is the antiestrogen Tamoxifen R which inhibits the proliferation or growth of estrogen dependent breast cancer. Inhibitors of the transduction of cellular proliferative signals are cytostatic agents. Representative examples include but are not limited to epidermal growth factor inhibitors, Her-2 inhibitors, MEK-1 kinase inhibitors, MAPK kinase inhibitors, PI3K inhibitors, Src kinase inhibitors, and PDGF inhibitors.

Methods of the invention include treating a subject with a MYC-dependent cancer, comprising administration of a compound of Formula I-IV. Subjects with MYC-dependent cancer can be determined by several methods including but not limited to determining MYC mRNA expression levels in the tumor and/or MYC protein expression in the tumor. Preferred subjects for treatment by methods of the invention can be identified by historical experience or known prevalence of MYC activation in certain cancers such as multiple myeloma (J. E. Delmore, Cell 2011, 146, 904-917), CLL (J. R. Brown et al., Clin. Cancer Res. 2012, 18, 3791-3802), leukemia (M. A. Dawson et al., Nature 2013, 478, 529-533), neuroblastoma (A. Puissant et al., Cancer Discov. 2013, 3, 308-323), or medulloblastoma (Y. J. Cho et al., J. Clin. Oncol. 2010, 29, 1424-1430).

Other diseases and conditions treatable according to methods of this invention include, but are not limited to, other proliferative disorders, sepsis, autoimmune disease, and infections including but not limited to viral infections. Diseases such as atherosclerosis and type 2 diabetes (V. A. DeWaskin et al., Nature Rev. Drug Disc. 2013, 12, 661-662), obesity and inflammation (A. C. Belkina et al., Nature Rev. Cancer 2012, 12, 465-474) are also treatable according to the methods of the invention.

Methods of the invention further include administering one or more compounds of Formula I-IV for treating non-cancer proliferative diseases or benign proliferative disorders including, but not limited to, meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

F. Administration and Dosage

Compounds or compositions of Formula I-IV for use in a therapeutic method of the present invention can be administered in any manner including but not limited to orally, parenterally, sublingually, transdermally, rectally, transmucosally, topically, pulmonarily, nasally, or bucally. Parenteral administration includes but is not limited to intravenous, intraarterial, intraperitoneal, subcutaneous, intramuscular, intrathecal, and intraarticular. Compounds or compositions of the invention may also be administered via slow controlled i.v. infusion or by release from an implant device.

A therapeutically effective amount of a compound of Formula I-IV for use in a method of the invention varies with the nature of the condition being treated, the length of treatment time desired, the age and the condition of the patient, and is ultimately determined by the attending physician. In general, however, doses employed for adult human treatment typically are in arrange of about 0.001 mg/kg to about 200 mg/kg per day, or about 1 μg/kg to about 100 μg/kg per day. The desired dose may be conveniently administered in a single dose, or as multiple doses administered at appropriate intervals, for example, as two, three, four or more sub-doses per day. Multiple doses over a 24-hour period may be desired or required.

A number of factors may lead to the compounds of Formula I-IV being administered according to the methods of the invention over a wide range of dosages. When given in combination with other therapeutic agents, compounds of the present invention may be provided at relatively lower dosages. In addition, the use of targeting agents on a conjugate is expected to lower the effective dosage required for treatment. As a result, the daily dosage of a targeted compound administered according to the methods of the present invention may be from about 1 ng/kg to about 100 mg/kg. The dosage of a compound of Formula I-IV according to the methods of the present invention may be at any dosage including, but not limited to, about 1 μg/kg, 25 μg/kg, 50 μg/kg. 75 μg/kg, 100 μg/kg, 125 μg/kg, 150 μg/kg, 175 μg/kg, 200 μg/kg. 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg kg, 30 mg/kg, 35 mg kg, 40 mg kg, 45 mg/kg, 50 mg/kg, 60 mg kg, 70 mg/kg, 80 mg/kg, 90 mg/kg, or 100 mg/kg.

The present invention has multiple aspects. illustrated by the following non-limiting examples. The examples are merely illustrative and do not limit the scope of the invention in any way.

EXAMPLES

HPLC traces for compounds synthesized were recorded using a HPLC consisting of Shimadzu or Agilent HPLC pumps, degasser and UV detector, equipped with an Agilent 1100 series auto-sampler. The UV detection provided a measure of purity by percent peak area. A MS detector (APCI) PE Sciex API 150 EX was incorporated for purposes of recording mass spectral data providing compound identification. HPLC/mass traces were obtained using one of three chromatographic methods listed below. If a method is not specifically identified in the example, then method A was utilized.

Method A: Column SunFire™ (Waters) C18, size 2.1 mm×50 mm;

Solvent A: 0.05% TFA in water, Solvent B: 0.05% TFA in acetonitrile;

Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.

Method B: Column Aquasil™ (Thermo) C18, size 2.1 mm×150 mm; particle size 5μ. Solvent A: 0.05% TFA in water, Solvent B: 0.05% TFA in acetonitrile;

Flow rate—0.3 mL/min; Gradient: 10% B to 95% B in 2.4 min, hold at 95% B for 6.25 min and 95% B to 10% B in 0.2 min, hold at 10% B for 1.5 min.; UV detector—channel 1=220 nm, channel 2=254 nm.

Method C: Column Phenomenex C18, size 2 mm×50 mm; particle size 5μ. Solvent A: 0.05% TFA in water, Solvent B: 0.05% TFA in acetonitrile; Flow rate-0.8 mL/min; Gradient: 10% B to 90% B in 2.4 min, hold at 90% B for 1.25 min and 90% B to 10% B in 0.25 min, hold at 10% B for 1.5 min.; UV detector-channel 1=220 nm, channel 2=254 nm.

Example 1. Preparation of Triple BTK/BRD4/PI3K Inhibitor Compound 7

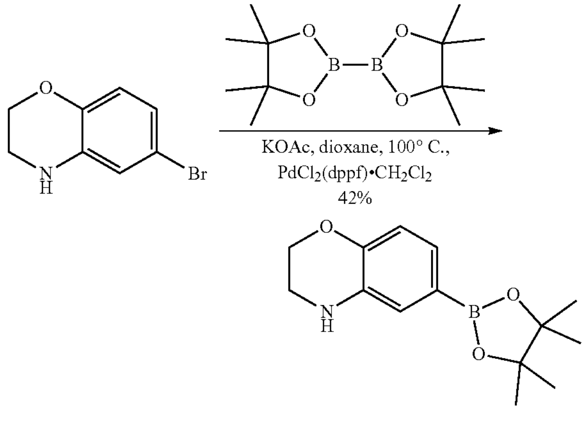

Step 1:4,4,5,5-Tetramethyl-2-(1-oxa-4-aza-3,4-dihydro-2H-naphth-6-yl)-1,3,2-dioxaborolane A mixture containing 6-bromo-1-oxa-4-aza-3,4-dihydro-2H-naphthalene (3.51 g, 16.4 mmol), anhydrous KOAc (3.62 g, 36.9 mmol), pinacol diborane (10.4 g, 41.0 mmol) in 1,4-dioxane was degassed under bubbling $N_2$ for 15 minutes. $PdCl_2$(dppf) dichloromethane adduct (670 mg, 0.82 mmol) was added and the resulting mixture was stirred and heated to 100° C. for 18 hours, after which time the reaction was deemed complete by LCMS. The reaction was cooled, filtered through a short pad of CELITE and concentrated in vacuo. The crude residue was purified by silica gel chromatography, eluting with 0-15% hexanes/EtOAc gradient. The product was obtained as a colorless oil. Yield=1.81 g (6.9 mmol, 42%).

LC/MS-HPLC (254 nm)—Rt 2.65 min. MS (ESI) m/z 262.4 $[M^++H^+]$. Purity=95% by UV (254 nm).

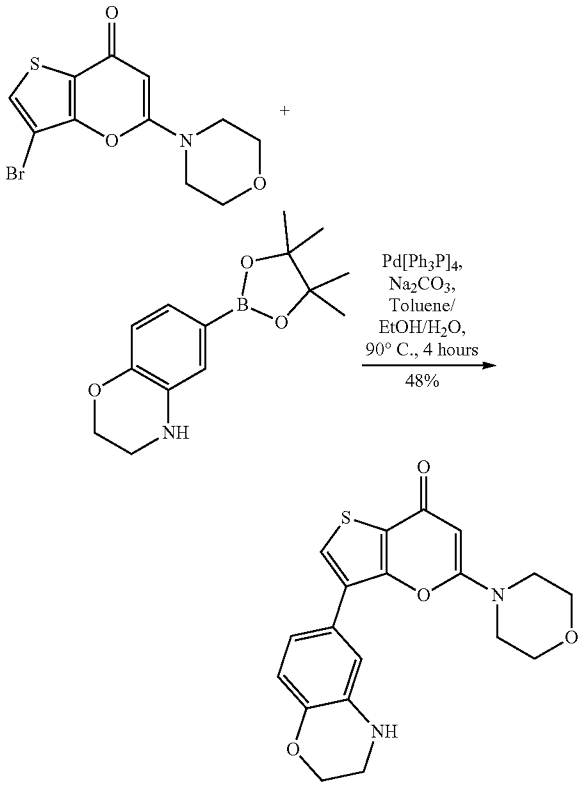

Step 2:5-Morpholino-3-(1-oxa-4-aza-3,4-dihydro-2H-naphth-6-yl)-4-oxa-1-thia-7-indenone A mixture of 3-bromo-5-morpholino-4-oxa-1-thia-7-indenone (1.68 g., 5.30 mmol) and 4,4,5,5-tetramethyl-2-(1-oxa-4-aza-3,4-dihydro-2H-naphth-6-yl)-1,3,2-dioxaborolane (1.80 g, 6.89 mmol) $Na_2CO_3$ 2M aqueous solution (18 mL), toluene:ethanol 2:1 v/v (55 mL) and $Pd[Ph_3P]_4$ (360 mg, 0.31 mmol) were stirred together at 90° C. for 4 h. Then the reaction mixture was cooled and diluted with ethyl acetate (200 mL) and filtered. The filtrate was washed with water and dried ($Na_2SO_4$), filtered and concentrated to yield crude which was purified on silica column using 0-5% MeOH/EtOAc gradient system. Useful fractions were pulled together and concentrated to yield pure final product (950 mg, 48% yield).

LC/MS-HPLC (254 nm)—Rt 2.34 min. MS (ESI) m/z 371.3 [$M^{+}$+$H^{+}$]. Purity=98% by UV (254 nm).

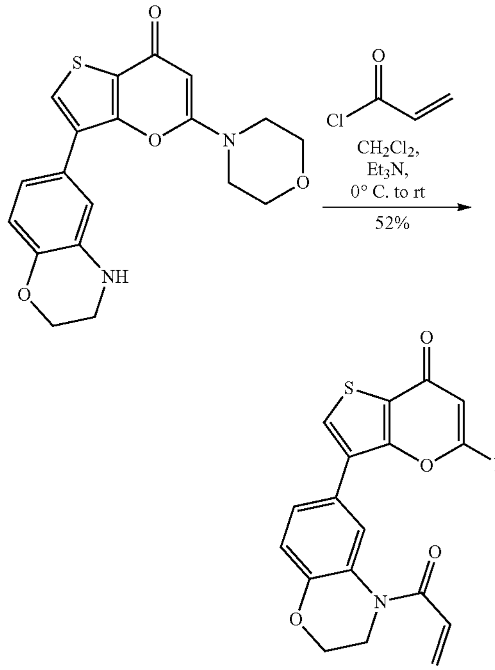

Step 3:1-[7-(5-Morpholino-7-oxo-4-oxa-1-thia-3-indenyl)-4-oxa-1-aza-2,3-dihydro-1H-naphth-1-yl]-2-propen-1-one A mixture 5-morpholino-3-(1-oxa-4-aza-3,4-dihydro-2H-naphth-6-yl)-4-oxa-1-thia-7-indenone (950 mg, 2.57 mmol), triethylamine (1080 μL, 7.70 mmol) in DCM (25 mL) was cooled to 0° C. and added acryloyl chloride (245 μL, 3.08 mmol). Stirred at RT for 3 hours and then diluted with DCM, washed with water and concentrated to yield crude product which was purified on silica column using 0-5% MeOH/EtOAc (gradient) to give the final product Compound 7 as a off white solid (569 mg, 1.34 mmol, 52%).

LC/MS-HPLC (254 nm)—Rt 2.25 min. MS (ESI) m/z 425.5 [$M^{+}$+$H^{+}$]. Purity=99.5% by UV (254 nm).

Example 2. Preparation of Triple BTK/BRD4/PI3K Inhibitor Compound 1 (and Compound 13)

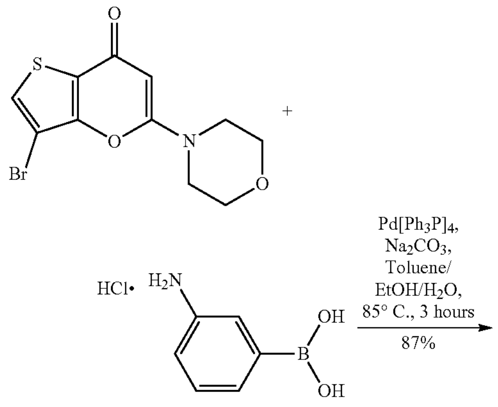

-continued

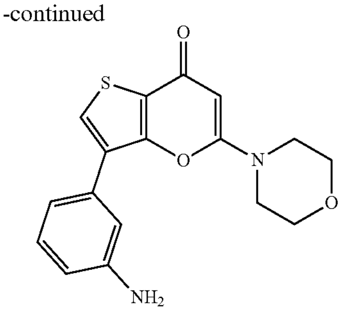

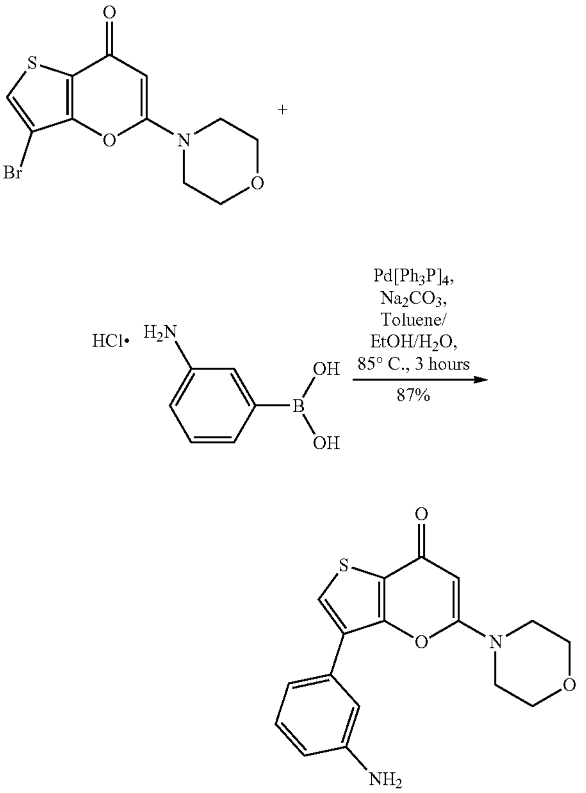

49FT121
MW = 328.39

Step 1:3-(m-Aminophenyl)-5-morpholino-4-oxa-1-thia-7-indenone

3-Bromo-5-morpholino-4-oxa-1-thia-7-indenone (632 mg, 2.0 mmol) and 3-amino-phenylboronic acid hydrochloride (520 mg, 3.0 mmol, 1.5 eq.) were dissolved in a 2:1 v/v mixture of toluene and ethanol (20 mL). The mixture was treated with $Na_2CO_3$ 2M aqueous solution (6.7 mL) and deoxygenated by bubbling $N_2$ for 10 minutes. Pd[$PPh_3$]$_4$ (116 mg, 0.1 mmol) was added and the mixture was heated to 85° C. for 3 hours. LCMS indicates complete conversion to product. The cooled reaction mixture was diluted with EtOAc (200 mL) washed with water and brine. The combined organics were dried over anhydrous $MgSO_4$, filtered and concentrated in vacuo. The crude residue was purified by silica gel chromatography, eluting with a EtOAc/MeOH gradient to yield the pure product. Yield=570 mg (1.74 mmol, 87%). LC/MS-HPLC (254 nm)—Rt 1.78 min. MS (ESI) m/z 329.5 [$M^{+}$+$H^{+}$]. Purity=97.0% by UV (254 nm).

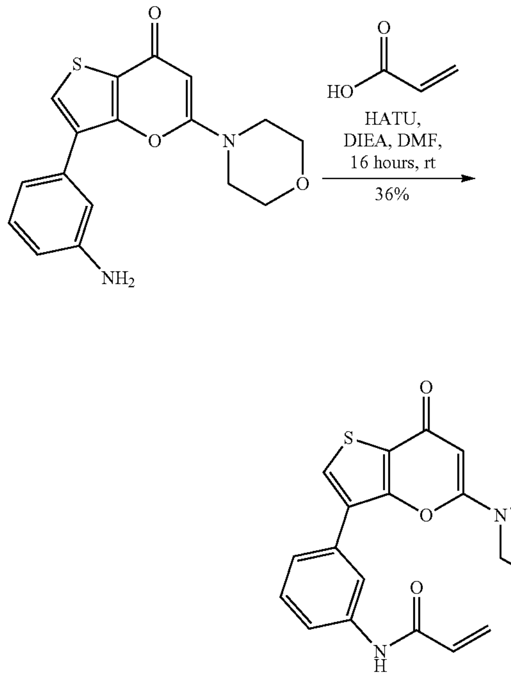

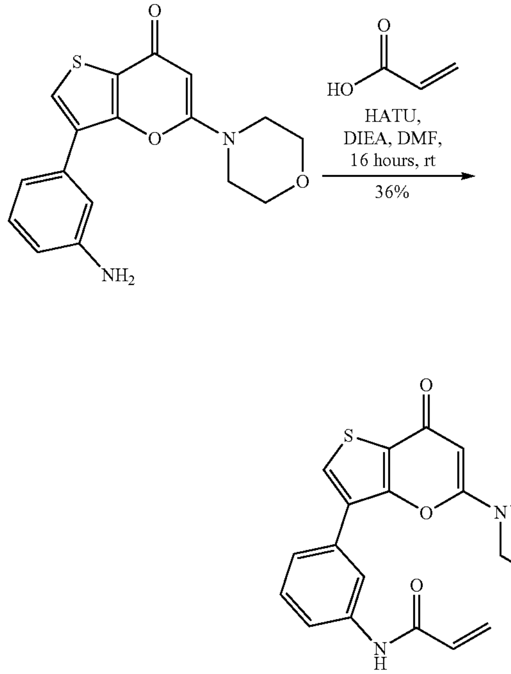

49FT80
MW = 382.4

Step 2:1-[m-(5-Morpholino-7-oxo-4-oxa-1-thia-3-indenyl)phenylamino]-2-propen-1-one 3-(m-Aminophenyl)-5-morpholino-4-oxa-1-thia-7-indenone (164 mg, 0.5 mmol) was dissolved in anhydrous DMF (2.5 mL) and treated with N,N-diisopropylethylamine (358 μL, 2.0 mmol) and acrylic acid (51 μL, 0.55 mmol). To this stirring solution, HATU (247 mg, 0.65 mmol) was added and the resulting mixture was stirred at room temperature for 16 hours. LCMS indicated complete conversion to the product. The reaction was quenched by addition of $H_2O$ and the product was extracted with 10% iPrOH in $CH_2Cl_2$. The organic layer was washed with 0.1N HCl aqueous, dried over $MgSO_4$, filtered and concentrated in vacuo. The crude residue was purified by preparative thin layer chromatography, eluting with 9:1 v/v $CH_2Cl_2$/MeOH. The product was obtained as a beige solid. Yield=69 mg (0.181 mmol, 36%).

LC/MS-HPLC (254 nm)—Rt 2.36 min. MS (ESI) m/z 383.4 [$M^+$+$H^+$]. Purity=93.4% by UV (254 nm).

Likewise, Compound 13 was made using this procedure except substituting 4-amino-phenylboronic acid hydrochloride for the 3-amino-phenylboronic acid hydrochloride in step 1 to then give Compound 13 product after acylation in step 2: MS (ESI) m/z 383.4 [$M^+$+$H^+$].

Example 3. Preparation of Dual BRD4/PI3K Inhibitor Compound 2

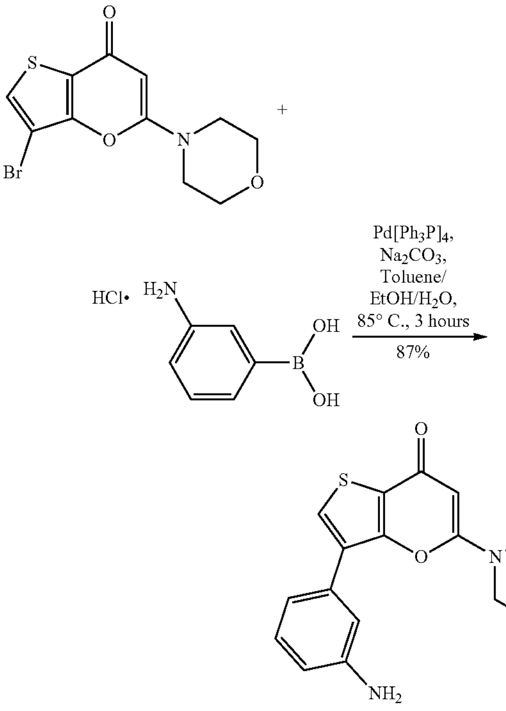

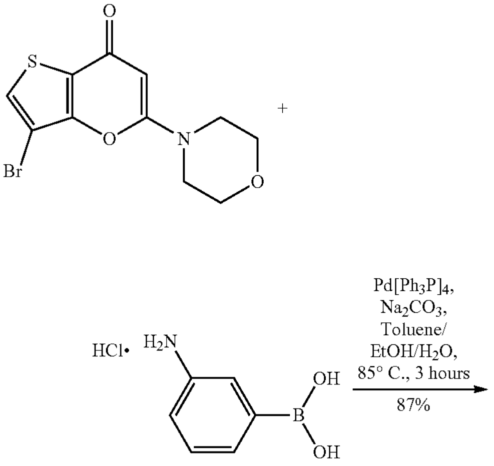

-continued

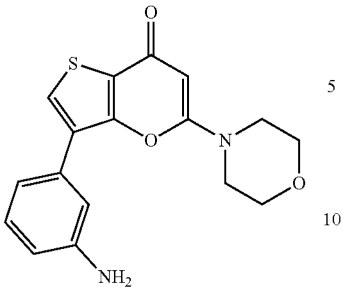

49FT121
MW = 328.39

Step 1:3-(m-Aminophenyl)-5-morpholino-4-oxa-1-thia-7-indenone

3-Bromo-5-morpholino-4-oxa-1-thia-7-indenone (632 mg, 2.0 mmol) and 3-amino-phenylboronic acid hydrochloride (520 mg, 3.0 mmol, 1.5 eq.) were dissolved in a 2:1 v/v mixture of toluene and ethanol (20 mL). The mixture was treated with $Na_2CO_3$ 2M aqueous solution (6.7 mL) and deoxygenated by bubbling $N_2$ for 10 minutes. $Pd[PPh_3]_4$ (116 mg, 0.1 mmol) was added and the mixture was heated to 85° C. for 3 hours. LCMS indicates complete conversion to product. The cooled reaction mixture was diluted with EtOAc (200 mL) washed with water and brine. The combined organics were dried over anhydrous $MgSO_4$, filtered and concentrated in vacuo. The crude residue was purified by silica gel chromatography, eluting with a EtOAc/MeOH gradient to yield the pure product. Yield=570 mg (1.74 mmol, 87%).

LC/MS-HPLC (254 nm)—Rt 1.78 min. MS (ESI) m/z 329.5 [$M^+$+$H^+$]. Purity=97.0% by UV (254 nm).

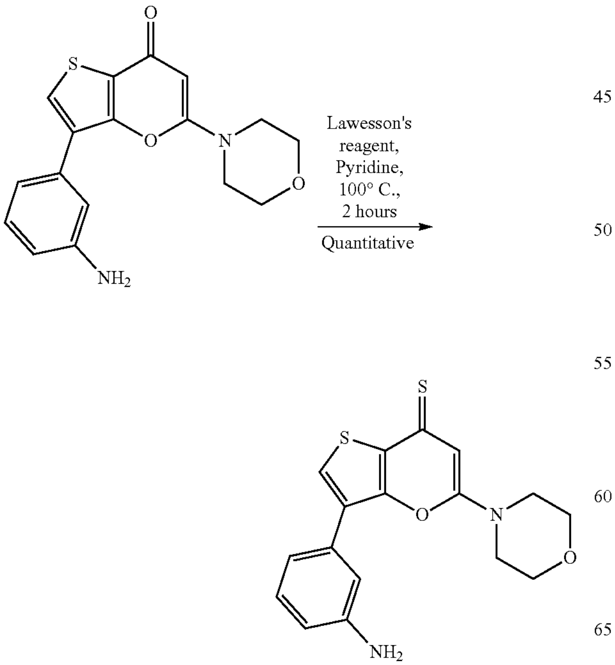

-continued

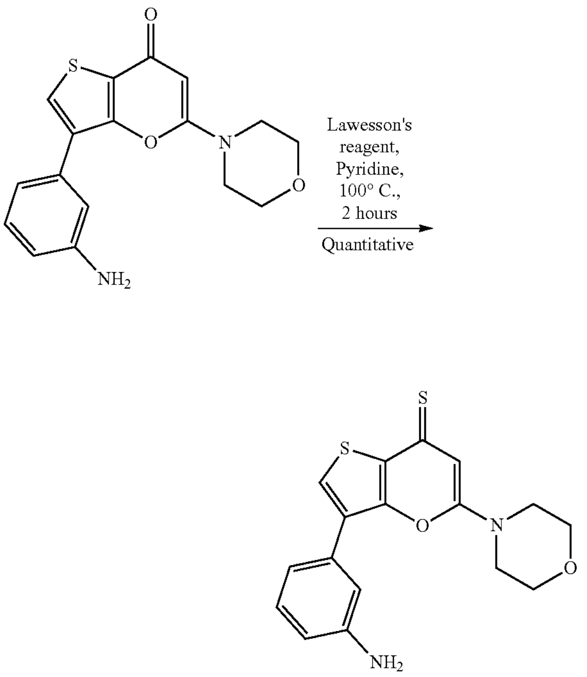

49FT150

Step 2:3-(m-Aminophenyl)-5-morpholino-4-oxa-1-thia-7-indenethione

In a 20 mL scintillation vial, 3-(m-aminophenyl)-5-morpholino-4-oxa-1-thia-7-indenone (221 mg, 0.67 mmol) was dissolved in pyridine (6.7 mL) and treated with Lawesson's reagent [2,4-bis(4-methoxyphenyl)-1,3,2,4-dithiadiphosphetane-2,4-dithione] (162 mg, 0.402 mmol, 0.6 eq.) under magnetic stirring. The resulting solution was heated to 100° C. and stirred at that temperature for 2 hours. LCMS indicated clean conversion to the product. The reaction was cooled, diluted with EtOAc (50 mL) and washed with saturated $NH_4Cl$ aqueous solution and brine (50 mL). The organic layer was dried over anhydrous $MgSO_4$, filtered and concentrated in vacuo. The crude residue used without further purification in the next step. Yield=287 mg (>100%). LC/MS-HPLC (254 nm)—Rt 0.11 min. MS (ESI) m/z 345.1 [$M^+$+$H^+$]. Purity=95% by UV (254 nm).

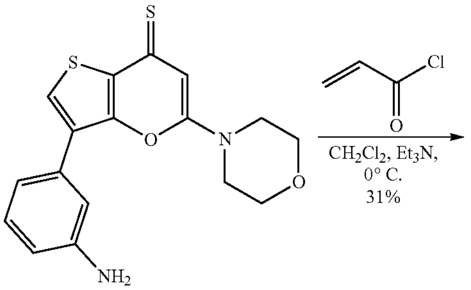

-continued

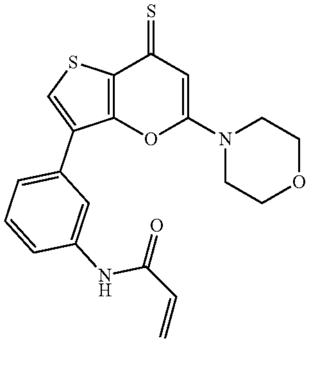

Step 3:1-[m-(5-Morpholino-7-thioxo-4-oxa-1-thia-3-indenyl)phenylamino]-2-propen-1-one (Compound 2): A stirring solution of 3-(m-aminophenyl)-5-morpholino-4-oxa-1-thia-7-indenethione (230 mg, 0.67 mmol) and triethylamine (282 μL, 2.01 mmol) in $CH_2Cl_2$ (6.7 mL) was cooled to 0° C. under an inert atmosphere of $N_2$. Acryloyl chloride (60 μL, 0.74 mmol) was added via syringe and the resulting mixture was stirred at 0° C. for 1 hour. Analysis by LCMS indicated clean conversion to the product. The reaction mixture was concentrated in vacuo and directly purified by silica gel chromatography, eluting with a 1:1 v/v hexanes/EtOAc mixture. The product was obtained as a yellow solid. Yield=84 mg (0.211 mmol, 31%).

LC/MS-HPLC (254 nm)—Rt 2.46 min. MS (ESI) m/z 399.3 $[M^{+}+H^{+}]$. Purity=98.9% by UV (254 nm).

Example 4. Preparation of Dual BRD4/BTK Inhibitor Compound 3

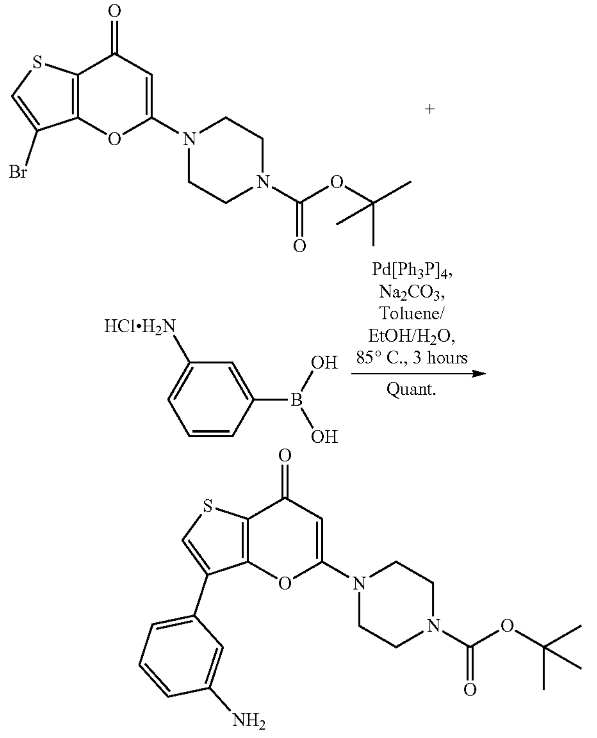

-continued

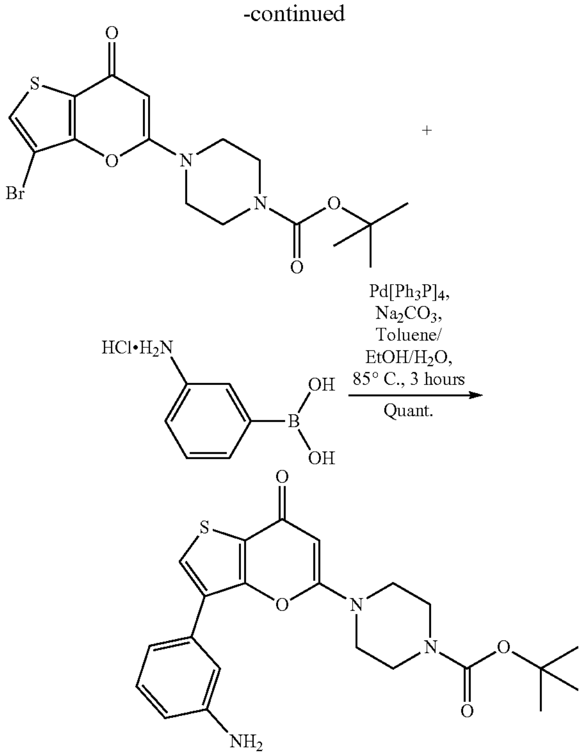

49FT123
MW = 427.52

Step 1: tert-Butyl 4-13-(m-aminophenyl)-7-oxo-4-oxa-1-thia-5-indenyl-1-piperazinecarboxylate tert-Butyl 4-(3-bromo-7-oxo-4-oxa-1-thia-5-indenyl)-1-piperazinecarboxylate (414 mg, 1.0 mmol) and 3-aminophenylboronic acid hydrochloride (260 mg, 1.5 mmol, 1.5 eq.) were dissolved in a 2:1 v/v mixture of toluene and ethanol (10 mL). The mixture was treated with $Na_2CO_3$ 2M aqueous solution (3.3 mL) and deoxygenated by bubbling $N_2$ for 20 minutes. $Pd[PPh_3]_4$ (58 mg, 0.05 mmol) was added and the mixture was heated to 85° C. for 3 hours. LCMS indicates complete conversion to product. The cooled reaction mixture was diluted with EtOAc (100 mL) washed with water and brine. The organics were dried over anhydrous $MgSO_4$, filtered and concentrated in vacuo. The crude residue was purified by silica gel chromatography, eluting with EtOAc first, then with 10% MeOH in EtOAc. The pure product is a tan solid. Yield=482 mg (1.0 mmol, quant.).

LC/MS-HPLC (254 nm)—Rt 2.28 min. MS (ESI) m/z 428.5 $[M^{+}+H^{+}]$. Purity=99.3% by UV

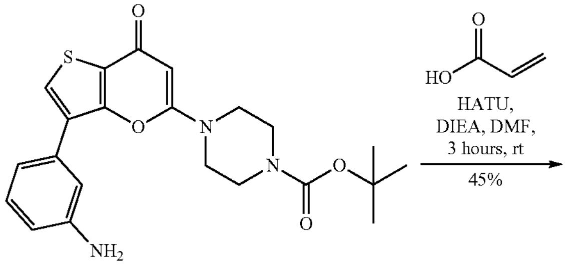

-continued

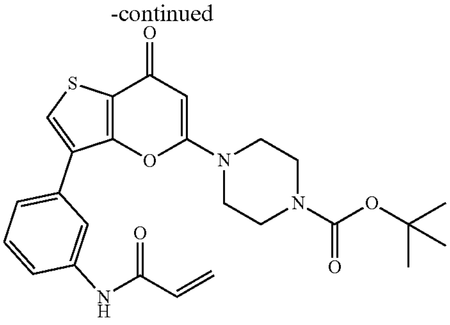

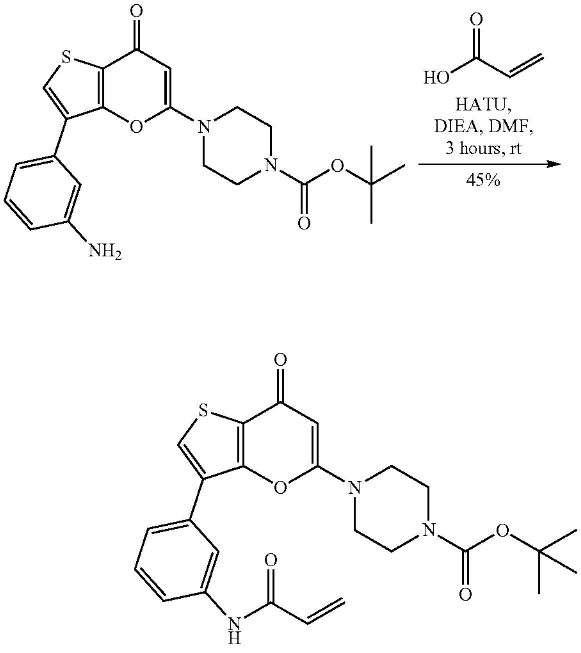

49FT126
MW = 481.5

Step 2: tert-Butyl 4-{3-[m-(acryloylamino)phenyl]-7-oxo-4-oxa-1-thia-5-indenyl}-1-piperazinecarboxylate tert-Butyl 4-[3-(m-aminophenyl)-7-oxo-4-oxa-1-thia-5-indenyl]-1-piperazinecarboxylate (128 mg, 0.3 mmol) was dissolved in anhydrous DMF (3 mL) and treated with N,N-diisopropylethylamine (205 μL, 1.2 mmol) and acrylic acid (32 μL, 0.39 mmol). To this stirring solution, HATU (148 mg, 0.39 mmol) was added and the resulting mixture was stirred at room temperature for 3 hours. LCMS indicated complete conversion to the product. The reaction was quenched by addition of $H_2O$ and the product was extracted with EtOAc. The organic layer was washed with 0.1N HCl aqueous and brine, dried over $MgSO_4$, filtered and concentrated in vacuo. The crude residue was purified by silica gel chromatography, eluting with a hexanes/EtOAc gradient. The product was obtained as a film. Yield=65 mg (0.135 mmol, 45%).

LC/MS-HPLC (254 nm)—Rt 2.75 min. MS (ESI) m/z 482.2 [$M^+$+$H^+$]. Purity=95% by UV

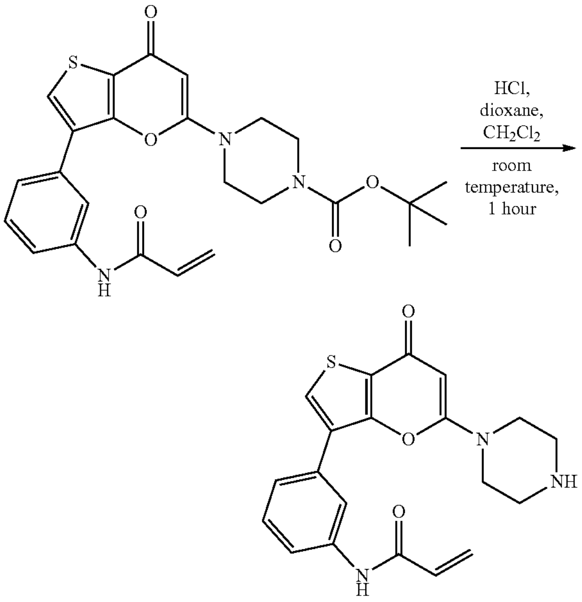

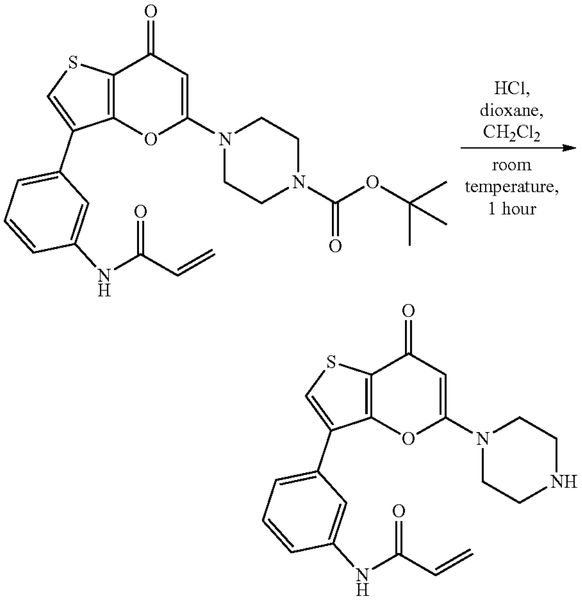

SRX 3261
49FT129
MW = 381.5

Step 3: 1-{m-[7-Oxo-5-(1-piperazinyl)-4-oxa-1-thia-3-indenyl] phenylamino}-2-propen-1-one (Compound 3)

A solution of tert-butyl 4-{3-[m-(acryloylamino)phenyl]-7-oxo-4-oxa-1-thia-5-indenyl}-1-piperazinecarboxylate (65 mg, 0.135 mmol) in $CH_2Cl_2$ (1.4 mL) was treated with a 4N solution of HCl in dioxane (135 μL) at room temperature. The resulting mixture was stirred for 1 hour, after which time LCMS indicated reaction completed. The reaction mixture was concentrated to dryness in vacuo and the residue was purified by reverse phase column chromatography on C18 column, eluting with $H_2O$/MeCN containing 0.1% trifluroacetic acid. The product was obtained as a white solid. Yield=21 mg (0.055 mmol, 41%).

LC/MS-HPLC (254 nm)—Rt 1.99 min. MS (ESI) m/z 382.3 [$M^{+}$+$H^{+}$]. Purity=99% by UV (254 nm).

Example 5. Preparation of Triple BTK/BRD4/PI3K Inhibitor Compound 8

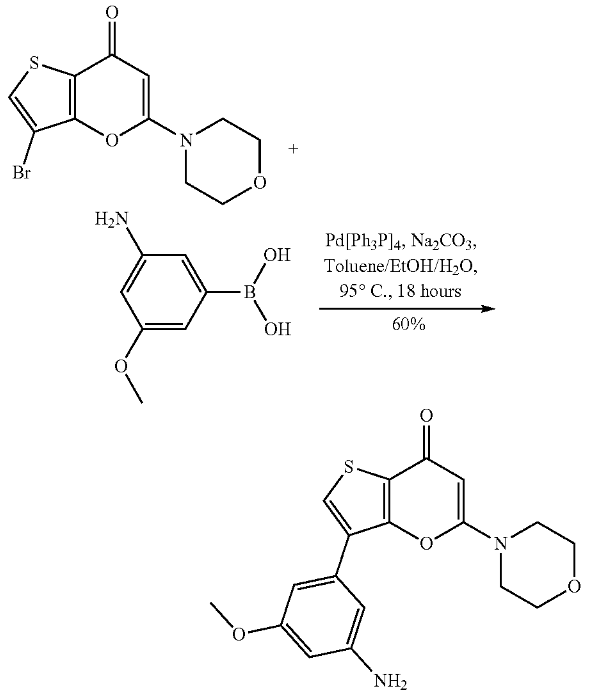

Step 1:3-(3-Amino-5-methoxyphenyl)-5-morpholino-4-oxa-1-thia-7-indenone A mixture of 3-bromo-5-morpholino-4-oxa-1-thia-7-indenone (120 mg, 0.38 mmol), 3-amino-5-Methoxy boronic acid (100 mg, 0.49 mmol), $Na_2CO_3$ 2M aqueous solution (1.5 mL), toluene:ethanol 2:1 v/v (4.5 mL) and $Pd[Ph_3P]_4$ (24 mg., 0.02 mmol) were stirred together at 95° C. for 18 h. Then the reaction mixture was cooled and diluted with ethyl acetate (50 mL) and filtered. The filtrate was washed with water and dried ($Na_2SO_4$), filtered and concentrated to yield crude 3-(3-amino-5-methoxyphenyl)-5-morpholino-4-oxa-1-thia-7-indenone (150 mg). The crude was purified on silica gel column using 0-100% acetone/hexane gradient system. Useful fractions were pulled together and concentrated to yield pure final product (150 mg, 60% yield).

LC/MS-HPLC (254 nm)—Rt 1.73 min. MS (ESI) m/z 359.5 [$M^{+}$+$H^{+}$]. Purity=99% by UV

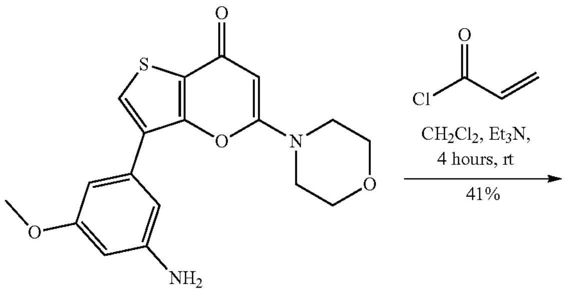

-continued

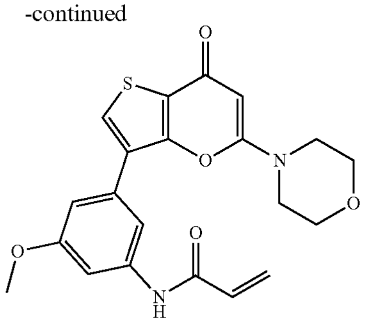

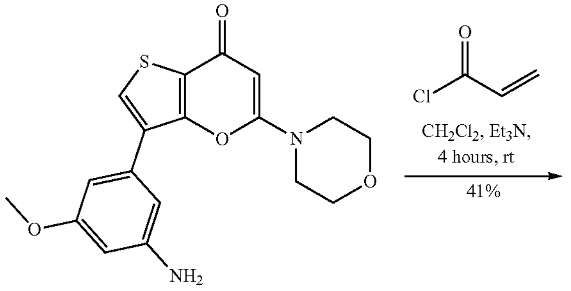

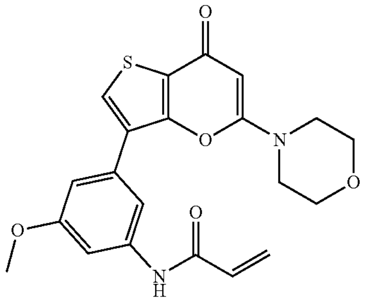

48CR169-2
MW = 412.46

Step 2: 1-[5-Methoxy-3-(5-morpholino-7-oxo-4-oxa-1-thia-3-indenyl)phenylamino]-2-propen-1-one (Compound 8)

3-(3-Amino-5-methoxyphenyl)-5-morpholino-4-oxa-1-thia-7-indenone (129 mg, 0.36 mmol) was dissolved into DCM (3 mL). Added triethylamine (101 μL, 0.72 mmol) and cooled to 0° C. Added acryloyl chloride (44 μL, 0.54 mmol). Then reaction mixture was stirred at RT for 4 h. Diluted with DCM and washed with water, concentrated to oily crude compound. The crude compound was purified on silica gel column using 0-100% acetone/hexane gradient system. The final pure product, 1-[5-methoxy-3-(5-morpholino-7-oxo-4-oxa-1-thia-3-indenyl)phenylamino]-2-propen-1-one was obtained (60 mg, 41% yield).

LC/MS-HPLC (254 nm)—Rt 0.36 min. MS (ESI) m/z 413.5 [$M^{+}$+$H^{+}$]. Purity=99% by UV (254 nm).

Example 6. Preparation of Dual BRD4/PI3K Inhibitors Compound 5 and Compound 6 Via Boc-Piperidine Intermediate Compound 4

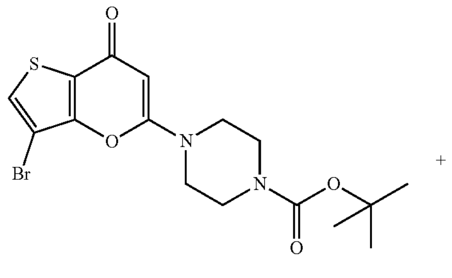

Step 1: tert-Butyl-4-3-(1-oxa-4-aza-3,4-dihydro-2H-naphth-6-yl)-5-(1-piperazinyl)-4-oxa-1-thia-7-indenone A mixture of tert-butyl 4-(3-bromo-7-oxo-4-oxa-1-thia-5-indenyl)-1-piperazinecarboxylate (267 mg., 0.645 mmol) and 4,4,5,5-tetramethyl-2-(1-oxa-4-aza-3,4-dihydro-2H-naphth-6-yl)-1,3,2-dioxaborolane (219 mg, 0.838 mmol) $Na_2CO_3$ 2M aqueous solution (2.5 mL), toluene:ethanol 2:1 v/v (7.5 mL) and $Pd[Ph_3P]_4$ (45 mg, 0.04 mmol) were stirred together at 95° C. for 13 h. Then the reaction mixture was cooled and diluted with ethyl acetate (50 mL) and filtered. The filtrate was washed with water and dried ($Na_2SO_4$), filtered and concentrated to yield crude which was purified on silica column using 0-20% acetone/DCM gradient system. Useful fractions were pooled and concentrated to yield pure final product (226 mg, 75% yield).

LC/MS-HPLC (254 nm)—Rt 2.56 min. MS (ESI) m/z 470.9 $[M^+ + H^+]$. Purity=99% by UV (254 nm).

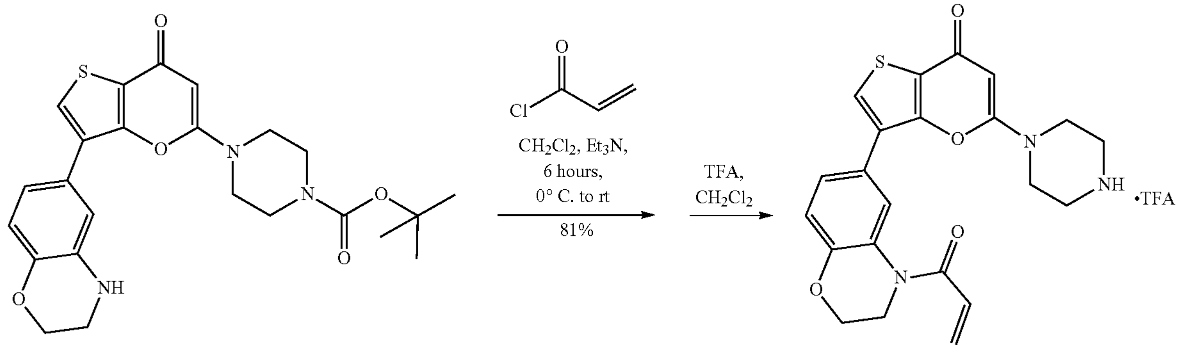

-continued

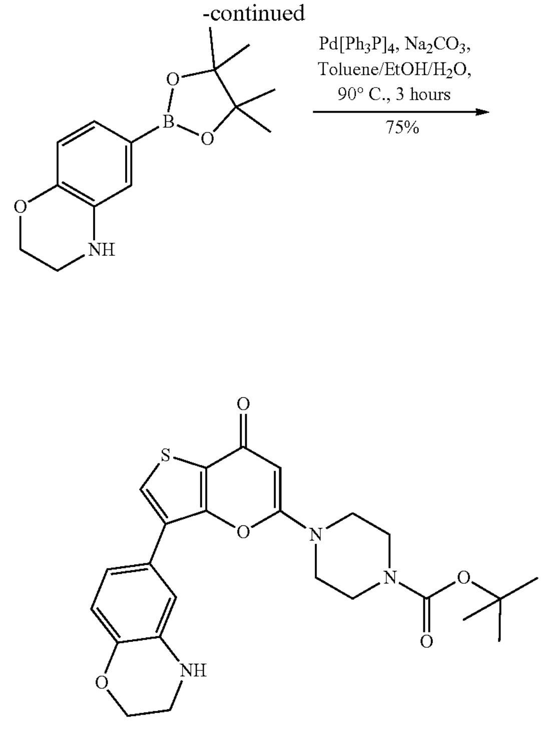

Step 2: 1-{7-[7-Oxo-5-(1-piperazinyl)-4-oxa-1-thia-3-indenyl]-4-oxa-1-aza-2,3-dihydro-1H-naphth-1-yl}-2-propen-1-one (Compound 5)

A mixture tert-butyl-4-3-(1-oxa-4-aza-3,4-dihydro-2H-naphth-6-yl)-5-(1-piperazinyl)-4-oxa-1-thia-7-indenone (225 mg, 0.48 mmol), triethylamine (205 μL, 1.44 mmol) in DCM (10 mL) was cooled to 0° C. and added acryloyl chloride (50 mg, 0.42 mmol). Stirred at RT for 6 h and then diluted with DCM, washed with water and concentrated to yield crude product which was purified on silica column using 0-20% acetone/DCM (gradient) to give Boc derivative tert-butyl 4-[3-(4-acryloyl-1-oxa-4-aza-3,4-dihydro-2H-naphth-6-yl)-7-oxo-4-oxa-1-thia-5-indenyl]-1-piperazinecarboxylate=Compound 4 (230 mg, 0.4 mmol, 81%).

LC/MS-HPLC (254 nm)—Rt 2.64 min. MS (ESI) m/z 524.8 $[M^+ + H^+]$. Purity=99% by UV (254 nm).

The Boc derivative was dissolved into DCM (15 mL) with stirring and then treated with TFA (1 mL). Stirred for two additional hours and concentrated to dryness to yield final pure product in the form of TFA salt, Compound 5 (210 mg).

LC/MS-HPLC (254 nm)—Rt 1.62 min. MS (ESI) m/z 424.5 $[M^+ + H^+]$. Purity=99% by UV

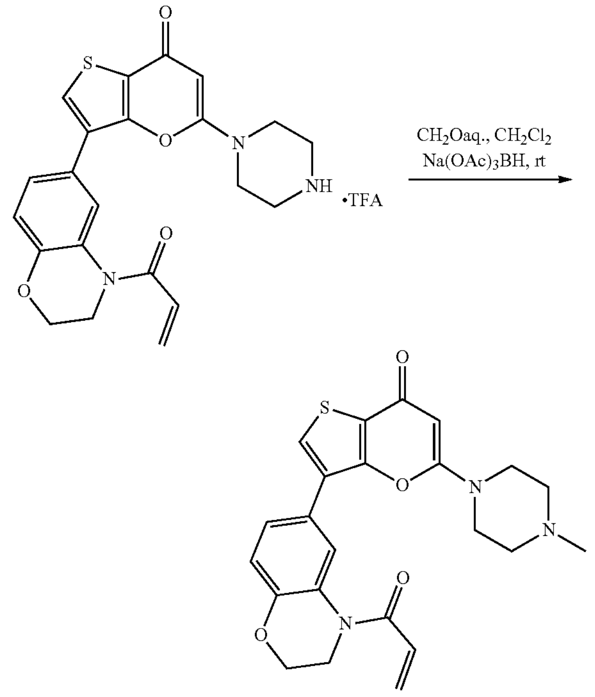

Step 3: 1-(7[5-(4-Methyl-1-piperazinyl)-7-oxo-4-oxa-1-thia-3-indenyl]-4-oxa-1-aza-2,3-dihydro-1H-naphth-1-yl]-2-propen-1-one (Compound 6)

1-{7-[7-Oxo-5-(1-piperazinyl)-4-oxa-1-thia-3-indenyl]-4-oxa-1-aza-2,3-dihydro-1H-naphth-1-yl}-2-propen-1-one trifluoroacetate salt (129 mg, 0.24 mmol) was taken into DCM. 10 drops of aqueous formaldehyde was added and then sodium triacetoxyborohydride (203 mg, 0.96 mmol) was added and the resulting mixture was stirred for 2 hours at room temperature. Diluted with more DCM and washed with water, dried ($Na_2SO_4$), filtered and concentrated to yield final pure product Compound 6 (24 mg, 0.055 mmol, 23%).

LC/MS-HPLC (254 nm)—Rt 1.96 min. MS (ESI) m/z 438.1 [$M^+$+$H^+$]. Purity=99% by UV (254 nm).

Example 7. Preparation of Triple BTK/BRD4/PI3K Inhibitor Compound 9

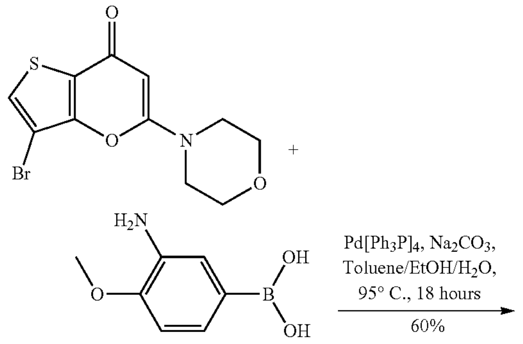

-continued

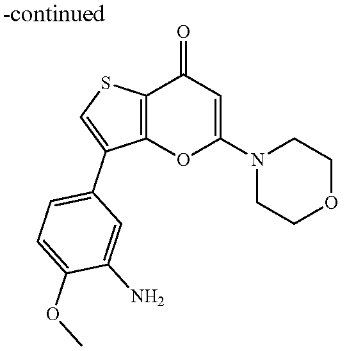

Step 1:3-(3-Amino-4-methoxyphenyl)-5-morpholino-4-oxa-1-thia-7-indenone: A mixture of 3-bromo-5-morpholino-4-oxa-1-thia-7-indenoe (120 mg, 0.38 mmol), 3-amino-4-methoxy boronic acid (100 mg, 0.49 mmol), $Na_2CO_3$ 2M aqueous solution (1.5 mL), toluene:ethanol 2:1 v/v (4.5 mL) and $Pd[Ph_3P]_4$ (24 mg, 0.02 mmol) were stirred together at 95° C. for 18 h. Then the reaction mixture was cooled and diluted with ethyl acetate (50 mL) and filtered. The filtrate was washed with water and dried ($Na_2SO_4$), filtered and concentrated to yield crude 3-(3-amino-4-methoxyphenyl)-5-morpholino-4-oxa-1-thia-7-indenone (200 mg). The crude was purified on silica gel column using 0-100% acetone/hexane gradient system. Useful fractions were pulled together and concentrated to yield pure final product (70 mg, 60% yield). LC/MS-HPLC (254 nm)—Rt 1.82 min. MS (ESI) m/z 359.6 [$M^+$+$H^+$]. Purity=99% by UV (254 nm).

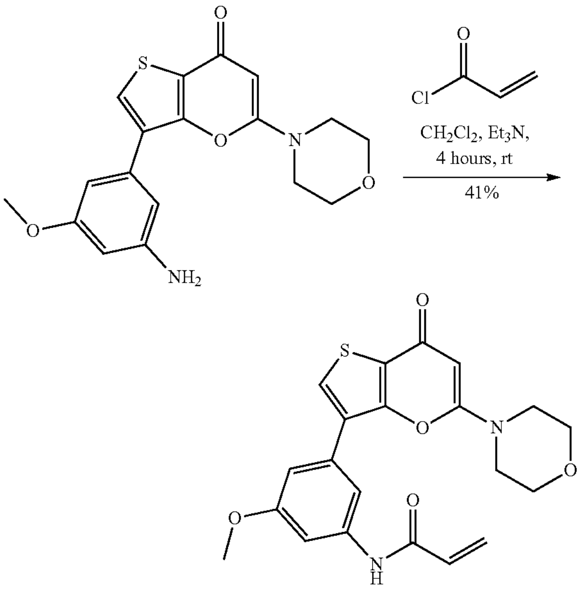

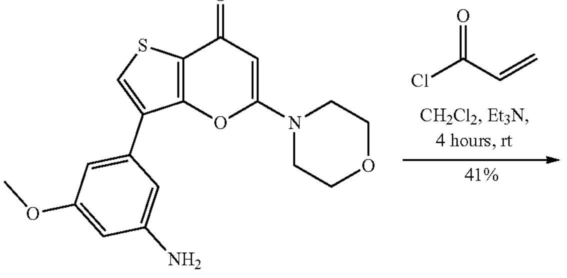

-continued

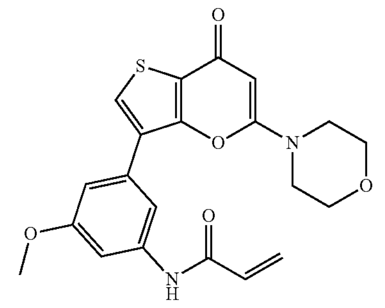

48CR169-2
MW = 412.46

Step 2: 1-[4-Methoxy-3-(5-morpholino-7-oxo-4-oxa-1-thia-3-indenyl)phenylamino]-2-propen-1-one (Compound 9)

3-(3-Amino-4-methoxyphenyl)-5-morpholino-4-oxa-1-thia-7-indenone (70 mg, 0.20 mmol) was dissolved into DCM (3 mL). Added triethylamine (85 μL, 0.60 mmol) and cooled to 0° C. Added acryloyl chloride (20 μL, 0.24 mmol). Then reaction mixture was stirred at RT for 4 h. Diluted with DCM and washed with water, concentrated to oily crude compound. The crude compound was purified on silica gel column using 0-100% acetone/hexane gradient system. The final pure product, 1-[4-methoxy-3-(5-morpholino-7-oxo-4-oxa-1-thia-3-indenyl)phenylamino]-2-propen-1-one was obtained (80 mg, 95% yield).

LC/MS-HPLC (254 nm)—Rt 2.50 min. MS (ESI) m/z 413.6 [$M^{+}$+$H^{+}$]. Purity=99% by UV (254 nm).

Example 8. Preparation of Compound 10

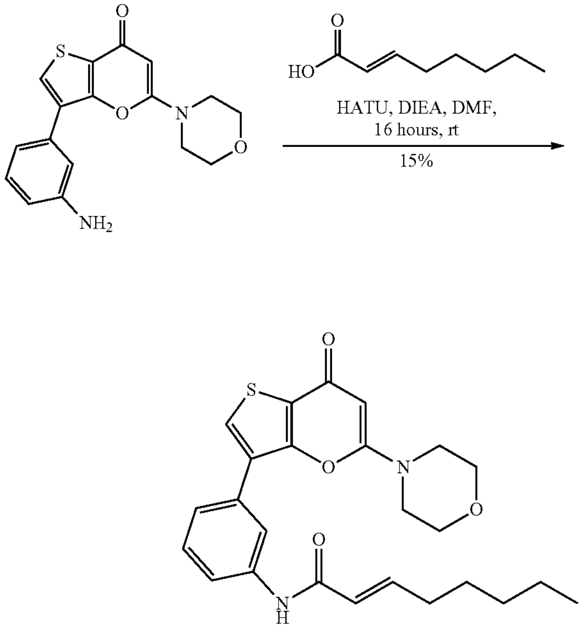

-continued

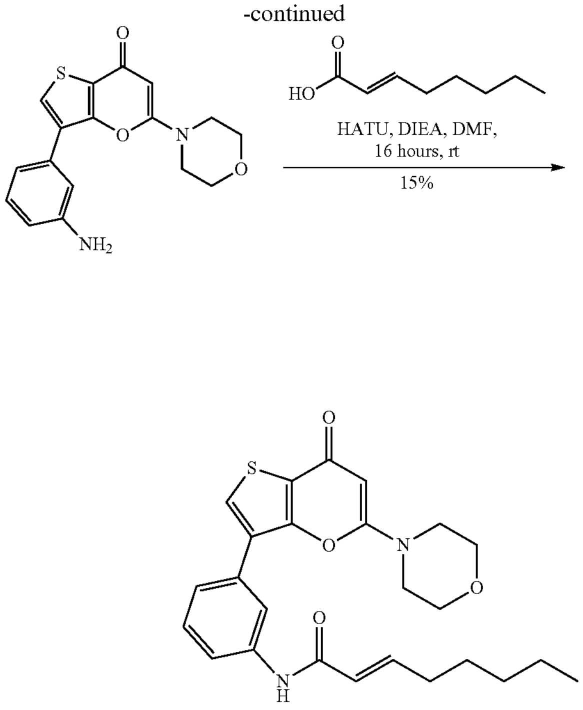

53FT07
MW = 452.5

Step 1: (E)-1-[m-(5-Morpholino-7-oxo-4-oxa-1-thia-3-indenyl)phenylamino]-2-octen-1-one (Compound 10)

3-(m-Aminophenyl)-5-morpholino-4-oxa-1-thia-7-indenone (98 mg, 0.3 mmol) was dissolved in anhydrous DMF (3 mL) and treated with N,N-diisopropylethylamine (209 μL, 2.0 mmol) and trans-2-octenoic acid (64 mg, 0.45 mmol). To this stirring solution, HATU (148 mg, 0.39 mmol) was added and the resulting mixture was stirred at room temperature for 16 hours. LCMS indicated complete conversion to the product. The reaction was quenched by addition of $H_2O$ and the product was extracted with EtOAc. The organic layer was washed with 0.1N HCl aqueous and brine, dried over $MgSO_4$, filtered and concentrated in vacuo. The crude residue was purified by silica gel chromatography, eluting with EtOAc. The product obtained consisted of a 3:1 mixture of cis/trans isomers. This material was repurified by reverse phase C-18 chromatography eluting with water/MeCN modified with 0.1% of trifluoroacetic acid. The product was obtained as a white solid. Yield=20 mg (0.044 mmol, 15%).

$^1$H NMR (DMSO-$d_6$) δ 10.09 (s, 1H): 8.35 (s, 1H): 8.15 (s, 1H): 7.44-7.37 (m, 3H): 6.83 (dd, $J_1$=15.5 Hz, $J_2$=6.5 Hz): 6.11 (d, J=15.5 Hz): 5.53 (s, 1H): 3.72-3.70 (m, 4H): 3.47-3.45 (m, 4H): 2.22-2.20 (m, 2H); 1.45 (m, 2H): 1.31-1.29 (m, 4H): 0.88 (t, J=6.5 Hz, 3H).

LC/MS-HPLC (254 nm)—Rt 2.81 min. MS (ESI) m/z 453.3 [$M^{+}$+$H^{+}$]. Purity=96.5% by UV (254 nm).

Example 9. Preparation of Compound 11

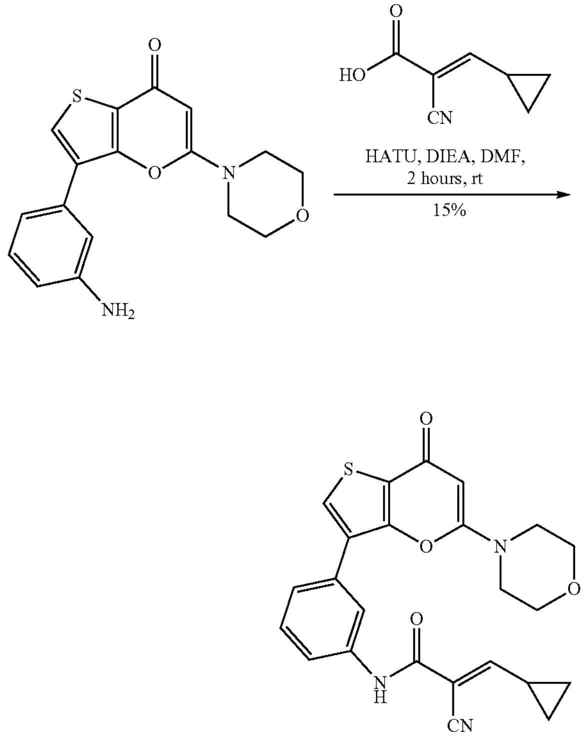

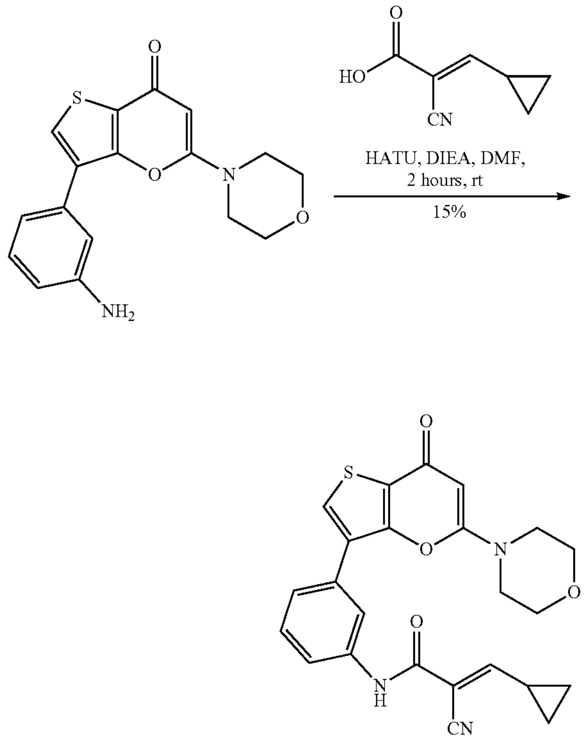

53FT16
MW = 447.5

Step 1: (E)-3-Cyclopropyl-2-{[m-(5-morpholino-7-oxo-4-oxa-1-thia-3-indenyl)phenylamino]carbonyl}acrylonitrile (Compound 11)

3-(m-Aminophenyl)-5-morpholino-4-oxa-1-thia-7-indenone (217 mg, 0.663 mmol) was dissolved in anhydrous DMF (6.6 mL) and treated with N,N-diisopropylethylamine (346 μL, 2.0 mmol) and (E)-2-cyano-3-cyclopropylacrylic acid (100 mg, 0.729 mmol). To this stirring solution, HATU (380 mg, 1.00 mmol) was added and the resulting mixture was stirred at room temperature for 2 hours. LCMS indicated clean conversion to the product. The reaction was quenched by addition of $H_2O$ and the product was extracted with EtOAc. The organic layer was washed with 0.1N HCl aqueous and brine, dried over $MgSO_4$, filtered and concentrated in vacuo. The crude residue was purified by silica gel chromatography, eluting with EtOAc and MeOH gradient. The product was obtained as a yellow solid. Yield=45 mg (0.100 mmol, 15%).

LC/MS-HPLC (254 nm)—Rt 2.46 min. MS (ESI) m/z 448.2 $[M^{+}+H^{+}]$. Purity=99% by UV (254 nm).

Example 10. Preparation of Acetylenic Triple BTK/BRD4/PI3K Inhibitor Compound 12

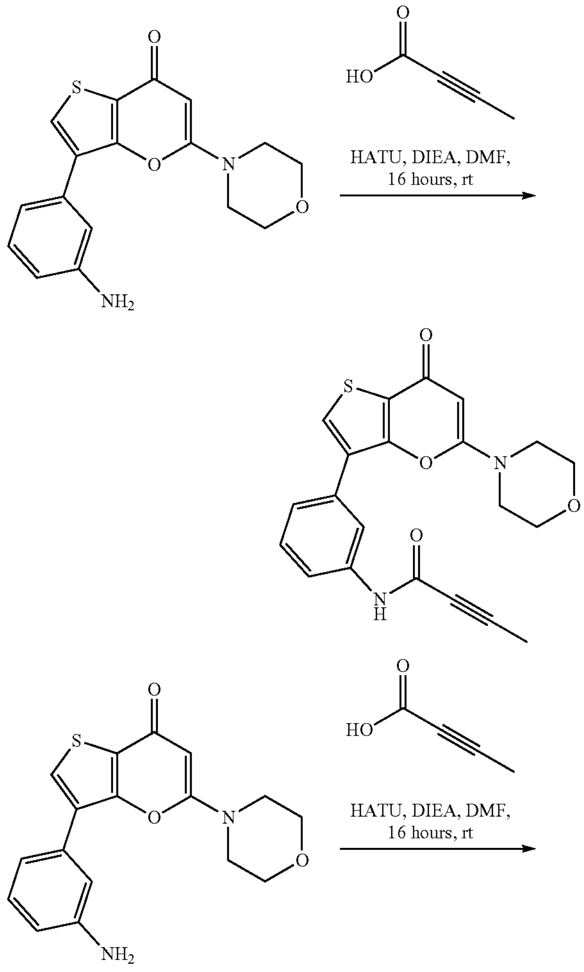

-continued

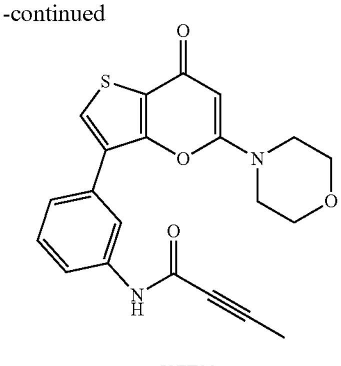

53FT08
MW = 394.4

Step 1:1-[m-(5-Morpholino-7-oxo-4-oxa-1-thia-3-indenyl)phenylamino]-2-butyn-1-one (Compound 12)

3-(m-Aminophenyl)-5-morpholino-4-oxa-1-thia-7-indenone (98 mg, 0.3 mmol) was dissolved in anhydrous DMF (3 mL) and treated with N,N-diisopropylethylamine (209 μL, 2.0 mmol) and 2-butynoic acid (38 mg, 0.45 mmol). To this stirring solution, HATU (148 mg, 0.39 mmol) was added and the resulting mixture was stirred at room temperature for 16 hours. LCMS indicated complete conversion to the product. The reaction was quenched by addition of $H_2O$ and the product was extracted with EtOAc. The organic layer was washed with 0.1N HCl aqueous and brine, dried over $MgSO_4$, filtered and concentrated in vacuo. The crude residue was purified by silica gel chromatography, eluting with EtOAc. The product obtained was still impure. This material was repurified by reverse phase C-18 chromatography eluting with water/MeCN modified with 0.1% of trifluoroacetic acid. The product was obtained as a white solid. Yield=2.6 mg.

LC/MS-HPLC (254 nm)—Rt 2.24 min. MS (ESI) m/z 395.5 $[M^{+}+H^{+}]$. Purity=95% by UV (254 nm).

Example 11. $IC_{50}$ Data for Compounds of the Invention for BTK, BRD4, and PI3K Compounds of the invention were analyzed for their ability to inhibit target proteins in vitro. PI3K alpha, gamma, and delta inhibition activity was determined by Thermo Fisher Scientific-Biosciences Life Sciences Solutions, Madison, WI. The bromodomain protein inhibition (binding domain 1 and 2 of BRD4) was determined at Reaction Biology Corp., Malvern, PA. BTK inhibition was performed by Reaction Biology Corp., Malvern, PA. In addition to native BTK inhibition, the compounds were assayed against the cysteine mutant C481S (BTK having cysteine at position 481 replaced by Serine which is incapable of forming a covalent bond (e.g., Michael addition) between the electrophilic group on the compounds of the invention and the cysteine C481 in the binding pocket. The ratio of the IC50 inhibitions determined for the two BTK proteins (i.e., wild-type and C481S) was calculated and is displayed in the rightmost column of Table 6. While not wishing to be bound by theory a high number indicates that the compound of the invention binds covalently to BTK via Michael addition by the cysteine C481 of BTK to the electrophilic group of the compound of the invention.

Additional information regarding the testing procedures is available at each company's website on the internet. The IC50 data was calculated from a 10-point curve by the vendor and is compiled in ranges in the Table 6 below.

TABLE 6

Compiled IC50 data for compounds of the invention.

| Compound | | Target IC50 (nM) | | | | | | | |
|---|---|---|---|---|---|---|---|---|---|
| No. | MW | BRD4-1 | BRD4-2 | PI3K α | PI3K β | PI3K γ | BTK (WT) | BTK (C481S) | Ratio C481S/WT |
| 1 | 382.4 | + | ++ | + | + | ++ | + | ND | >81 |
| 2 | 398.5 | +++ | ++ | + | + | + | ++ | +++ | 8.1 |
| 3 | 381.5 | + | ++ | +++++ | +++++ | +++++ | ++ | ++++ | 24.5 |
| 4 | 523.6 | + | ++ | +++ | ++ | +++ | + | +++ | 212 |
| 5 | 423.1 | + | ++ | +++ | ++ | +++++ | + | +++ | 52.0 |
| 6 | 437.5 | ++ | +++ | ++++ | ++ | +++++ | + | ++ | 11.2 |
| 7 | 474.5 | + | + | + | + | + | + | +++ | 728 |
| 8 | 412.5 | + | ++ | + | + | + | + | +++++ | >60 |
| 9 | 412.5 | + | + | + | + | ++ | ++ | ++ | 3.3 |
| 10 | 452.2 | ++ | +++ | ++ | ++ | +++ | ND | ND | -- |
| 11 | 447.5 | ++ | + | + | + | ++ | +++ | +++ | 1.3 |
| 12 | 394.4 | + | + | + | + | + | ++ | +++ | 15.8 |
| 21 | 460.5 | + | + | + | + | + | + | + | 1402 |
| II-18 | 418.5 | + | + | + | + | + | + | + | >20K |
| 0 | 371.4 | + | ++ | + | + | + | +++ | +++ | ~1 |

+ = less than 1,000 nM
++ = between 1,000 nM and 10,000 nM
+++ = between 10,000 nM and 30,000 nM
++++ = between 30,000 nM and 50,000 nM
+++++ = more than 50,000 nM
ND = Not Determined

Figure 1B:
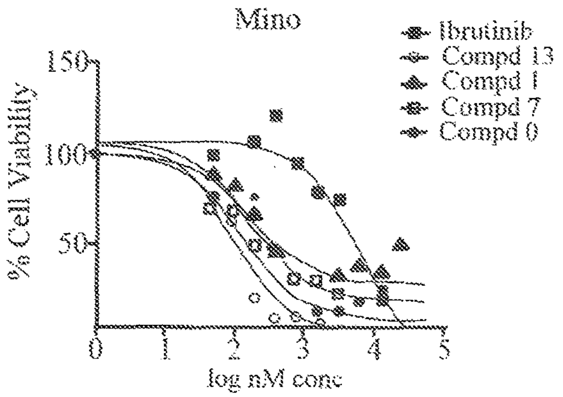
FIG. 1B shows the inhibitory effects of compounds of the invention including Compds 0, 1, 7, and 13 and Ibrutinib in Mino cells, a human mantle cell lymphoma cell line.
Figure 1C:
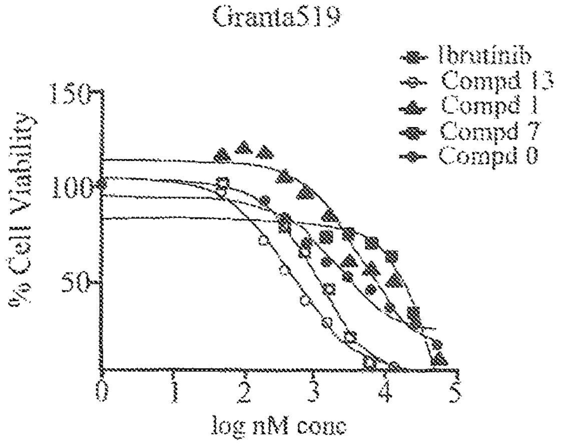
FIG. 1C shows the inhibitory effects of compounds of the invention including Compds 0, 1, 7, and 13 and Ibrutinib in Granta 519 cells, a human mantle cell lymphoma cell line.

Example 12. Compound 7 is a Novel PI3K/BRD4/BTK Inhibitor that Inhibits the Growth of Mantle Cell Lymphoma Cell Lines The results of this experiment are shown in FIGS. 1A-1C, and in Table 7 below. Human mantle cell lymphoma cell lines were grown in 96 well plates with 5000 cells per well in RPMI 1640 media supplemented with 10% fetal bovine serum. Cells were treated for 48 hours with a concentration range of each compound from 50 nM to 50 μM. Cell viability a measure of viable cell numbers was determined using a Celltiter-Glo® reagent for each concentration in order to construct an IC50 curve for each compound in each cell line. Semiquantitation of the IC50 sensitivity of each cell line is shown in Table 7. Conclusion: Compounds 13, 1, 7 and 0 are markedly more potent at subnanomolar concentration as compared to Ibrutinib in reducing mantle cell lymphoma viability in vitro.

TABLE 7

Compound IC50 data (nM) in JeKo-1, Mino, and Granta519.

| Compound | JeKo-1 | Mino | Granta519 |
|---|---|---|---|
| Ibrutinib | +++++ | ++ | +++ |
| Compound 13 | + | + | + |
| Compound 1 | ++ | + | ++ |
| Compound 7 | + | + | ++ |
| Compound 0 | + | + | ++ |

+ = less than 1,000 nM
++ = between 1,000 nM and 10,000 nM
+++ = between 10,000 nM and 30,000 nM
++++ = between 30,000 nM and 50,000 nM
+++++ = more than 50,000 nM

Figure 2A:
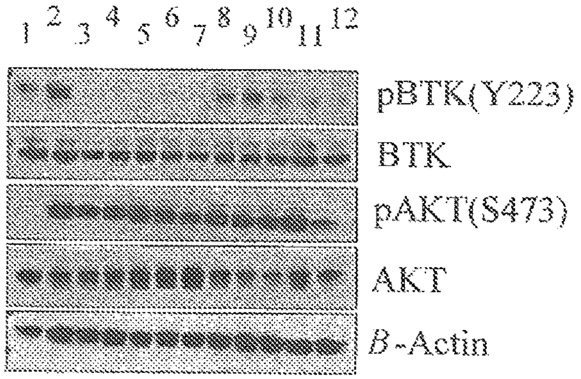
FIG. 2A shows a Western blot analysis in JeKo cells comparing Ibrutinib with Compd 7 of the invention on BTK and PI3K signaling in IgM stimulated cells. Lane 1-DMSO; lane 2-DMSO+IgM; lane 3-Ibrutinib, 50 nM; lane 4-Ibrutinib, 250 nM; lane 5-Ibrutinib, 500 nM; lane 6-Ibrutinib, 750 nM; lane 7-Ibrutinib, 1 μM; lane 8-Compd 7, 50 nM; lane 9-Compd 7, 250 nM; lane 10-Compd 7, 500 nM; lane 11-Compd 7, 750 nM; lane 12-Compd 7, 1 μM.
Figure 2B:
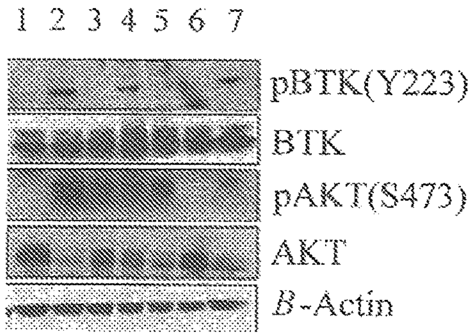
FIG. 2B shows a Western blot analysis in JeKo cells comparing Ibrutinib, and various compounds including Compd 0 and compounds of the invention 1, 7, and 13. Lane 1-DMSO; lane 2-DMSO+IgM; lane 3-Ibrutinib, 5 μM; lane 4-Compd 13, 5 μM; lane 5-Compd 1, 5μ; lane 6-Compd 7, 5μ; lane 7-Compd 0, 5 μM.
Figure 2C:
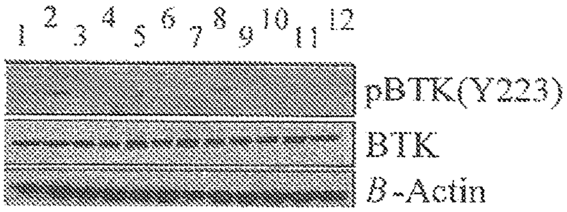
FIG. 2C shows a Western blot analysis in Mino cells comparing Ibrutinib with Compd 7 of the invention on BTK and PI3K signaling in IgM stimulated cells. Lane 1—DMSO; lane 2—DMSO+IgM; lane 3—Ibrutinib, 50 nM; lane 4—Ibrutinib, 250 nM; lane 5—Ibrutinib, 500 nM; lane 6—Ibrutinib, 750 nM; lane 7—Ibrutinib, 1 μM; lane 8—Compd 7, 50 nM; lane 9—Compd 7, 250 nM; lane 10—Compd 7, 500 nM; lane 11—Compd 7, 750 nM; lane 12—Compd 7, 1 μM.
Figure 2D:
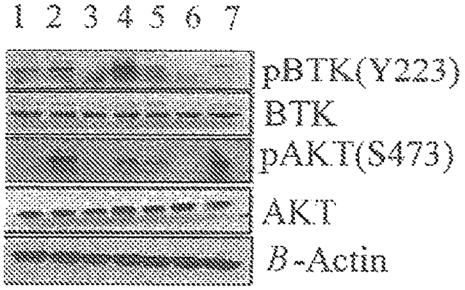
FIG. 2D shows a Western blot analysis in Mino cells comparing Ibrutinib, and various compounds including Compd 0 and compounds of the invention 1, 7, and 13. Lane 1—DMSO; lane 2—DMSO+IgM; lane 3—Ibrutinib, 1 μM; lane 4—Compd 13, 1 μM; lane 5—Compd 1, 1 μM; lane 6—Compd 7, 1 μM; lane 7—Compd 0, 1 μM.

Example 13. Compound 7 Inhibits BTK and PI3K Signaling in IgM Stimulated JeKo and Mino Mantle Cell Lymphoma Cell Lines To test the ability of compounds of the invention to inhibit BTK and PI3K signaling, F(ab') and anti-IgM stimulated JeKo and Mino cells were incubated with Ibrutinib and with compound 1, 7, 13 and 0. Phosphorylation of BTK at Tyr223 and AKT at Ser 473 were determined by Western blot analysis. The results are shown in FIGS. 2A-2B (JeKo cells) and FIGS. 2C-2D (Mino cells). Blots were reprobed for total BTK, AKT, and β-actin. The compounds of the invention demonstrate suppression of both pAKT and pBTK whereas ibrutinib only shows suppression of pBTK. Notably compounds 1 and 7 block the catalytic activity of both BTK and AKT under anti-IgM stimulation (B cell receptor stimulation) conditions in multiple mantle cell lymphoma cell lines.

Example 14. Compounds of the Invention Inhibit BTK and PI3K Signaling

Figure 3A:
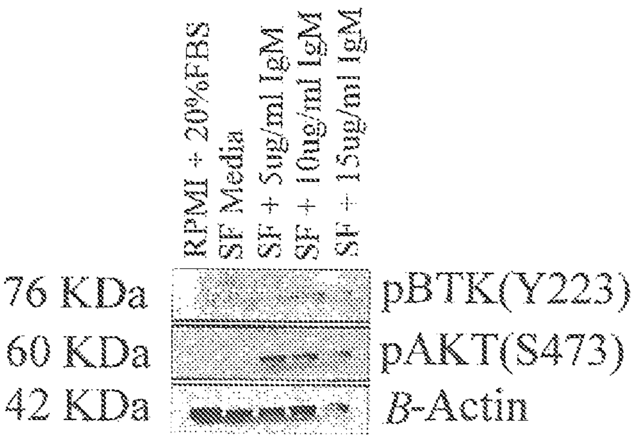
FIG. 3A shows the results of a Western blot analysis of pBTK(Y223) and pAKT(S473) in JeKo cells stimulated with different concentrations of F(ab) anti-human IgM.
Figure 3B:
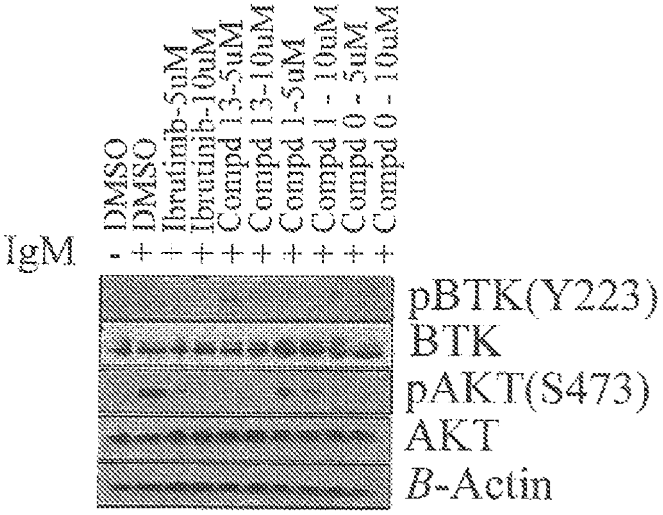
FIG. 3B shows the results of a Western blot analysis of phosphorylation of pBTK(Y223) and pAKT(S473) incubated with varying concentrations of Ibrutinib and Compounds 0, 1, and 13.

As shown in FIG. 3A, phosphorylation of pBTK(Y223) and pAKT(S473) was examined by Western blot analysis in JeKo cells stimulated with different concentrations of F(ab') and anti-human IgM in serum free medium (SF) and shows dose dependent activation of the PI3K pathway. FIG. 3B shows the results of a Western blot analysis for phosphorylation of pBTK(Y223) and pAKT(S473) in JeKo cells stimulated with F(ab') and anti-human IgM and treated with various concentrations of Ibrutinib and compounds 1, 13, and 0. Compounds 1 and 13 show that in cells stimulated in this way both the pAKT and pBTK components of their different pathways are suppressed.

Example 15. Compound 7 Induces Apoptosis and Cell Cycle Arrest in MCL Cells

Figure 4:
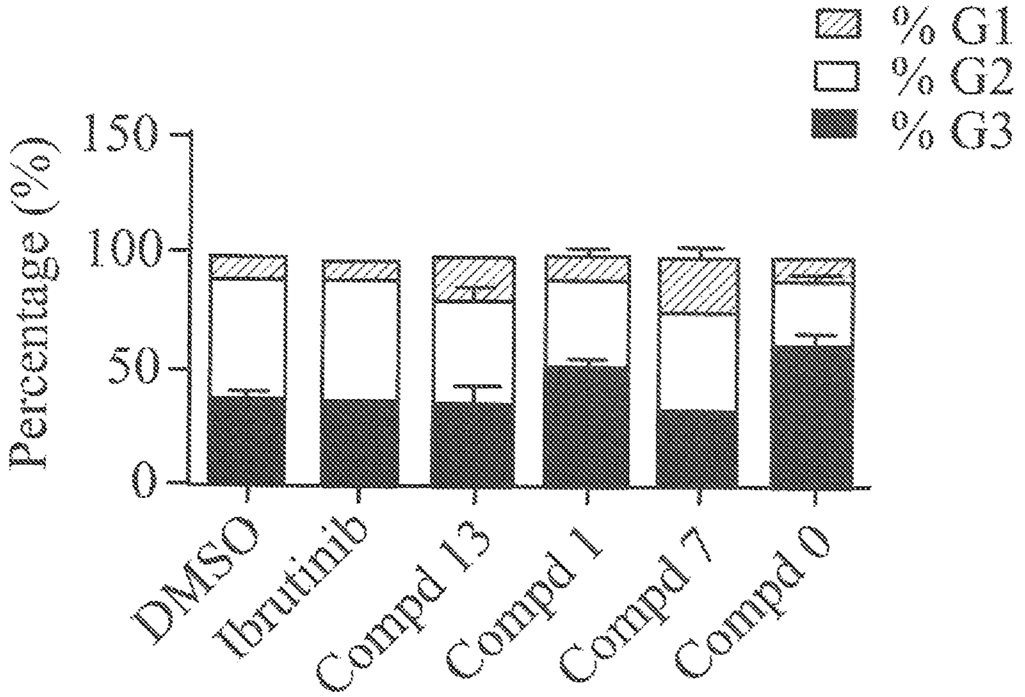
FIG. 4 shows cell cycle profile data generated in JeKo cells treated with 5 μM Ibrutinib, 5 μM Compd 13; 5 μM Compd 1; 5 μM Compd 7; and 5 μM Compd 0.

Cell cycle analysis data in JeKo cells after treatment with 5 μM concentrations of Ibrutinib, Compound 13, Compound 7, Compound 1, and Compound 0 are shown in FIG. 4. Additionally apoptosis data was obtained in both JeKo and Mino cells for compound 7. Table 8 provides a summary of the percentage of cells in apoptosis in JeKo-1 and Mino cells treated with Staurosporine, Ibrutinib, and Compound 7. The data indicates much more apoptosis from exposure to compound 7 than from exposure to Ibrutinib in both mantle cell lymphoma lines.

TABLE 8

Percentage cells in apoptosis in JeKo and Mino cells.

| Cells | Time | Apoptotic Phase | DMSO | Staurosporine | Ibrutinib | Compound 7 |
|---|---|---|---|---|---|---|
| JeKo-1 | 24-hour | Early | + | ++ | + | + |
| | | Late | + | + | + | +++ |
| | | Total | + | +++ | + | +++ |
| | 48-hour | Early | + | +++ | + | +++ |
| | | Late | + | +++ | + | +++ |
| | | Total | + | ++++ | ++ | ++++ |
| Mino | 24-hour | Early | + | ++++ | ++ | +++ |
| | | Late | + | ++++ | + | ++ |
| | | Total | ++ | +++++ | +++ | +++ |

+ = less than 5%
++ = between 5% and 10%
+++ = between 10% and 30%
++++ = between 30% and 50%
+++++ = more than 50%

Example 16. Compound 1 is a Covalent Irreversible BTK Inhibitor

Figure 5A:
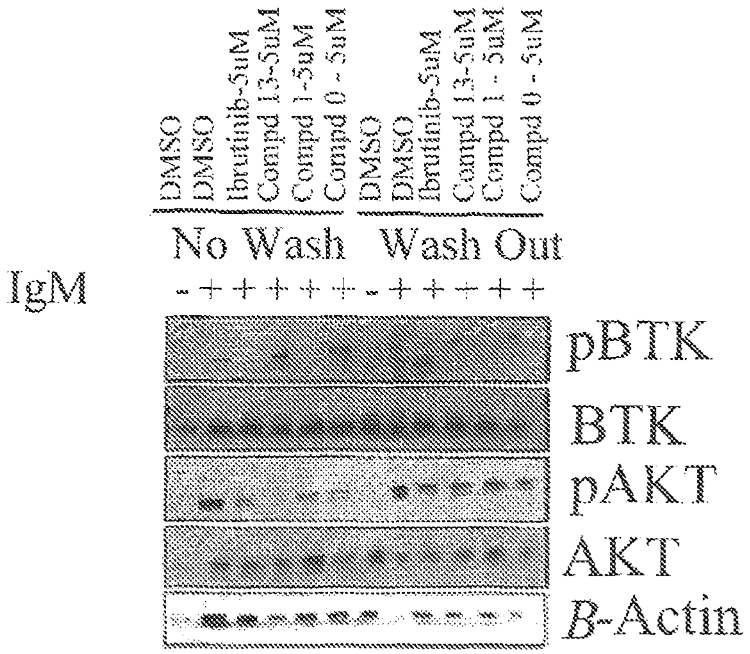
FIG. 5A shows Western blot analysis for pBTK, BTK, pAKT, AKT, and β-Actin in IgM stimulated JeKo cells treated with 5 μM Ibrutibib, 5 μM Compd 13, 5 μM Compd 1, and 5 μM Compd 0.
Figure 5B:
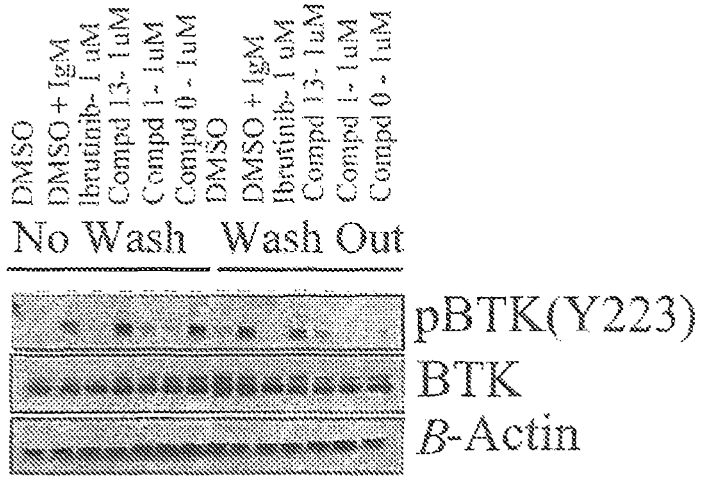
FIG. 5B shows Western blot analysis for pBTK(Y223), BTK, and β-Actin in IgM stimulated JeKo cells treated with 1 μM Ibrutibib, 1 μM Compd 13, 1 μM Compd 1, and 1 μM Compd 0.

Referring to FIGS. 5A and 5B, IgM-stimulated JeKo cells were treated with DMSO, DMSO+IgM, and with 5 μM (FIG. 5A) or 1 μM (FIG. 5B) Ibrutinib, Compound 13, Compound 1, and Compound 0 for 3 hours, washed extensively with PBS three (3) times, allowed to recover for 4 hours, lysed and subjected to Western blot analysis for pBTK, BTK, pAKT, AKT, and β-actin. The pBTK inhibiting properties of Compound 1 were not diminished by washing whereas pAKT was restored after washing indicating irreversible BTK inhibition and reversible PI3K pathway inhibition.

Example 17. Compound 7 Targets BTK and AKT to Overcome BTK Resistance

Figure 6A:
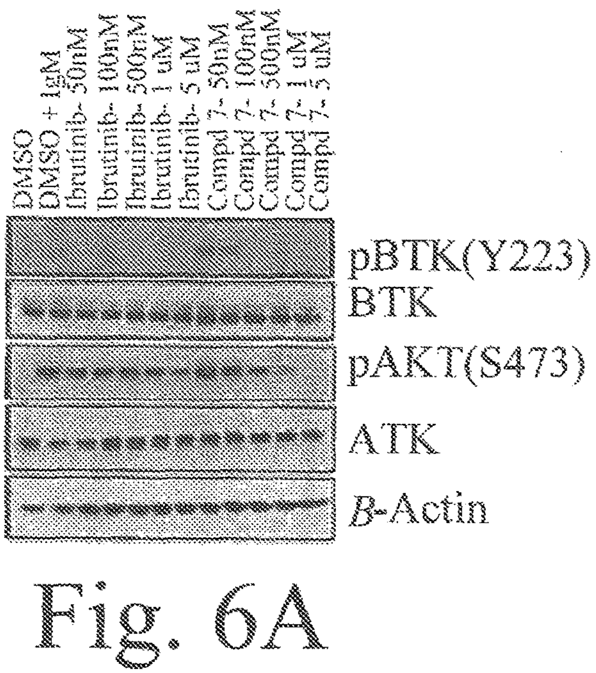
FIG. 6A shows immunoblotting data in JeKo-BTK-WT cells for the indicated targets at differing concentrations of Ibrutinib and Compd 7.
Figure 6B:
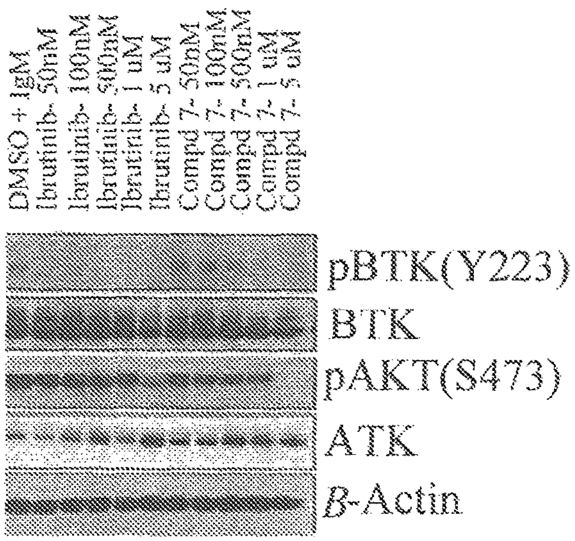
FIG. 6B shows immunoblotting data in JeKo-BTK-C481S cells for the indicated targets at differing concentrations of Ibrutinib and Compd 7.
Figure 6C:
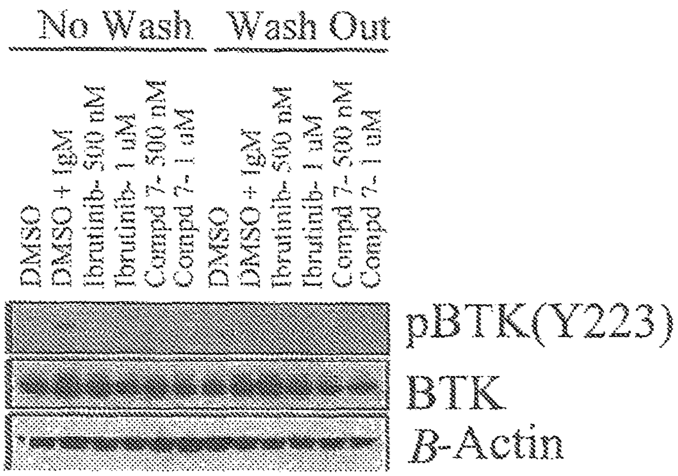
FIG. 6C shows immunoblotting data in JeKo-BTK-C481S cells for the indicated targets at differing concentrations of Ibrutinib and Compd 7 after the cells were washed and allowed to recover for 4 hours prior to lysing.

Referring to FIGS. 6A-6C, Western blot analyses are shown for JeKo-BTK wild-type cells (FIG. 6A) and JeKo-BTK-C418S cells (FIG. 6B) that were exposed for 1 hour to different concentrations of Ibrutinib and Compound 7 and probed for pBTK(Y223), BTK, pAKT(S473), AKT, and β-actin. FIG. 6C shows the results for JeKo-BTK-C481S cells treated with different concentrations of Compound 7 and Ibrutinib for 3 hours, washed with PBS and allowed to recover for 4 hours prior to lysis and immunoblotting for pBTK, BTK, and β-actin. FIGS. 6A and 6B show that both Ibrutinib and Compound 7 inhibit pBTK but only Compound 7 inhibits pAKT and in a dose dependent manner. The washout experiment data shown in 6C indicates that the pBTK suppression activity of Ibrutinib and Compound 7 are irreversible as they do not diminish upon washout.

Example 18. Compound 7 has BRD4 Inhibitory Activity

Figure 7:
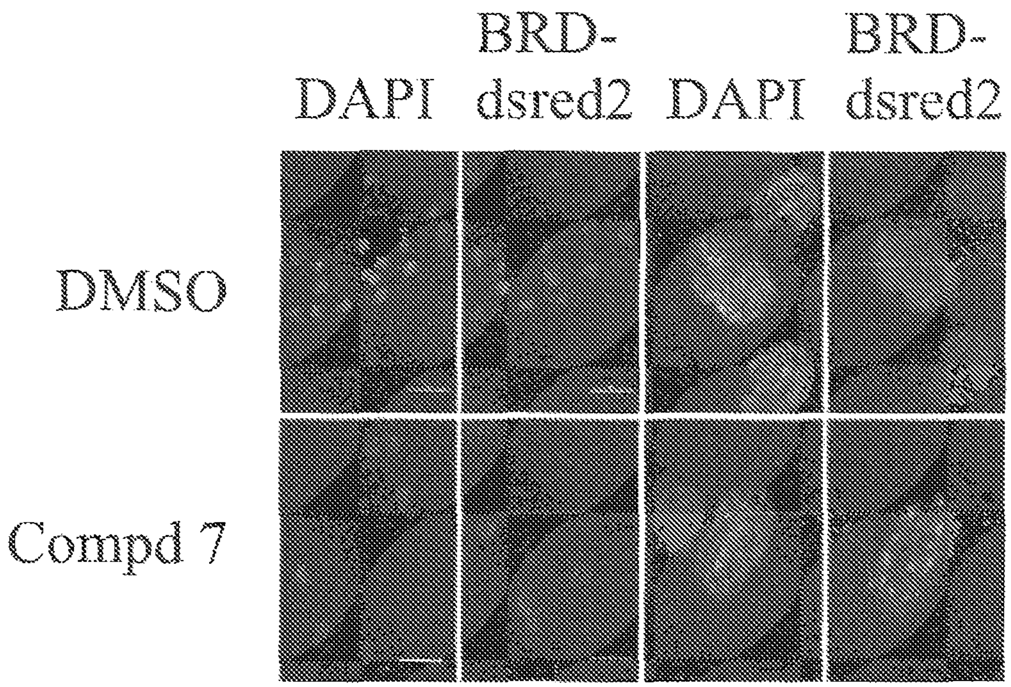
FIG. 7 shows the results of a chromatin-release assay performed in JeKo cells treated with 1 μM Compd 7.

A chromatin-release assay was performed on JeKo cells treated with 1 μM Compound 7. FIG. 7 shows that Compound 7 released a fluorophore-tagged BRD4 fusion protein from chromatin as assessed by confocal microscopy. This demonstrates the inhibition of the function of BRD4 which is to bind to the acetyl-lysine group of chromatin as part of it epigenetic regulation.

Example 19. Preparation of Compound 21

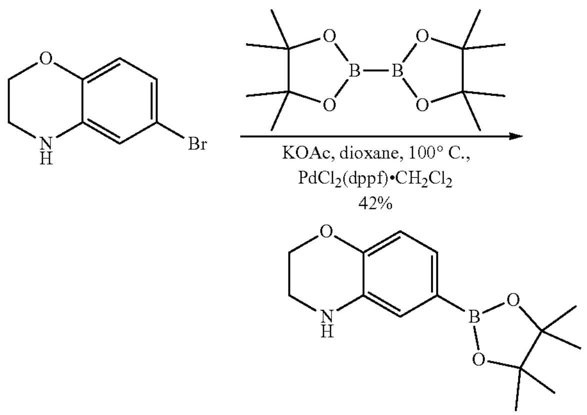

Step 1:4,4,5,5-Tetramethyl-2-(1-oxa-4-aza-3,4-dihydro-2H-naphth-6-yl)-1,3,2-dioxaborolane A mixture containing 6-bromo-1-oxa-4-aza-3,4-dihydro-2H-naphthalene (3.51 g, 16.4 mmol), anhydrous KOAc (3.62 g, 36.9 mmol), pinacol diborane (10.4 g, 41.0 mmol) in 1,4-dioxane was degassed under bubbling $N_2$ for 15 minutes. $PdCl_2$ (dppf) dichloromethane adduct (670 mg, 0.82 mmol) was added and the resulting mixture was stirred and heated to 100° C. for 18 hours, after which time the reaction was deemed complete by LCMS analysis. The reaction was cooled, filtered through a short pad of CELITE and concentrated in vacuo. The crude residue was purified by silica gel chromatography, eluting with a 0-15% hexanes/EtOAc gradient. The product was obtained as a colorless oil. Yield=1.81 g (6.9 mmol, 42%).

LC/MS-HPLC (254 nm)—Rt 2.65 min. MS (ESI) m/z 262.4 [$M^+$+$H^+$]. Purity=95% by UV (254 nm).

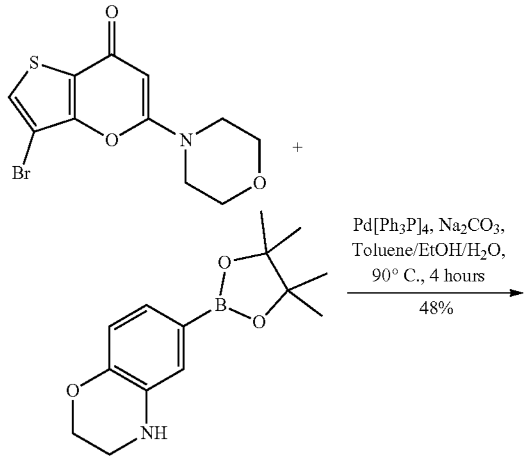

-continued

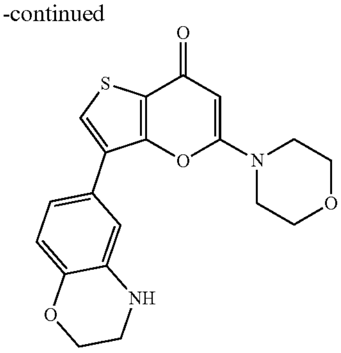

Step 2:5-Morpholino-3-(1-oxa-4-aza-3,4-dihydro-2H-naphth-6-yl)-4-oxa-1-thia-7-indenone A mixture of 3-bromo-5-morpholino-4-oxa-1-thia-7-indenone (1.68 g., 5.30 mmol) and 4,4,5,5-tetramethyl-2-(1-oxa-4-aza-3,4-dihydro-2H-naphth-6-yl)-1,3,2-dioxaborolane (1.80 g, 6.89 mmol) $Na_2CO_3$ 2M aqueous solution (18 mL), toluene:ethanol 2:1 v/v (55 mL) and $Pd[Ph_3P]_4$ (360 mg, 0.31 mmol) were stirred together at 90° C. for 4 h. Then the reaction mixture was cooled and diluted with ethyl acetate (200 mL) and filtered. The filtrate was washed with water and dried ($Na_2SO_4$), filtered and concentrated to yield crude product which was purified on silica column using 0-5% MeOH/EtOAc gradient system. Useful fractions were pulled together and concentrated to yield pure final product (950 mg, 48% yield).

LC/MS-HPLC (254 nm)—Rt 2.34 min. MS (ESI) m/z 371.3 [$M^+$+$H^+$]. Purity=98% by UV (254 nm).

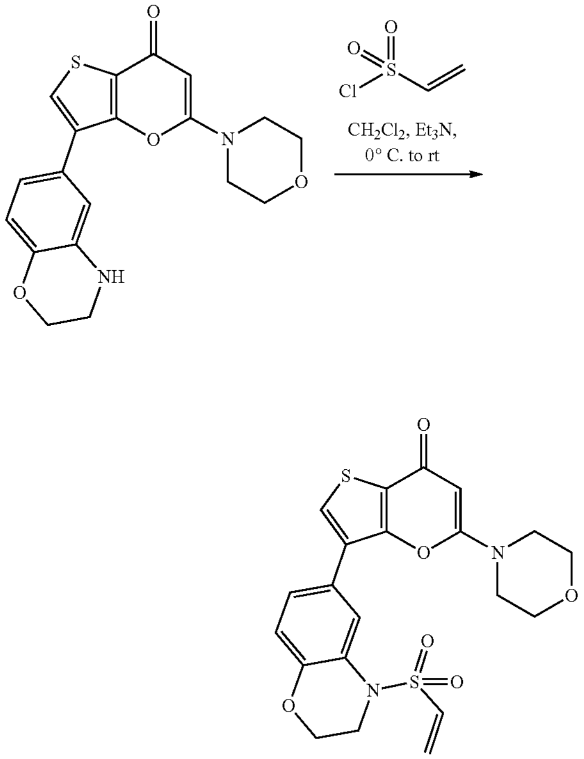

Step 3:5-Morpholino-3-[4-(vinylsulfonyl)-1-oxa-4-aza-3,4-dihydro-2H-naphth-6-yl]-4-oxa-1-thia-7-indenone (Compound 21)

A mixture 5-morpholino-3-(1-oxa-4-aza-3,4-dihydro-2H-naphth-6-yl)-4-oxa-1-thia-7-indenone (370 mg, 1.0 mmol), triethylamine (842 μL, 6.0 mmol) in DCM (5 mL) was cooled to 0° C. and treated with ethenesulfonyl chloride (508 mg, 4.0 mmol). Resulting mixture was stirred at RT overnight and then diluted with DCM, washed with water and concentrated to yield crude product which was purified by silica-gel column chromatography using 0-100% hexanes/EtOAc (gradient) to give the final product Compound 21 as an off white solid (190 mg, 0.41 mmol, 41%). LC/MS-HPLC (254 nm)—Rt 2.42 min. MS (ESI) m/z 461.5 [$M^{+}$+$H^{+}$]. Purity=98% by UV (254 nm).

Example 20. Preparation of Compound II-18

Step 1: Synthesis of 3-(m-aminophenyl)-5-morpholino-4-oxa-1-thia-7-indenone

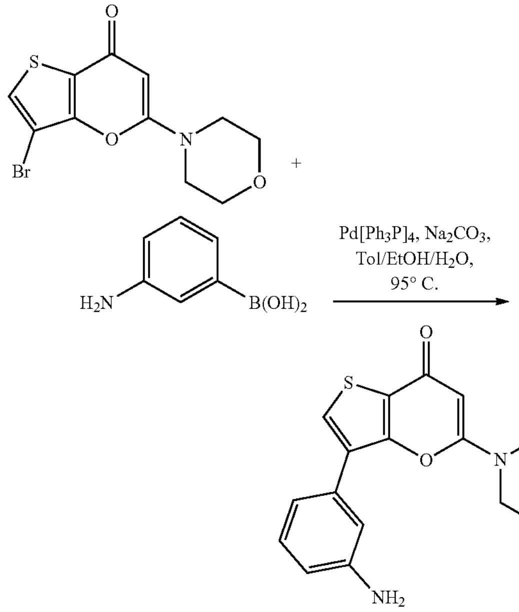

A stirred solution of 3-bromo-5-morpholino-4-oxa-1-thia-7-indenone (2.58 g, 8.2 mmol), 3-amino-phenyl boronic acid (1.57 g, 11.4 mmol) and $Pd[Ph_3P]_4$ (320 mg, 0.28 mmol) in a mixture of toluene/ethanol (2:1 v/v, 90 mL) was treated with a 2 M aqueous $Na_2CO_3$ solution (30 mL) under nitrogen at 95° C. for 18 hours. The resulting mixture was cooled, diluted with ethyl acetate (100 mL), filtered through a pad of CELITE and the filtrate was washed with water (2×50 mL), dried ($Na_2SO_4$), filtered and concentrated to yield the crude amine. The crude material was purified on a silica gel column eluting with 50-100% ethyl acetate/hexane gradient, followed by 2-10% methanol in ethyl acetate, yielding pure amine (1.69 g, 63% yield). LC/MS: Peak at 0.08 minutes 329.2 (m/z). Purity: 99.5%. TLC on silica gel plate: 5% MeOH/EA, Single spot, $R_f$=0.16

Step 2: Synthesis of 5-morpholino-3-[m-(vinylsulfonylamino)phenyl]-4-oxa-1-thia-7-indenone (Compound II-18)

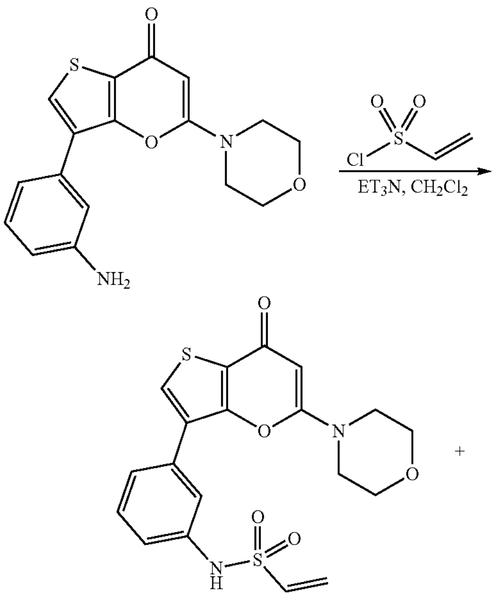

Compound II-18

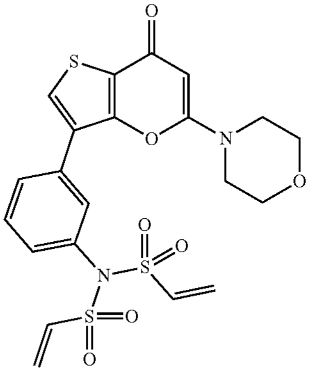

Compound II-6

3-(m-Aminophenyl)-5-morpholino-4-oxa-1-thia-7-indenone (1.68 g, 5.13 mmol) and triethylamine (1.8 mL, 12.83 mmol) were dissolved in dichloromethane (1.8 mL) and the resulting mixture was cooled −78° C., under nitrogen with vigorous stirring. To this mixture, ethene sulphonyl chloride (650 mg, 5.13 mmol) was added dropwise in two to three minutes. The resulting mixture was stirred for an additional hour at −78° C. and then warmed to 0° C. and kept at that temperature for one hour. The reaction was then immediately quenched with 1 mL of water and diluted with dichloromethane (50 mL). The organic layer was washed with water, dried ($Na_2SO_4$), filtered and concentrated to yield the crude sulfonamide. This material was purified on silica gel column chromatography using 0-15% acetone/dichloromethane twice. The faster moving compound was isolated as the disulfonamide, Compound II-6 (274 mg, 11%).

LC/MS: Peak at 2.45 min 509.3 (m/z). Purity: 99.5%. The disulfonamide was assigned Compound II-6.

The slower moving compound was the desired mono sulfonamide Compound II-18 (75 mg, 4% yield).

LC/MS: Peak at 2.28 min 419.4 (m/z), Purity: 99.5%.

What is claimed is:

1. A compound of Formula II or a pharmaceutically acceptable salt thereof,

Formula II

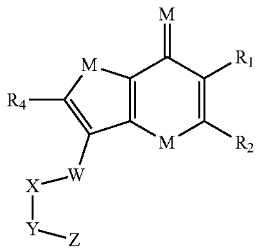

wherein M is independently O or S;

R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1;

R4 is selected from R1;

W is null, NR1, O, S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

X is null or O, N, NR1 or S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

provided that if Wis N, O, or S then X cannot be N, O, or S; and if X is N, O, or S then W cannot be N, O, or S;

Y is null, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate; and Z is a BTK covalent binding group selected from a Michael acceptor, olefin, substituted olefin, acetylenic, substituted acetylenic, alpha-chloroacetamide, and chlorofluoro-acetamide; and wherein W, X, and Y are not all null.

2. A compound of claim 1 wherein said compound has the Formula III or a pharmaceutically acceptable salt thereof, Formula III

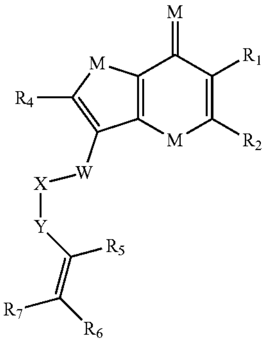

wherein M is independently O or S;

R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1;

R4 is selected from R1;

W is null, NR1, O, S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

X is null or O, N, NR1 or S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

provided that if Wis N, O, or S then X cannot be N, O, or S; and if X is N, O, or S then W cannot be N, O, or S;

Y is null, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate; and R5, R6, R7 are each independently selected from R1.

3. A compound of claim 1 wherein said compound has the Formula IV or a pharmaceutically acceptable salt thereof, Formula IV

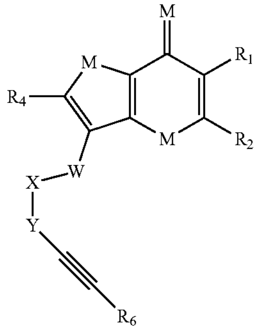

wherein M is independently O or S;

R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1;

R4 is selected from R1;

W is null, NR1, O, S, $CH_2$, Ar, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

X is null or O, N, NR1 or S, $CH_2$, Ar, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N, N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

provided that if Wis N, O, or S then X cannot be N, O, or S; and if X is N, O, or S then W cannot be N, O, or S;

Y is null, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate; and R8 is selected from R1.

4. A compound or a pharmaceutically acceptable salt thereof selected from the group consisting of

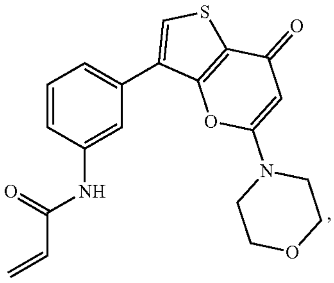
,
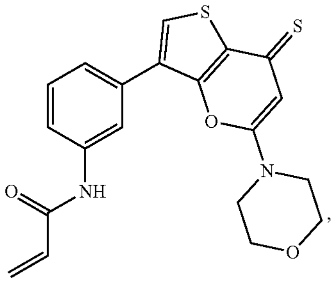
,
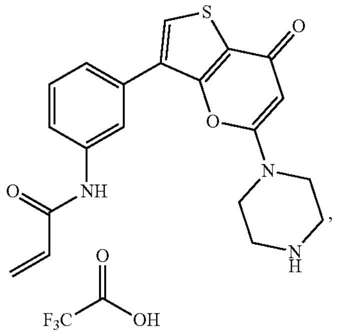
,
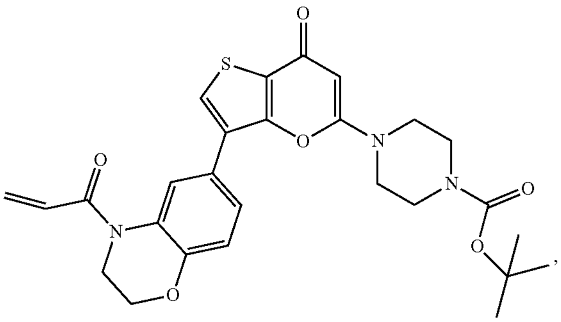
,
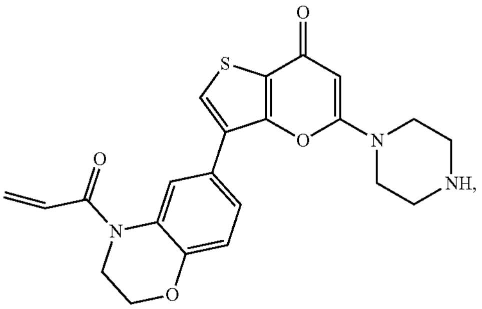
,
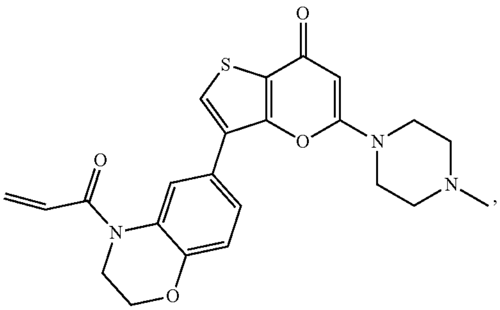
,
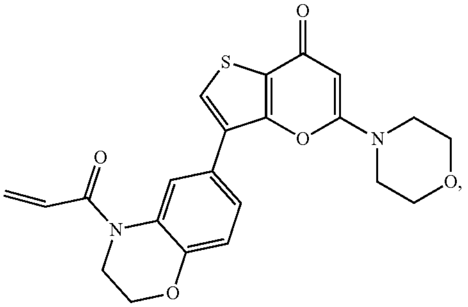
, -continued
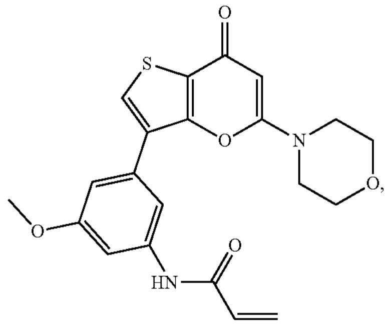
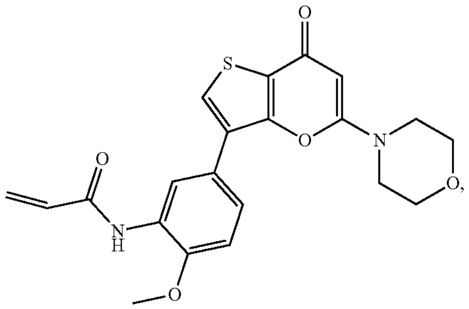
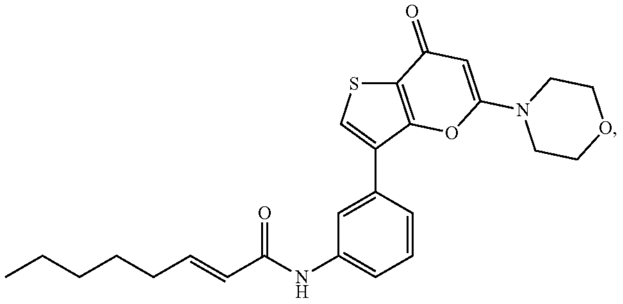
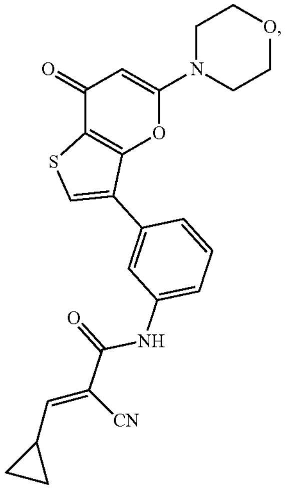
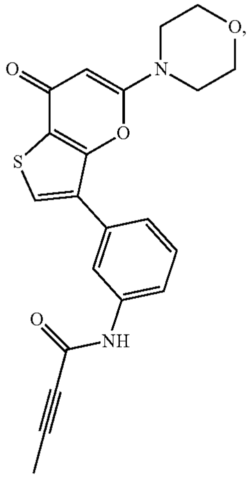
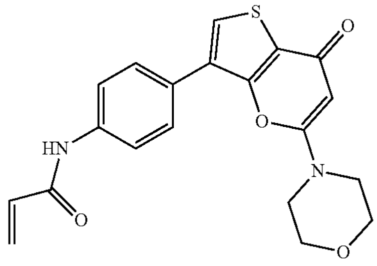
,
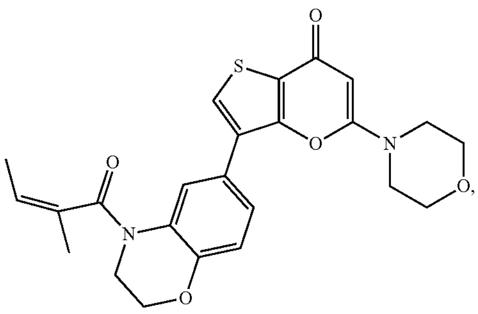
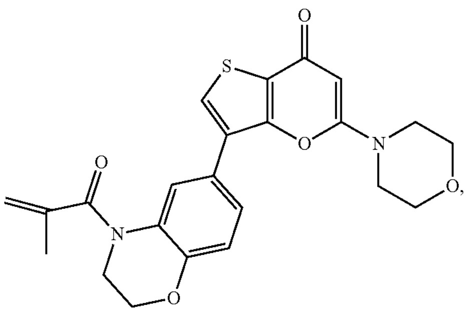

-continued
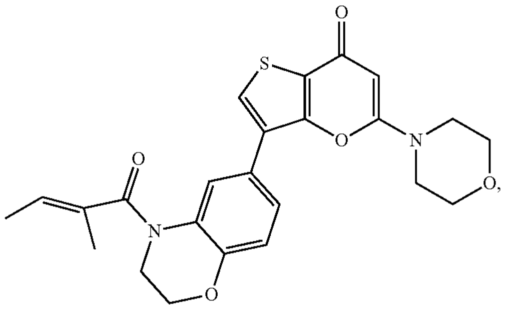
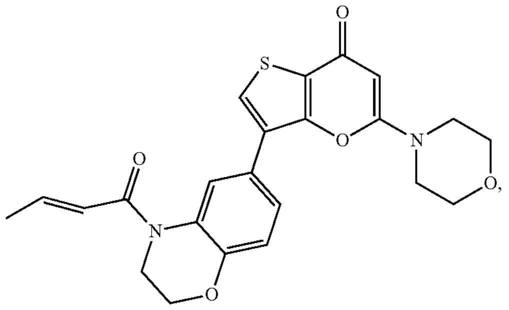
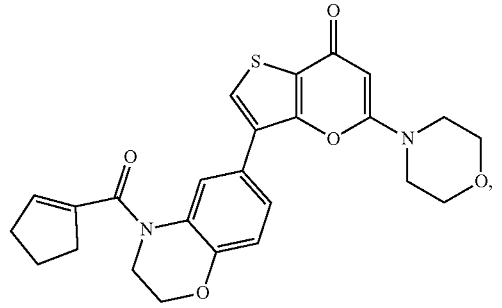
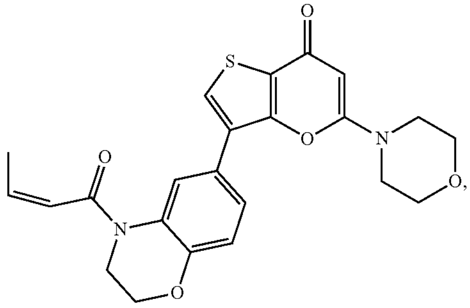
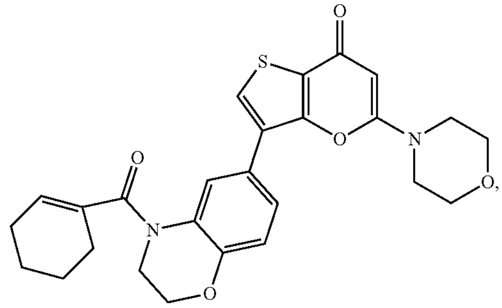
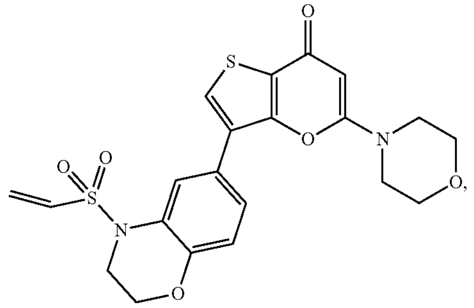
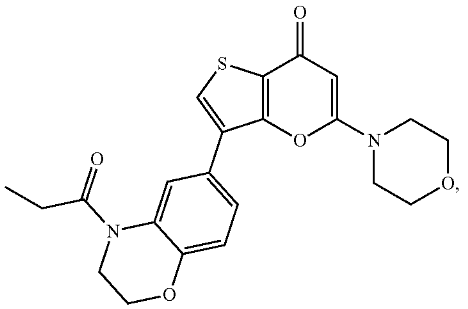
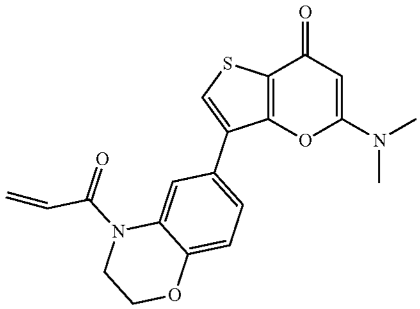
,
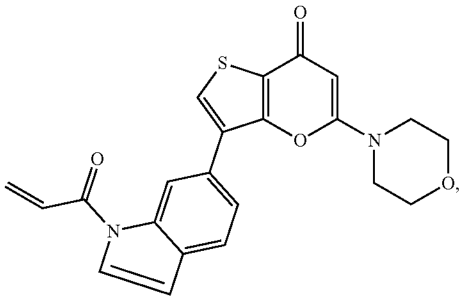
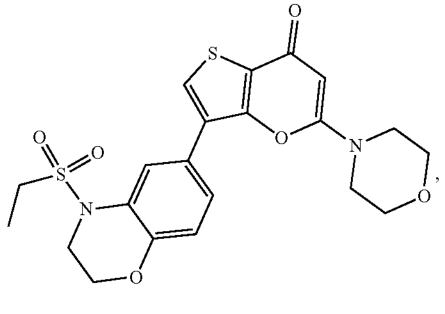

-continued
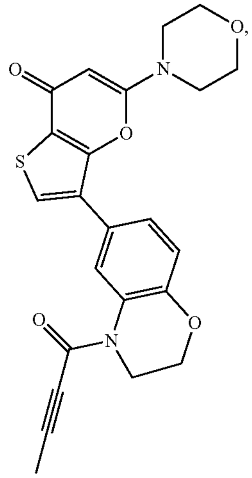
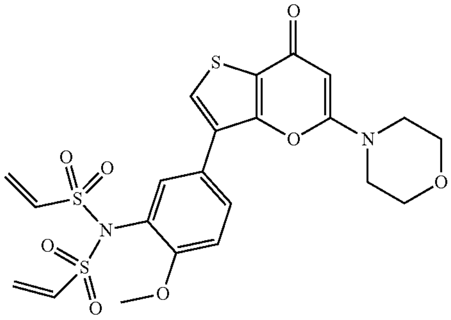
,
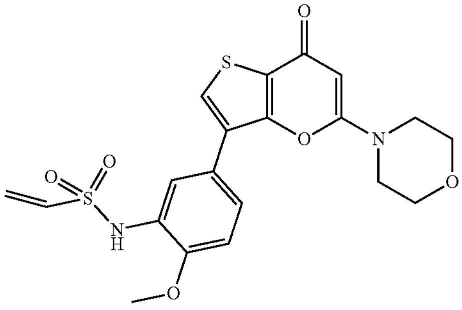
,
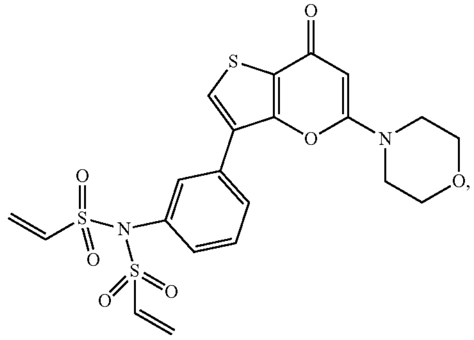
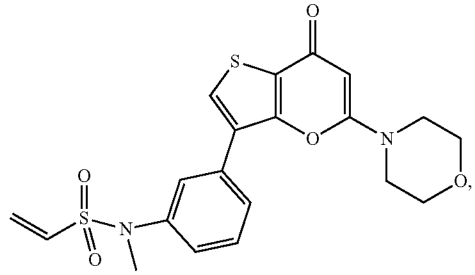
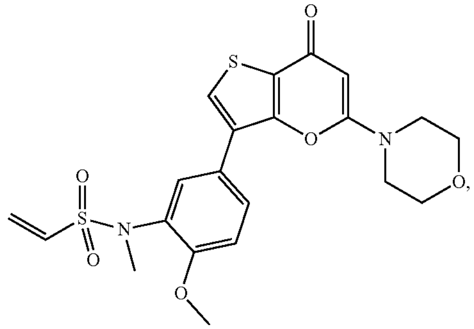
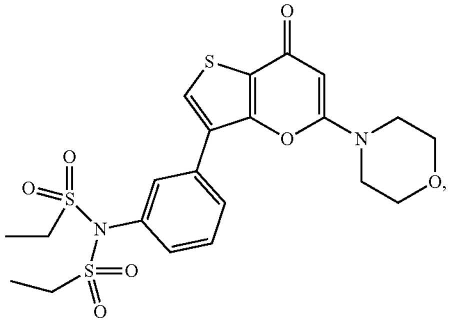
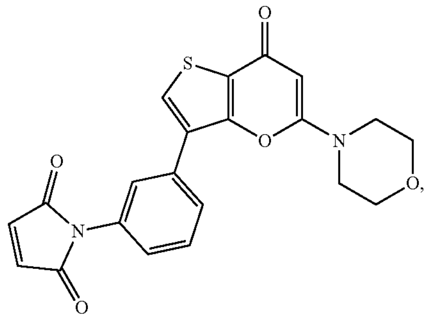
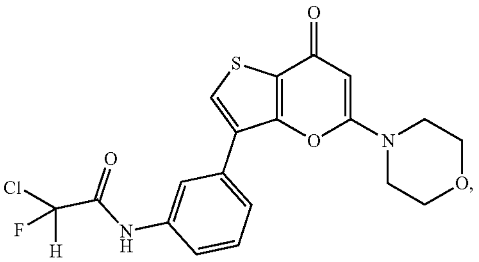

-continued
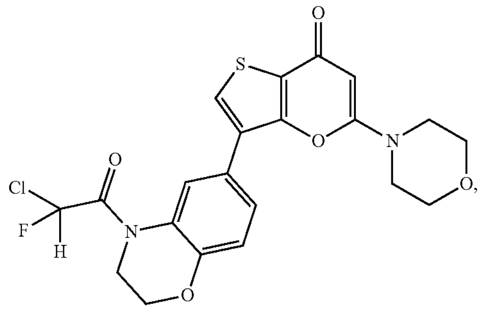
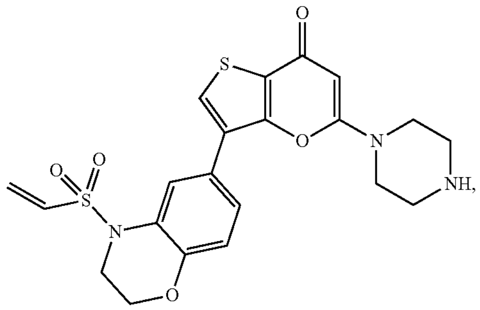
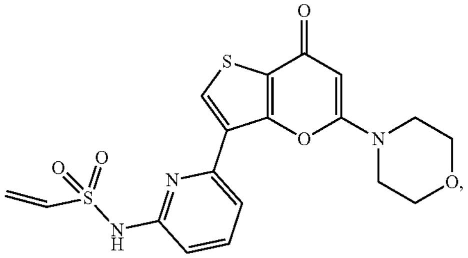
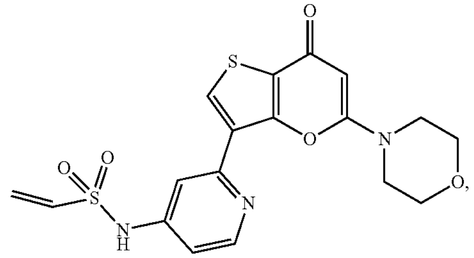
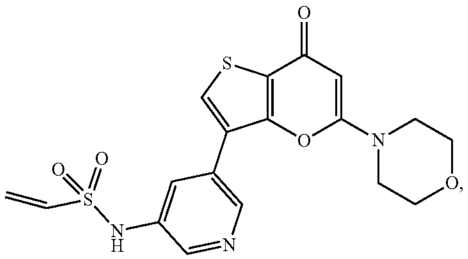
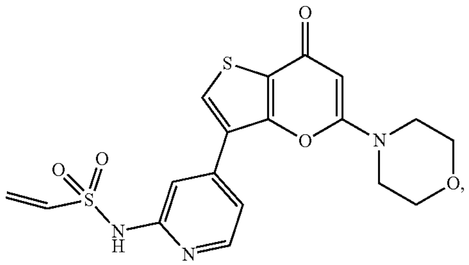
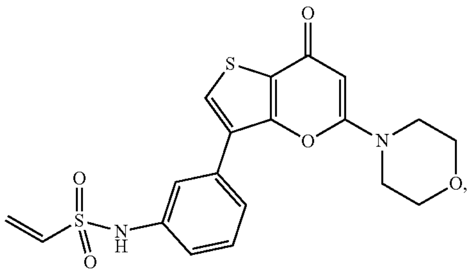
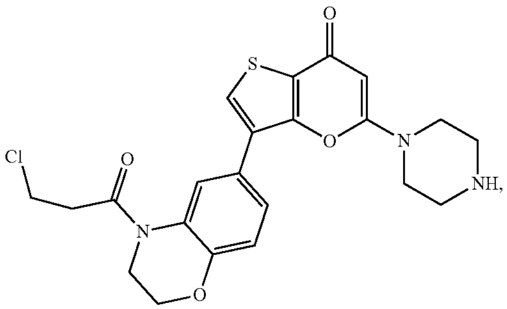
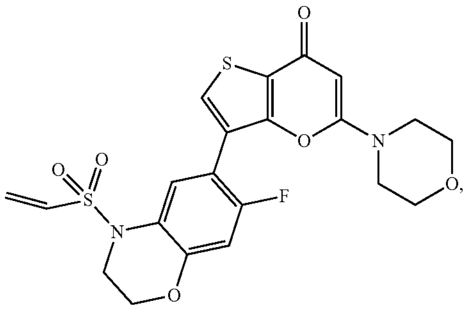
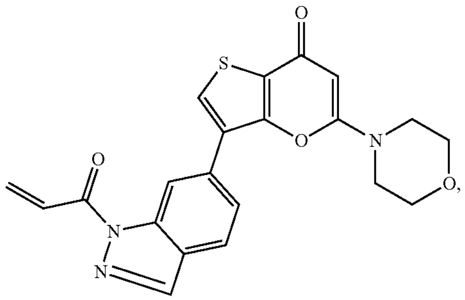

-continued
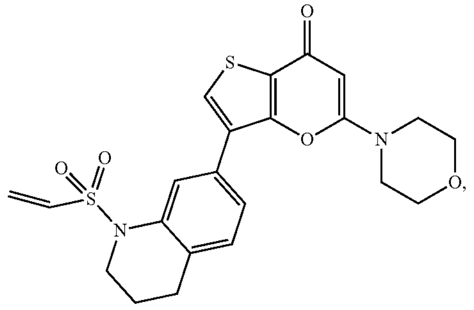
,
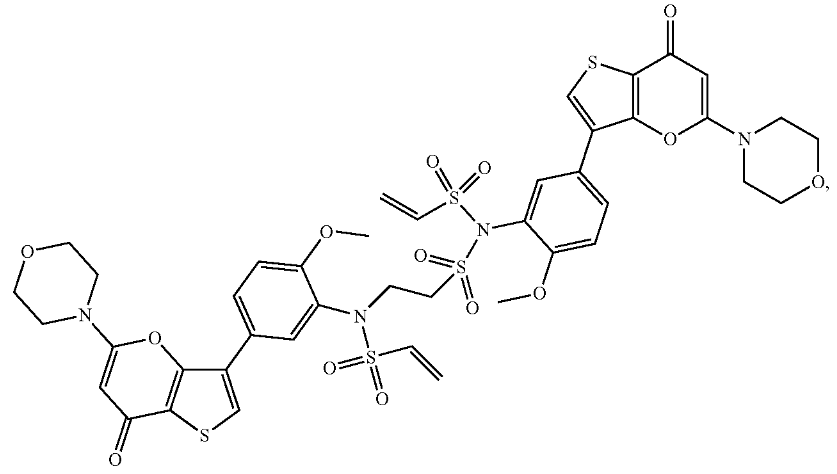
,
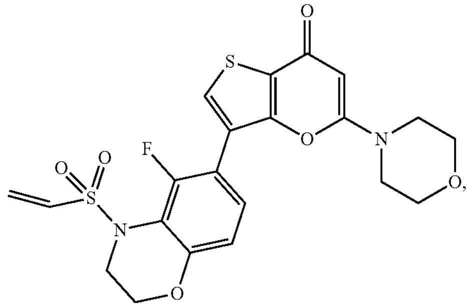
,
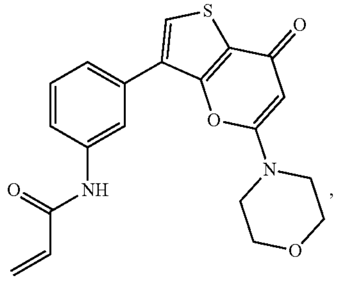
,
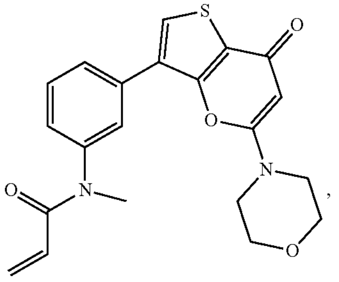
,
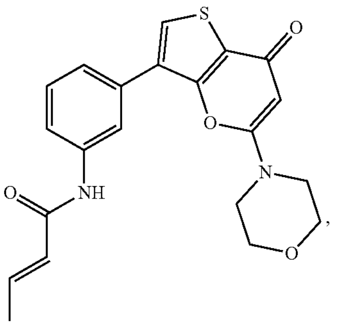
,
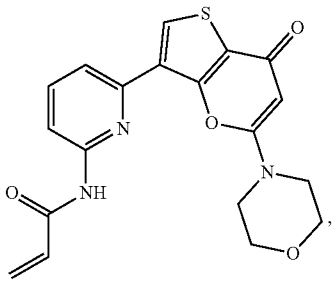
,
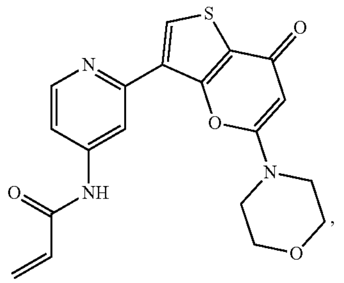
,
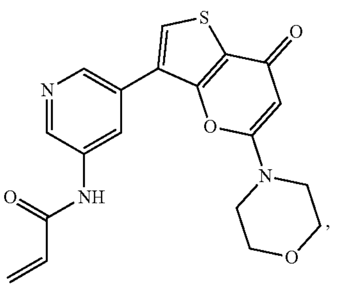
,
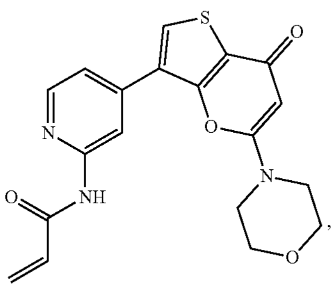
,
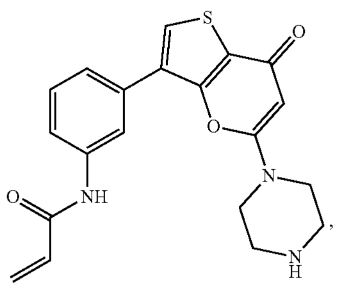
, -continued
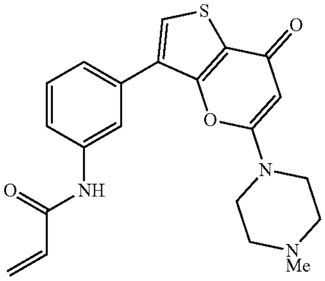,
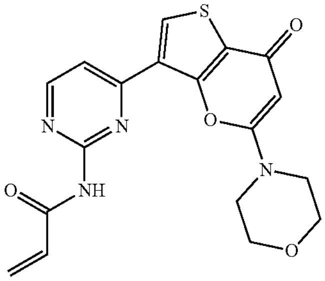,
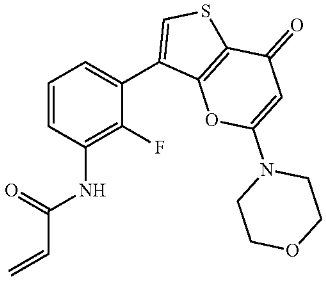,
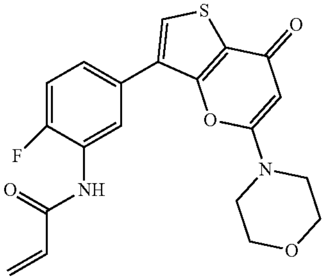,
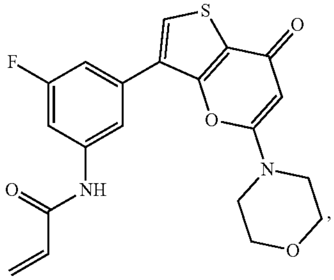,
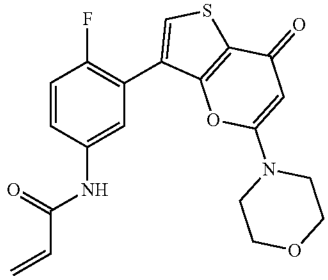,
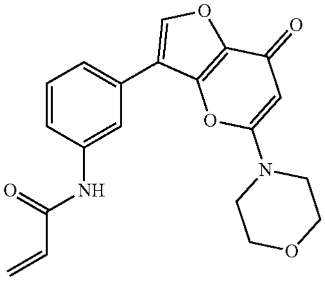,
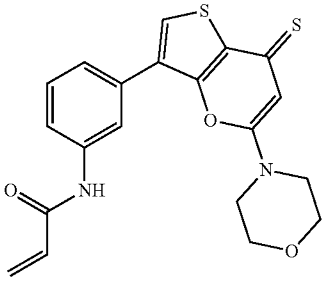,
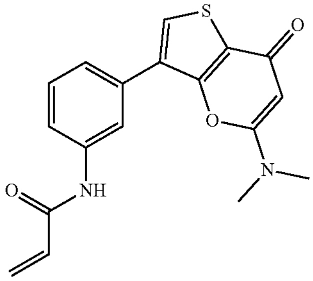,
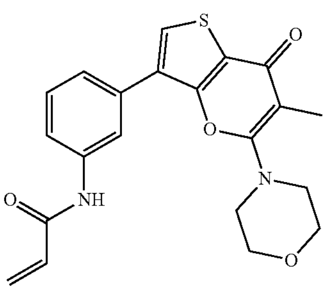,
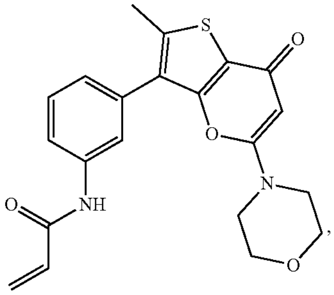,
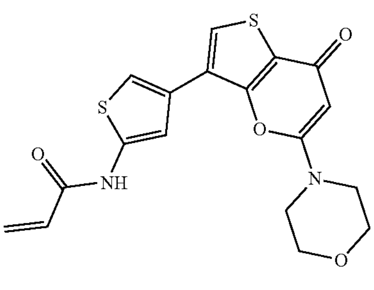,
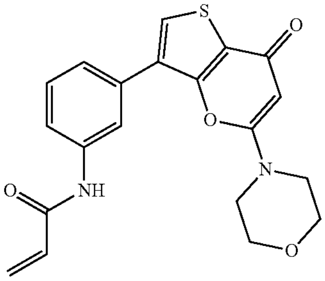,
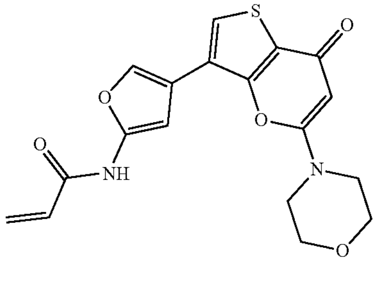,
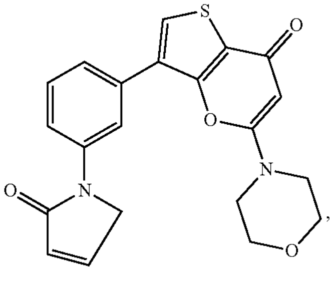,
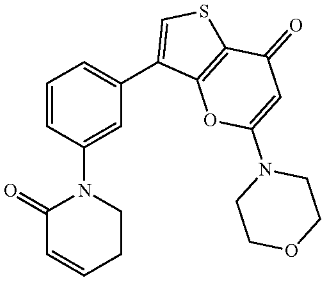,
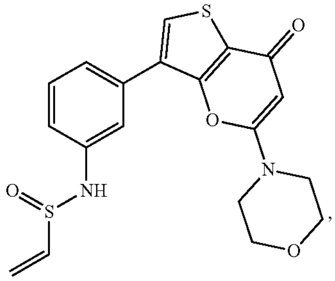,
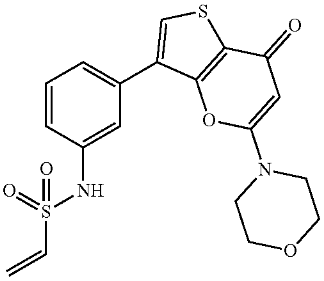, -continued
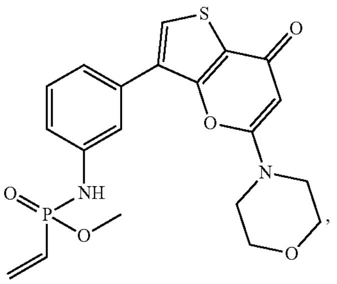
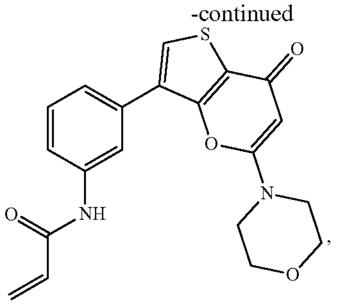
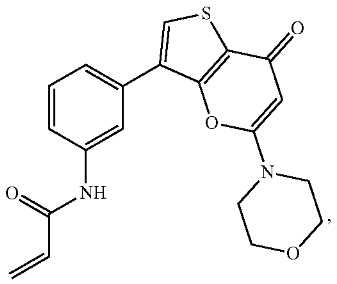
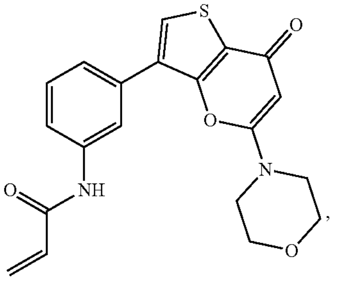
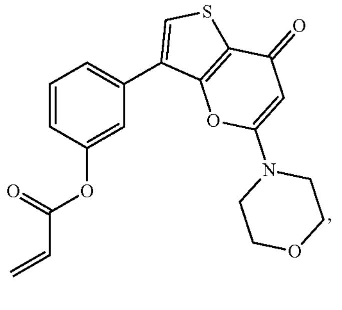
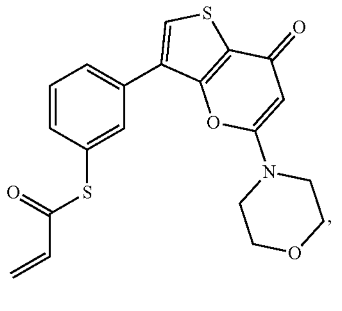
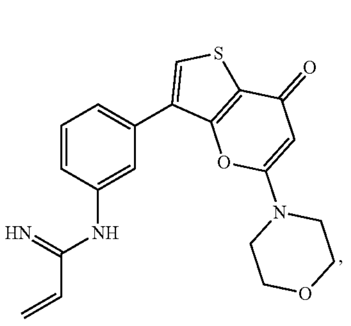
-continued
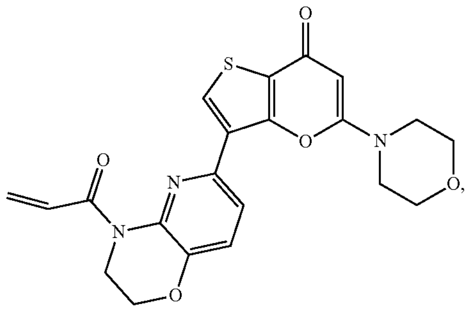
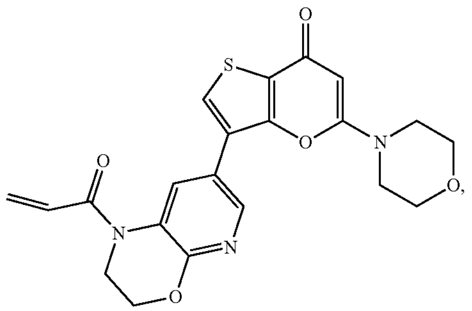
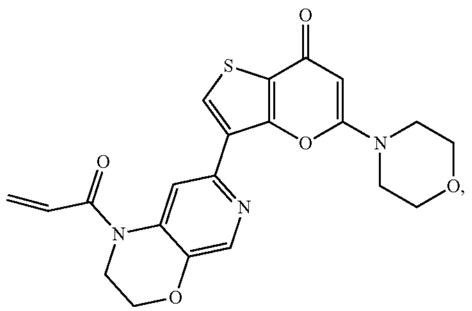

-continued
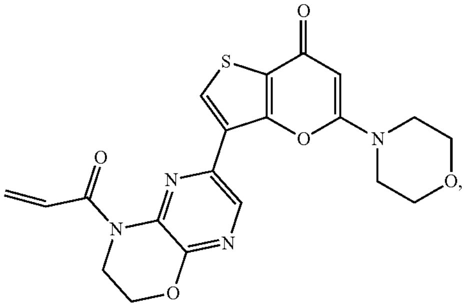
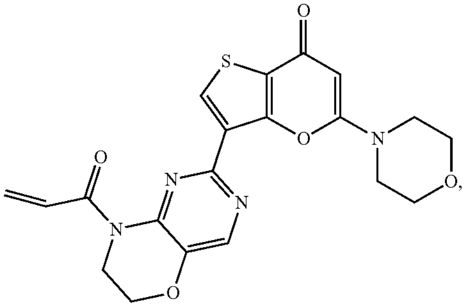
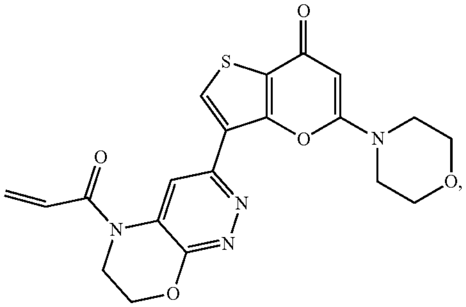
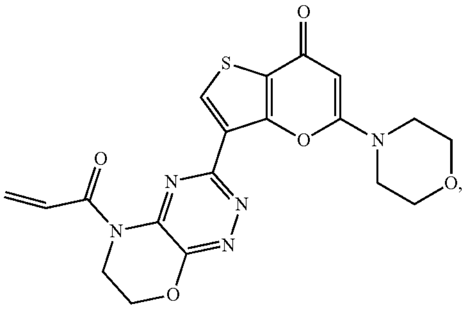
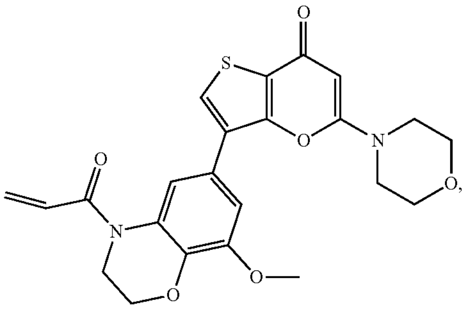
-continued
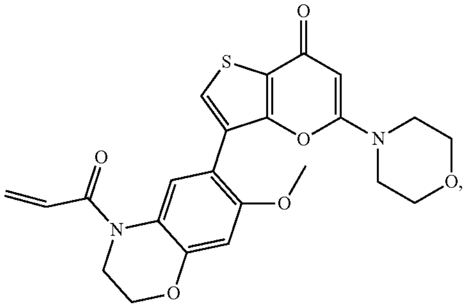
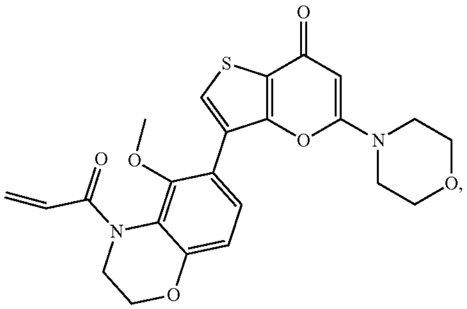
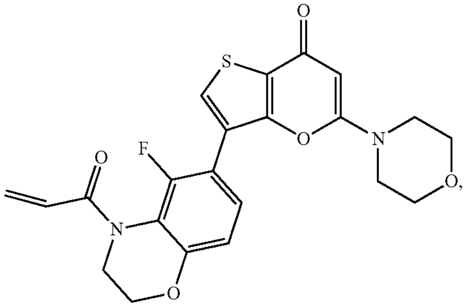
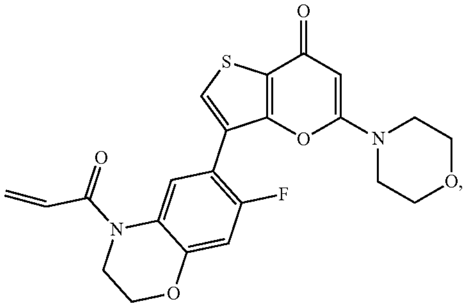
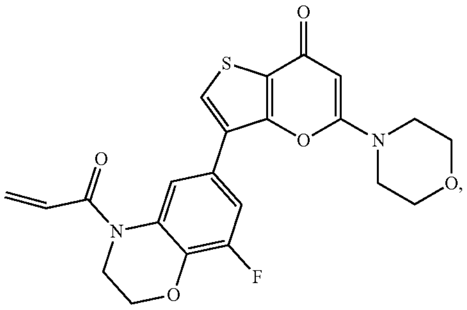

-continued
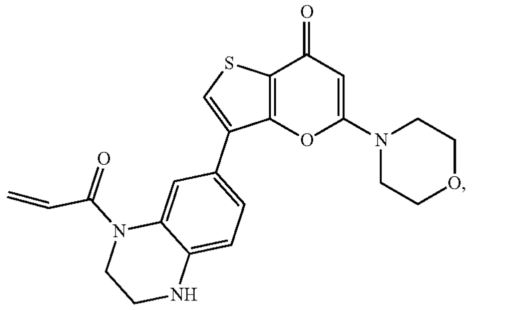
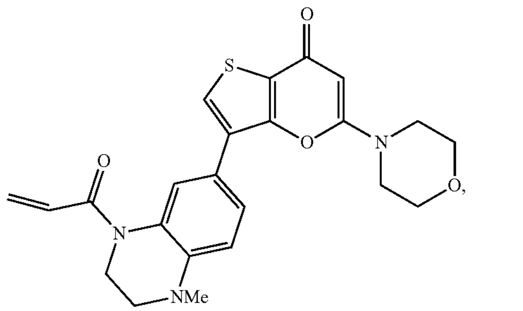
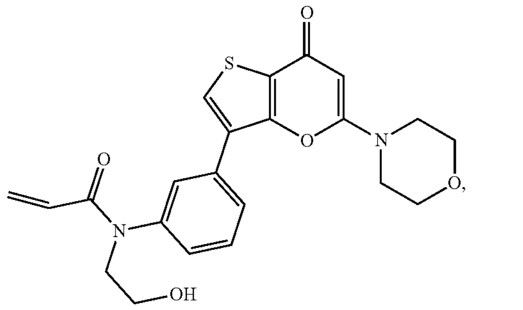
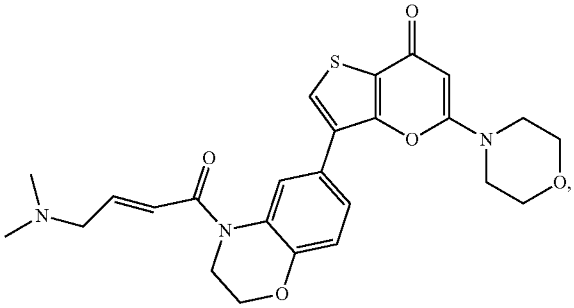
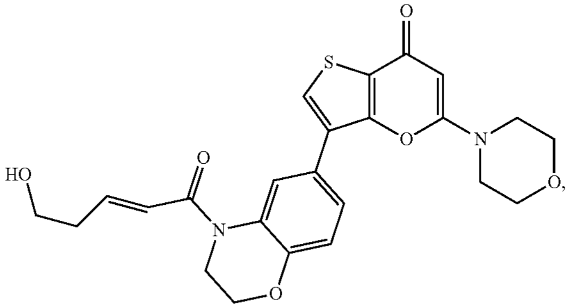
-continued
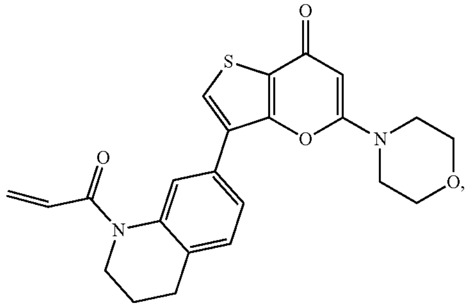
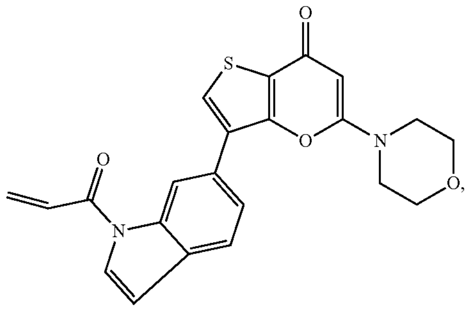
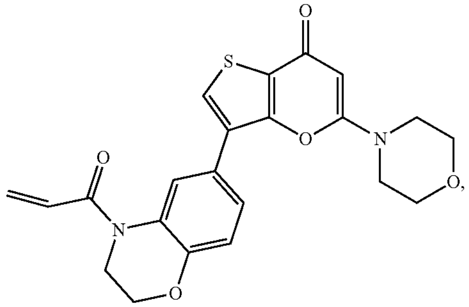
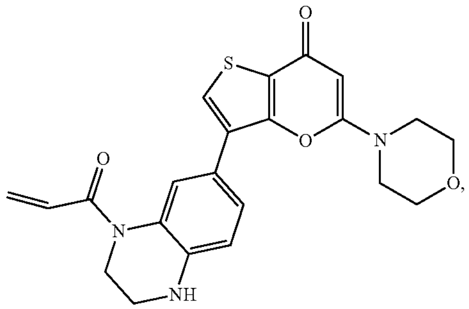
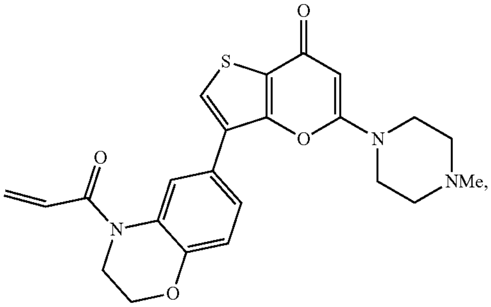

-continued
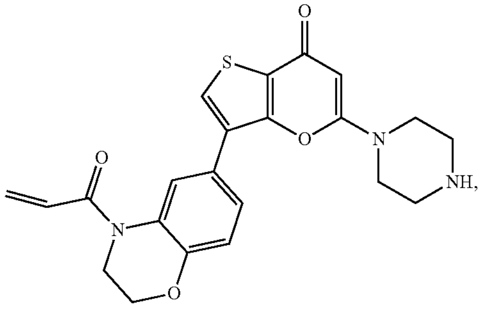
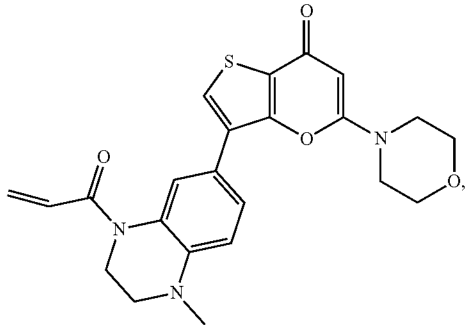
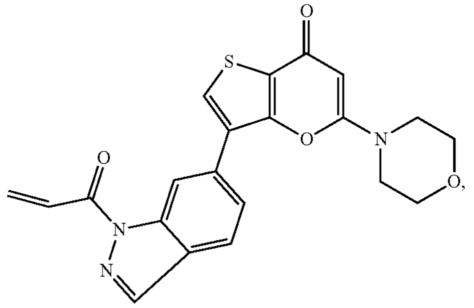
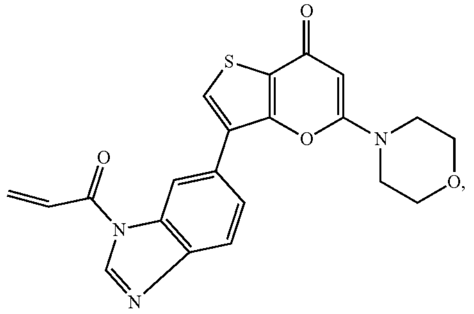
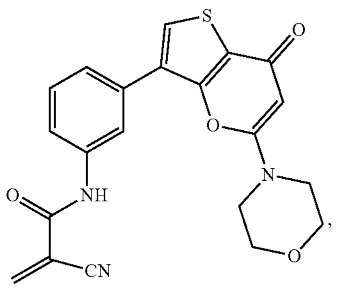
-continued
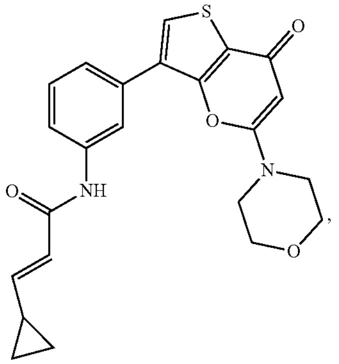
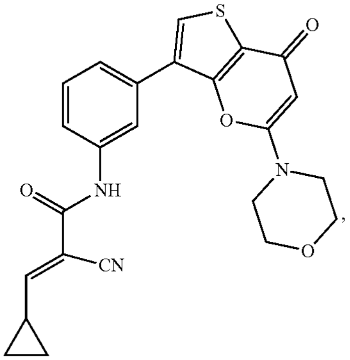
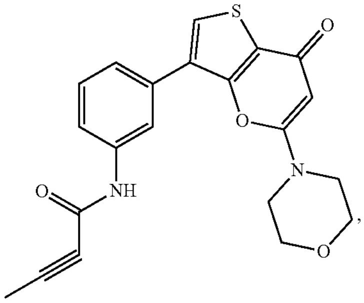
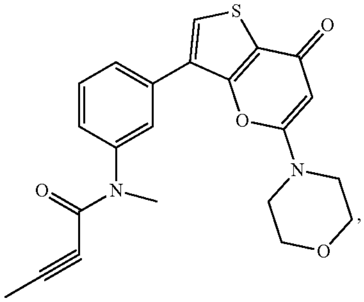
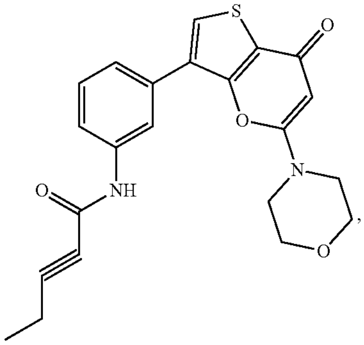

-continued
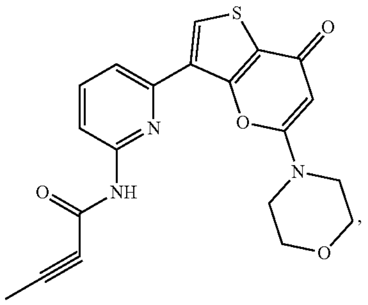
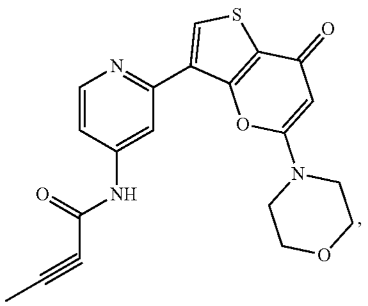
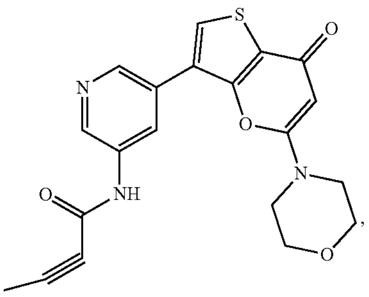
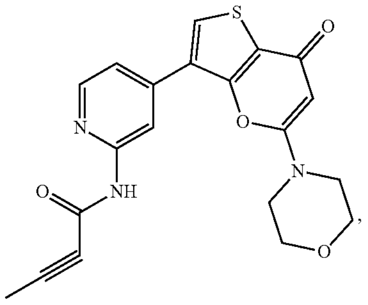
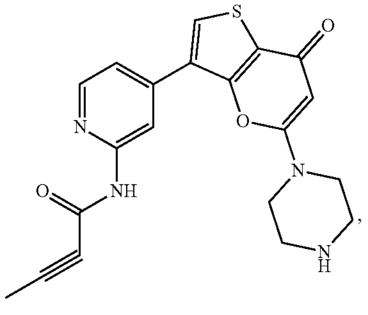
-continued
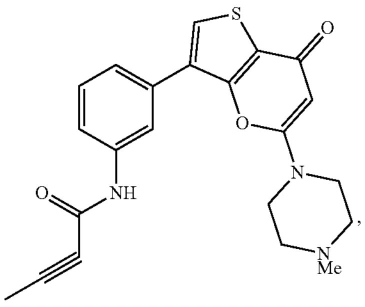
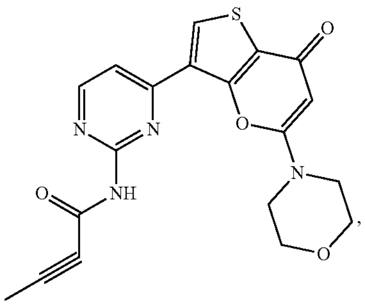
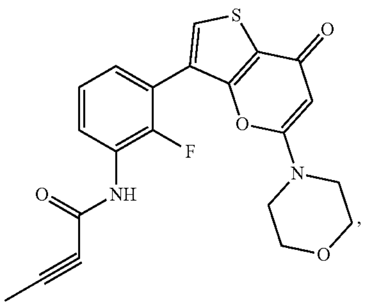
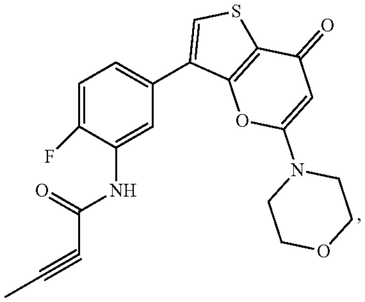
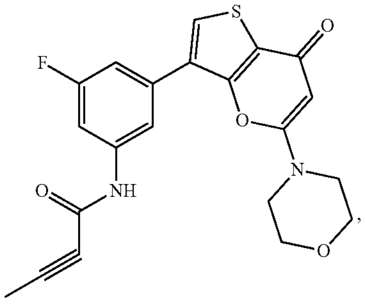

-continued
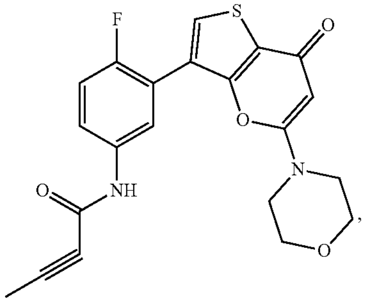,
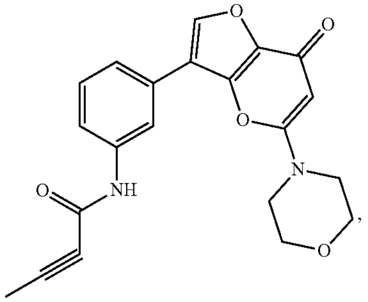,
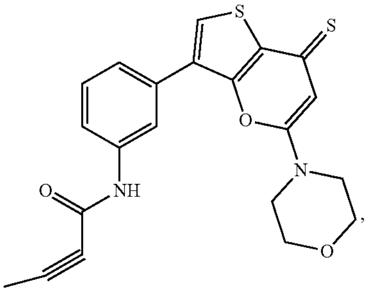,
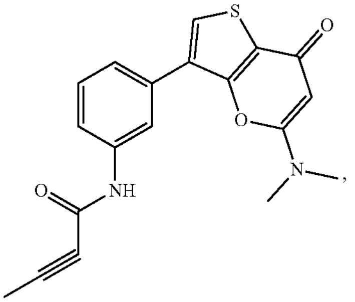,
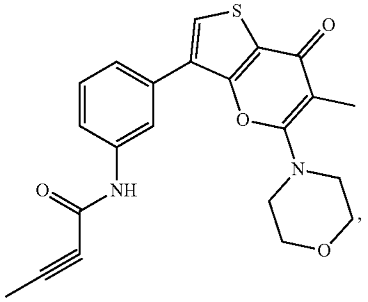,
-continued
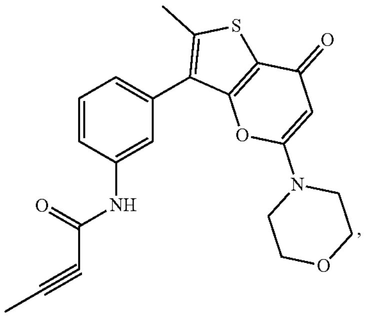,
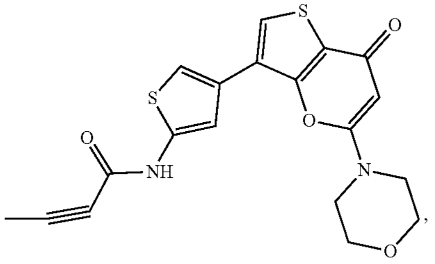,
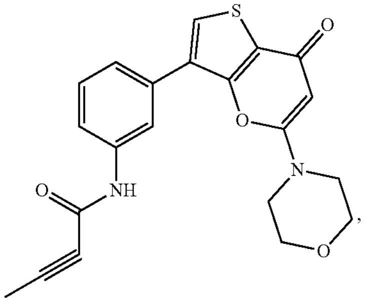,
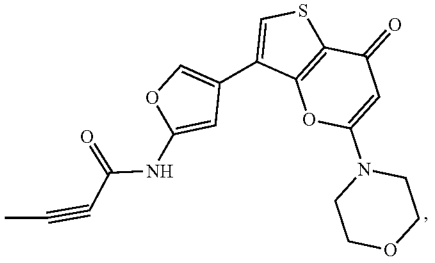,
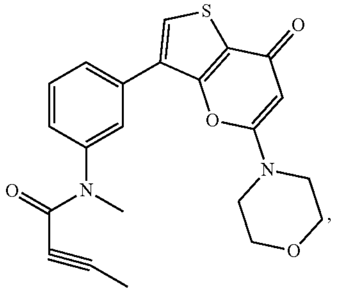,
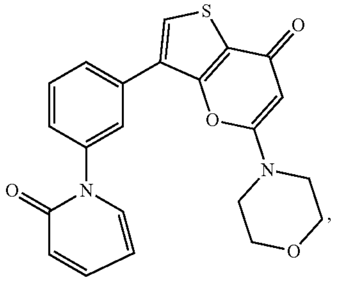, -continued
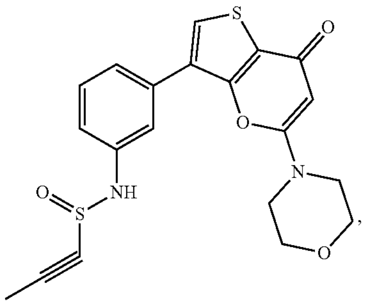
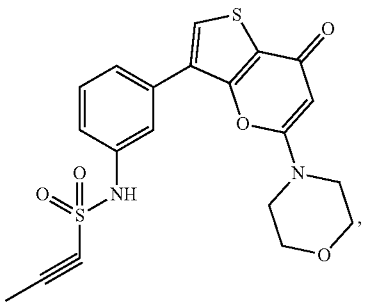
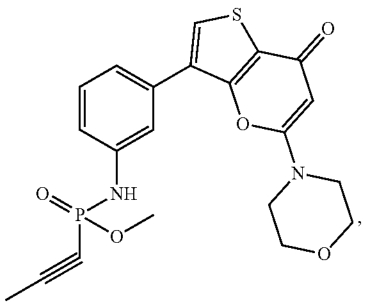
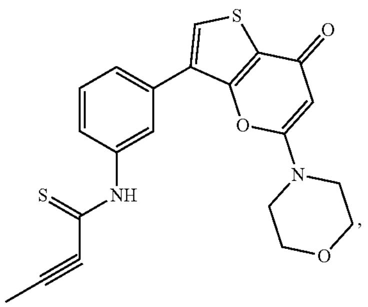
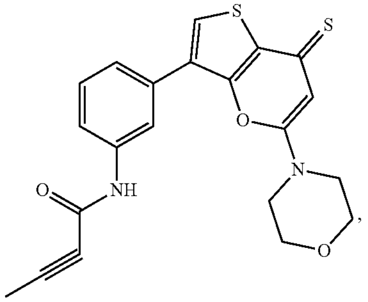
-continued
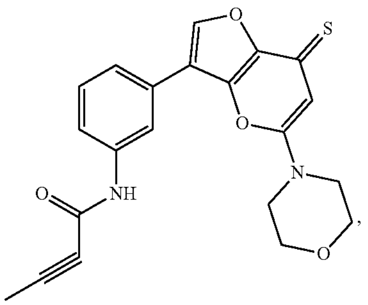
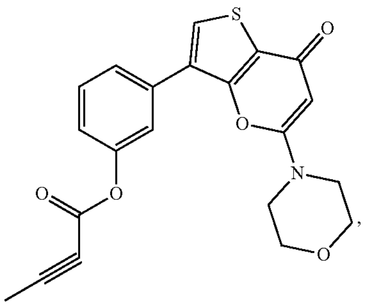
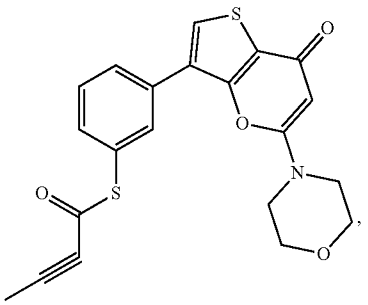
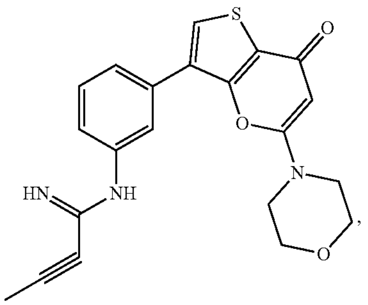
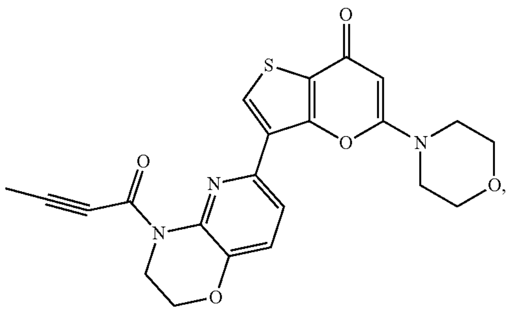

-continued
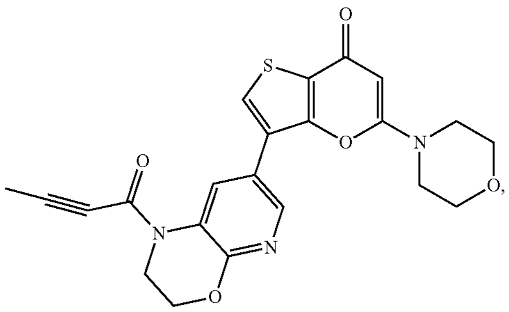
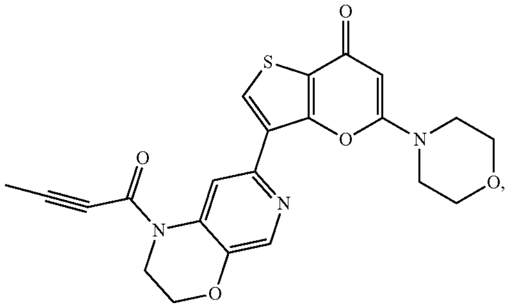
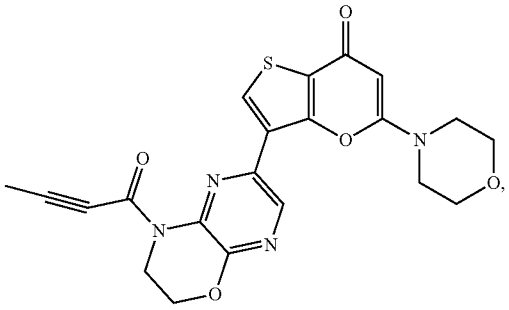
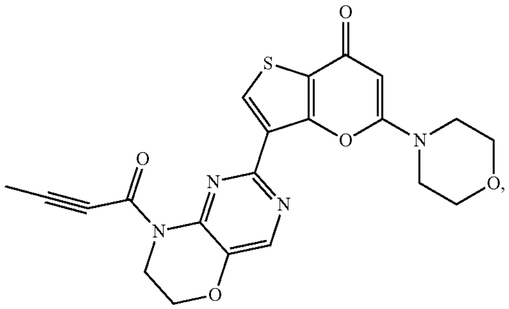
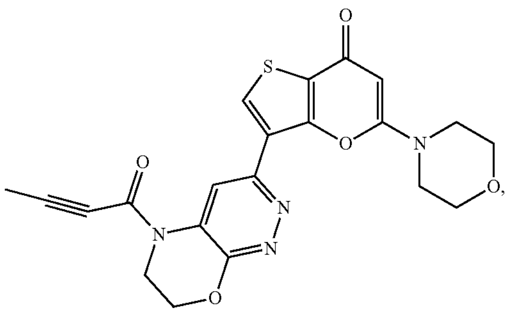
-continued
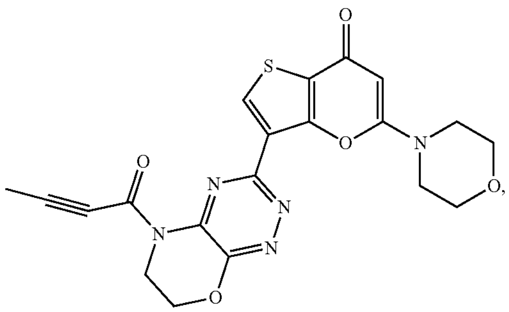
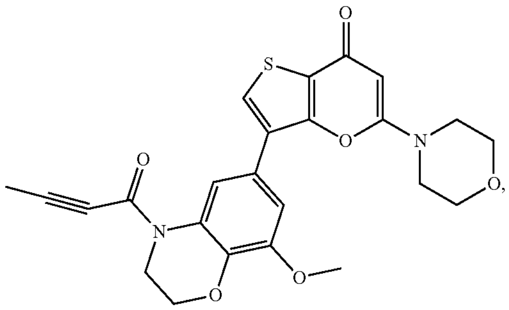
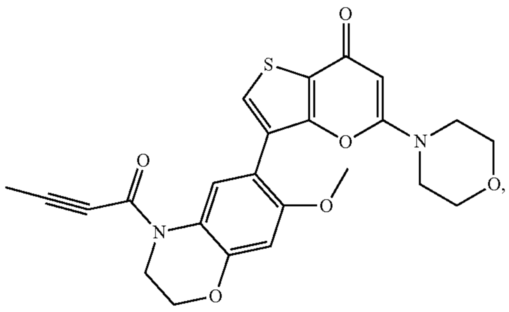
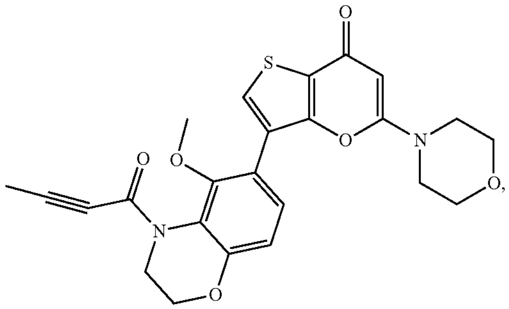
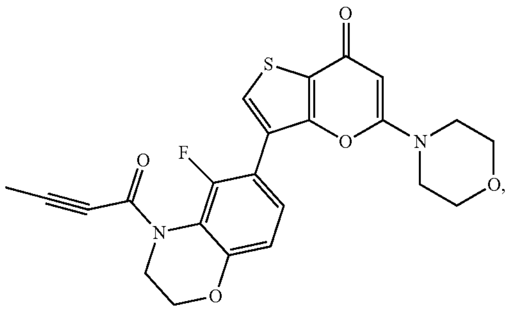

-continued
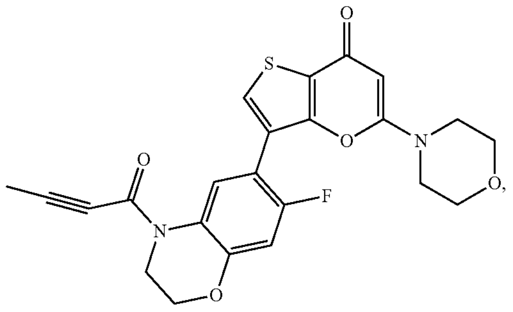
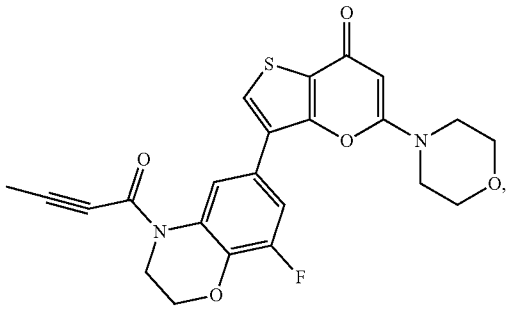
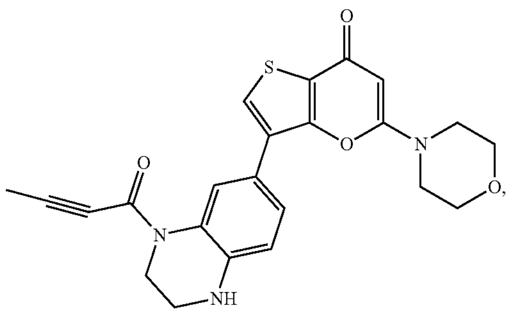
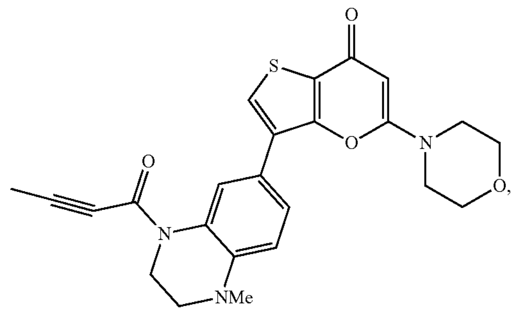
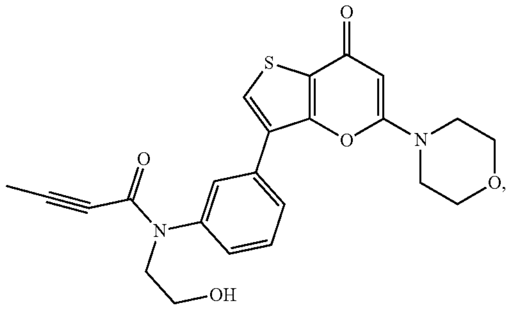
-continued
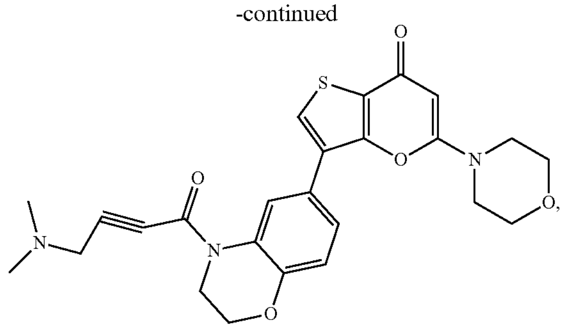
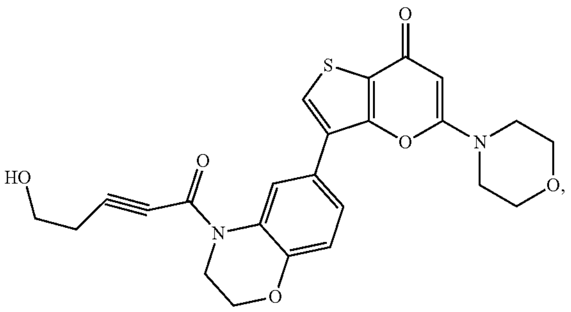
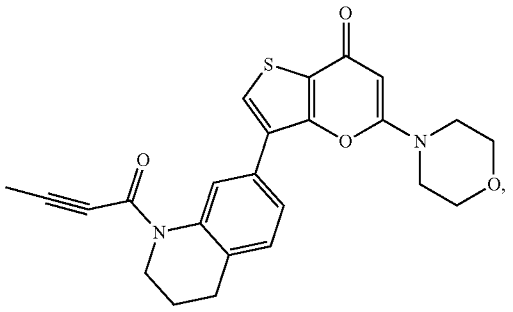
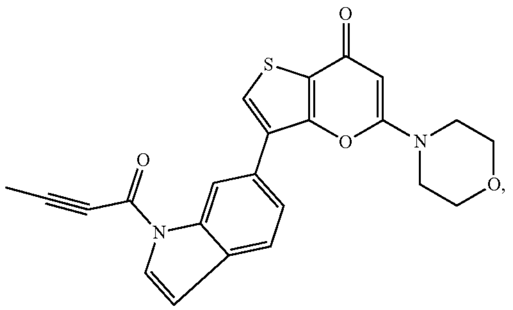
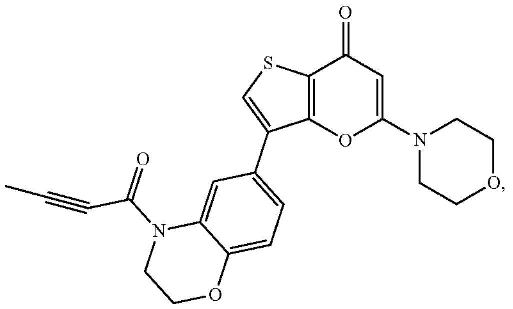

-continued

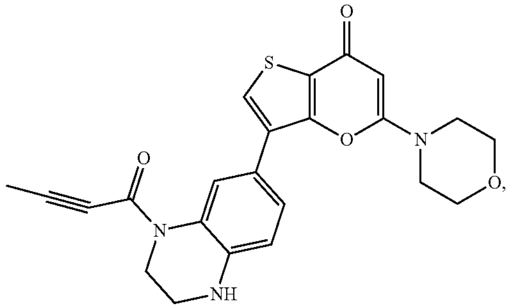

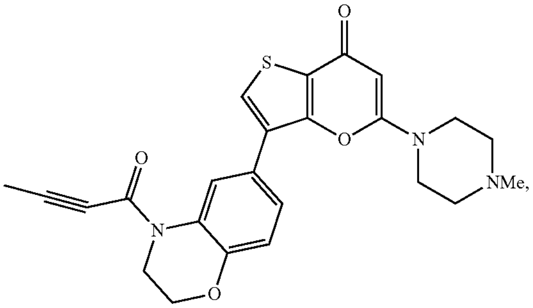

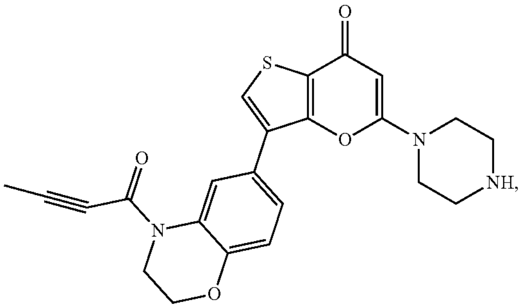

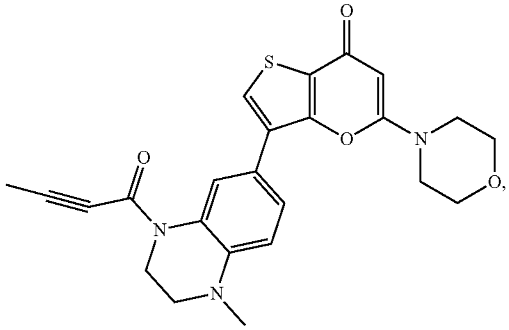

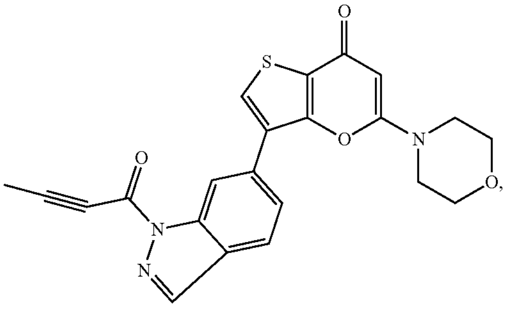

and

-continued

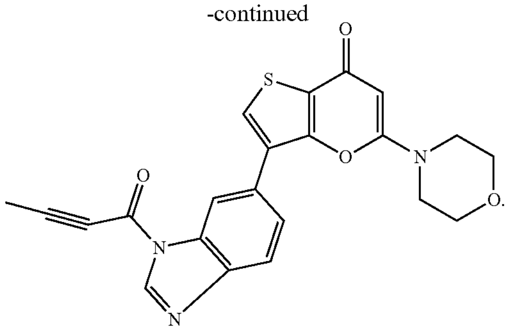

5. A pharmaceutical formulation comprising a compound of claim 1 in association with a pharmaceutically acceptable carrier, diluent, or excipient.

6. A method for treating a disease in a mammal in need thereof wherein said disease is cancer or a non-cancer proliferative disease comprising administering a therapeutically effective amount of a compound of Formula II-IV:

Formula II

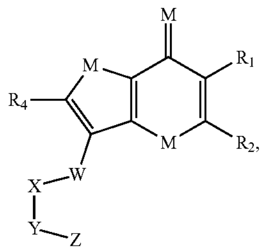

Formula III

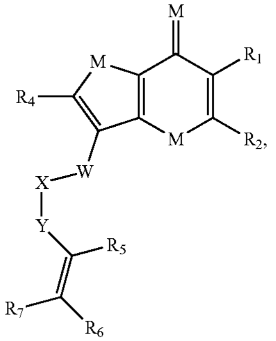

Formula IV

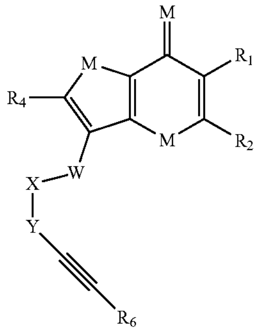

wherein M is independently O or S;

R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2, R4, R5, R6, R7 and $R^8$ are each independently selected from R1;

W is null, NR1, O, S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate;

X is null or O, N, NR1 or S, $CH_2$, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy substituted aryloxy, thioether, substituted thioether, carbamate, substituted carbamate;

provided that if Wis N, O, or S then X cannot be N, O, or S; and if X is N, O, or S then W cannot be N, O, or S;

Y is null, aryl, substituted aryl, heteroaryl, substituted heteroaryl, heterocyclic or substituted heterocyclic, alkyl, alkenyl, alkynyl, carbocycle, aryl, heterocycle, heteroaryl, amino, carboxylic acid, carboxylic ester, carboxyl amide, reverse carboxyamide, substituted alkyl, substituted alkenyl, substituted alkynyl, substituted carbocycle, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, imino, substituted imino, oxime, substituted oxime, alkoxy, substituted alkoxy, aryloxy, substituted aryloxy, thioether, substituted thioether, carbamate, substituted carbamate; and Z is a BTK covalent binding group selected from a Michael acceptor, olefin, substituted olefin, acetylenic, alpha-chloroacetamide, and chlorofluoro-acetamide.

7. A method as in claim 6 wherein said compound is selected from the group consisting of

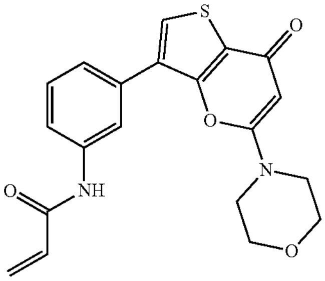

,

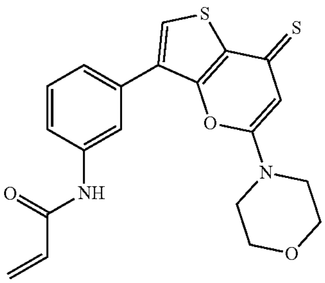

,

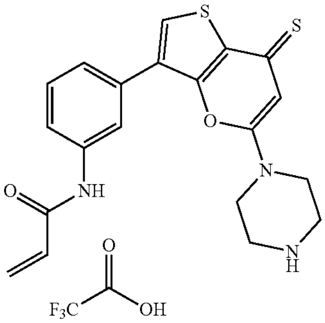

,

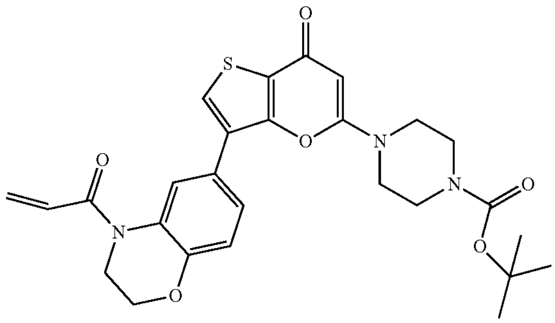

,

-continued
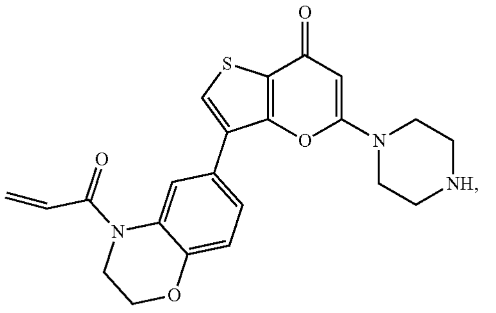
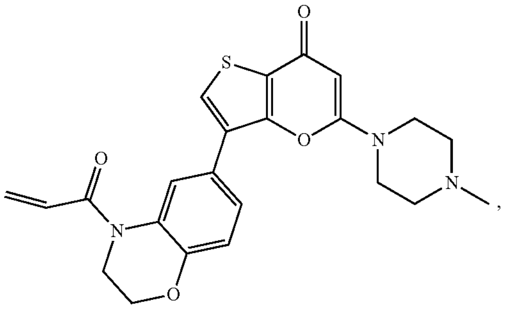
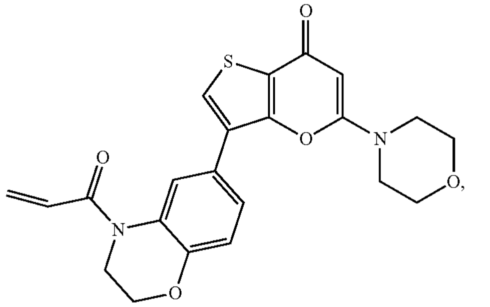
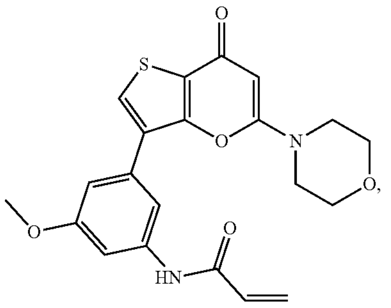
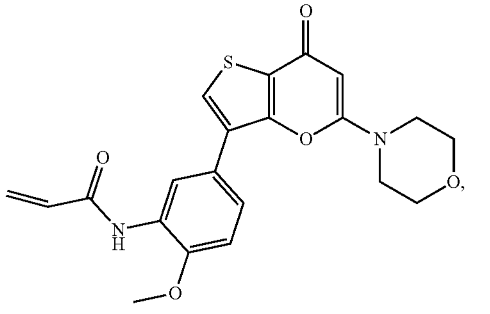
-continued
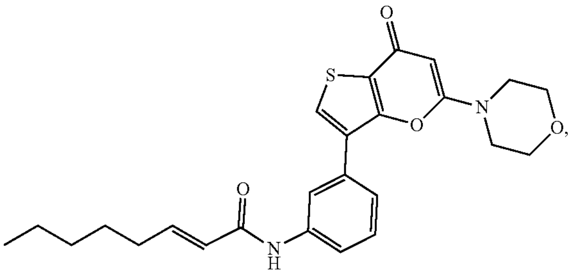
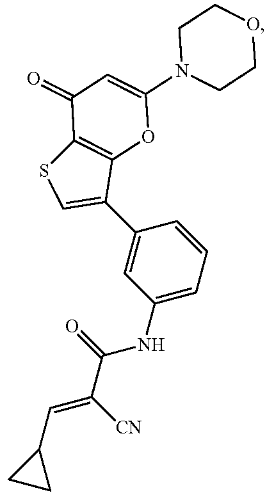
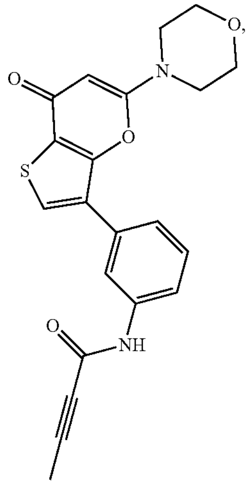
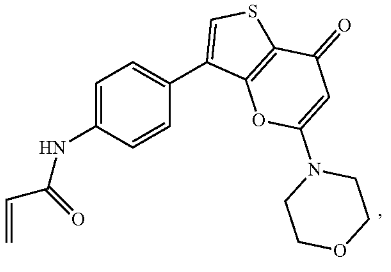

-continued
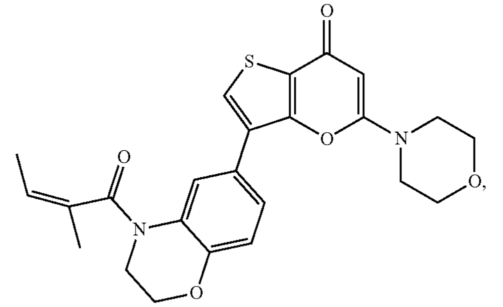
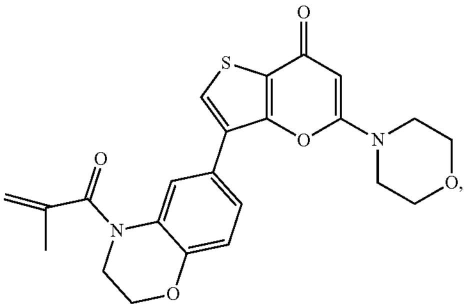
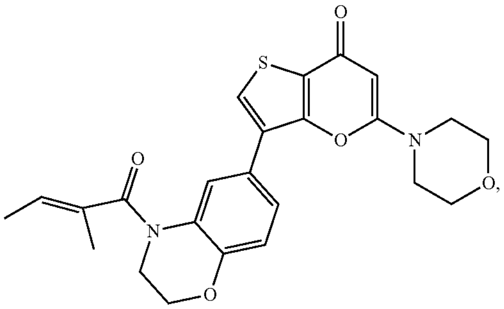
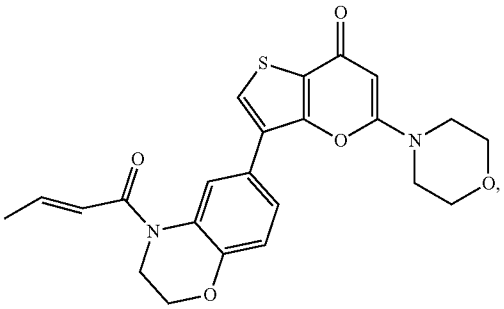
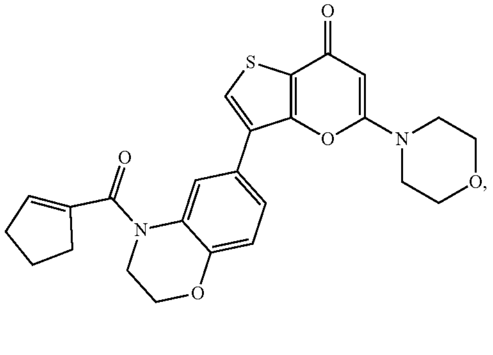
-continued
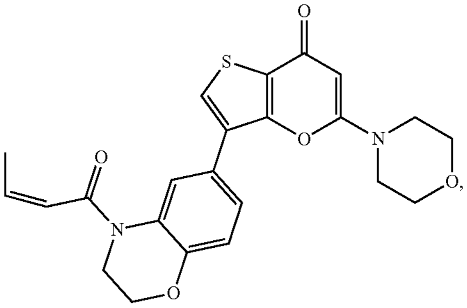
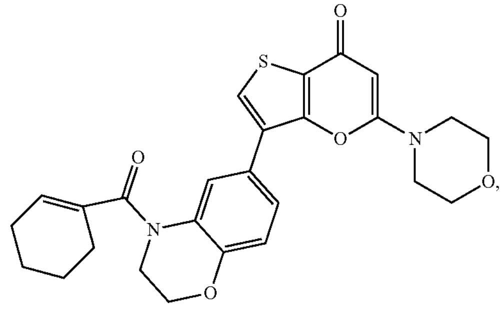
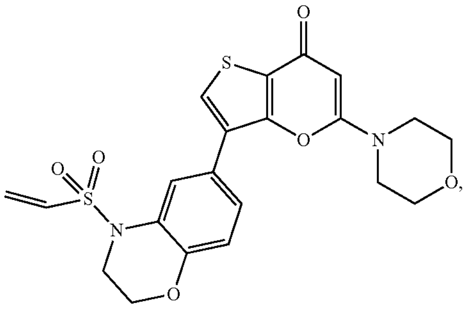
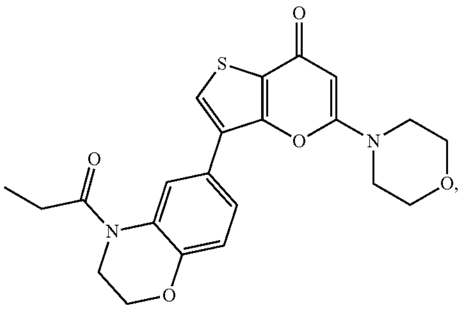
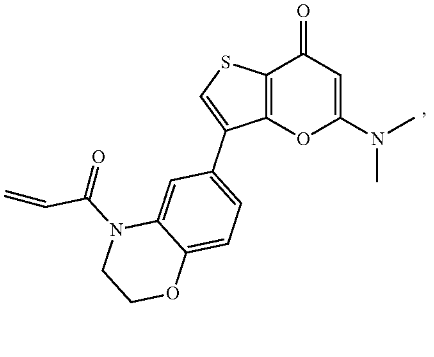

-continued
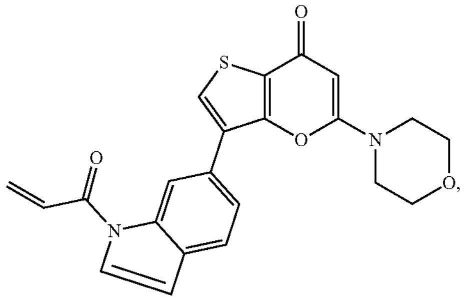
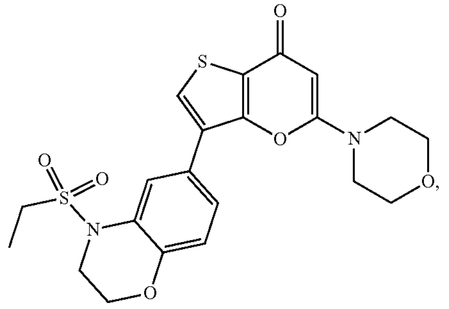
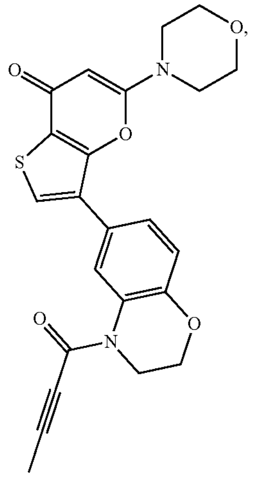
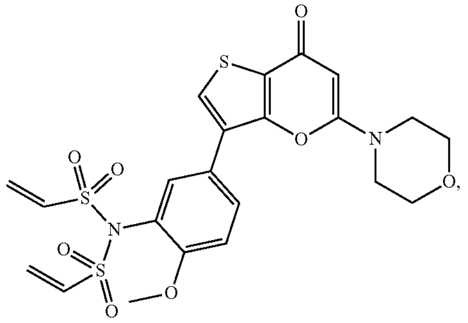
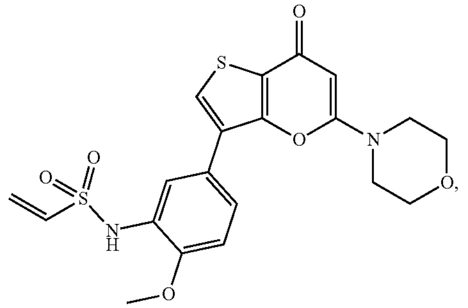
-continued
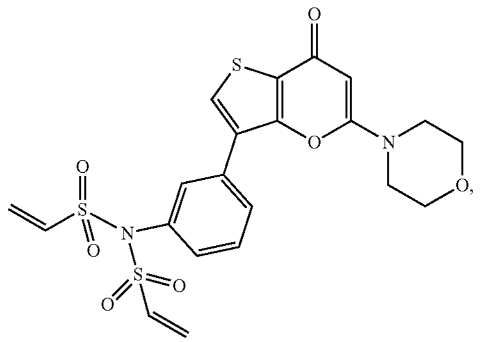
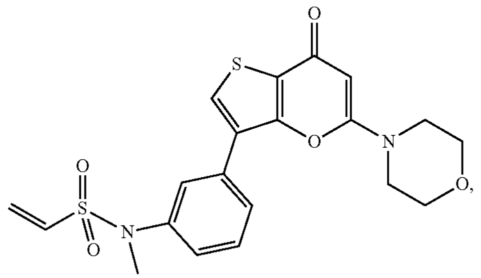
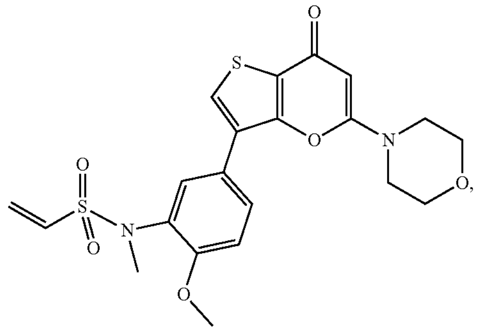
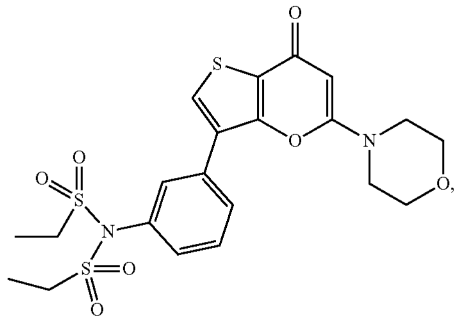
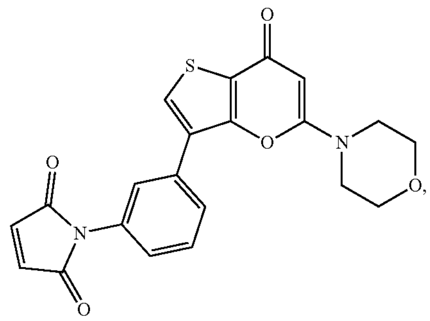

-continued
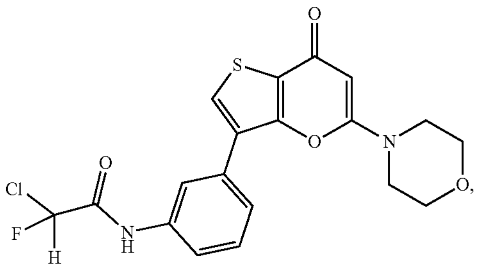
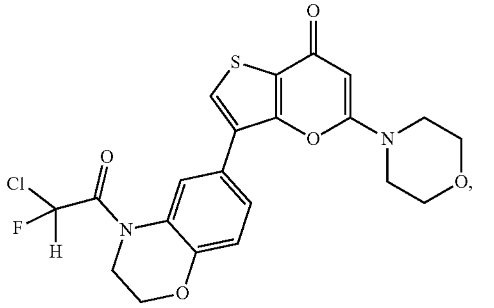
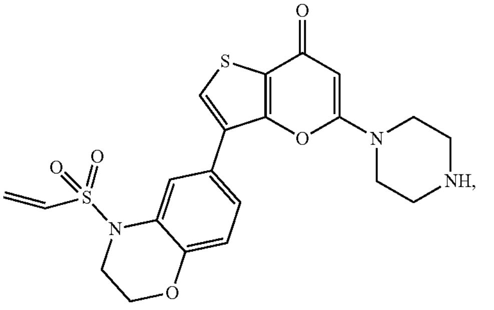
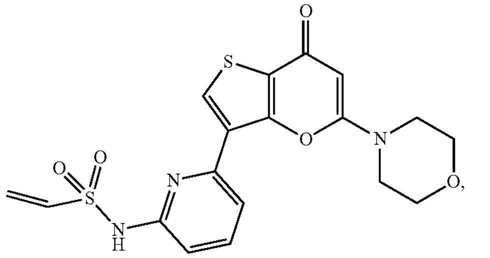
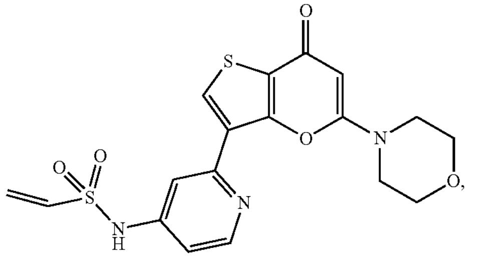
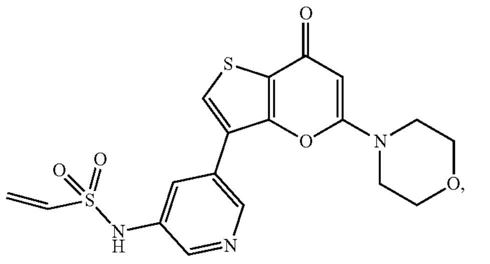
-continued
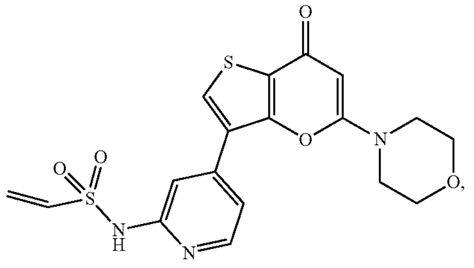
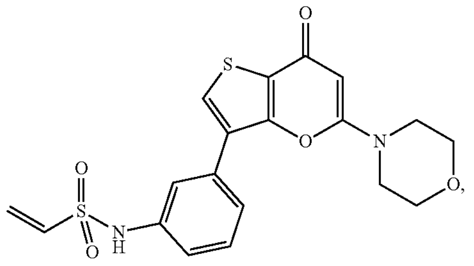
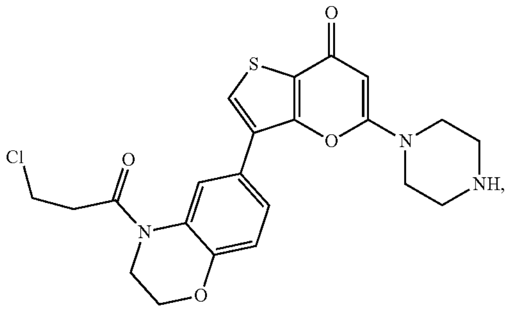
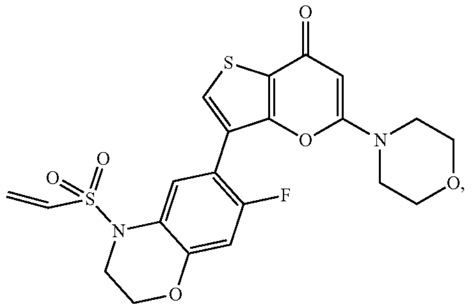
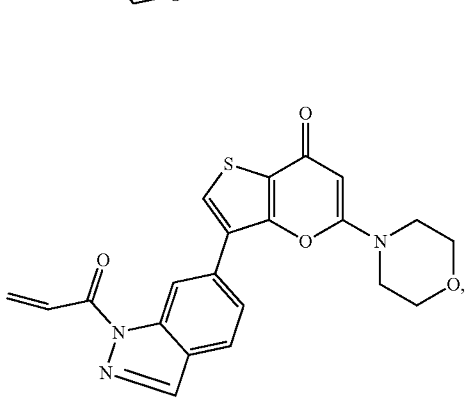

-continued
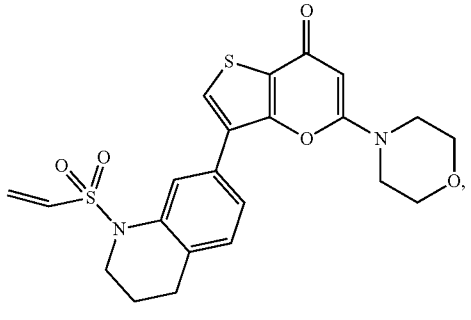
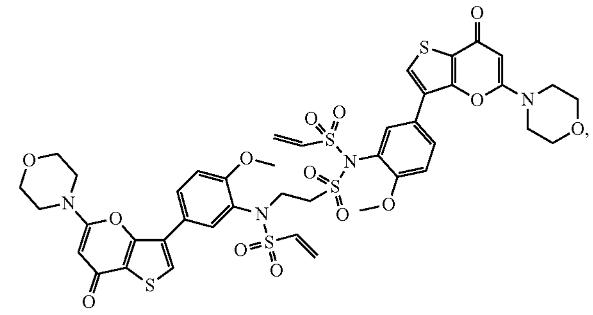
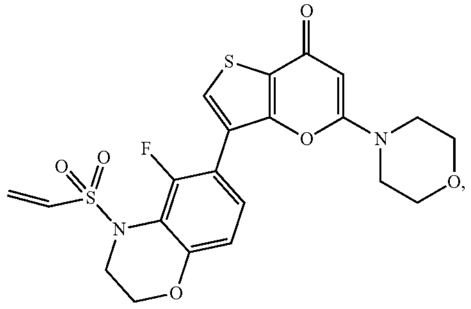
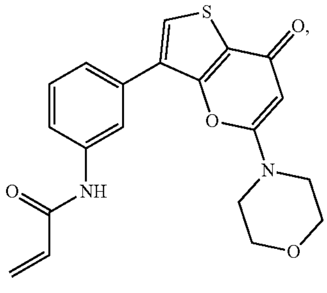
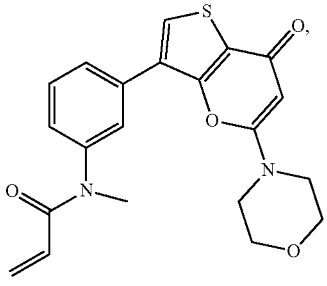
-continued
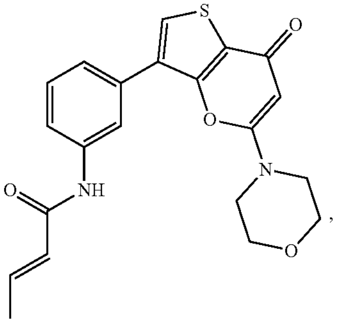
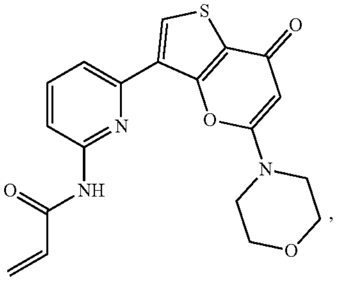
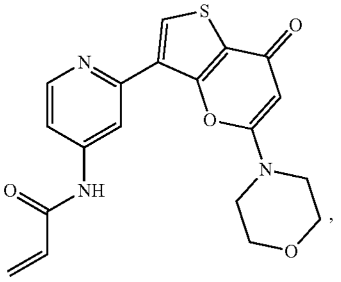
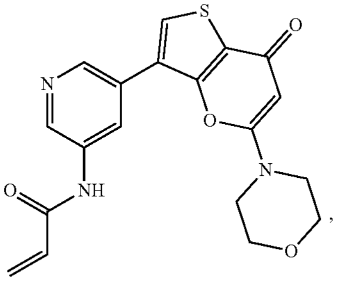
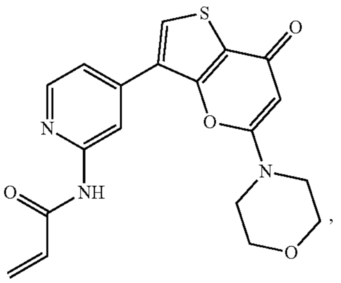
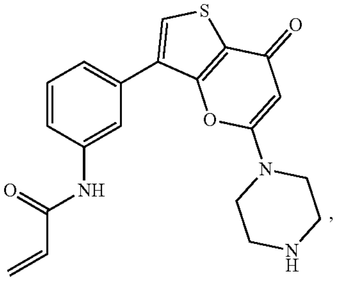

-continued
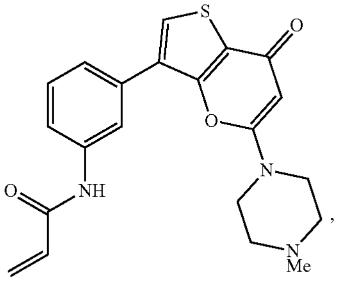
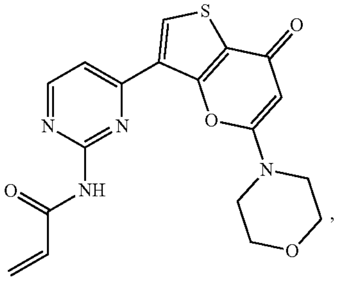
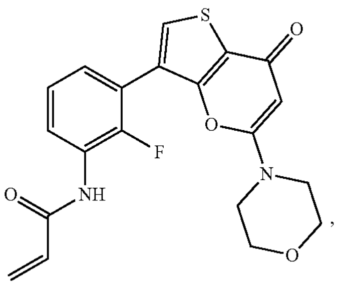
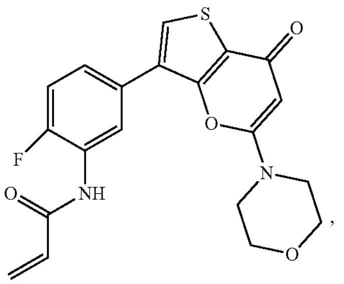
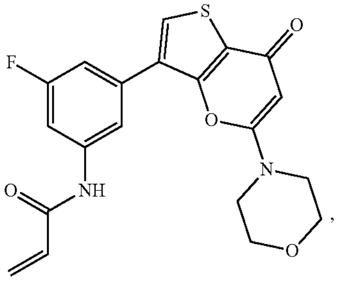
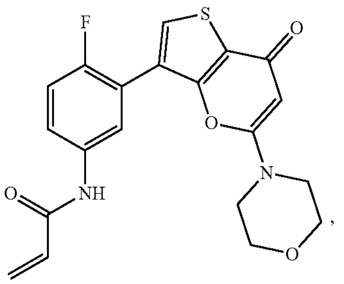
-continued
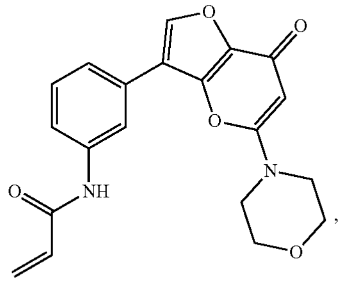
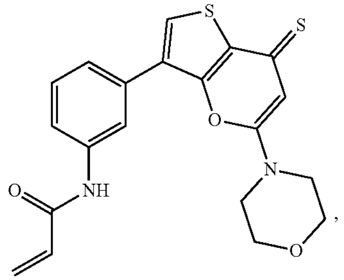
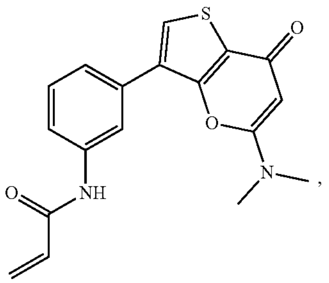
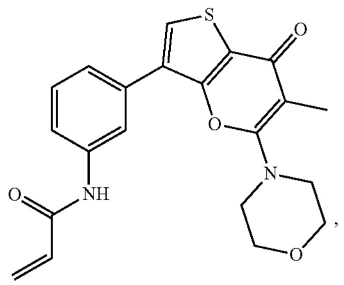
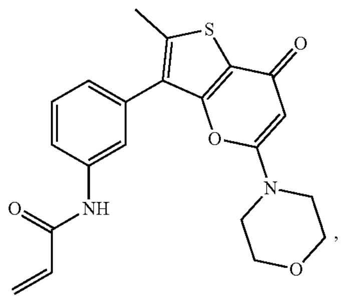
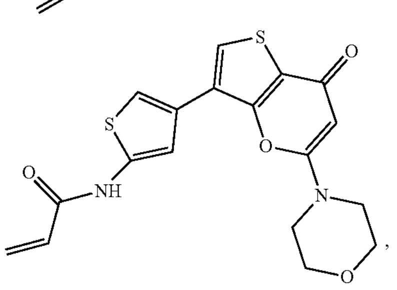

-continued
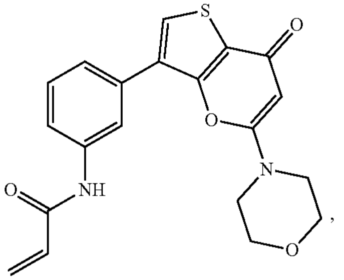
,
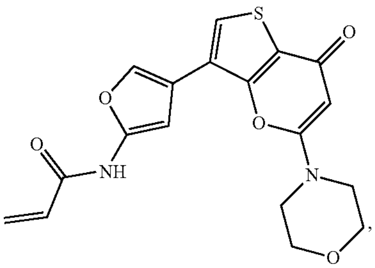
,
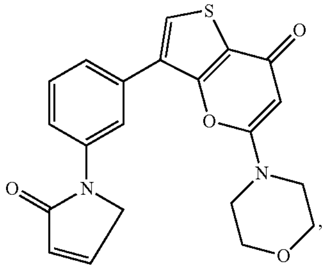
,
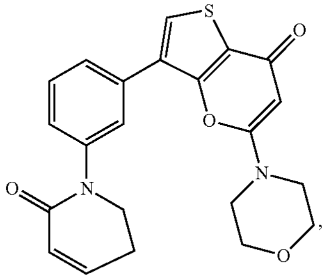
,
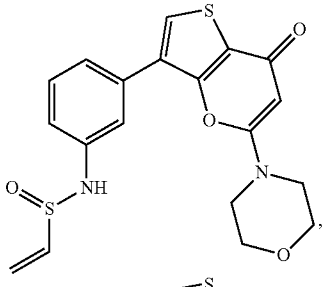
,
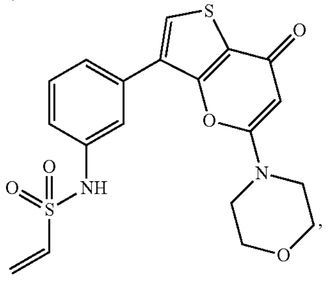
,
-continued
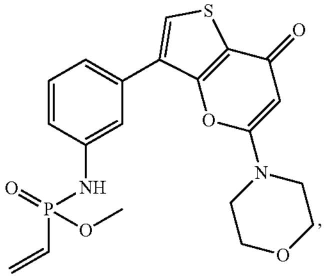
,
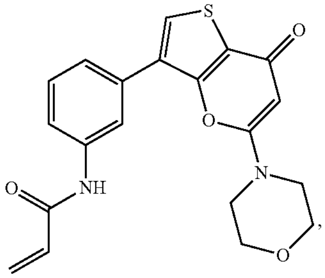
,
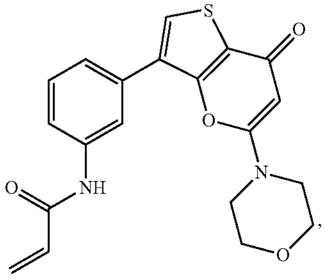
,
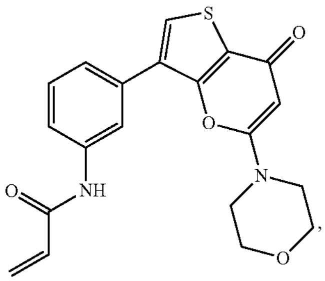
,
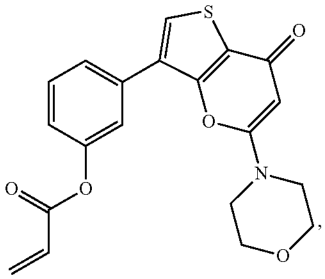
,
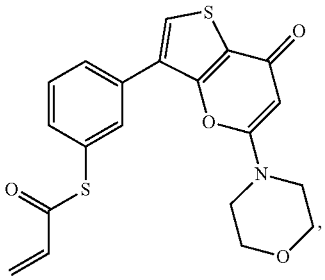
, -continued
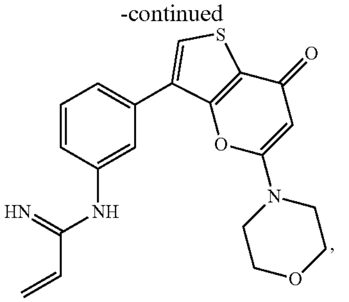
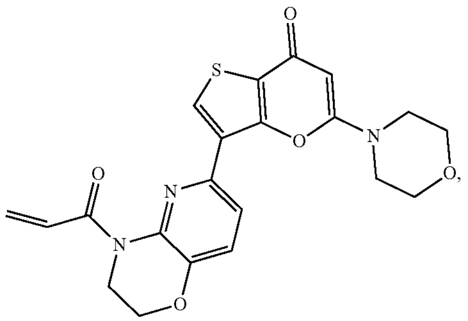
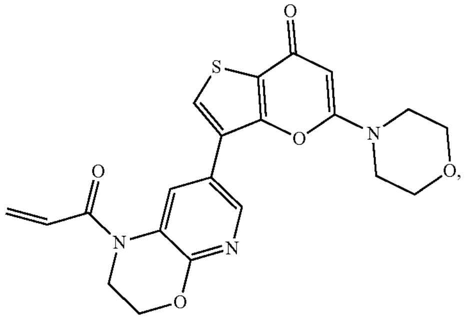
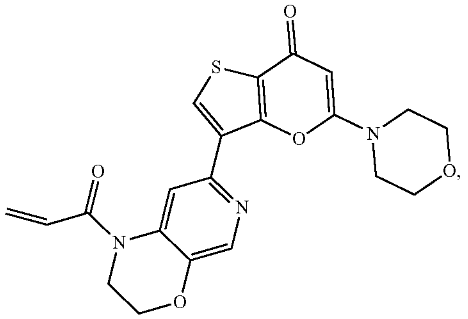
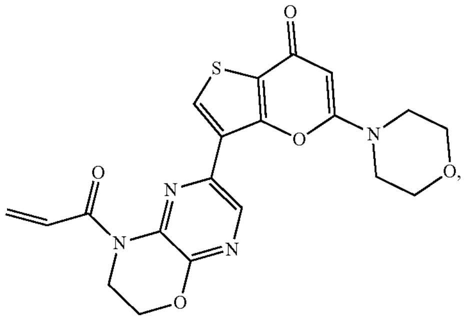
-continued
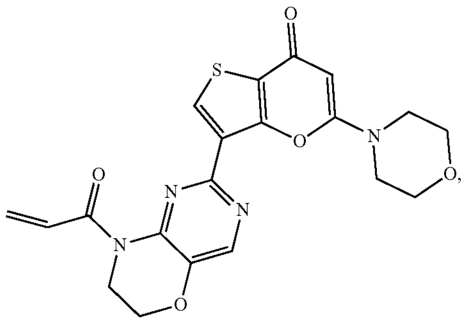
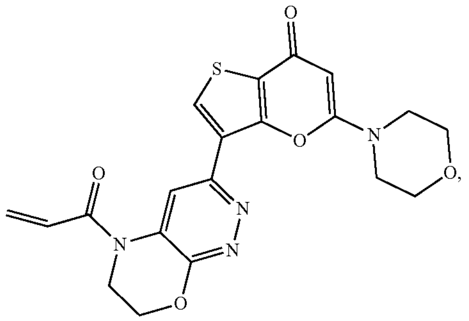
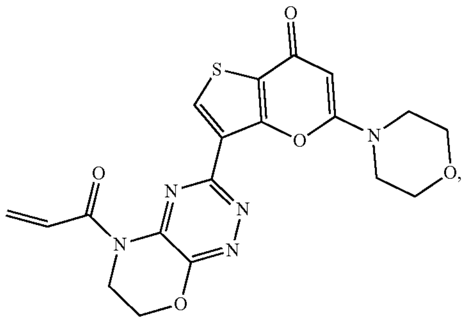
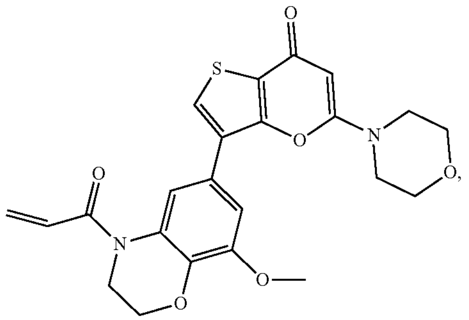
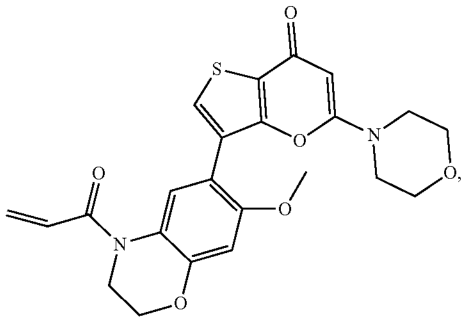

-continued
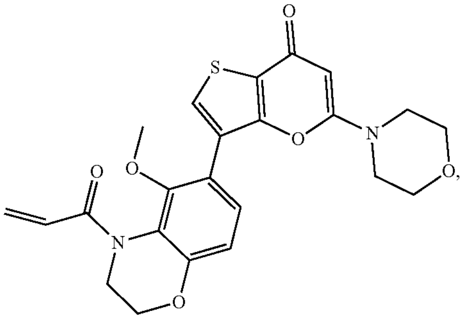
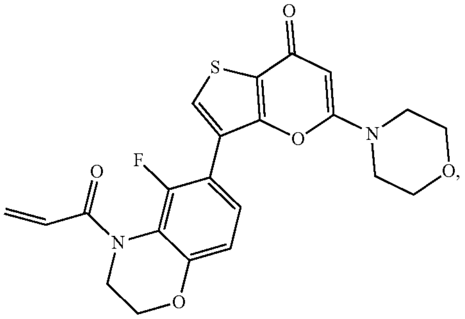
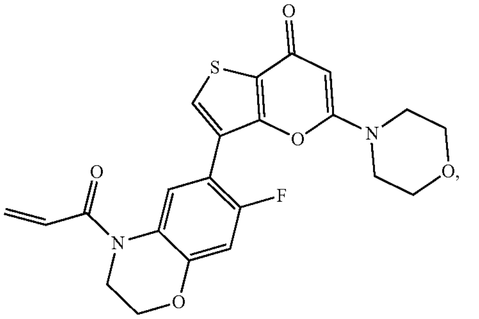
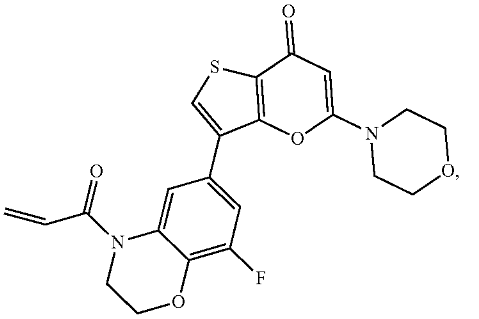
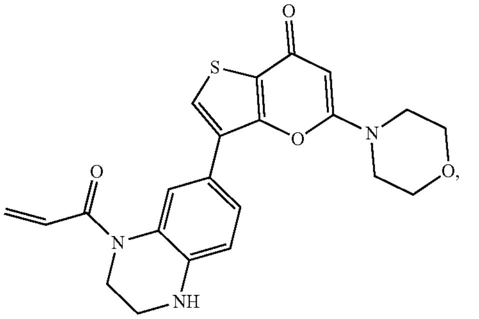
-continued
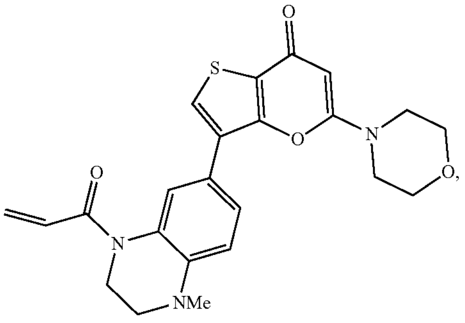
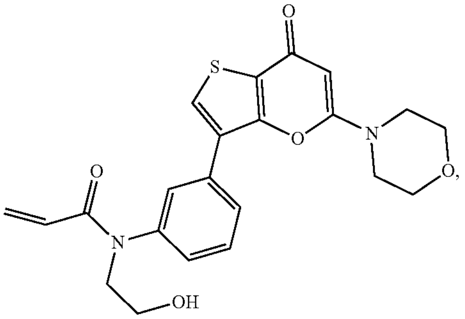
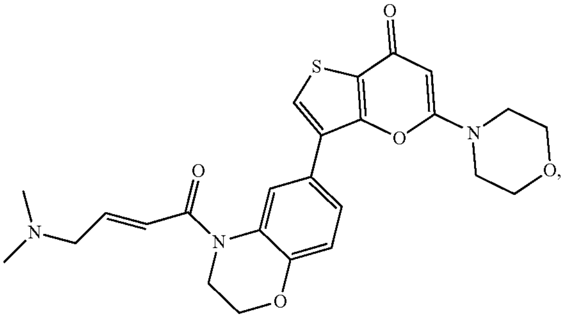
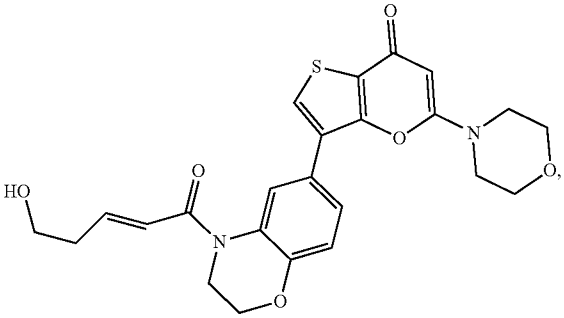
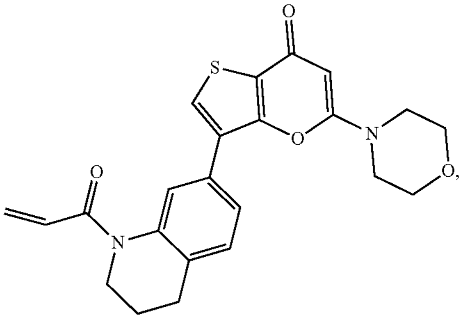

-continued
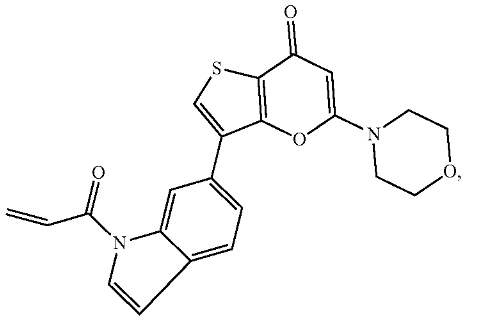
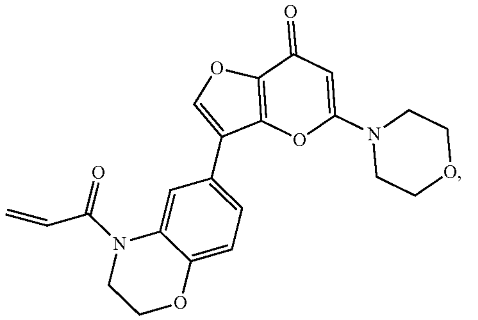
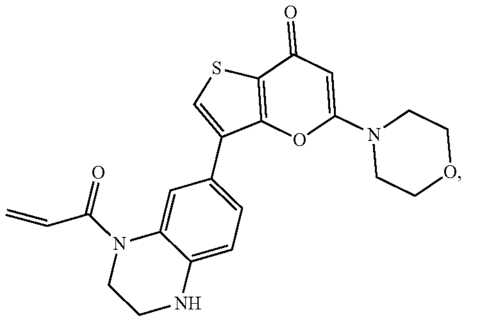
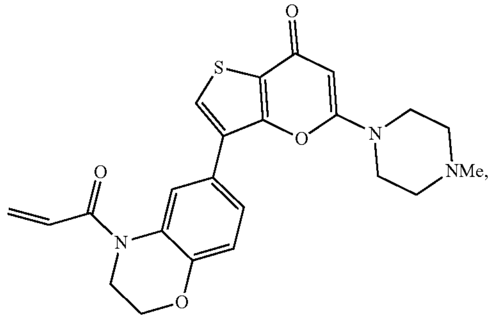
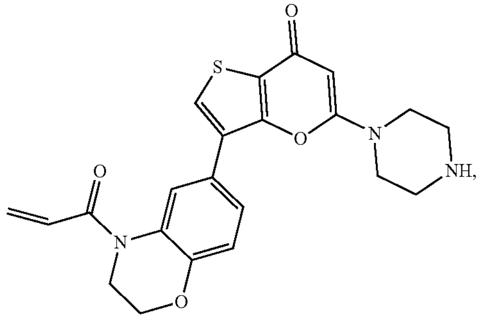
-continued
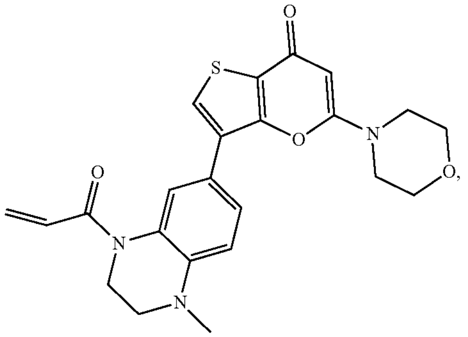
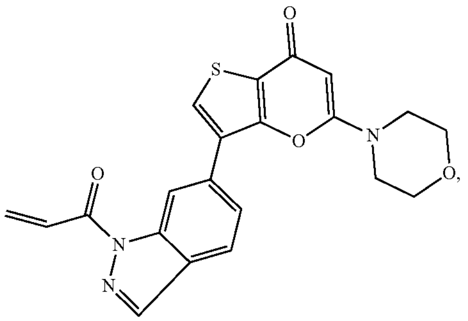
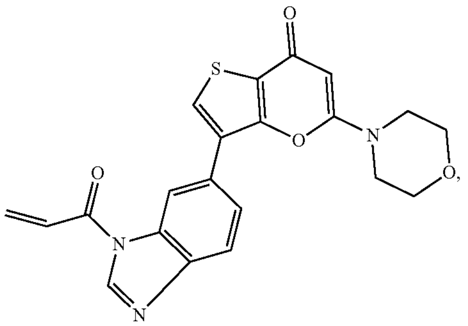
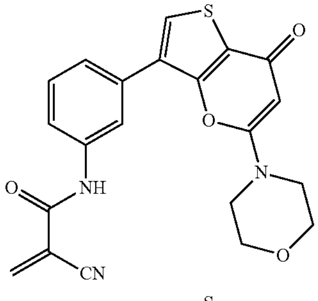
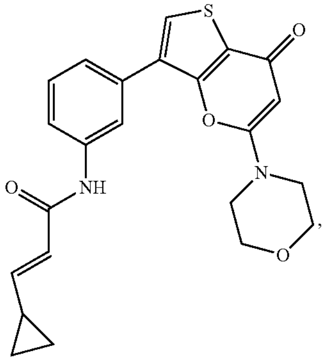

-continued
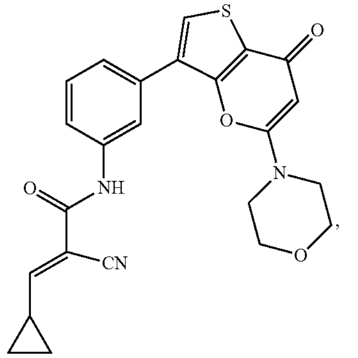 [SMILES: N#C/C(=C\C1CC1)C(=O)Nc1cccc(-c2csc3c(=O)cc(N4CCOCC4)oc23)c1]
,
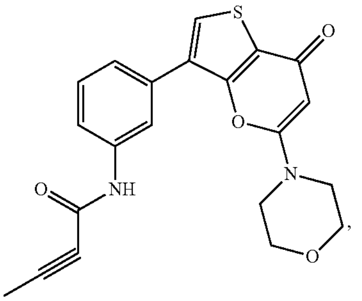
,
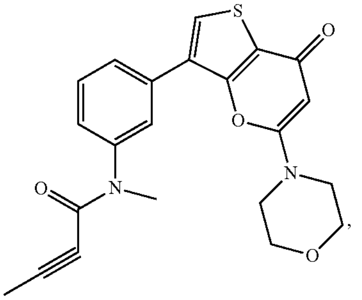
,
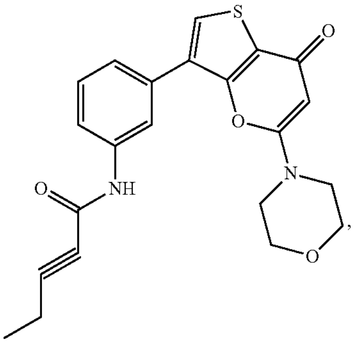
,
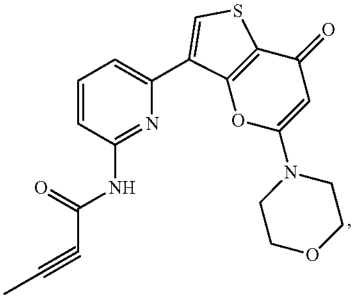
,
-continued
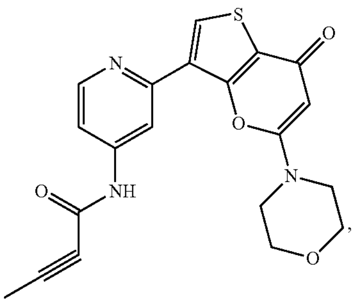
,
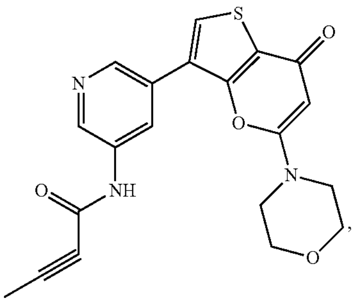
,
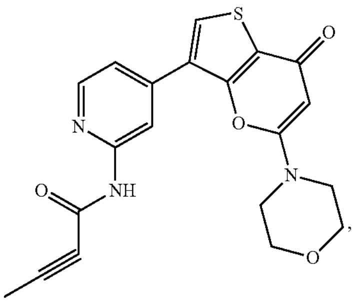
,
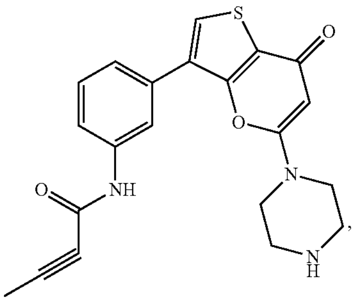
,
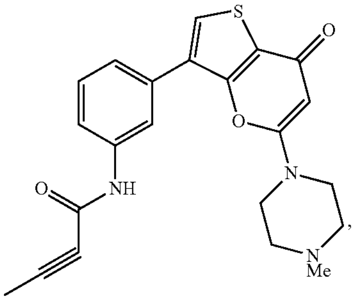
, -continued
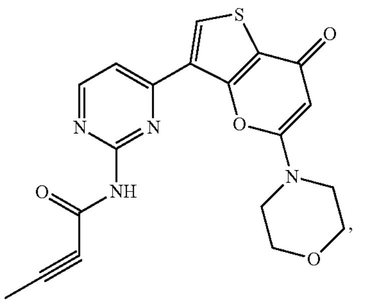
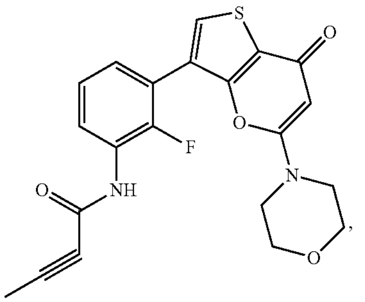
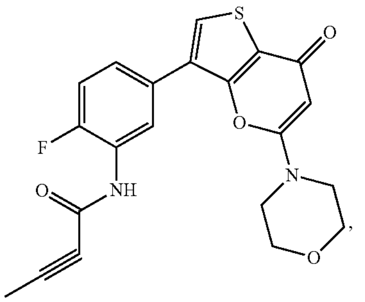
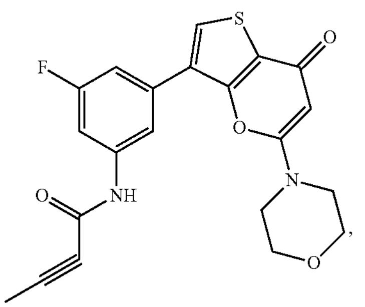
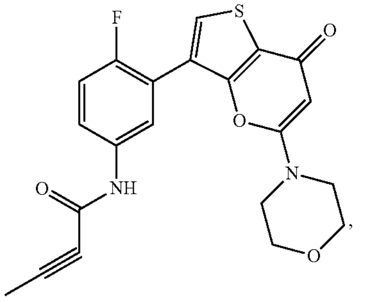
-continued
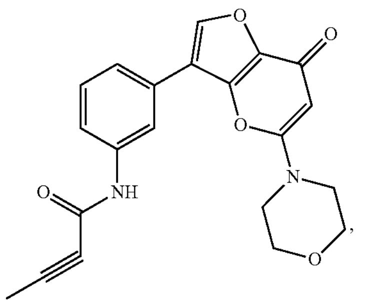
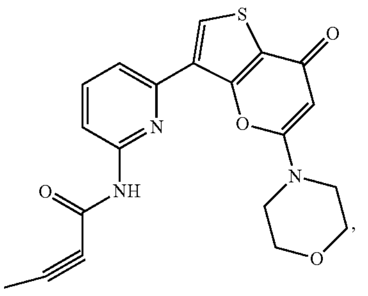
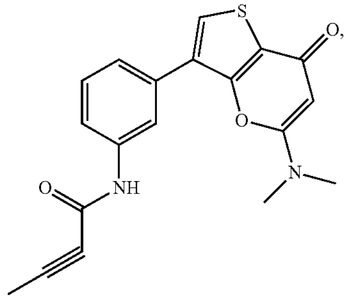
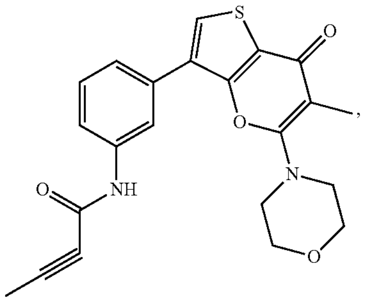
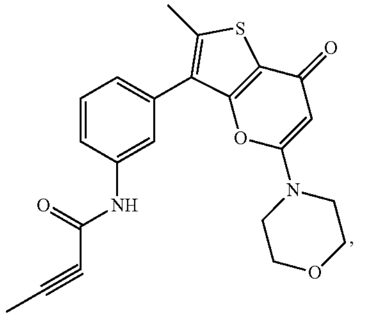

-continued
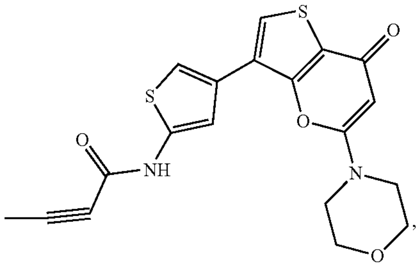
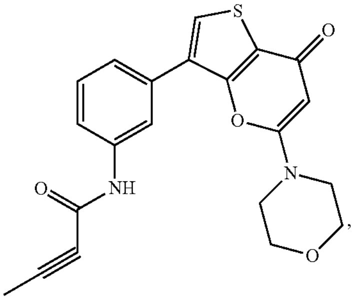
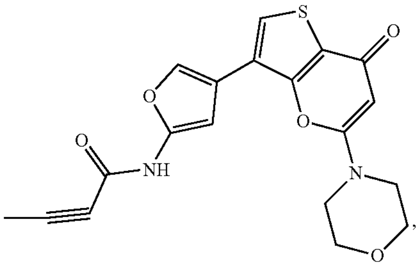
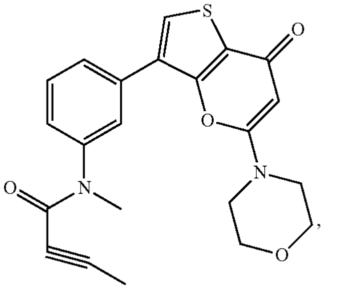
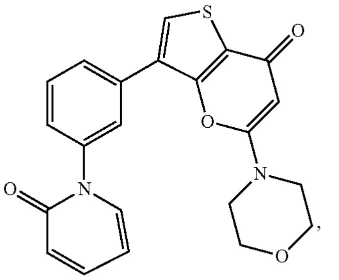
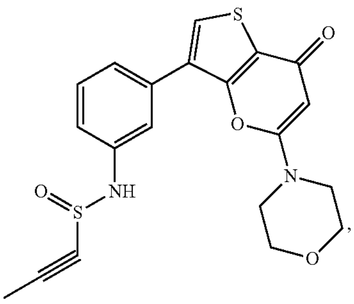
-continued
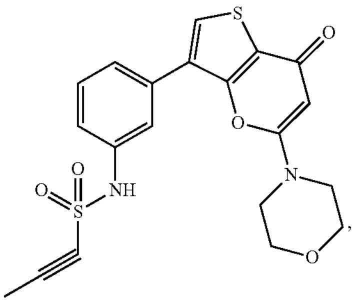
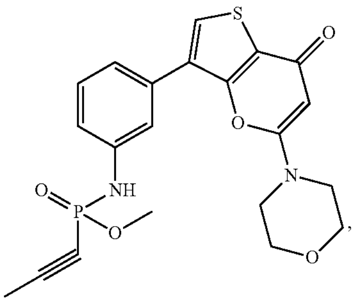
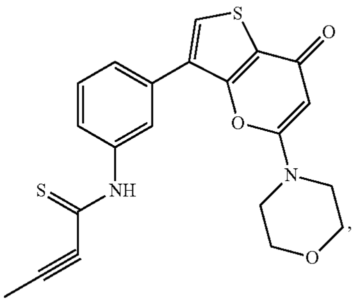
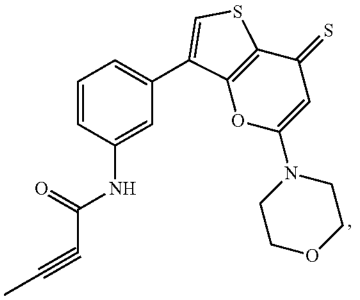
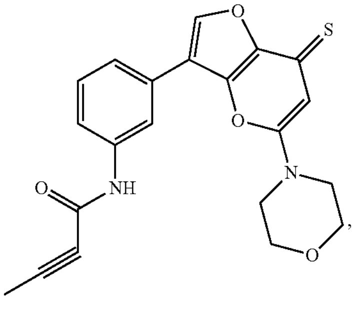

-continued
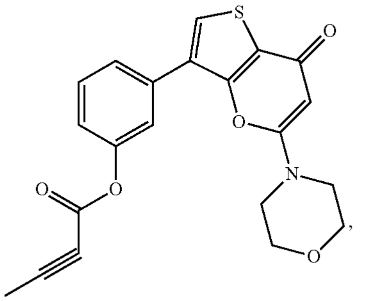,
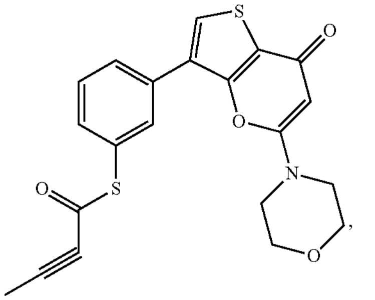,
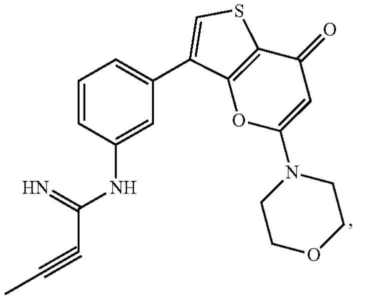,
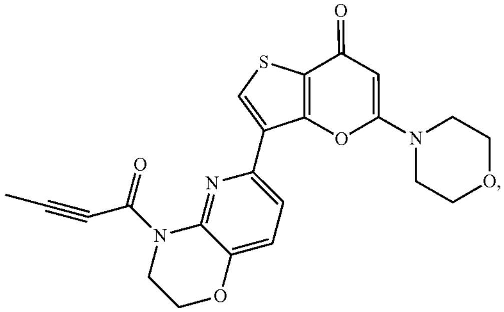,
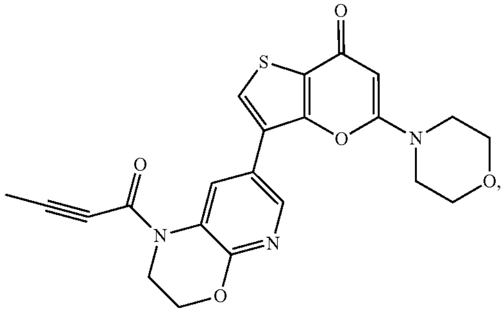,
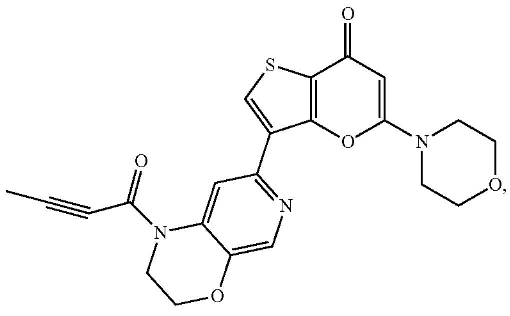,
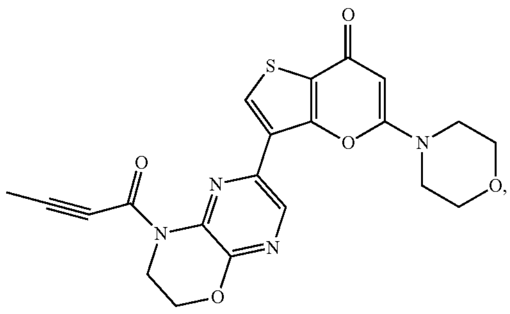,
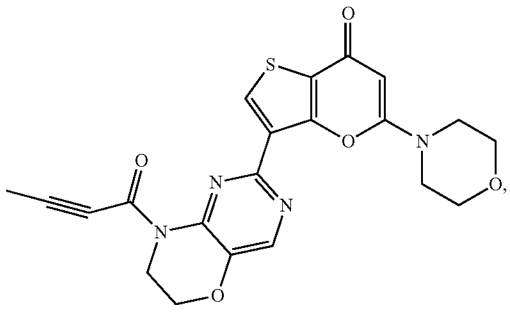,
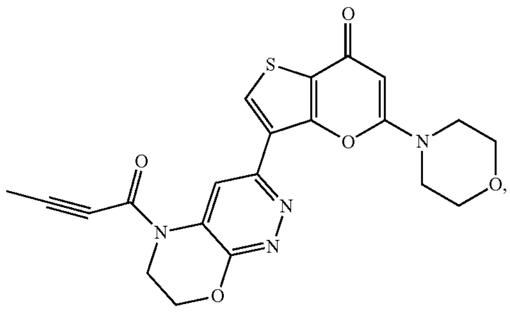,
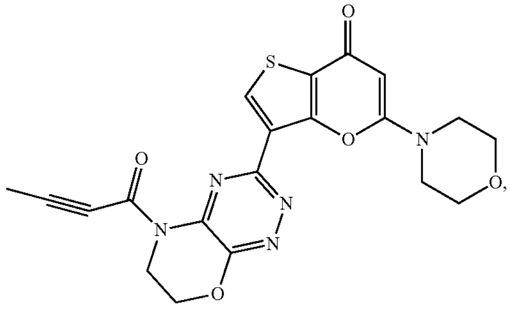, -continued
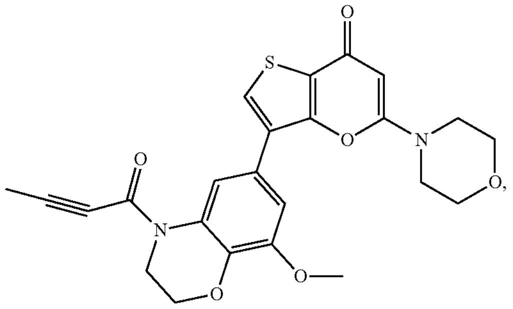
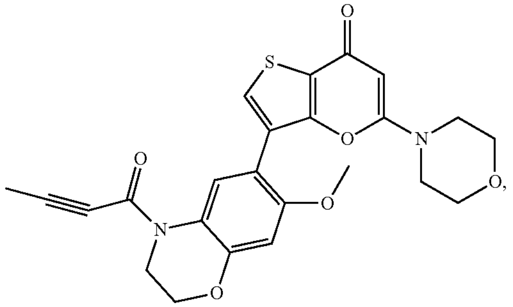
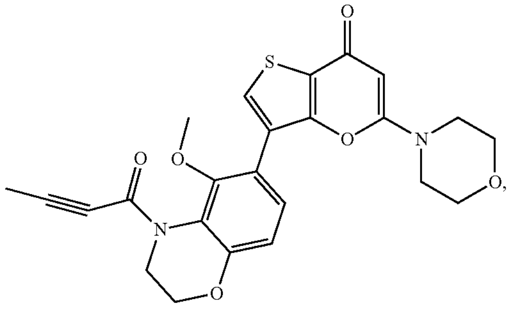
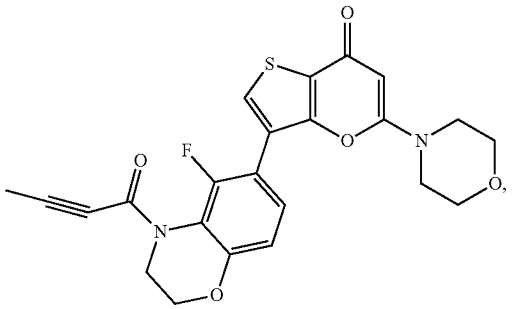
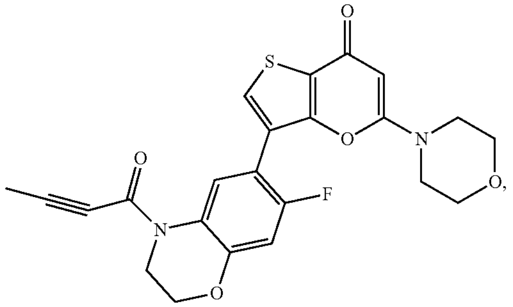
-continued
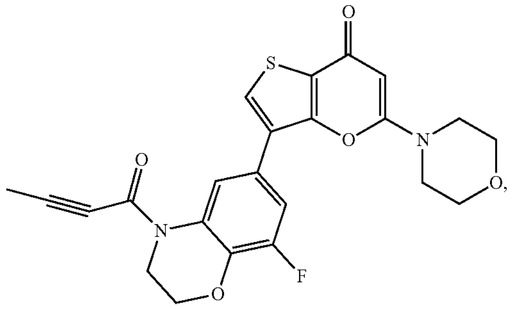
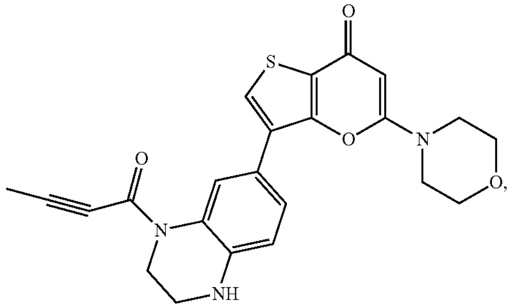
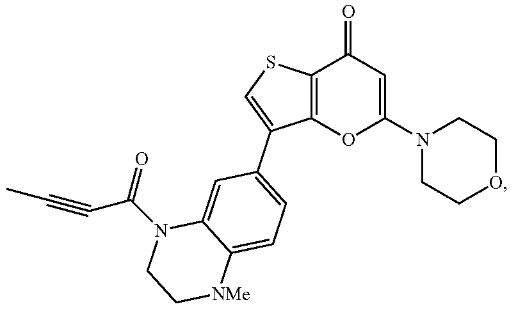
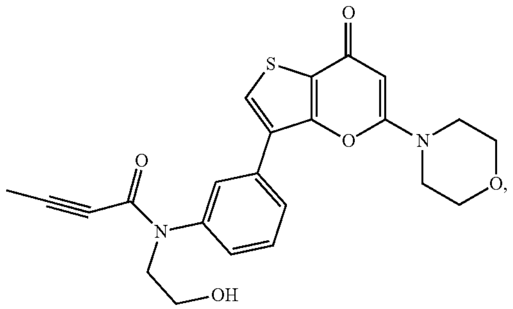
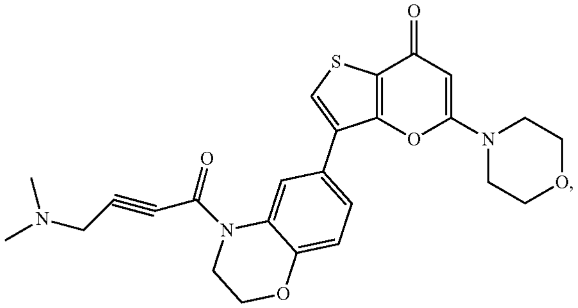

-continued

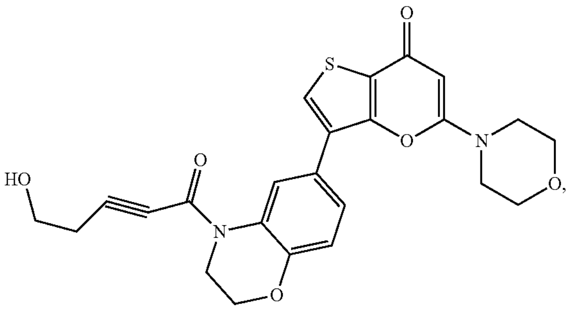

,

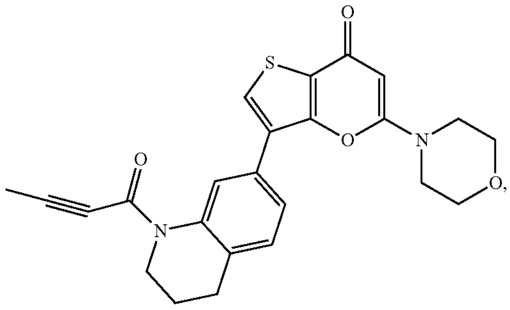

,

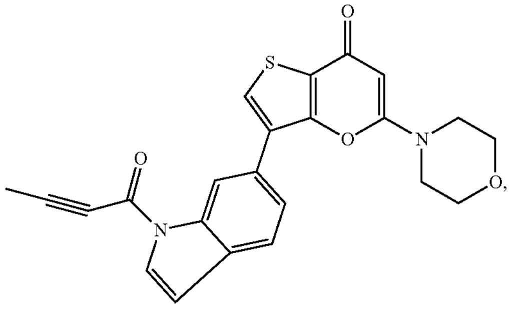

,

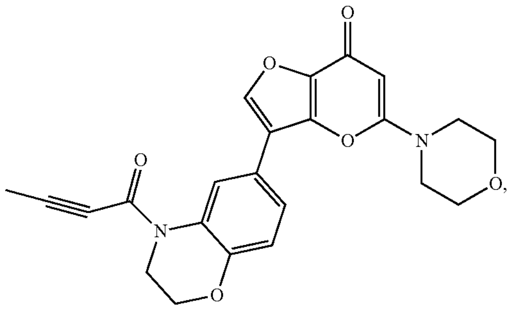

,

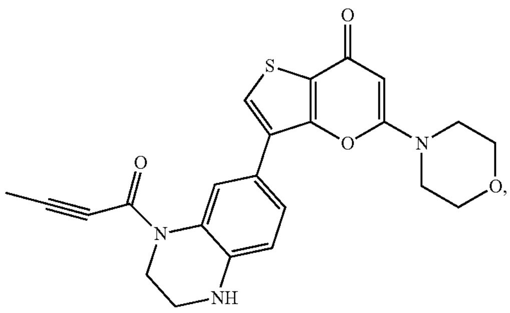

,

-continued

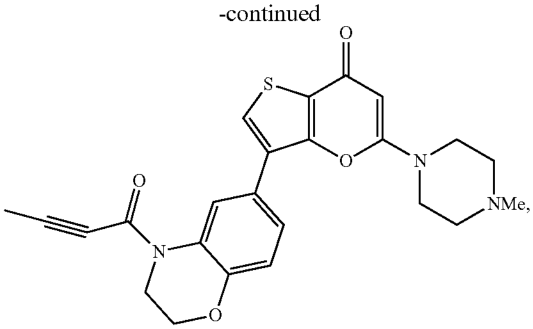

,

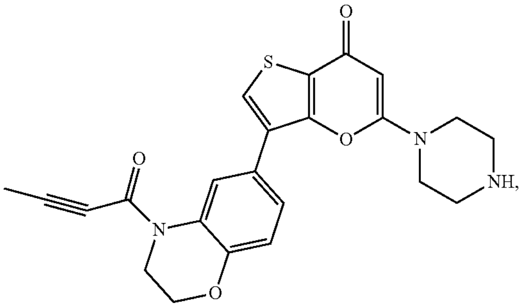

,

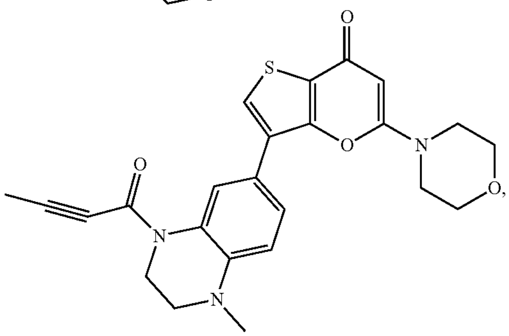

,

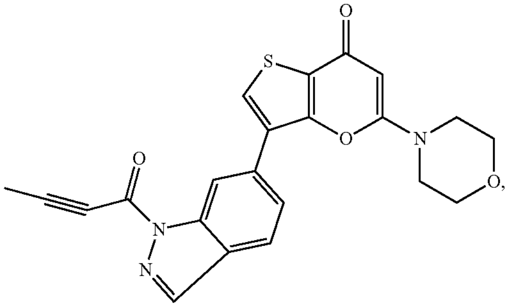

, and

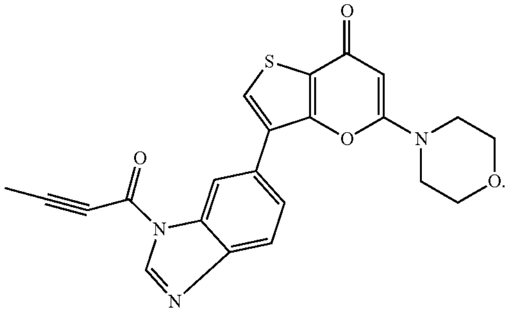

.

8. A method of claim 6 wherein said disease is cancer selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangio sarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom macroglobulinemia, Warthin's tumor, and Wilms' tumor.

9. A method of claim 8 wherein said cancer is a BTK-dependent cancer.

10. A method of claim 8 wherein said cancer is medulloblastoma or neuroblastoma.

11. A method of claim 8 wherein said cancer is a Myc-dependent cancer.

12. A method of claim 11 wherein said Myc-dependent cancer is selected from CLL, multiple myeloma, neuroblastoma, pancreatic, breast, prostate cancer, lymphoid malignancy, myeloid malignancy, medulloblastoma or any other Myc-dependent cancer.

13. A method of claim 6 wherein said disease is a non-cancer pr oliferative disease.

14. A method of claim 13 wherein said non-cancer proliferative disease is selected from the group consisting of fibrotic disease, meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

15. A method of claim 14 wherein said non-cancer proliferative disease is fibrotic disease selected from the group consisting of primary biliary cholangitis (PBC), non-alcoholic steatohepatitis (NASH), scleroderma and idiopathic pulmonary fibrosis (IPF).

16. A pharmaceutical formulation comprising a compound of claim 1 in association with a pharmaceutically acceptable carrier, diluent, or excipient.

17. A pharmaceutical formulation comprising a compound of claim 2 in association with a pharmaceutically acceptable carrier, diluent, or excipient.

18. A pharmaceutical formulation comprising a compound of claim 3 in association with a pharmaceutically acceptable carrier, diluent, or excipient.

19. A pharmaceutical formulation comprising a compound of claim 4 in association with a pharmaceutically acceptable carrier, diluent, or excipient.

* * * * *